(12) United States Patent
Damour et al.

(10) Patent No.: US 7,473,701 B2
(45) Date of Patent: Jan. 6, 2009

(54) SUBSTITUTED INDAZOLES, COMPOSITIONS CONTAINING THEM, METHOD OF PRODUCTION AND USE

(75) Inventors: Dominique Damour, Orly (FR); Jean-Christophe Carry, Saint-Maur (FR); Patrick Nemecek, Thiais (FR); Corinne Terrier, Livry-Gargan (FR); Frederico Nardi, Paris (FR); Bruno Filoche-Romme, Creteil (FR); Marie-Pierre Cherrier, Ivry sur Seine (FR); Daniel Bezard, Bagnolet (FR)

(73) Assignee: Aventis Pharma S.A., Antony (FR)

(*) Notice: Subject to any disclaimer, the term of this patent is extended or adjusted under 35 U.S.C. 154(b) by 430 days.

(21) Appl. No.: 10/963,880

(22) Filed: Oct. 13, 2004

(65) Prior Publication Data

US 2005/0059722 A1  Mar. 17, 2005

Related U.S. Application Data

(62) Division of application No. 10/385,870, filed on Mar. 11, 2003, now Pat. No. 6,858,638.

(30) Foreign Application Priority Data

Mar. 11, 2002  (FR) .................................. 02 02996

(51) Int. Cl.
*A61K 31/415*  (2006.01)
*C07D 231/54*  (2006.01)

(52) U.S. Cl. ........................ 514/405; 514/306; 514/337; 548/360.1; 548/361.1; 548/364.1; 546/134; 546/268.4

(58) Field of Classification Search ................. 514/405, 514/306, 337, 2; 548/360.1, 361.1, 364.1; 546/134, 268.4
See application file for complete search history.

(56) References Cited

U.S. PATENT DOCUMENTS

| 5,880,151 | A | 3/1999 | Medina et al. | |
|---|---|---|---|---|
| 6,858,638 | B2 * | 2/2005 | Damour et al. | 514/405 |
| 6,949,579 | B2 | 9/2005 | Dutruc-Rosset | |
| 6,982,274 | B2 * | 1/2006 | Oinuma et al. | 514/338 |
| 7,064,215 | B2 * | 6/2006 | Renhowe et al. | 548/125 |
| 7,199,147 | B2 | 4/2007 | Imazaki et al. | |
| 2005/0282880 | A1 | 12/2005 | Oinuma et al. | |

FOREIGN PATENT DOCUMENTS

| JP | 47021425 | 6/1972 |
|---|---|---|
| JP | 62025747 | 2/1987 |
| WO | WO 98/05315 | 2/1998 |
| WO | WO 99/15500 | 4/1999 |
| WO | WO 99/64004 | 12/1999 |
| WO | WO 00/27627 | 5/2000 |
| WO | WO 00/73264 | 12/2000 |
| WO | WO 01/53268 | 7/2001 |
| WO | WO 01/85726 | 11/2001 |
| WO | WO 02/10137 | 2/2002 |
| WO | WO 02/083648 | 10/2002 |
| WO | WO 02/100833 | 12/2002 |
| WO | WO 03/004488 | 1/2003 |
| WO | WO 03/024969 | 3/2003 |

* cited by examiner

*Primary Examiner*—Rei-tsang Shiao
(74) *Attorney, Agent, or Firm*—Kelly L. Bender; Balaram Gupta

(57) ABSTRACT

Substituted indazoles, compositions containing them, method of production and use. The present invention relates in particular to novel specific substituted indazoles exhibiting kinase-inhibiting activity, having therapeutic activity, in particular in oncology.

14 Claims, No Drawings

SUBSTITUTED INDAZOLES, COMPOSITIONS CONTAINING THEM, METHOD OF PRODUCTION AND USE

This application is a division of U.S. application Ser. No. 10/385,870, filed Mar. 11, 2003, now allowed, which claims the benefit of priority of French Patent Application No. 02/02, 996, filed Mar. 11, 2002, which is incorporated herein by reference in its entirety.

The present invention relates in particular to novel chemical compounds, particularly novel substituted indazoles, to the compositions containing them, and to their use as medicinal products.

More particularly, the invention relates to novel specific indazoles exhibiting anticancer activity via the modulation of the activity of proteins, in particular of kinases.

To date, most of the commercial compounds used in chemotherapy pose considerable problems of side effects and of tolerance in patients. These effects may be limited insofar as the medicinal products used act selectively on cancer cells, with the exclusion of healthy cells. One of the solutions for limiting the undesirable effects of chemotherapy may therefore consist in using medicinal products which act on metabolic pathways or elements constituting these pathways, expressed mainly in cancer cells, and which would be expressed very little or not at all in healthy cells.

Protein kinases are a family of enzymes which catalyze the phosphorylation of hydroxyl groups of specific protein residues such as tyrosine, serine or threonine residues. Such phosphorylations can widely modify the function of proteins; thus, protein kinases play an important role in regulating a large variety of cell processes, including in particular metabolism, cell proliferation, cell differentiation, cell migration or cell survival. Among the various cellular functions in which the activity of a protein kinase is involved, certain processes represent attractive targets for treating cancer-related diseases and also other diseases.

Thus, one of the objects of the present invention is to provide compositions having anticancer activity, acting in particular with respect to kinases. Among the kinases for which modulation of the activity is sought, FAK (Focal Adhesion Kinase) is preferred.

FAK is a cytoplasmic tyrosine kinase which plays an important role in transduction of the signal transmitted by integrins, a family of heterodimeric cell adhesion receptors. FAK and the integrins are co-localized in perimembrane structures called adhesion plaques. It has been shown, in many cell types, that the activation of FAK, and also phosphorylation thereof on tyrosine residues and in particular autophosphorylation thereof on tyrosine 397, are dependent on the binding of integrins to their extracellular ligands and are therefore induced during cell adhesion [L. Kornberg, et al. J. Biol. Chem. 267(33): 23439-442. (1992)]. The autophosphorylation of FAK, on tyrosine 397, represents a binding site for another tyrosine kinase, Src, via its SH2 domain [Schaller et al. Mol. Cell. Biol. 14:1680-1688. 1994; Xing et al. Mol. Cell. Biol. 5: 413-421. 1994]. Src can then phosphorylate FAK on tyrosine 925, thus recruiting the Grb2 adaptor protein and inducing, in certain cells, activation of the ras and MAP Kinase pathway involved in the control of cell proliferation [Schlaepfer et al. Nature; 372:786-791. 1994; Schlaepfer et al. Prog. Biophy. Mol. Biol. 71:435-478. 1999; Schlaepfer and Hunter, J. Biol. Chem. 272:13189-13195. 1997]. The activation of FAK can also induce the jun NH2-terminal kinase (JNK) signaling pathway and result in the progression of cells for the G1 phase of the cell cycle [Oktay et al., J. Cell. Biol.145: 1461-1469. 1999]. Phosphatidylinositol-3-OH kinase (P13-kinase) also binds to FAK on tyrosine 397, and this interaction might be necessary for the activation of P13-kinase [Chen and Guan, Proc. Nat. Acad. Sci. USA. 91: 10148-10152. 1994; Ling et al. J. Cell. Biochem. 73: 533-544. 1999]. The FAK/Src complex phosphorylates various substrates, such as paxillin and p130CAS in fibroblasts [Vuori et al. Mol. Cell. Biol. 16: 2606-2613. 1996].

The results of many studies support the hypothesis that FAK inhibitors might be used in the treatment of cancer. Studies have suggested that FAK may play an important role in cell proliferation and/or survival in vitro. For example, in CHO cells, some authors have demonstrated that overexpression of p125FAK leads to an acceleration of the G1 to S transition, suggesting that p125FAK promotes cell proliferation [J.-H Zhao et al. J. Cell Biol. 143:1997-2008. 1998].

Other authors have shown that tumor cells treated with FAK antisense oligonucleotides lose their adhesion and enter into apoptosis (Xu et al, Cell Growth Differ. 4:413-418. 1996). It has also been demonstrated that FAK promotes cell migration in vitro. Thus, fibroblasts deficient for the expression of FAK (mice which are knockout for FAK) exhibit a rounded morphology and deficiencies in cell migration in response to chemotactic signals, and these deficiencies are eliminated by reexpression of FAK [DJ. Sieg et al., J. Cell Science. 112:2677-91. 1999]. Overexpression of the C-terminal domain of FAK (FRNK) blocks the extension of adherent cells and decreases cell migration in vitro [A. Richardson and J. T. Parsons Nature. 380:538-540.1996]. Overexpression of FAK in CHO or COS cells or in human astrocytoma cells promotes migration of the cells. The involvement of FAK in the promotion of cell proliferation and migration in many cell types in vitro suggests the potential role of FAK in neoplastic processes. A recent study has effectively demonstrated an increase in the proliferation of tumor cells in vivo after induction of FAK expression in human astrocytoma cells [L. A. Cary L. A. et al. J. Cell Sci. 109:1787-94. 1996; D. Wang et al. J. Cell Sci. 113:4221-4230. 2000]. In addition, immunohistochemical studies of human biopsies have demonstrated that FAK is overexpressed in prostate cancer, breast cancer, thyroid cancer, colon cancer melanoma, brain cancer and lung cancer, the level of FAK expression being directly correlated with the tumors exhibiting the most aggressive phenotype [T M Weiner, et al. Lancet. 342(8878):1024-1025. 1993; Owens et al. Cancer Research. 55:2752-2755. 1995; K. Maung et al. Oncogene. 18:6824-6828. 1999; D Wang et al. J. Cell Sci. 113:4221-4230. 2000].

Indazoles are not very common in pharmaceutical products on the market. Included among the indazoles substituted at position 5 are essentially sulfonic acids, which are widely used in the field of photosensitization, with a predilection in the photographic field. Moreover, a sulfonamide is known, from JP 62025747, which claims N-(1H-indazol-5-yl)-methanesulfonamide as a film preserver and inhibitor of shadow formation. A therapeutic use is neither described nor envisioned here.

The following documents propose the therapeutic use of indazoles substituted at position 5.

Patent application WO 99/64004 discloses quinazoline derivatives, some of which contain an N-(1H-indazol-5-yl) sulfonamide substituent. These products are reputed to be of use for inhibiting a cGMP phosphodiesterase, and for the treatment of cardiovascular diseases. The use of these products in oncology is not envisioned.

U.S. Pat. No. 5,880,151 claims pentafluorophenylsulfonamide derivatives for treating atherosclerosis. This patent gives an example of indazole substituted at position 5 with a pentafluorophenylsulfonamide group. The same series of products is claimed in application WO 98/05315, for use as anti-proliferative agents, and also for treating inflammatory diseases, myocardial infarction, glomerular nephritis, transplant rejection, and infectious diseases such as HIV infections and malaria. In particular, product 15, the preparation of which is described on page 37, is the only indazole which appears in the patent application. The use of these products as kinase inhibitors is not mentioned. On the contrary, these products are aimed at inhibiting tubulin polymerization, which is a result of different mechanisms of inhibition of cell proliferation.

Patent application WO 00/73264 claims cell proliferation inhibitors, and in particular tubulin polymerization inhibitors. That patent application gives the preparation of many products, including a single indazole (page 42, example 34: N-(1H-indazol-5-yl)-3,4,5-trimethoxybenzenesulfonamide). This product is tested (page 20) at a concentration of 100 µM against NCI-H460 cells (18.5% growth inhibition) and HCT-15 cells (47.6% growth inhibition). The activity of this product is very modest compared to that obtained for the other compounds tested. In addition, it should be noted that the use of these products as kinase inhibitors is neither described nor suggested, the applicant placing the emphasis particularly on the 3,4,5-trimethoxybenzenesulfonamide group to which it is possible to add a large number of substituents, including an indazole.

Patent application WO 01/53268 claims 3,5-disubstituted indazoles as CDK kinase inhibitors, and for inhibiting cell proliferation. The substituents at position 5 are always hydrocarbon-based chains or cyclic, aromatic or heteroaromatic groups.

Patent application WO 02/10137 claims indazoles substituted at positions 3 and 5 with many different groups. Out of the 438 examples of indazoles described, only example 42 is an indazole substituted at position 5 with a phenylsulfonylamino group. The products described here are of use for inhibiting the JNK protein.

Patent application WO 02/083648, published on Oct. 24, 2002, claims indazoles which inhibit JNK protein. In that application, only the products 1-18 to 1-20 and 1-64 to 1-71 are 5-sulfonylaminoindazoles substituted at position 3 with an aryl group.

Patent application WO 03/004488, published on Jan. 16, 2003, discloses 2-(3-benzimidazolyl)indazoles of use as inhibitors of tyrosine and serine/threonine kinases. These products are indifferently substituted at positions 4 to 7 of the indazole and/or the imidazole. Examples 843 to 854 are indazoles substituted at position 3 with a benzimidazol-2-yl substituent, and at position 5 with an (alkyl/aryl)sulfonamido substituent. All these benzimidazoles are substituted at position 6 with N,N-dialkylamino substituents. No test on FAK is given. No relationship between the activity of the compounds and their structure is discussed.

Now, surprisingly, it has been found that indazoles substituted at position 5 with a series of substituents Z-X— as defined below, and optionally substituted at position 3, exhibit considerable kinase-inhibiting activity, in particular against FAK.

Another of the merits of the invention is to have found that substitution of the indazole at position 5 with a suitable group leads to considerable inhibition of FAK kinase, even when the indazole is not substituted on any other position, in particular at position 3.

Another of the merits of the invention is to have found that substitution of the indazole ring at a position other than position 5 systematically leads to a decrease in activity against the kinases tested here. Thus, when a series of substituents Z-X— is placed at one of positions 1, 4, 6 or 7 of the indazole ring, this results in a very large loss of activity which then makes the product unsuitable for use as a kinase inhibitor, particularly FAK. In addition, insofar as the indazole is substituted at position 5 with a suitable group Z-X— as claimed, it is possible to substitute the indazole at position 6 with a small substituent, such as a C1-C3 alkyl group, although this is not preferred.

In addition, one of the merits of the invention is to have demonstrated that, even when the indazole is correctly substituted with a suitable group X, it is essential for the nitrogen at position 1 of the indazole not to be substituted, in order to conserve satisfactory inhibitory activity.

These products correspond to the following formula (I)

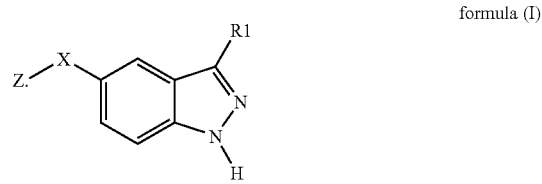

formula (I)

in which:
a) R1 is selected from the group consisting of H, halogen, alkyl, alkenyl, alkynyl, aryl, heteroaryl, cycloalkyl, heterocyclyl, substituted alkyl, substituted alkenyl, substituted alkynyl, substituted aryl, substituted heteroaryl, substituted cycloalkyl, substituted heterocyclyl, CN, O(R2), OC(O)(R2), OC(O)N(R2)(R3), OS(O$_2$)(R2), N(R2)(R3), N═C(R2)(R3), N(R2)C(O)(R3), N(R2)C(O)O(R3), N(R4)C(O)N(R2)(R3), N(R4)C(S)N(R2)(R3), N(R2)S(O$_2$)(R3), C(O)(R2), C(O)O(R2), C(O)N(R2)(R3), C(═N(R3))(R2), C(═N(OR3))(R2), S(R2), S(O)(R2), S(O$_2$)(R2), S(O$_2$)N(R2)(R3), in which each R2, R3 and R4 is independently selected from the group consisting of H, alkyl, aryl, heteroaryl, cycloalkyl, heterocyclyl, substituted alkyl, substituted aryl, substituted heteroaryl, substituted cycloalkyl, substituted heterocyclyl, alkenyl, substituted alkenyl;
b) X is selected from the group consisting of S(O$_2$)—NH; S(O$_2$)—O; NH—S(O$_2$); O—S(O$_2$);
c) Z is selected from the group consisting of alkyl, aryl, heteroaryl, cycloalkyl, heterocyclyl, substituted alkyl, substituted aryl, substituted heteroaryl, substituted cycloalkyl, substituted heterocyclyl;

with the proviso that the product of formula (I) is not one of the following compounds:

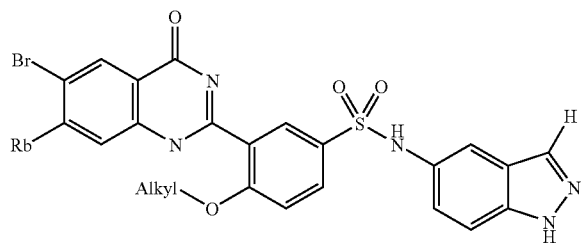

in which alkyl is n-propyl, and in which Ra and Rb are independently selected from the group consisting of NH$_2$, NO$_2$ and Cl, or Ra and Rb form a ring —NH—CH═N—;

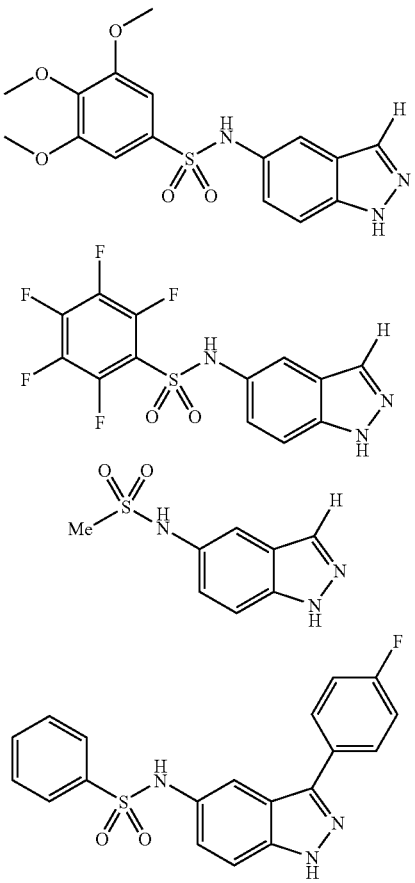

X may advantageously be S(O₂)—NH or S(O₂)—O.

It has been observed that, quite unexpectedly, products of general formula (I) in which Z-X— is Z-SO₂O— exhibit levels of activity similar to those observed when Z-X— is Z-SO₂NH—.

Preferably, R1 will not be H.

Specifically, another of the merits of the invention is to have discovered that substitution of the indazole at position 3 with a group R1 other than H significantly improves the inhibitory properties against kinases.

Z may advantageously be substituted aryl. More preferably, Z may be phenyl substituted with one to three substituents.

According to a very preferred variant, Z may be phenyl substituted with one or more substituents selected from the group consisting of: 3-fluoro; 3,4-dichloro; 3,4-difluoro; 2-methylsulfonyl.

Preferably, R1 may be selected from the group consisting of H, CH₃, C₂-C₆ alkyl, Cl, Br, I, CN, C(O)NH(R2), NHC(O)(R2), aryl, substituted aryl, alkenyl and substituted alkenyl.

The products according to the invention may advantageously be chosen from the group consisting of
N-(3-chloro-1H-indazol-5-yl)-2-methylsulfonylbenzenesulfonamide;
N-(3-chloro-1H-indazol-5-yl)-3,4-dichlorobenzenesulfonamide;
N-(3-chloro-1H-indazol-5-yl)-3-fluorobenzenesulfonamide;
N-(3-cyano-1H-indazol-5-yl)-3-fluorobenzenesulfonamide;
N-(3-cyano-1H-indazol-5-yl)-2-methylsulfonylbenzenesulfonamide;
3-fluoro-N-(3-phenyl-1H-indazol-5-yl)benzenesulfonamide;
2-methylsulfonyl-N-(3-phenyl-1H-indazol-5-yl)benzenesulfonamide;
3,4-dichloro-N-(3-phenyl-1H-indazol-5-yl)benzenesulfonamide;
3-fluoro-N-(3-methyl-1H-indazol-5-yl)benzenesulfonamide;
2-methylsulfonyl-N-(3-methyl-1H-indazol-5-yl)benzenesulfonamide;
N-(3-fluorophenyl)-(1H-indazol-5-yl)sulfonamide;
3-fluoro-N-(3-iodo-1H-indazol-5-yl)benzenesulfonamide;
2-methylsulfonyl-N-(1H-indazol-5-yl)benzenesulfonamide;
3,4-dichloro-N-(1H-indazol-5-yl)benzenesulfonamide;
3-fluoro-N-(1H-indazol-5-yl)benzenesulfonamide;
3-fluoro-N-(3-hydroxy-1H-indazol-5-yl)benzenesulfonamide;
1H-indazol-5-yl 3-fluorobenzenesulfonate;
N-phenyl-5-(2-methylsulfonylbenzenesulfonylamino)-1H-indazole-3-carboxamide;
N-methyl-5-(3-fluorobenzenesulfonylamino)-1H-indazole-3-carboxamide;
5-(2-methylsulfonylbenzenesulfonylamino)-1H-indazole-3-carboxamide;
5-(3-fluorobenzenesulfonylamino)-1H-indazole-3-carboxamide;
N-phenyl-5-(3-fluorobenzenesulfonylamino)-1H-indazole-3-carboxamide;
N-[5-(3-fluorobenzenesulfonylamino)-1H-indazol-3-yl]-benzamide.

More generally, the list of the products below is representative of the invention:
N-(1H-indazol-5-yl)-2-methysulfonylbenzenesulfonamide
N-(3-chloro-1H-indazol-5-yl)-2-methylsulfonylbenzenesulfonamide
N-(3-hydroxy-1H-indazol-5-yl)-2-methylsulfonylbenzenesulfonamide
N-(3-cyano-1H-indazol-5-yl)-2-methylsulfonylbenzenesulfonamide
N-(3-phenyl-1H-indazol-5-yl)-2-methylsulfonylbenzenesulfonamide
N-(3-methyl-1H-indazol-5-yl)-2-methylsulfonylbenzenesulfonamide
N-(3-iodo-1H-indazol-5-yl)-2-methylsulfonylbenzenesulfonamide
N-[5-(2-methylsulfonylbenzenesulfonylamino)-1H-indazol-3-yl]benzamide
N-phenyl-5-(2-methylsulfonylbenzenesulfonylamino)-1H-indazole-3-carboxamide
N-methyl-5-(2-methylsulfonylbenzenesulfonylamino)-1H-indazole-3-carboxamide;
5-(2-methylsulfonylbenzenesulfonylamino)-1H-indazole-3-carboxamide
N-(1H-indazol-5-yl)-3-fluorobenzenesulfonamide
N-(3-chloro-1H-indazol-5-yl)-3-fluorobenzenesulfonamide
N-(3-hydroxy-1H-indazol-5-yl)-3-fluorobenzenesulfonamide
N-(3-cyano-1H-indazol-5-yl)-3-fluorobenzenesulfonamide
N-(3-phenyl-1H-indazol-5-yl)-3-fluorobenzenesulfonamide
N-(3-methyl-1H-indazol-5-yl)-3-fluorobenzenesulfonamide
N-(3-iodo-1H-indazol-5-yl)-3-fluorobenzenesulfonamide
N-[5-(3-fluorobenzenesulfonylamino)-1H-indazol-3-yl]benzamide
N-phenyl-5-(3-fluorobenzenesulfonylamino)-1H-indazole-3-carboxamide
N-methyl-5-(3-fluorobenzenesulfonylamino)-1H-indazole-3-carboxamide;

5-(3-fluorobenzenesulfonylamino)-1H-indazole-3-carboxamide
N-(1H-indazol-5-yl)-3,4-dichlorobenzenesulfonamide
N-(3-chloro-1H-indazol-5-yl)-3,4-dichlorobenzenesulfonamide
N-(3-hydroxy-1H-indazol-5-yl)-3,4-dichlorobenzenesulfonamide
N-(3-cyano-1H-indazol-5-yl)-3,4-dichlorobenzenesulfonamide
N-(3-phenyl-1H-indazol-5-yl)-3,4-dichlorobenzenesulfonamide
N-(3-methyl-1H-indazol-5-yl)-3,4-dichlorobenzenesulfonamide
N-(3-iodo-1H-indazol-5-yl)-3,4-dichlorobenzenesulfonamide
N-[5-(3,4-dichlorobenzenesulfonylamino)-1H-indazol-3-yl]benzamide
N-phenyl-5-(3,4-dichlorobenzenesulfonylamino)-1H-indazole-3-carboxamide
N-methyl-5-(3,4-dichlorobenzenesulfonylamino)-1H-indazole-3-carboxamide
5-(3,4-dichlorobenzenesulfonylamino)-1H-indazole-3-carboxamide
N-(2-methylsulfonylphenyl)-(1H-indazol-5-yl)sulfonamide
3-chloro-N-(2-methylsulfonylphenyl)-(1H-indazol-5-yl)sulfonamide
3-hydroxy-N-(2-methylsulfonylphenyl)-(1H-indazol-5-yl)sulfonamide
3-cyano-N-(2-methylsulfonylphenyl)-(1H-indazol-5-yl)sulfonamide
N-(2-methylsulfonylphenyl)-3-phenyl-(1H-indazol-5-yl)sulfonamide
N-(2-methylsulfonylphenyl)-3-methyl-(1H-indazol-5-yl)sulfonamide
3-iodo-N-(2-methylsulfonylphenyl)-(1H-indazol-5-yl)sulfonamide
N-[5-(2-methylsulfonylphenylaminosulfonyl)-1H-indazol-3-yl]benzamide
N-phenyl-5-(2-methylsulfonylphenylaminosulfonyl)-1H-indazole-3-carboxamide
N-methyl-5-(2-methylsulfonylphenylaminosulfonyl)-1H-indazole-3-carboxamide
5-(2-methylsulfonylphenylaminosulfonyl)-1H-indazole-3-carboxamide
N-(3-fluorophenyl)-(1H-indazol-5-yl)sulfonamide
3-chloro-N-(3-fluorophenyl)-(1H-indazol-5-yl)sulfonamide
3-hydroxy-N-(3-fluorophenyl)-(1H-indazol-5-yl)sulfonamide
3-cyano-N-(3-fluorophenyl)-(1H-indazol-5-yl)sulfonamide
N-(3-fluorophenyl)-3-phenyl-(1H-indazol-5-yl)sulfonamide
N-(3-fluorophenyl)-3-methyl-(1H-indazol-5-yl)sulfonamide
3-iodo-N-(3-fluorophenyl)-(1H-indazol-5-yl)sulfonamide
N-[5-(3-fluorophenylaminosulfonyl)-1H-indazol-3-yl]benzamide
N-phenyl-5-(3-fluorophenylaminosulfonyl)-1H-indazole-3-carboxamide
N-methyl-5-(3-fluorophenylaminosulfonyl)-1H-indazole-3-carboxamide
5-(3-fluorophenylaminosulfonyl)-1H-indazole-3-carboxamide
N-(3,4-dichlorophenyl)-(1H-indazol-5-yl)sulfonamide
3-chloro-N-(3,4-dichlorophenyl)-(1H-indazol-5-yl)sulfonamide
3-hydroxy-N-(3,4-dichlorophenyl)-(1H-indazol-5-yl)sulfonamide
3-cyano-N-(3,4-dichlorophenyl)-(1H-indazol-5-yl)sulfonamide
N-(3,4-dichlorophenyl)-3-phenyl-(1H-indazol-5-yl)sulfonamide
N-(3,4-dichlorophenyl)-3-methyl-(1H-indazol-5-yl)sulfonamide
3-iodo-N-(3,4-dichlorophenyl)-(1H-indazol-5-yl)sulfonamide
N-[5-(3,4-dichlorophenylaminosulfonyl)-1H-indazol-3-yl]benzamide
N-phenyl-5-(3,4-dichlorophenylaminosulfonyl)-1H-indazole-3-carboxamide
N-methyl-5-(3,4-dichlorophenylaminosulfonyl)-1H-indazole-3-carboxamide
5-(3,4-dichlorophenylaminosulfonyl)-1H-indazole-3-carboxamide
2-methylsulfonylphenyl 1H-indazol-5-ylsulfonate
2-methylsulfonylphenyl 3-chloro-1H-indazol-5-ylsulfonate
2-methylsulfonylphenyl 3-hydroxy-1H-indazol-5-ylsulfonate
2-methylsulfonylphenyl 3-cyano-1H-indazol-5-ylsulfonate
2-methylsulfonylphenyl 3-phenyl-1H-indazol-5-ylsulfonate
2-methylsulfonylphenyl 3-methyl-1H-indazol-5-ylsulfonate
2-methylsulfonylphenyl 3-iodo-1H-indazol-5-ylsulfonate
N-[5-(2-methylsulfonylphenyloxysulfonyl)-1H-indazol-3-yl]benzamide
N-phenyl-5-(2-methylsulfonylphenyloxysulfonyl)-1H-indazole-3-carboxamide
N-methyl-5-(2-methylsulfonylphenyloxysulfonyl)-1H-indazole-3-carboxamide
5-(2-methylsulfonylphenyloxysulfonyl)-1H-indazole-3-carboxamide
3-fluorophenyl 1H-indazol-5-ylsulfonate
3-fluorophenyl 3-chloro-1H-indazol-5-ylsulfonate
3-fluorophenyl 3-hydroxy-1H-indazol-5-ylsulfonate
3-fluorophenyl 3-cyano-1H-indazol-5-ylsulfonate
3-fluorophenyl 3-phenyl-1H-indazol-5-ylsulfonate
3-fluorophenyl 3-methyl-1H-indazol-5-ylsulfonate
3-fluorophenyl 3-iodo-1H-indazol-5-ylsulfonate
N-[5-(3-fluorophenyloxysulfonyl)-1H-indazol-3-yl]benzamide
N-phenyl-5-(3-fluorophenyloxysulfonyl)-1H-indazole-3-carboxamide
N-methyl-5-(3-fluorophenyloxysulfonyl)-1H-indazole-3-carboxamide
5-(3-fluorophenyloxysulfonyl)-1H-indazole-3-carboxamide
3,4-dichlorophenyl 1H-indazol-5-ylsulfonate
3,4-dichlorophenyl 3-chloro-1H-indazol-5-ylsulfonate
3,4-dichlorophenyl 3-hydroxy-1H-indazol-5-ylsulfonate
3,4-dichlorophenyl 3-cyano-1H-indazol-5-ylsulfonate
3,4-dichlorophenyl 3-phenyl-1H-indazol-5-ylsulfonate
3,4-dichlorophenyl 3-methyl-1H-indazol-5-ylsulfonate
3,4-dichlorophenyl 3-iodo-1H-indazol-5-ylsulfonate
N-[5-(3,4-dichlorophenyloxysulfonyl)-1H-indazol-3-yl]benzamide
N-phenyl-5-(3,4-dichlorophenyloxysulfonyl)-1H-indazole-3-carboxamide
N-methyl-5-(3,4-dichlorophenyloxysulfonyl)-1H-indazole-3-carboxamide
5-(3,4-dichlorophenyloxysulfonyl)-1H-indazole-3-carboxamide
1H-indazol-5-yl 2-methylsulfonylbenzenesulfonate
3-chloro-1H-indazol-5-yl 2-methylsulfonylbenzenesulfonate
3-hydroxy-1H-indazol-5-yl 2-methylsulfonylbenzenesulfonate
3-cyano-1H-indazol-5-yl 2-methylsulfonylbenzenesulfonate
3-phenyl-1H-indazol-5-yl 2-methylsulfonylbenzenesulfonate 3-methyl-1H-indazol-5-yl 2-methylsulfonylbenzenesulfonate
3-iodo-1H-indazol-5-yl 2-methylsulfonylbenzenesulfonate
N-[5-(2-methylsulfonylphenylsulfonyloxy)-1H-indazol-3-yl]benzamide
N-phenyl-5-(2-methylsulfonylphenylsulfonyloxy)-1H-indazole-3-carboxamide
N-methyl-5-(2-methylsulfonylphenylsulfonyloxy)-1H-indazole-3-carboxamide
5-(2-methylsulfonylphenylsulfonyloxy)-1H-indazole-3-carboxamide
1H-indazol-5-yl 3-fluorobenzenesulfonate
3-chloro-1H-indazol-5-yl 3-fluorobenzenesulfonate
3-hydroxy-1H-indazol-5-yl 3-fluorobenzenesulfonate
3-cyano-1H-indazol-5-yl 3-fluorobenzenesulfonate
3-phenyl-1H-indazol-5-yl 3-fluorobenzenesulfonate
3-methyl-1H-indazol-5-yl 3-fluorobenzenesulfonate
3-iodo-1H-indazol-5-yl 3-fluorobenzenesulfonate
N-[5-(3-fluorophenylsulfonyloxy)-1H-indazol-3-yl]benzamide
N-phenyl-5-(3-fluorophenylsulfonyloxy)-1H-indazole-3-carboxamide
N-methyl-5-(3-fluorophenylsulfonyloxy)-1H-indazole-3-carboxamide
5-(3-fluorophenylsulfonyloxy)-1H-indazole-3-carboxamide
1H-indazol-5-yl 3,4-dichlorobenzenesulfonate
3-chloro-1H-indazol-5-yl 3,4-dichlorobenzenesulfonate
3-hydroxy-1H-indazol-5-yl 3,4-dichlorobenzenesulfonate
3-cyano-1H-indazol-5-yl 3,4-dichlorobenzenesulfonate
3-phenyl-1H-indazol-5-yl 3,4-dichlorobenzenesulfonate
3-methyl-1H-indazol-5-yl 3,4-dichlorobenzenesulfonate
3-iodo-1H-indazol-5-yl 3,4-dichlorobenzenesulfonate
N-[5-(3,4-dichlorophenylsulfonyloxy)-1H-indazol-3-yl]benzamide
N-phenyl-5-(3,4-dichlorophenylsulfonyloxy)-1H-indazole-3-carboxamide
N-methyl-5-(3,4-dichlorophenylsulfonyloxy)-1H-indazole-3-carboxamide
5-(3,4-dichlorophenylsulfonyloxy)-1H-indazole-3-carboxamide According to a second aspect, the invention relates to products corresponding to the following formula (I)

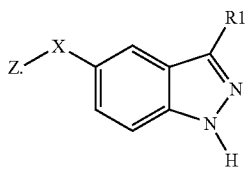

formula (I)

in which:
d) R1 is selected from the group consisting of H, halogen, alkyl, alkenyl, alkynyl, aryl, heteroaryl, cycloalkyl, heterocyclyl, substituted alkyl, substituted alkenyl, substituted alkynyl, substituted aryl, substituted heteroaryl, substituted cycloalkyl, substituted heterocyclyl, CN, O(R2), OC(O)(R2), OC(O)N(R2)(R3), OS(O$_2$)(R2), N(R2)(R3), N=C(R2)(R3), N(R2)C(O)(R3), N(R2)C(O)O(R3), N(R4)C(O)N(R2)(R3), N(R4)C(S)N(R2)(R3), N(R2)S(O$_2$)(R3), C(O)(R2), C(O)O(R2), C(O)N(R2)(R3), C(=N(R3))(R2), C(=N(OR3))(R2), S(R2), S(O)(R2), S(O$_2$)(R2), S(O$_2$)N(R2)(R3), in which each R2, R3 and R4 is independently selected from the group consisting of H, alkyl, aryl, cycloalkyl, heterocyclyl, substituted alkyl, substituted aryl, substituted cycloalkyl, substituted heterocyclyl, alkenyl, substituted alkenyl;
e) X is selected from the group consisting of S(O$_2$)—NH; S(O$_2$)—O; NH—S(O$_2$); O—S(O$_2$);
f) Z is selected from the group consisting of alkyl, alkenyl, aryl, heteroaryl, cycloalkyl, heterocyclyl, substituted alkyl, substituted alkenyl, substituted aryl, substituted heteroaryl, substituted cycloalkyl, substituted heterocyclyl;
g) R is chosen from H and C1-C3 alkyl;

with the proviso that the product of formula (I) is not one of the following compounds:

1)

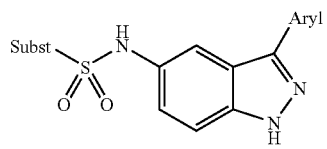

in which
(i) Aryl is 3-fluorophenyl and Subst is chosen from methyl, 2,2,2-trifluoromethyl, 4-methylphenyl,

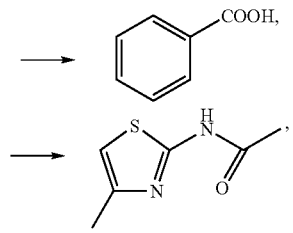

(ii) Aryl is chosen from 6-(2-dimethylaminomethyl-5-methylmorpholin-4-yl)-1H-benzimidazol-2-yl, 6-(4-methylpiperazin-1-yl)-1H-benzimidazol-2-yl, 6-(1,4'-bipiperidin-1'-yl)-1H-benzimidazol-2-yl and 6-(N,N-dialkylamino)-1H-benzimidazol-2-yl, and Subst is independently chosen from methyl, ethyl, trifluoromethyl, phenyl, 4-methoxyphenyl and thien-2-yl,
(iii) Aryl is 4-fluorophenyl and Subst is phenyl,
(iv) Aryl is 4-trifluoromethylphenyl and Subst is N,N-dimethylamino,
(v) Aryl is thien-2-yl and Subst is 3,5-bis(trifluoromethyl)phenyl,
(vi) Aryl is 3,4-methylenedioxyphenyl and Subst is 1-methylethyl,
(vii) Aryl is 3,5-bis(trifluoromethyl)phenyl and Subst is 5-(pyrid-2-yl)-thien-2-yl,
(viii) Aryl is 4-methoxyphenyl and Subst is 4-phenylsulfonylthien-2-yl,

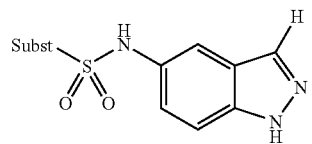

in which

Subst is chosen from 3,4,5-trimethoxyphenyl, 2,3,4,5,6-pentafluorophenyl, methyl, and

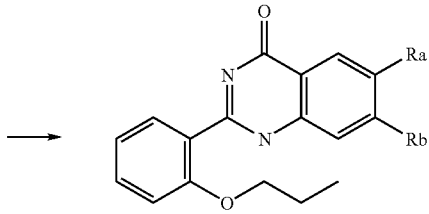

in which Ra and Rb are independently selected from the group consisting of NH₂, NO₂ and Cl, or Ra and Rb form a ring —NH—CH=N—.

According to its second aspect, a product in accordance with the invention is advantageously a product of formula (I) in which Z-X is chosen from Z-S(O₂)—NH and Z-S(O₂)—O.

According to its second aspect, R is preferably a hydrogen atom.

According to its second aspect, the invention relates to a product of formula (I) in which Z is substituted aryl, preferably phenyl substituted with one to three substituents. Z is particularly advantageously chosen from 2-methylsulfonylphenyl, 3-fluorophenyl and 3,5-difluorophenyl. This product is particularly of use for inhibiting FAK.

According to its second aspect, R1 is advantageously selected from the group consisting of NH₂, NHCOPh, NHCOMe, CONH₂, CONHPh, phenyl, 3-cyanophenyl, 3-CO₂MePh, 3-(Me₃SiC≡C—)Ph, 3-nitrophenyl, 3-aminophenyl, 3-methylphenyl, 3-chlorophenyl, 3-fluorophenyl, 3-bromophenyl, 4-carboxyphenyl, 4-methoxyphenyl, 4-aminophenyl, 4-hydroxyphenyl, 4-dimethylaminophenyl, thiophen-2-yl, 5-methoxy-1H-indol-2-yl, benzofuran-2-yl, 1H-indol-2-yl, pyrrol-2-yl, 1H-benzimidazol-2-yl, pyrid-4-yl and pyrid-3-yl. This product is particularly of use for inhibiting FAK.

According to its second aspect, the invention relates to a product of formula (I) in which Z is substituted aryl, preferably phenyl substituted with one to three substituents. Z is particularly advantageously chosen from 2-methylsulfonylphenyl, 3-fluorophenyl, 2-trifluoromethoxyphenyl, thiophen-2-yl, quinolin-8-yl and phenyl. This product is particularly of use for inhibiting Aurora2.

According to its second aspect, R1 is advantageously selected from the group consisting of 4-carboxyphenyl, 4-hydroxyphenyl, 4-dimethylaminophenyl, 5-methoxy-1H-indol-2-yl, 1H-indol-2-yl, 1H-benzimidazol-2-yl, pyrid-4-yl, pyrid-3-yl, benzothiophen-2-yl, styryl, 4-fluorophenylethylen-2-yl and 4-chlorophenylethylen-2-yl. This product is particularly of use for inhibiting Aurora2.

Products according to the invention may advantageously be chosen from the group consisting of:
N-(1H-indazol-5-yl)benzenesulfonamide;
3,4-dichloro-N-(3-methyl-1H-indazol-5-yl)benzenesulfonamide;
N-(3-amino-1H-indazol-5-yl)-3-fluorobenzenesulfonamide;
3-fluoro-N-(3-methylsulfonylamino-1H-indazol-5-yl)benzenesulfonamide;
N-[5-(3-fluorobenzenesulfonylamino)-1H-indazol-3-yl)acetamide;
N-cyclohexyl-5-(2-methylsulfonylbenzenesulfonylamino)-1H-indazole-3-carboxamide;
N-[3-(4-chlorophenyl)-1H-indazol-5-yl]-2-methylsulfonylbenzenesulfonamide;
N-[3-(4-methoxyphenyl)-1H-indazol-5-yl]benzenesulfonamide;
N-[3-(4-methoxyphenyl)-1H-indazol-5-yl]-2-methylsulfonybenzenesulfonamide;
N-[3-(4-fluorophenyl)-1H-indazol-5-yl]-2-methylsulfonylbenzenesulfonamide;
N-[3-(4-hydroxyphenyl)-1H-indazol-5-yl]benzenesulfonamide;
N-[3-(4-hydroxyphenyl)-1H-indazol-5-yl]-2-methylsulfonylbenzenesulfonamide;
N-(3-benzylamino-1H-indazol-5-yl)-2-methylsulfonylbenzenesulfonamide;
N-(3-methylamino-1H-indazol-5-yl)-2-methylsulfonylbenzenesulfonamide;
N-(3-bromo-1H-indazol-5-yl)-2-methylsulfonylbenzenesulfonamide;
N-(3-amino-1H-indazol-5-yl)-2-methylsulfonylbenzenesulfonamide;
N-(3-amino-1H-indazol-5-yl)-2,6-difluorobenzenesulfonamide;
N-(3-amino-1H-indazol-5-yl)-2,6-dichlorobenzenesulfonamide;
N-(3-amino-1H-indazol-5-yl)-3,5-difluorobenzenesulfonamide;
N-[5-(2-methylsulfonylbenzenesulfonylamino)-1H-indazol-3-yl)acetamide;
N-[5-(3,5-difluorobenzenesulfonylamino)-1H-indazol-3-yl)acetamide;
N-[5-(2-methylsulfonylbenzenesulfonylamino)-1H-indazol-3-yl)benzamide;
N-[5-(3,5-difluorobenzenesulfonylamino)-1H-indazol-3-yl)benzamide;
N-{2-[5-(3-fluorobenzenesulfonylamino)-1H-indazol-3-yl]phenyl}acetamide;
N-{2-[5-(2-methylsulfonylbenzenesulfonylamino)-1H-indazol-3-yl]phenyl}-acetamide;
N-[3-(2-aminophenyl)-1H-indazol-5-yl]-2-methylsulfonylbenzenesulfonamide;
2-methylsulfonyl-N-(3-thiophen-2-yl-1H-indazol-5-yl)benzenesulfonamide;
2-methylsulfonyl-N-(3-thiophen-3-yl-1H-indazol-5-yl)benzenesulfonamide;
N-(3-furan-3-yl-1H-indazol-5-yl)-2-methylsulfonylbenzenesulfonamide;
N-(3-furan-2-yl-1H-indazol-5-yl)-2-methylsulfonylbenzenesulfonamide;
2-methylsulfonyl-N-(3-pyridin-4-yl-1H-indazol-5-yl)benzenesulfonamide;
methyl 3-[5-(2-methylsulfonylbenzenesulfonamino)-1H-indazol-3-yl]benzoate;
3-[5-(2-methylsulfonylbenzenesulfonamino)-1H-indazol-3-yl]benzoic acid;
2-methylsulfonyl-N-[3-(1H-pyrrolo[2,3-b]pyridin-2-yl)-1H-indazol-5-yl]benzenesulfonamide;
2-methylsulfonyl-N-[3-(5-methoxy-1H-indol-2-yl)-1H-indazol-5-yl]benzenesulfonamide;
2-methylsulfonyl-N-(3-pyridin-3-yl-1H-indazol-5-yl)benzenesulfonamide;
2-methylsulfonyl-N-[3-(1H-pyrrol-2-yl)-1H-indazol-5-yl]benzenesulfonamide;
N-[3-(1H-indol-2-yl)-1H-indazol-5-yl]-2-methylsulfonylbenzenesulfonamide;
N-[3-(3-aminophenyl)-1H-indazol-5-yl]-2-methylsulfonylbenzenesulfonamide;

N-[3-(4-dimethylaminophenyl)-1H-indazol-5-yl]-2-methyl-sulfonylbenzenesulfonamide;
N-(3-benzo[b]thiophen-3-yl-1H-indazol-5-yl)-2-methylsulfonylbenzenesulfonamide;
N-(3-benzo[b]thiophen-2-yl-1H-indazol-5-yl)-2-methylsulfonylbenzenesulfonamide;
N-[3-(4-nitrophenyl)-1H-indazol-5-yl]-2-methylsulfonyl-benzenesulfonamide;
2-methylsulfonyl-N-(3-quinolin-8-yl-1H-indazol-5-yl)benzenesulfonamide;
methyl 4-[5-(2-methylsulfonylbenzenesulfonamino)-1H-indazol-3-yl]benzoate;
4-[5-(2-methylsulfonylbenzenesulfonamino)-1H-indazol-3-yl]benzoic acid;
N-[3-(4-aminophenyl)-1H-indazol-5-yl]-2-methylsulfonyl-benzenesulfonamide;
N-[3-(3-cyanophenyl)-1H-indazol-5-yl]-2-methylsulfonyl-benzenesulfonamide;
2-methylsulfonyl-N-(3-naphthalen-1-yl-1H-indazol-5-yl)benzenesulfonamide;
2-methylsulfonyl-N-(3-naphthalen-2-yl-1H-indazol-5-yl)benzenesulfonamide;
N-{3-[(E)-2-(4-fluorophenyl)vinyl]-1H-indazol-5-yl}-2-methylsulfonylbenzenesulfonamide;
N-{3-[2-(4-fluorophenyl)ethyl]-1H-indazol-5-yl}-2-methylsulfonylbenzenesulfonamide;
N-{3-[(E)-2-(4-chlorophenyl)vinyl]-1H-indazol-5-yl}-2-methylsulfonylbenzenesulfonamide;
N-{3-[2-(4-chlorophenyl)ethyl]-1H-indazol-5-yl}-2-methylsulfonylbenzenesulfonamide;
2-methylsulfonyl-N-[3-((E)-styryl)-1H-indazol-5-yl]benzenesulfonamide;
methyl(E)-3-[5(2-methylsulfonylbenzenesulfonylamino)-1H-indazol-3-yl]-acrylate;
(E)-3-[5(2-methylsulfonylbenzenesulfonylamino)-1H-indazol-3-yl]acrylic acid;
N-[3-(1H-benzimidazol-2-yl)-1H-indazol-5-yl]-2-methyl-sulfonylbenzenesulfonamide;
N-[3-(1H-indol-2-yl)-1H-indazol-5-yl]benzenesulfonamide;
2-methylsulfonyl-N-(3-phenylamino-1H-indazol-5-yl)benzenesulfonamide;
N-[3-(1H-indol-2-yl)-1H-indazol-5-yl]-2-trifluoromethoxy-benzenesulfonamide;
3-fluoro-N-[3-(1H-indol-2-yl)-1H-indazol-5-yl]benzenesulfonamide;
4-dimethylamino-2,3,5,6-tetrafluoro-N-[3-(1H-indol-2-yl)-1H-indazol-5-yl]benzenesulfonamide;
{N-[3-(1H-indol-2-yl)-1H-indazol-5-yl]}thiophene-2-sulfonamide;
2-methylsulfonyl-N-(3-phenylsulfanyl-1H-indazol-5-yl)benzenesulfonamide;
2-methylsulfonyl-N-(3-phenylethynyl-1H-indazol-5-yl)benzenesulfonamide;
2-methylsulfonyl-N-(3-phenethyl-1H-indazol-5-yl)benzenesulfonamide;
2-methylsulfonyl-N-[3-(3-trimethylsilanylethynylphenyl)-1H-indazol-5-yl]benzenesulfonamide;
2-methylsulfonyl-N-(6-methyl-3-phenyl-1H-indazol-5-yl)benzenesulfonamide;
5-fluoro-2-methylsulfonyl-N-(3-phenyl-1H-indazol-5-yl)benzenesulfonamide;
4-amino-N-(3-phenyl-1H-indazol-5-yl)benzenesulfonamide;
N-[4-(3-phenyl-1H-indazol-5-ylsulfamoyl)phenyl]acetamide;
N-(3-phenyl-1H-indazol-5-yl)pyridine-3-sulfonamide;
3-nitro-N-(3-phenyl-1H-indazol-5-yl)benzenesulfonamide;
3-amino-N-(3-phenyl-1H-indazol-5-yl)benzenesulfonamide;
N-(3-phenyl-1H-indazol-5-yl)cyclohexanesulfonamide;
N-(3-phenyl-1H-indazol-5-yl)piperidine-4-sulfonamide;
N-[3-(3,5-bis-trifluoromethylphenyl)-1H-indazol-5-yl]-2-methylsulfonylbenzenesulfonamide;
N-[3-(3,5-difluorophenyl)-1H-indazol-5-yl]-2-methylsulfonylbenzenesulfonamide;
2-methylsulfonyl-N-[3-(2-methylsulfanylphenyl)-1H-indazol-5-yl]benzenesulfonamide;
N-[3-(1H-indol-5-yl)-1H-indazol-5-yl]-2-methylsulfonyl-benzenesulfonamide;
2-methylsulfonyl-N-(3-o-tolyl-1H-indazol-5-yl)benzene-sulfonamide;
N-(3-phenyl-1H-indazol-5-yl)naphthalene-1-sulfonamide;
5-dimethylamino-N-(3-phenyl-1H-indazol-5-yl)naphthalene-1-sulfonamide;
N-(3-phenyl-1H-indazol-5-yl)naphthalene-2-sulfonamide;
N-(3-phenyl-1H-indazol-5-yl)-2-trifluoromethylbenzene-sulfonamide;
N-(3-phenyl-1H-indazol-5-yl)thiophene-2-sulfonamide;
N-(3-phenyl-1H-indazol-5-yl)quinoline-8-sulfonamide;
N-(3-phenyl-1H-indazol-5-yl)benzenesulfonamide;
2-nitro-N-(3-phenyl-1H-indazol-5-yl)benzenesulfonamide;
2,4,6-triisopropyl-N-(3-phenyl-1H-indazol-5-yl)benzene-sulfonamide;
2,4,6-trimethyl-N-(3-phenyl-1H-indazol-5-yl)benzene-sulfonamide;
4-bromo-N-(3-phenyl-1H-indazol-5-yl)benzenesulfonamide;
4-fluoro-N-(3-phenyl-1H-indazol-5-yl)benzenesulfonamide;
N-[4-(3-phenyl-1H-indazol-5-ylsulfamoyl)phenyl]acetamide;
4-nitro-N-(3-phenyl-1H-indazol-5-yl)benzenesulfonamide;
4-methoxy-N-(3-phenyl-1H-indazol-5-yl)benzenesulfonamide;
4-tert-butyl-N-(3-phenyl-1H-indazol-5-yl)benzenesulfonamide;
4-methyl-N-(3-phenyl-1H-indazol-5-yl)benzenesulfonamide;
1-methyl-N-(3-phenyl-1H-indazol-5-yl)ethanesulfonamide;
N-(3-phenyl-1H-indazol-5-yl)methanesulfonamide;
1-phenyl-N-(3-phenyl-1H-indazol-5-yl)methanesulfonamide;
(E)-2-phenyl-N-(3-phenyl-1H-indazol-5-yl)ethylene-sulfonamide;
N-(3-phenyl-1H-indazol-5-yl)ethanesulfonamide;
N-(3-phenyl-1H-indazol-5-yl)propanesulfonamide;
N-(3-phenyl-1H-indazol-5-yl)butanesulfonamide;
3-trifluoromethyl-N-(3-phenyl-1H-indazol-5-yl)benzene-sulfonamide;
2,5-dimethoxy-N-(3-phenyl-1H-indazol-5-yl)benzene-sulfonamide;
2-methyl-N-(3-phenyl-1H-indazol-5-yl)benzenesulfonamide;
3-(3-phenyl-1H-indazol-5-ylsulfamoyl)benzoic acid;
2-fluoro-N-(3-phenyl-1H-indazol-5-yl)benzenesulfonamide;
5-chloro-N-(3-phenyl-1H-indazol-5-yl)thiophene-2-sulfonamide;
3-chloro-N-(3-phenyl-1H-indazol-5-yl)benzenesulfonamide;
3,5-dichloro-N-(3-phenyl-1H-indazol-5-yl)benzenesulfonamide;

3-methyl-N-(3-phenyl-1H-indazol-5-yl)benzenesulfonamide;
2-bromo-N-(3-phenyl-1H-indazol-5-yl)benzenesulfonamide;
N-[5-(3-phenyl-1H-indazol-5-ylsulfamoyl)thiophen-2-ylmethyl]benzamide;
3-bromo-N-(3-phenyl-1H-indazol-5-yl)benzenesulfonamide;
N-(3-phenyl-1H-indazol-5-yl)-2-trifluoromethoxybenzenesulfonamide;
4-cyano-N-(3-phenyl-1H-indazol-5-yl)benzenesulfonamide;
2-cyano-N-(3-phenyl-1H-indazol-5-yl)benzenesulfonamide;
4-butoxy-N-(3-phenyl-1H-indazol-5-yl)benzenesulfonamide;
N-[2-chloro-4-(3-phenyl-1H-indazol-5-ylsulfamoyl)phenyl]acetamide;
5-dibutylamino-N-(3-phenyl-1H-indazol-5-yl)naphthalene-1-sulfonamide;
C-(7,7-dimethyl-2-oxobicyclo[2.2.1]hept-1-yl)-N-(3-phenyl-1H-indazol-5-yl)-methanesulfonamide;
N-(3-phenyl-1H-indazol-5-yl)benzo[1,2,5]oxadiazole-4-sulfonamide;
N-(3-phenyl-1H-indazol-5-yl)-(5-isoxazol-3-ylthiophene)-2-sulfonamide;
C-(2-nitrophenyl)-N-(3-phenyl-1H-indazol-5-yl)methanesulfonamide;
3,4-difluoro-N-(3-phenyl-1H-indazol-5-yl)benzenesulfonamide;
N-(3-phenyl-1H-indazol-5-yl)-(5-chloro-3-methylbenzo[b]thiophene)-2-sulfonamide;
3-cyano-N-(3-phenyl-1H-indazol-5-yl)benzenesulfonamide;
4-methanesulfonyl-N-(3-phenyl-1H-indazol-5-yl)benzenesulfonamide;
3-methoxy-N-(3-phenyl-1H-indazol-5-yl)benzenesulfonamide;
N-(3-phenyl-1H-indazol-5-yl)diphenyl-3-sulfonamide;
3,5-difluoro-N-(3-phenyl-1H-indazol-5-yl)benzenesulfonamide;
2-amino-4,6-dichloro-N-(3-phenyl-1H-indazol-5-yl)benzenesulfonamide;
4-trifluoromethoxy-N-(3-phenyl-1H-indazol-5-yl)benzenesulfonamide;
N-[3-(4-bromophenyl)-1H-indazol-5-yl]-2-methanesulfonylbenzenesulfonamide;
2-methanesulfonyl-N-[3-(3-nitrophenyl)-1H-indazol-5-yl]benzenesulfonamide;
N-[3-(2,4-dichlorophenyl)-1H-indazol-5-yl]-2-methanesulfonylbenzenesulfonamide;
2-methanesulfonyl-N-(3-p-tolyl-1H-indazol-5-yl)benzenesulfonamide;
2-methanesulfonyl-N-(3-m-tolyl-1H-indazol-5-yl)benzenesulfonamide;
N-{3-[5-(2-methanesulfonylbenzenesulfonylamino)-1H-indazol-3-yl]phenyl}-5-dimethylaminonaphthalene-1-sulfonamide;
N-[3-(3-chloro-4-fluorophenyl)-1H-indazol-5-yl]-2-methanesulfonylbenzenesulfonamide;
N-[3-(3,5-dichlorophenyl)-1H-indazol-5-yl]-2-methanesulfonylbenzenesulfonamide;
N-(3-(dibenzofuran-4-yl)-1H-indazol-5-yl)-2-methanesulfonylbenzenesulfonamide;
N-(3-biphenyl-4-yl-1H-indazol-5-yl)-2-methanesulfonylbenzenesulfonamide;
2-methanesulfonyl-N-[3-(4-phenoxy-phenyl)-1H-indazol-5-yl]-benzenesulfonamide;
2-methanesulfonyl-N-[3-(4-methylsulfanylphenyl)-1H-indazol-5-yl]-benzenesulfonamide;
N-(3-biphenyl-2-yl-1H-indazol-5-yl)-2-methanesulfonylbenzenesulfonamide;
2-methanesulfonyl-N-(3-thiophen-2-yl-1H-indazol-5-yl)benzenesulfonamide;
N-[3-(3-trifluoromethylphenyl)-1H-indazol-5-yl]-2-methanesulfonylbenzenesulfonamide;
N-[3-(4-trifluoromethylphenyl)-1H-indazol-5-yl]-2-methanesulfonylbenzenesulfonamide;
N-[3-(3-chlorophenyl)-1H-indazol-5-yl]-2-methanesulfonylbenzenesulfonamide;
2-methanesulfonyl-N-[3-(3-methoxyphenyl)-1H-indazol-5-yl]-benzenesulfonamide;
2-methanesulfonyl-N-[3-(3,5-dimethylphenyl)-1H-indazol-5-yl]-benzenesulfonamide;
N-(3-benzofuran-2-yl-1H-indazol-5-yl)-2-methanesulfonylbenzenesulfonamide;
N-[3-(5-chlorothiophen-2-yl)-1H-indazol-5-yl]-2-methanesulfonylbenzenesulfonamide;
N-[3-(3-fluorophenyl)-1H-indazol-5-yl]-2-methanesulfonylbenzenesulfonamide;
2-methanesulfonyl-N-[3-(2-methoxyphenyl)-1H-indazol-5-yl]-benzenesulfonamide;
N-[3-(3-bromophenyl)-1H-indazol-5-yl]-2-methanesulfonylbenzenesulfonamide;
2-methanesulfonyl-N-[3-(4-vinylphenyl)-1H-indazol-5-yl]benzenesulfonamide;
N-[3-(3-ethoxyphenyl)-1H-indazol-5-yl]-2-methanesulfonylbenzenesulfonamide;
N-[3-(2-chlorophenyl)-1H-indazol-5-yl]-2-methanesulfonylbenzenesulfonamide;
N-[3-(2-fluorophenyl)-1H-indazol-5-yl]-2-methanesulfonylbenzenesulfonamide;
N-[3-(2-ethoxyphenyl)-1H-indazol-5-yl]-2-methanesulfonylbenzenesulfonamide;
N-[3-(4-ethoxyphenyl)-1H-indazol-5-yl]-2-methanesulfonylbenzenesulfonamide;
N-[3-(4-hydroxymethylphenyl)-1H-indazol-5-yl]-2-methanesulfonylbenzenesulfonamide;
N-[3-(3,4-difluorophenyl)-1H-indazol-5-yl]-2-methanesulfonylbenzenesulfonamide;
N-[3-(4-ethylphenyl)-1H-indazol-5-yl]-2-methanesulfonylbenzenesulfonamide;
N-[3-(4-benzyloxy-3-fluorophenyl)-1H-indazol-5-yl]-2-methanesulfonylbenzenesulfonamide;
2-methanesulfonyl-N-[3-(3,4-dimethylphenyl)-1H-indazol-5-yl]-benzenesulfonamide;
N-[3-(benzo[1,3]dioxol-5-yl)-1H-indazol-5-yl]-2-methanesulfonylbenzenesulfonamide;
N-[3-(4-tert-butylphenyl)-1H-indazol-5-yl]-2-methanesulfonylbenzenesulfonamide;
2-methanesulfonyl-N-[3-(3,4-dimethoxyphenyl)-1H-indazol-5-yl]-benzenesulfonamide;
2-methanesulfonyl-N-[3-(2,4-dimethoxyphenyl)-1H-indazol-5-yl]-benzenesulfonamide;
N-[3-(3-hydroxyphenyl)-1H-indazol-5-yl]-2-methanesulfonylbenzenesulfonamide;
N-[3-(4-isopropylphenyl)-1H-indazol-5-yl]-2-methanesulfonylbenzenesulfonamide;
N-[3-(4-hydroxyphenyl)-1H-indazol-5-yl]-2-methanesulfonylbenzenesulfonamide;
N-[3-(3-isopropylphenyl)-1H-indazol-5-yl]-2-methanesulfonylbenzenesulfonamide;

N-[3-(3-amino-4-methylphenyl)-1H-indazol-5-yl]-2-methanesulfonylbenzenesulfonamide;
N-[3-(3,4-dichlorophenyl)-1H-indazol-5-yl]-2-methanesulfonylbenzenesulfonamide;
N-[3-(4-trifluoromethoxyphenyl)-1H-indazol-5-yl]-2-methanesulfonylbenzenesulfonamide;
N-[3-(4-acetylphenyl)-1H-indazol-5-yl]-2-methanesulfonylbenzenesulfonamide;
N-[3-(2,3-dichlorophenyl)-1H-indazol-5-yl]-2-methanesulfonylbenzenesulfonamide;
N-[3-(4-benzyloxyphenyl)-1H-indazol-5-yl]-2-methanesulfonylbenzenesulfonamide;
N-[3-(2-fluorobiphenyl-4-yl)-1H-indazol-5-yl]-2-methanesulfonylbenzenesulfonamide;
N-[3-(3,5-dibromophenyl)-1H-indazol-5-yl]-2-methanesulfonylbenzenesulfonamide;
N-[3-(4-bromo-2-fluorophenyl)-1H-indazol-5-yl]-2-methanesulfonylbenzenesulfonamide;
N-[3-(4-ethylsulfanylphenyl)-1H-indazol-5-yl]-2-methanesulfonylbenzenesulfonamide;
2-methanesulfonyl-N-[3-(2,3,4-trimethoxyphenyl)-1H-indazol-5-yl]-benzenesulfonamide;
N-[3-(5-chloro-2-methoxyphenyl)-1H-indazol-5-yl]-2-methanesulfonylbenzenesulfonamide;
N-[3-(4-cyanophenyl)-1H-indazol-5-yl]-2-methanesulfonylbenzenesulfonamide;
N-[3-(2,4-difluorophenyl)-1H-indazol-5-yl]-2-methanesulfonylbenzenesulfonamide;
N-[3-(4-iodophenyl)-1H-indazol-5-yl]-2-methanesulfonylbenzenesulfonamide;
N-[3-(3-trifluoromethoxyphenyl)-1H-indazol-5-yl]-2-methanesulfonylbenzenesulfonamide;
2-methanesulfonyl-N-[3-(4-methanesulfonylphenyl)-1H-indazol-5-yl]-benzenesulfonamide;
N-[3-(2,3-difluorophenyl)-1H-indazol-5-yl]-2-methanesulfonylbenzenesulfonamide;
N-[3-(4-fluoro-3-methylphenyl)-1H-indazol-5-yl]-2-methanesulfonylbenzenesulfonamide;
N-[3-(3-benzyloxyphenyl)-1H-indazol-5-yl]-2-methanesulfonylbenzenesulfonamide;
N-[3-(3-fluoro-4-methylphenyl)-1H-indazol-5-yl]-2-methanesulfonylbenzenesulfonamide;
N-[3-(2,5-dichlorophenyl)-1H-indazol-5-yl]-2-methanesulfonylbenzenesulfonamide.

A product in accordance with the invention can exist in the:
1) nonchiral form, or
2) racemic form, or
3) form enriched in a stereoisomer, or
4) form enriched in an enantiomer;

and can optionally be salified.

A product in accordance with the invention may be used for producing a medicinal product of use for treating a pathological condition, in particular a cancer.

The present invention also relates to the therapeutic compositions comprising a product according to the invention, in combination with a pharmaceutically acceptable excipient according to the method of administration chosen. The pharmaceutical composition can be in the form of a solid, of a liquid or of liposomes.

Among the solid compositions, mention may be made of powders, gelatin capsules or tablets. The oral forms can also include solid forms protected against the acidic environment of the stomach. The carriers used for the solid forms consist in particular of inorganic carriers, such as phosphates or carbonates, or of organic carriers, such as lactose, celluloses, starch or polymers. The liquid forms consist of solutions, of suspensions or of dispersions. They contain, as dispersing carrier, either water or an organic solvent (ethanol, NMP or others) or of mixtures of surfactants and of solvents or of complexing agents and of solvents.

The liquid forms will preferably be injectable and, as a result, will have a formulation acceptable for such a use.

Acceptable routes of administration by injection include intravenous, intraperitoneal, intramuscular and subcutaneous injection, intravenous injection usually being preferred.

The administered dose of the compounds of the invention will be adjusted by the practitioner as a function of the route of administration to the patient and of the patient's condition.

The compounds of the present invention can be administered alone or as a mixture with other anticancer agents. Among the possible combinations, mention may be made of:
alkylating agents and in particular cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine
platinum derivatives, such as, in particular, cisplatin, carboplatin or oxaliplatin
antibiotics, such as, in particular, bleomycin, mitomycin or dactinomycin
antimicrotubule agents, such as, in particular, vinblastine, vincristine, vindesine, vinorelbine or taxoids (paclitaxel and docetaxel)
anthracyclines, such as, in particular, doxorubicin, daunorubicin, idarubicin, epirubicin, mitoxantron or losoxantron
topoisomerase group I and II inhibitors, such as etoposide, teniposide, amsacrine, irinotecan, topotecan and tomudex
fluoropyrimidines, such as 5-fluorouracil, UFT or floxuridine
cytidine analogs, such as 5-azacytidine, cytarabine, gemcitabine, 6-mercaptomurine or 6-thioguanine
adenosine analogs, such as pentostatin, cytarabine or fludarabine phosphate
methotrexate and folinic acid
diverse enzymes and compounds, such as L-asparaginase, hydroxyurea, trans-retinoic acid, suramin, dexrazoxane, amifostine, herceptine and also estrogenic and androgenic hormones
antivascular agents, such as derivatives of combretastatin or colchicine and their prodrugs.

It is also possible to combine the compounds of the present invention with a radiation treatment. These treatments can be administered simultaneously, separately or sequentially. The treatment will be adjusted by the practitioner according to the patient to be treated.

The products of the invention are of use as agents for inhibiting a reaction catalyzed by a kinase. FAK is a kinase for which the products of the invention will be particularly useful as inhibitors. The products of the invention may also be of use as inhibitors of Aurora and/or KDR kinases. More generally, the products of the invention may also be of use as inhibitors of Src, Tie2, IGF1R, CDK2 and CDK4 kinases, preferably Src and Tie2 kinases.

Reasons for which these kinases are chosen are given below:

KDR

KDR (Kinase insert Domain Receptor), also known as VEGF-R2 (Vascular Endothelial Growth Factor Receptor 2), is expressed only in endothelial cells. This receptor binds to the angiogenic growth factor VEGF and thus acts as a mediator to a transduction signal via the activation of its intracellular kinase domain. Direct inhibition of the kinase activity of VEGF-R2 makes it possible to reduce the phenomenon of angiogenesis in the presence of exogenous VEGF (Vascular Endothelial Growth Factor:) (Strawn et al., *Cancer Research*, 1996, vol. 56, p.3540-3545). This process has been demonstrated in particular using VEGF-R2 mutants (Millauer et al., *Cancer Research*, 1996, vol. 56, p.1615-1620). The VEGF-R2 receptor does not appear to have any function in adults other than that related to the angiogenic activity of VEGF. Consequently, a selective inhibitor of the kinase activity of VEGF-R2 should show only slight toxicity.

In addition to this central role in the angiogenic dynamic process, recent results suggest that the expression of VEGF contributes to the survival of tumor cells after chemotherapy and radiotherapy, underlining the potential synergy of KDR inhibitors with other agents (Lee et al. *Cancer Research*, 2000, vol. 60, p.5565-5570).

Aurora2

Many proteins involved in chromosome segregation and spindle assembly have been identified in yeast and drosophilia. Disruption of these proteins leads to non-segregation of chromosomes and to monopolar or disorganized spindles. Among these proteins, certain kinases, including Aurora and Ipl1, originating respectively from *S. cerevisiae* and from drosophilia, are necessary for chromosome segregation and centrosome separation. A human analog of yeast Ipl1 has recently been cloned and characterized by various laboratories. This kinase, called aurora2, STK15 or BTAK, belongs to the serine/threonine kinase family. Bischoff et al. have shown that Aurora2 is oncogenic and is amplified in human colorectal cancers (EMBO J, 1998, 17, 3052-3065). This has also been exemplified in cancers involving epithelial tumors such as breast cancer.

Src

It has been noted that the Src kinase, involved in many signaling cascades, is often activated or overexpressed in many types of cancer, such as colon cancer or breast cancer (M M Moasser et al., Cancer Res. 1999. 59:6245-6152; Wiener et al. Clin. Cancer Res. 1999. 5:2164-2170). In addition, Src appears to play a predominant role in the development of bone metastases, by virtue of its involvement in the development of bone tissue (P. Soriano et al., Cell 1991. 64:693-702; Nakagawa et al, Int. J. Cancer 2000. 88:384-391).

Tie2

Tie-2 (TEK) is a member of a family of tyrosine kinase receptors, specific for endothelial cells. Tie2 is the first receptor possessing tyrosine kinase activity for which both the agonist (angiopoietin 1 or Ang1) which stimulates autophosphorylation of the receptor and cell signaling [S. Davis et al (1996) *Cell* 87, 1161-1169] and the antagonist (angiopoietin 2 or Ang2) [P. C. Maisonpierre et al. (1997) *Science* 277, 55-60] are known. Angiopoietin 1 can act synergistically with VEGF in the final stages of neoangiogenesis [Asahara T. *Circ. Res.* (1998) 233-240]. Knockout experiments and transgenic manipulations of the expression of Tie2 or of Ang1 result in animals which exhibit vascularization defects [D. J. Dumont et al (1994) *Genes Dev.* 8, 1897-1909 and C. Suri (1996) *Cell* 87, 1171-1180]. The binding of Ang1 to its receptor results in the autophosphorylation of the kinase domain of Tie2 which is essential for neovascularization and also for the recruitment and interaction of the vessels with pericytes and smooth muscle cells; these phenomena contribute to the maturation and stability of the newly formed vessels [P. C. Maisonpierre et al (1997) *Science* 277, 55-60]. Lin et al (1997) *J. Clin. Invest* 100, 8: 2072-2078 and P. Lin (1998) *PNAS* 95, 8829-8834, have shown an inhibition of tumor growth and vascularization and also a decrease in lung metastases during adenoviral infections or during injections of the extracellular domain of Tie-2 (Tek) in breast tumor and melanoma xenograft models.

Tie2 inhibitors can be used in situations where neovascularization takes place inappropriately (i.e. in diabetic retinopathy, chronic inflammation, psoriasis, Kaposi's sarcoma, chronic neovascularization due to macular degeneration, rheumatoid arthritis, infantile hemangioma and cancers).

IGF1R

The type 1 receptor for insulin-like growth factor (IGF-I-R) is a transmembrane receptor with tyrosine kinase activity which binds initially to IGFI but also to IGFII and to insulin with lower affinity. The binding of IGF1 to its receptor leads to oligomerization of the receptor, activation of the tyrosine kinase, intermolecular autophosphorylation and phosphorylation of cell substrates (main substrates: IRS1 and Shc). The receptor activated by its ligand induces mitogenic activity in normal cells. However, IGF-I-R plays an important role in "abnormal" growth.

Several clinical reports underline the important role of the IGF-I pathway in the development of human cancers:

IGF-I-R is often found overexpressed in many tumor types (breast, colon, lung, sarcoma, etc.) and its presence is often associated with a more aggressive phenotype.

High concentrations of circulating IGF1 correlate strongly with a risk of prostate cancer, lung cancer and breast cancer.

In addition, it has been widely documented that IGF-I-R is necessary for establishing and maintaining the transformed phenotype in vitro as in vivo [R Baserga, Exp. Cell. Res., 1999, 253, pages 1-6]. The kinase activity of IGF-I-R is essential to the transforming activity of several oncogenes: EGFR, PDGFR, SV40 virus large T antigen, activated Ras, Raf, and v-Src. The expression of IGF-I-R in normal fibroblasts induces a neoplastic phenotype, which can then lead to the formation of a tumor in vivo. The expression of IGF-I-R plays an important role in substrate-independent growth. IGF-I-R has also been shown to be a protector in apoptosis induced by chemotherapy and radiation, and apoptosis induced by cytokines. In addition, the inhibition of endogenous IGF-I-R by a dominant negative, the formation of a triple helix or the expression of an antisense causes suppression of the transforming activity in vitro and a decrease in tumor growth in animal models.

CDK2 and CDK4

Cyclin-dependent kinases (CDKs) constitute a family of protein kinases which are involved mainly in the control of progression between the various phases of the cell cycle. During the G1 phase, CDK4 associates with cyclin D and phosphorylates the Rb protein, which results in its inactivation, and induction of dissociation of the transcription factors E2F and DP1. These transcription factors then enter the nucleus, where they control the genic expression required for the G1/S transition and progression into S phase. The CDK2-cyclin E complex is also responsible for the G1/S transition and, in addition, regulates centrosome duplication. Deregulation of the kinase activity of CDKs in many tumors has stimulated an intensive search for inhibitors, for antiproliferative purposes (see, for example, TRENDS in Pharmacological Sciences Vol.23 No.9 September 2002).

Definitions

The term "halogen" refers to an element chosen from F, Cl, Br and 1.

The term "alkyl" refers to a saturated, linear or branched, hydrocarbon-based substituent having from 1 to 12 carbon atoms. The methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl and dodecyl substituents are examples of an alkyl substituent.

The term "alkenyl" refers to a linear or branched hydrocarbon-based substituent having one or more unsaturations and from 2 to 12 carbon atoms. The ethenyl, 1-methylethenyl, prop-1-enyl, prop-2-enyl, Z-1-methylprop-1-enyl, E-1-methylprop-1-enyl, Z-1,2-dimethylprop-1-enyl, E-1,2-dimethylprop-1-enyl, buta-1,3-dienyl, 1-methylinprop-2-enyl, Z-2-methylbuta-1,3-dienyl, E-2-methylbuta-1,3-dienyl, 2-methyl-1-methylinylprop-2-enyl, undec-1-enyl and undec-10-enyl substituents are examples of an alkenyl substituent.

The term "alkynyl" refers to a linear or branched hydrocarbon-based substituent having at least two unsaturations carried by a pair of vicinal carbon atoms, and having from 2 to 12 carbon atoms. The ethynyl; prop-1-ynyl; prop-2-ynyl and but-1-ynyl substituents are examples of an alkynyl substituent.

The term "aryl" refers to a mono- or polycyclic aromatic substituent having from 6 to 14 carbon atoms. The phenyl, naphth-1-yl; naphth-2-yl; 1,2,3,4-tetrahydronaphth-5-yl and 1,2,3,4-tetrahydronaphth-6-yl substituents are examples of an aryl substituent.

The term "heteroaryl" refers to a mono- or polycyclic heteroaromatic substituent having from 1 to 13 carbon atoms and from 1 to 4 heteroatoms. The pyrrol-1-yl; pyrrol-2-yl; pyrrol-3-yl; furyl; thienyl; imidazolyl; oxazolyl thiazolyl; isoxazolyl; 1,2,4-triazolyl; oxadiazolyl; thiadiazolyl; tetrazolyl; pyridyl; pyrimidyl; 1,3,5-triazinyl; indolyl; benzo[b]furyl; benzo[b]thienyl indazolyl; benzimidazolyl; azaindolyl; quinolyl; isoquinolyl and carbazolyl substituents are examples of a heteroaryl substituent.

The term "heteroatom" here refers to an at least divalent atom other than carbon. N; O; S and Se are examples of a heteroatom.

The term "cycloalkyl" refers to a saturated or partially unsaturated, cyclic hydrocarbon-based substituent having from 3 to 12 carbon atoms. The cyclopropyl, cyclobutyl, cyclopentyl, cyclopentenyl, cyclopentadienyl, cyclohexyl, cyclohexenyl, cycloheptyl, bicyclo[2.2.1]heptyl, cyclooctyl, bicyclo[2.2.2]octyl, adamantyl and perhydronapthyl substituents are examples of a cycloalkyl substituent.

The term "heterocyclyl" refers to a saturated or partially unsaturated, cyclic hydrocarbon-based substituent having from 1 to 13 carbon atoms and from 1 to 4 heteroatoms. Preferably the saturated or partially unsaturated cyclic hydrocarbon-based substituent will be monocyclic and will comprise 4 or 5 carbon atoms and 1 to 3 heteroatoms.

The term "substituted" refers to a substituent other than H, for example halogen, alkyl, aryl, heteroaryl, cycloalkyl, heterocyclyl, alkenyl, alkynyl, OH, O-alkyl, O-alkenyl, O-aryl, O-heteroaryl, NH$_2$, NH-alkyl, NH-aryl, NH-heteroaryl, SH, S-alkyl, S-aryl, S(O$_2$)H, S(O$_2$)-alkyl, S(O$_2$)-aryl, SO$_3$H, SO$_3$-alkyl, SO$_3$-aryl, CHO, C(O)-alkyl, C(O)-aryl, C(O)OH, C(O)O-alkyl, C(O)O-aryl; OC(O)-alkyl, OC(O)-aryl, C(O)NH$_2$; C(O)NH-alkyl, C(O)NH-aryl, NHCHO, NHC(O)-alkyl, NHC(O)-aryl, NH-cycloalkyl and NH-heterocyclyl.

A subject of the present invention is also the method for preparing the products of formula (I).

The compounds of formula (I) for which X is selected from the group consisting of S(O$_2$)—NH and S(O$_2$)—O can be prepared by reaction of a derivative of formula (II) in which R and R1 have the same meanings as in formula (I) and A represents a hydroxyl (OH) or amine (NH$_2$) function, with a sulfonyl chloride Z-S(O$_2$)Cl for which Z has the same meaning as in formula (I):

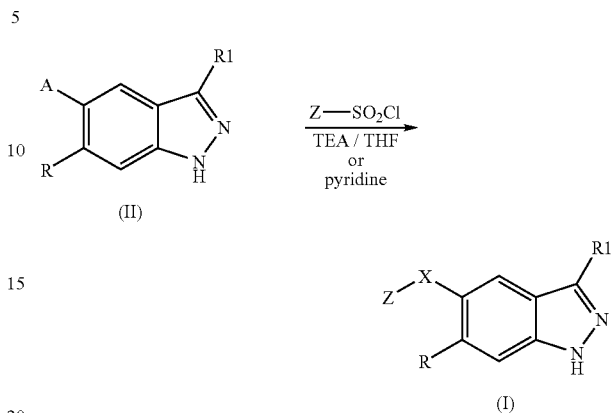

This reaction is preferably carried out in an inert solvent (tetrahydrofuran, dichloromethane, diethyl ether or dimethylformamide for example) in the presence of an acid acceptor, such as an alkylamine (triethylamine, cyclohexylamine, for example) or in the presence of a base, such as pyridine, sodium hydroxide or a hydride (sodium hydride for example), at a temperature of between 0° C. and the boiling point of the medium or by application or adaptation of the methods described by L. Z. FLORES-LOPEZ et al., Synth. Comm. 2000, 30(1), 147, J. BOSCH et al., Synthesis, 2000, (5), 721, G. THEODORIDIS et al., Tetrahedron Lett., 1998, 39(51), 9365, T. COHEN et al., Tetrahedron, 1997, 53(28), 9487, and T. B. GRINDLEY et al., Tetrahedron Lett., 1993, 34(33), 5231.

In some cases, it may be necessary to introduce protective groups for the amino functions in order to avoid side reactions. These groups are those which can be removed without affecting the remainder of the molecule. As examples of protective groups for the amine function, mention may be made of tert-butyl carbamate, which can be regenerated by means of iodotrimethylsilane or in an acidic medium (trifluoroacetic acid, or hydrochloric acid in a solvent such as dioxane for example), acetyl, which can be regenerated in an acid medium (hydrochloric acid for example), benzoyl, which can be regenerated in an acid medium (hydrochloric acid, for example), or 2-trimethylsilanylethoxymethyl, which can be regenerated in the presence of tetrabutylammonium fluoride or in an acid medium for example (hydrochloric acid for example). Other protective groups which can be used are described by T. W. GREENE et al. in Protective Groups in Organic Synthesis, third edition, 1999, Wiley-Interscience.

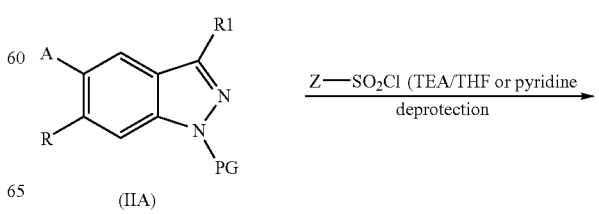

-continued

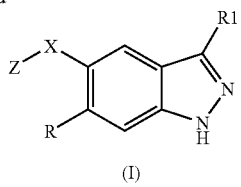

(I)

Compounds of formula (IIB) for which A represents NH₂ and R and R1 have the same meanings as in formula (I) may be commercially available or can be prepared by reduction of the compounds of formula (III):

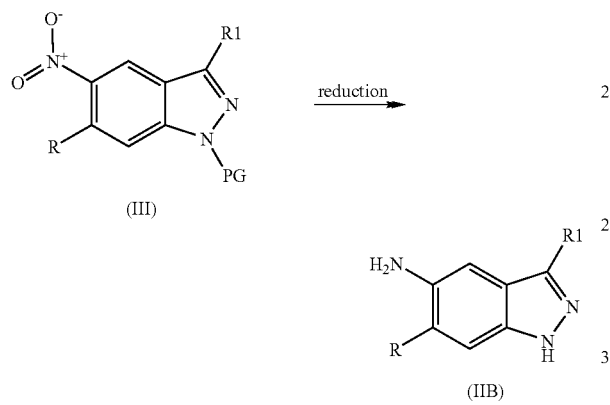

This reduction reaction can be carried out according to the usual methods known to those skilled in the art, such as, for example, using ammonium formate in the presence of palladium-on-charcoal (S. RAM et al., Tetrahedron Lett., 1984, 25, 3415) or using ferrous sulfate (S. CASTELLANO et al., J. Heterocycl., Chem., 2000, 37(6), 949) in an inert solvent such as an alcohol (methanol for example), or in the presence of iron and hydrochloric acid in a solvent such as a mixture of alcohol and water (ethanol-water for example) (S. A. MAHOOD et al., Org. Synth. Coll. Vol. 2, 1943, 160), or else using hydrogen in the presence of palladium-on-charcoal or of Raney nickel in an inert solvent such as ethyl acetate or ethanol, at a temperature of between 0° C. and the boiling temperature of the reaction mixture.

The compounds of formula (III) for which R and R1 have the same meanings as in formula (I) may be commercially available or can be prepared by nitration of compounds of formula (IV)

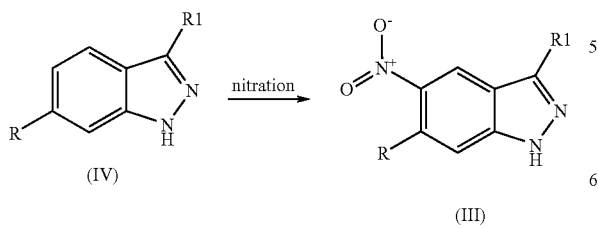

The nitration reaction can be carried out according to the usual methods known to those skilled in the art, such as, for example, using nitric acid or an alkali metal (potassium for example) nitrate in the presence of sulfuric acid (G. A. OLAH et al., Nitration: Methods and Mechanisms, VCH:NY, 1989) at a temperature of between 0° C. and the boiling temperature of the reaction mixture.

The compounds of formula (III) for which R and R1 have the same meanings as in formula (I) can also be prepared by cyclization of compounds of formula (V) in the presence of hydrazine hydrate or hydrochloride or by application or adaptation of the methods described for the preparation of the products (IV).

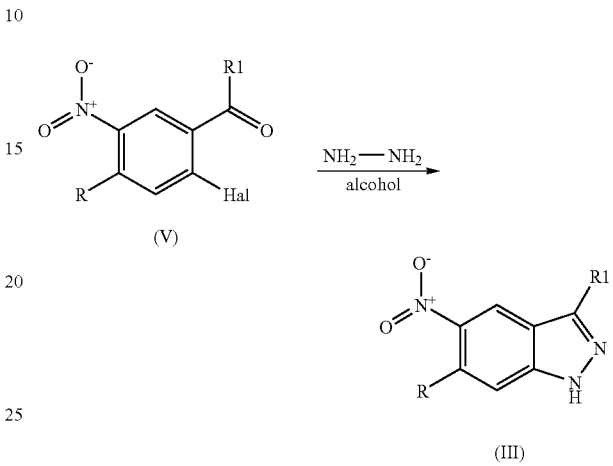

The reaction for cyclization of the compounds (V) is carried out in an inert solvent such as an alcohol (methanol or ethanol for example), at a temperature of between 0° C. and the boiling point of the reaction medium.

The compounds of formula (IV) for which R and R1 have the same meanings as in formula (I) may be commercially available or can be prepared by application or adaptation of the methods described by A. P. KRAPCHO et al., Bioorg. Med. Chem. Lett., 2000, 10(3), 305 and J. Heterocycl. Chem., 1997, 34(5), 1637, A. VARVARESOU et al., J. Heterocycl. Chem., 1996, 33(3), 831, F. HALLEY et al., Synth. Commun., 1997, 27(7), 1199, and R. F. KALTENBACH et al., Bioorg. Med. Chem. Lett., 1999, 9(15), 2259.

The compounds of formula (IV) for which R and R1 have the same meanings as in formula (I) can also be prepared by cyclization of the compounds of formula (VA) in the presence of nitrite R'ONO (sodium nitrite, tert-butyl nitrite or isoamyl nitrite, for example) in the presence of acid (acetic acid for example) or anhydride (acetic anhydride for example) at a temperature of between 0° C. and the boiling point of the reaction medium (C. RUECHARDT et al., Synthesis, 1972, 375, Ann. Chem., 1980, 6, 908).

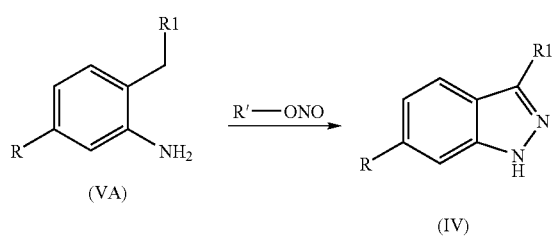

The compounds of formula (V) for which R and R1 have the same meanings as in formula (I) may be commercially available or can be prepared by application or adaptation of the methods described by E. KUMAZAWA et al., Chem. Pharm. Bull., 1997, 45(9), 1470, F. D. BELLAMY et al., J.

Med. Chem., 1991, 34(5), 1545, J. DEUTSCH et al., Synth. Commun., 1991, 21(4), 505, A. VARVARESOU et al., J. Heterocycl. Chem., 1996, 33(3), 831, in patent WO9322287 and by D. M. McKINNON et al., J. Heterocycl. Chem., 1991, 28(2), 347.

Compounds of formula (ICI) for which A=OH and R and R1 have the same meanings as in formula (I) can be prepared like the compounds (III) by cyclization of the compounds (VB) or by application or adaptation of the methods described by H. RAPOPORT et al., J. Am. Chem. Soc., 1951, 73, 2718 and D. THANG et al., C. R. Acad. Sci., Ser. C, 1971, 272, 1571.

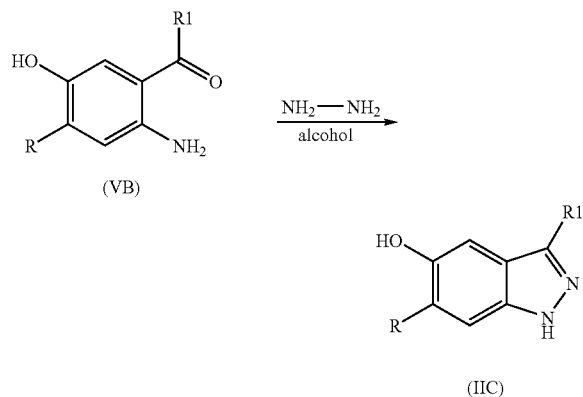

The compounds of formula (I) for which X is selected from the group consisting of NH—S(O$_2$) and O—S(O$_2$) can be prepared by reaction of a derivative of formula (VI) in which R and R1 have the same meanings as in formula (I) with an amine Z-NH$_2$ or an alcohol Z-OH for which Z has the same meaning as in formula (I)

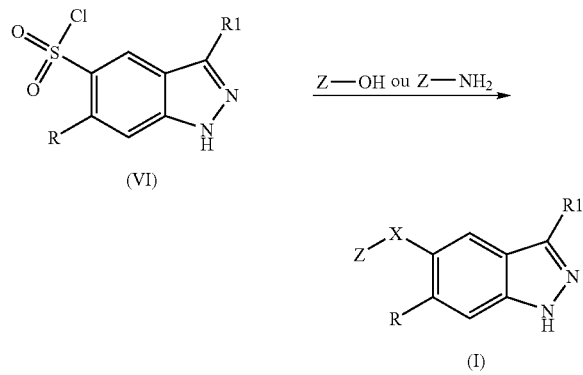

This reaction is carried out under the same conditions as those used for the preparation of the compounds of formula (I) from the compounds of formula (II).

The compounds of formula (VI) can be prepared by diazotization, followed by a chlorosulfonation reaction, of the derivatives of formula (IIB)

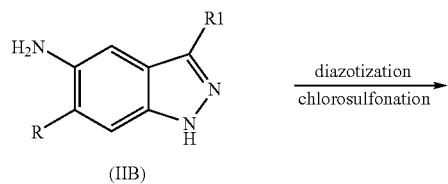

-continued

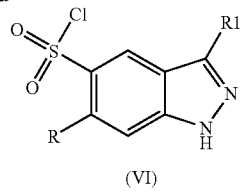

These reactions are carried out according to the usual methods known to those skilled in the art. The diazotization reaction is carried out, for example, using sodium nitrite in the presence of acid (hydrochloric acid and acetic acid, for example) at a temperature of between 0° C. and the boiling point of the reaction medium. The chlorosulfonation reaction is carried out, for example, using sulfur dioxide in the presence of copper salt (such as CuCl or CuCl$_2$). These compounds can also be prepared by application or adaptation of the methods described by A. E. WEBER et al., Bioorg. Med. Chem. Lett., 1999, 9(9), 1251, E. F. ELSLAGER et al., J. Med. Chem., 1984, 27(12), 1740, R. V. HOFFMAN et al., Org. Synth., 1981, 60, 121.

The compounds of formula (I) for which X and R have the same meanings as in formula (I) and R1 represents an O(R2) group can also be prepared by reaction of an alkylating agent R2-Hal with compounds of formula (I) for which R1 represents an OH group. This reaction is generally carried out in the presence of a base (sodium hydride or potassium carbonate, for example) in an inert solvent (diethyl ether, dimethylformamide or tetrahydrofuran, for example) at a temperature of between 0° C. and the boiling point of the reaction medium or by application or adaptation of the methods described by V. J. FLORES et al., Liebigs Ann., 1996, 5, 683 and M. YAMAGUCHI et al., Chem. Pharm. Bull., 1995, 43(2), 332.

The compounds of formula (I) for which X and R have the same meanings as in formula (I) and R1 represents an OC(O)(R2) group can also be prepared by acylation of the compounds of formula (I) for which R1 represents an OH group. These compounds can be obtained by reaction of an acid chloride (R2)C(O)Cl in the presence of a base, such as pyridine or triethylamine for example (J. K. GAWRONSKI et al., J. Am. Chem. Soc., 1987, 109, 6726, J. B. LAMBERT et al. J. Am. Chem. Soc., 1987, 109, 7838, and C. J. BLANKEY et al., Org. Synth. Coll. Vol. 5, 1973, 258.), by reaction of an anhydride ((R2)C(O))$_2$O in the presence of an acid (paratoluenesulfonic acid, for example, A. C. COPE et al., Org. Syn. Coll. Vol. 4, 1963, 304) or in the presence of a base (pyridine for example, J. B. LAMBERT et al. J. Am. Chem. Soc., 1987, 109, 7838) or by reaction with a carboxylic acid (R2)C(O)OH according to the well known methods of esterification (E. HASLAM et al., Tetrahedron, 1980, 36, 2409).

The compounds of formula (I) for which X and R have the same meanings as in formula (I) and R1 represents an OC(O)N(R2)(R3) group can also be prepared by acylation of the compounds of formula (I) for which R1 represents an OH group. These compounds can be obtained by reaction with a carbamoyl chloride (R2)(R3)NC(O)Cl in the presence of a base, such as pyridine (A. BORIONI, Heterocycl. Chem., 2000, 37 (4), 799), at a temperature of between 0° C. and the boiling point of the medium. The compounds of formula (I) for which X has the same meaning as in formula (I) and R1 represents an OC(O)N(R2)(R3) group in which R3 represents a hydrogen atom can also be prepared by reaction of an isocyanate (R2)—N═C═O in the presence of a base, such as triethylamine or pyridine (R. C. REYNOLDS, J. Med. Chem., 200, 43(8), 1484).

The compounds of formula (I) for which X and R have the same meanings as in formula (I) and R1 represents an OS(O$_2$)(R2) group can also be prepared by sulfonylation of the compounds of formula (I) for which R1 represents an OH group. These compounds can be obtained by reaction of a derivative (R2)S(O₂)Cl as described for the preparation of the compounds of formula (I) from the compounds of formula (ICI).

The compounds of formula (I) for which X and R have the same meanings as in formula (I) and R1 represents a C(O)(R2) group can also be prepared from the compounds of formula (I) for which R1 represents a CN group or else a (C=O)N(OMe)Me group by addition of an organometallic compound (a Grignard reagent R2MgX for example, M. B. SMITH and J. MARCH, Wiley Interscience, Advanced Organic Chemistry, 5th edition, 1217; A. ALBEROLA et al., Tetrahedron 1999, 55, 13211, or an alkyllithium reagent, M. KRATZEL et al. J. Chem. Soc. Perkin Trans. 1, 1997, 7, 1009; J. SINGH et al., J. Prakt. Chem. 2000, 342(4), 340.) at a temperature of between 0° C. and the boiling point of the medium.

The compounds of formula (I) for which X and R have the same meanings as in formula (I) and R1 represents a C(=N(R3))(R2) group can also be prepared from the compounds of formula (I) for which R1 represents a C(O)(R2) group by addition of amines (R3)NH₂ (M. B. SMITH and J. MARCH, Wiley Interscience, Advanced Organic Chemistry, 5th edition, 1185) at a temperature of between 0° C. and the boiling point of the medium.

The compounds of formula (I) for which X and R have the same meanings as in formula (I) and R1 represents a C(=N(OR3))(R2) group can also be prepared from the compounds of formula (I) for which R1 represents a C(O)(R2) group by addition of hydroxylamines NH₂O(R3) (M. B. SMITH and J. MARCH, Wiley Interscience, Advanced Organic Chemistry, 5th edition, 1194) at a temperature of between 0° C. and the boiling point of the medium.

The compounds of formula (I) for which X and R have the same meanings as in formula (I) and R1 is selected from the group consisting of C(O)O(R2) and C(O)N(R2)(R3) can be prepared from the compounds of formula (I) for which R1 represents a CN group according to the following scheme:

The hydrolysis of the nitrile function (step a) can be carried out in acidic or basic medium by methods known to those skilled in the art. For example, this reaction can be carried out in the presence of aqueous sodium hydroxide at a temperature of between 0° C. and the boiling point of the medium (P. L. COMPAGNON et al., Ann. Chem. (Paris), 1970, 14(5), 11 and 23).

The esterification reaction (step b) can be carried out by methods known to those skilled in the art, such as, for example, in the presence of an acid and by reaction with an alcohol (R2)OH (E. HASLAM et al., Tetrahedron, 1980, 36, 2409).

The derivatives of formula (ID) can be obtained by reaction (step c) of an amine (R2)(R3)NH in the presence of an activating agent (O-(7-azabenzotriazol-1-yl)-N,N,N',N'-tetramethyluronium hexafluorophosphate (HATU), or 1-hydroxybenzotriazole hydrate (HOBT)/1-ethyl-3-[3-(dimethylamino)propyl]carbodiimide hydrochloride (EDCl) for example), in the presence of a base (diisopropylethylamine or triethylamine for example) in an inert solvent (dimethylformamide or a dimethylformamide/dichloromethane or dimethylformamide/1-methyl-2-pyrrolidinone mixture for example) at a temperature of between 0° C. and the boiling point of the medium, or according to the well known coupling methods of peptide chemistry (M. BODANSZKY et al., Principles of Peptide Synthesis, Spinger-Verleg, New York, N.Y., 1984, 9-58) or the well known methods for the formation of an amide.

Alternatively, the derivatives of formula (IB) for which X represents SO₂NH can be prepared from the compounds of formula (I) for which R1 represents a (C=O)N(OMe)Me group according to the following scheme:

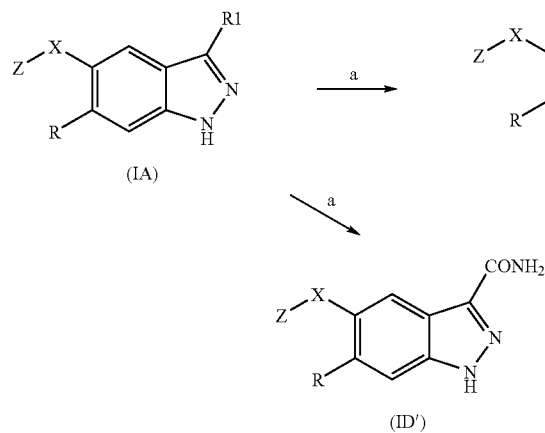

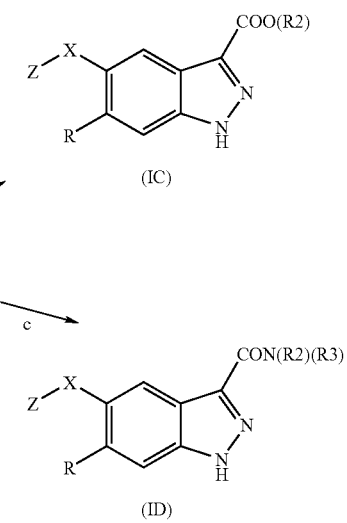

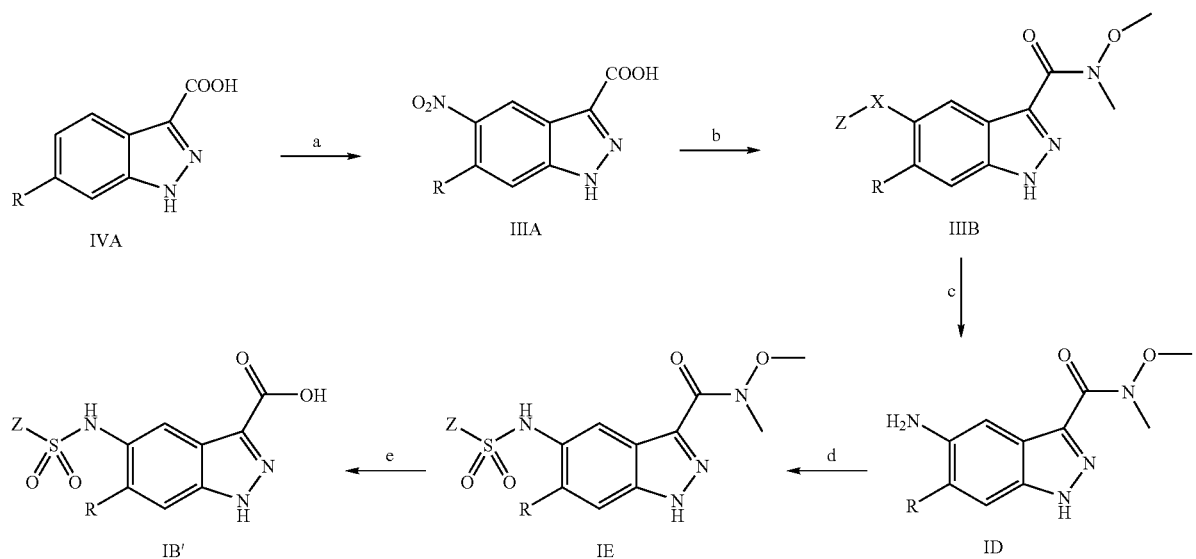

The nitration (step a) can be carried out as described previously. The synthesis of the amide intermediate IIIB (step b) can be carried out using N,O-dimethylhydroxylamine, in the presence of an activating agent (1-hydroxybenzotriazole hydrate (HOBT)/1-ethyl-3-[3-(dimethylamino)propyl]-carbodiimide hydrochloride (EDCl) for example), in the presence of a base (triethylamine for example) in an inert solvent (dichloromethane for example) at a temperature of between 0° C. and the boiling point of the medium, or according to the well known coupling methods of peptide chemistry (M. BODANSZKY et al., Principles of Peptide Synthesis, Spinger-Verleg, New York, N.Y., 1984, 9-58) or the well known methods for the formation of an amide. The reduction step (step c) and step d can be carried out as described previously. The hydrolysis of the amide function (step e) can be carried out in acidic or basic medium by methods known to those skilled in the art. For example, this reaction can be carried out in the presence of aqueous sodium hydroxide at a temperature of between 0° C. and the boiling point of the medium.

The compounds of formula (I) for which X and R have the same meanings as in formula (I) and R1 represents an N(R2)(R3) group can also be prepared from the compounds of formula (I) for which R1 represents an NH₂ group.

These compounds can be obtained by an alkylation reaction from a derivative (R2)(R3)-Hal in the presence of a base at a temperature of between 0° C. and the boiling point of the medium by application or adaptation of the methods described by H. KAWAKUBO et al., Chem. Pharm. Bull., 1987, 35(6), 2292.

The compounds of formula (I) for which X and R have the same meanings as in formula (I) and R1 represents the N(R2)(R3) group in which R2 represents a hydrogen atom and R3 represents a disubstituted alkyl radical can also be prepared from the compounds of formula (I) for which R1 represents an NH₂ group. These compounds can be obtained by reaction of an aldehyde or of a ketone in the presence of a reducing agent (M. B. SMITH and J. MARCH, Wiley Interscience, Advanced Organic Chemistry, 5th edition, 1185) at a temperature of between 0° C. and the boiling point of the medium.

The compounds of formula (I) for which X and R have the same meanings as in formula (I) and R1 represents an N=C(R2)(R3) group can also be prepared from the compounds of formula (I) for which R1 represents an NH₂ group. These compounds can be obtained by reaction of a derivative (R2)(R3)C(O) (M. B. SMITH and J. MARCH, Wiley Interscience, Advanced Organic Chemistry, 5th edition, 1185) at a temperature of between 0° C. and the boiling point of the medium.

The compounds of formula (I) for which X and R have the same meanings as in formula (I) and R1 represents an N(R2)C(O)(R3) group in which R2 represents a hydrogen atom can also be prepared by acylation from the compounds of formula (I) for which R1 represents an NH₂ group, using an acid chloride (R3)C(O)Cl in the presence of a base, such as pyridine, triethylamine or diisopropylethylamine, in an inert solvent (dimethylformamide or tetrahydrofuran for example), at a temperature of between 0° C. and the boiling point of the medium (G. DAIDONE et al, Heterocycles, 1996, 43(11), 2385), using an anhydride ((R3)CO)₂O in an inert solvent (dimethylformamide, tetrahydrofuran or dichloromethane for example) or in the anhydride itself at a temperature of between 0° C. and the boiling point of the medium (F. ALBERICIO, Synth. Commun., 2001, 31(2), 225, G. PROCTER, Tetrahedron, 1995, 51(47), 12837), using an acid (R3)C(O)OH in the presence of an activating agent (1-hydroxybenzotriazole hydrate (HOBT)/1-ethyl-3-[3-(dimethylamino)propyl]carbodiimide hydrochloride (EDCl), or O-benzotriazol-1-yl-N,N,N',N'-tetramethyluronium hexafluorophosphate (HBTU) for example), in the presence of a base (diisopropylethylamine or triethylamine for example) in an inert solvent (dimethylformamide for example) at a temperature of between 0° C. and the boiling point of the medium, or according to the well known coupling methods of peptide chemistry (M. BODANSZKY et al., Principles of Peptide Synthesis, Spinger-Verleg, New York, N.Y., 1984, 9-58) or the well known methods for the formation of an amide.

The compounds of formula (I) for which X and R have the same meanings as in formula (I) and R1 represents an N(R2)C(O)O(R3) group in which R2 represents a hydrogen atom can also be prepared by acylation of the compounds of formula (I) for which R1 represents an $NH_2$ group. These compounds can be obtained by reaction of a chloroformate (R3)(O)C(O)Cl in the presence of a base at a temperature of between 0° C. and the boiling point of the medium by application or adaptation of the methods described by B. BARAGATTI et al., Eur. J. Med. Chem. 2000, 35 (10), 949, or by reaction of a dicarbonate ((R3(O)C(O))$_2$O by application or adaptation of the methods described by T. ERKER et al., Heterocycles 2001, 55 (2), 255-264.

The compounds of formula (I) for which X and R have the same meanings as in formula (I) and R1 represents an N(R4)C(O)N(R2)(R3) group in which R4 and R2 represent a hydrogen atom can also be prepared from the compounds of formula (I) for which R1 represents an $NH_2$ group. These compounds can be obtained by reaction of an isocyanate (R3)—N=C=O at a temperature of between 0° C. and the boiling point of the medium by application or adaptation of the methods described in the references cited by D. P. N. SATCHELL et al., Chem. Soc. Rev., 1975, 4, 231.

The compounds of formula (I) for which X and R have the same meanings as in formula (I) and R1 represents an N(R4)C(S)N(R2)(R3) group in which R2 and R4 represent a hydrogen atom can also be prepared from the compounds of formula (I) for which R1 represents an $NH_2$ group. These compounds can be obtained by reaction of an isothiocyanate (R3)—N=C=S by application or adaptation of the methods described by M. PALKO et al., J. Heterocycl. Chem. 2000, 37 (4), 779.

The compounds of formula (I) for which X and R have the same meanings as in formula (I) and R1 represents an N(R2)S(O$_2$)(R3) group in which R2 represents a hydrogen atom can also be prepared from the compounds of formula (I) for which R1 represents an $NH_2$ group. These compounds can be obtained by reaction of a derivative (R3)S(O$_2$)Cl as described for the preparation of the compounds of formula (I) from the compounds of formula (II).

The compounds of formula (I) for which X and R have the same meanings as in formula (I) and R1 is selected from the group consisting of S(O)(R2) and S(O$_2$)(R2) can also be prepared by oxidation of the compounds of formula (I) for which R1 represents an S(R2) group at a temperature of between 0° C. and the boiling point of the medium by application or adaptation of the methods described by (M. B. SMITH and J. MARCH, Wiley Interscience, Advanced Organic Chemistry, 5th edition, 1541).

The compounds of formula (I) for which X and R have the same meanings as in formula (I) and R1 represents an S(O$_2$)N(R2)(R3) group can also be prepared from the compounds of formula (I) for which R1 represents the $NH_2$ group as described for the preparation of the compounds (I) for which X represents an NH—S(O$_2$) group from the compounds (IIB).

The compounds for which R1 represents the alkyl, alkenyl, alkynyl, aryl, cycloalkyl, heterocyclyl, substituted alkyl, substituted alkenyl, substituted alkynyl, substituted aryl, substituted cycloalkyl, substituted heterocyclyl, CN, O(R2), N(R2)(R3), N(R2)S(O$_2$)(R3), N(R2)C(O)(R3), N(R2)C(O)O(R3), S(R2), C(O)(R2), C(O)O(R2) or C(O)N(R2)(R3) groups can also be obtained by reactions involving palladium chemistry: SUZUKI (A. SUZUKI, Pure Appl. Chem., 1991, 63, 419), STILLE (J. STILLE, Angew. Chem. Int. Ed., 1986, 25, 508), HECK (R. F. HECK, Org. React., 1982, 27, 345), SONOGASHIRA (K. SONOGASHIRA, Synthesis, 1977, 777), BUCHWALD (S. L. BUCHWALD, Acc. Chem. Res., 1998, 31, 805; S. L. BUCHWALD, J. Org. Chem., 2001, 66, 2560) or by reactions involving copper chemistry (BUCHWALD, Organic Letters, 2002, 4(4), 581) from the corresponding halogenated, triflate and mesylate derivatives. The derivatives (IG) and (IH) for which X represents SO$_2$NH, R1 represents an iodo group and for which R and Z have the same meaning as in formula (I), for example, can be obtained from the compounds of formula (IICI) for which R1 represents an iodo group and R has the same meaning as in formula (I), according to the following scheme:

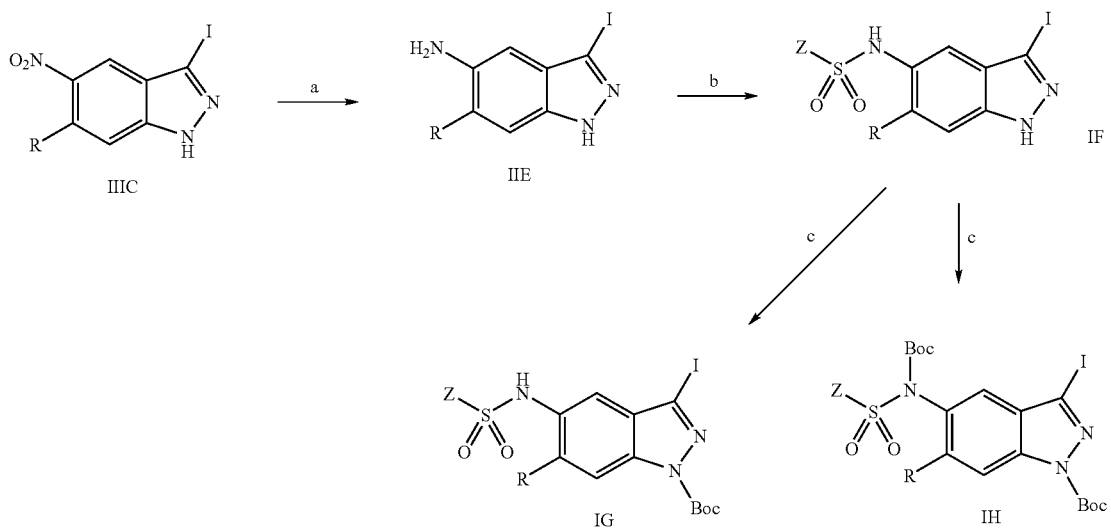

The step of reduction of the nitro group (step a) and step b can be carried out as described previously. The protection steps (steps c and d) can be carried out using di-tert-butyl dicarbonate in the presence of a base, such as triethylamine, in an inert solvent (dichloromethane for example) at a temperature of between −10° C. and the boiling point of the medium, or according to the well known methods of protection of the amine function (T. W. GREENE et al. in Protective Groups in Organic Synthesis, third edition, 1999, Wiley-Interscience). The derivative of formula (IICI) for which R represents a hydrogen atom is described by S. RAULT (S. RAULT et al. Tetrahedron Lett., 2002, 43, 2695). The derivatives of formula (IICI) for which R has the same meaning as in formula (I) and R represents an atom other than hydrogen can be prepared from the corresponding derivatives of formula (III) for which R1 represents a hydrogen atom, by application or adaptation of the method described by S. RAULT (S. RAULT et al. Tetrahedron Lett., 2002, 43, 2695).

The derivatives of formula (IIH) for which R1 represents an iodo group and for which R has the same meaning as in formula (I), for example, can be obtained from the compounds of formula (IIF) for which R has the same meaning as in formula (I), according to the following scheme:

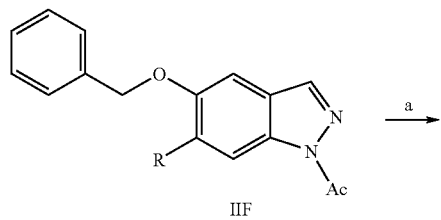

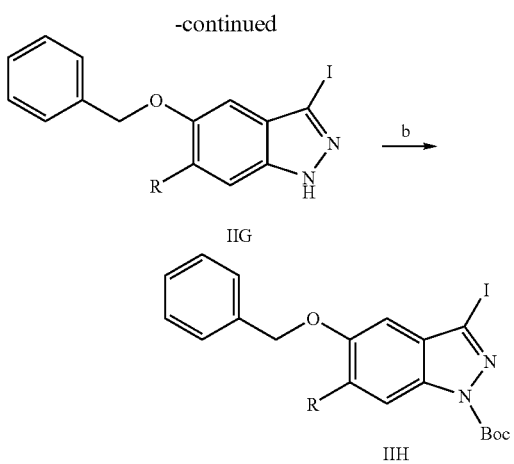

The iodination step (step a) can be carried out using iodine in the presence of a base such as potassium hydroxide, in an inert solvent (dimethylformamide for example) at a temperature of between 25° C. and the boiling point of the medium, by application or adaptation of the method described by S. RAULT (S. RAULT et al. Tetrahedron Lett., 2002, 43, 2695). The protection step b can be carried out as described previously. The derivatives of formula (IIF) for which R has the same meaning as in formula (I) can be prepared as described previously.

The compounds of formula (I) for which X represents $SO_2NH$, R1 represents a 1H-benzimidazol-2-yl group and R has the same meaning as in formula (I) can be prepared from the corresponding compounds of formula (IIIA) according to the following scheme:

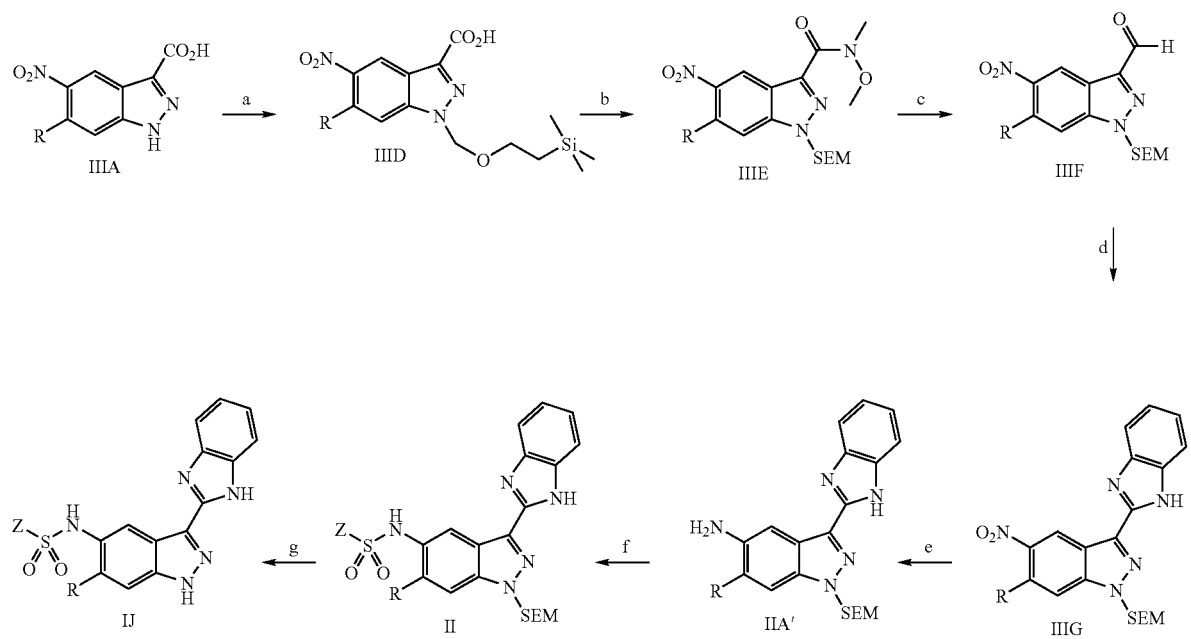

The protection (step a) can be carried out using 2-(trimethylsilyl)ethoxymethyl chloride in the presence of a base, such as sodium hydride, in an inert solvent (dimethylformamide for example) at a temperature between −10° C. and the boiling point of the medium, or according to the well known methods of protection of the amine function (T. W. GREENE et al. in Protective Groups in Organic Synthesis, third edition, 1999, Wiley-Interscience). The synthesis of the amide intermediate IIIE (step b) can be carried out using N,O-dimethylhydroxylamine, in the presence of an activating agent (1-hydroxybenzotriazole hydrate (HOBT)/1-ethyl-3-[3-(dimethylamino)propyl]-carbodiimide hydrochloride (EDCl) for example), in the presence of a base (triethylamine for example) in an inert solvent (dichloromethane for example) at a temperature of between 0° C. and the boiling point of the medium, or according to the well known coupling methods of peptide chemistry (M. BODANSZKY et al., Principles of Peptide Synthesis, Spinger-Verleg, New York, N.Y., 1984, 9-58) or the well known methods for the formation of an amide. The step of reduction of the amide function (step c) can be carried out using diisobutylaluminum hydride in an inert solvent such as an ether (tetrahydrofuran for example) at a temperature of between −10° C. and the boiling point of the medium, or according to the well known methods for reduction of this function (J. SINGH et al., J. Prakt. Chem., 2000, 342(4), 340). Step d can be carried out using 1,2-diaminobenzene, in the presence of sulfur (0) in an inert solvent (dimethylformamide for example) at a temperature of between 0° C. and the boiling point of the medium, or according to the well known methods of benzimidazole synthesis (P. N. PRESTON, Chem. Rev., 1974, 74, 279; P. N. PRESTON et al., Chem. Rev., 1972, 72, 627; J. B. WRIGHT, Chem. Rev., 1951, 48, 397. The step of reduction of the nitro group (step e) and step f can be carried out as described previously. The deprotection step (step g) can be carried out in an acidic medium (hydrochloric acid for example) in an alcohol (ethanol for example) at a temperature of between 0° C. and the boiling point of the medium, or according to the well known methods for deprotection of the amine function (T. W. GREENE et al. in Protective Groups in Organic Synthesis, third edition, 1999, Wiley-Interscience).

The compounds of formula (IK) for which X represents $SO_{2O}$, R1 represents a 1H-benzimidazol-2-yl group, and Z and R have the same meaning as in formula (I) can be prepared from corresponding compounds of formula (II I) according to the following scheme:

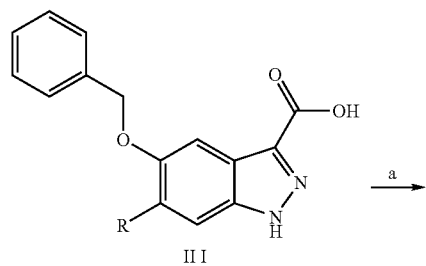

The compound (II I) in which R═H can be prepared according to the method described in EP-A-708105, pp.13-15. Similarly, derivatives of formula (III) for which R has the same meaning as in formula (I) can be prepared from suitable precursors. Step a can be carried out using 1,2-diaminobenzene in the presence of an activating agent (N,N′-diisopropylcarbodiimide for example), in an inert solvent (dimethylformamide for example), at a temperature of between 0° C. and the boiling point of the medium, or according to the well known coupling methods of peptide chemistry (M. BODANSZKY et al., Principles of Peptide Synthesis, Spinger-Verleg, New York, N.Y., 1984, 9-58) or the well known methods for the formation of an amide. The deprotection step b can be carried out, for example, by means of hydrogen or of a hydrogen donor, such as cyclohexene, in the presence of a catalyst (palladium-on-charcoal for example), in an inert solvent such as an alcohol (methanol for example), at a temperature of between 25° C. and the boiling point of the medium, or according to the well known methods of deprotection of the alcohol function (T. W. GREENE et al. in Protective Groups in Organic Synthesis, third edition, 1999, Wiley-Interscience). The last step (step c) can be carried out as described previously.

It is understood by those skilled in the art that, generally and for ease of synthesis, the R1 group may be introduced first and then the series of Z-X substituents may be introduced onto the indazole or, conversely, the sequence of Z=X substituents may be introduced first and then the R1 group may be introduced onto the indazole according to the following scheme, with B and R'1 as suitable precursors of the series of Z-X substituents and of the R1 group respectively:

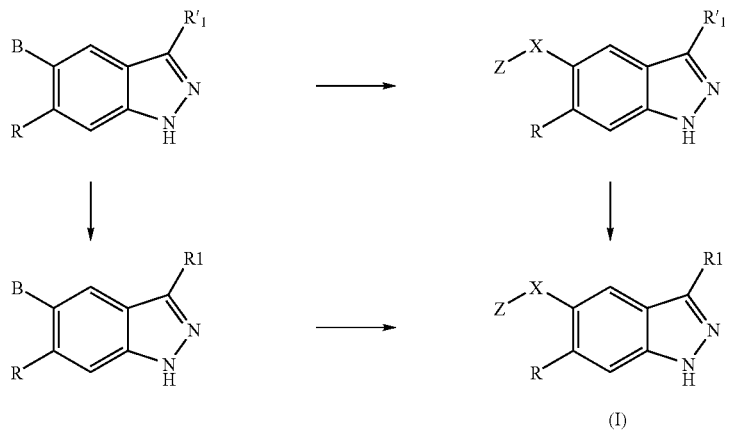

(I)

It is understood by those skilled in the art that, for the implementation of the methods according to the invention described above, it may be necessary to introduce protective groups for the amine, carboxyl and alcohol functions in order to avoid side reactions. These groups are those which can be removed without affecting the remainder of the molecule. As examples of protective groups for the amine function, mention may be made of tert-butyl carbamate, which can be regenerated by means of iodotrimethylsilane or in an acidic medium (trifluoroacetic acid, or hydrochloric acid in a solvent such as dioxane for example), benzyl carbamate, which can be regenerated in the presence of hydrogen or in the presence of a mixture of a thiol (benzenethiol for example) and of a Lewis acid (boron trifluoride etherate for example), acetyl which can be regenerated in an acidic medium (hydrochloric acid for example), benzoyl, which can be regenerated in an acidic medium (hydrochloric acid for example), or 2-trimethylsilanylethoxymethyl, which can be regenerated in the presence of tetrabutylammonium fluoride or in an acidic medium for example (hydrochloric acid for example). Protective groups for the carboxyl function which may be mentioned are the esters (methoxymethyl ester, benzyl ester, methyl ester for example) which can be regenerated by the methods described by T. W. GREENE et al. in Protective Groups in Organic Synthesis, third edition, 1999, Wiley-Interscience. Protective groups for the alcohol function which may be mentioned are the esters (benzoyl ester for example) which can be regenerated in an acidic medium or by catalytic hydrogenation, or else the ethers, such as methyl ether, for example, which can be regenerated in the presence of boron tribromide. Other protective groups which can be used are described by T. W. GREENE et al. in Protective Groups in Organic Synthesis, third edition, 1999, Wiley-Interscience.

The compounds of formula (I) are isolated and can be purified by the usual known methods, for example by crystallization, chromatography or extraction.

The enantiomers and diastereoisomers of the compounds of formula (I) are also part of the invention.

The compounds of formula (I) comprising a basic residue can optionally be converted to addition salts with an inorganic or organic acid by the action of such an acid in an organic solvent, such as an alcohol, a ketone, an ether or a chlorinated solvent.

The compounds of formula (I) comprising an acidic residue can optionally be converted to metal salts or to addition salts with nitrogenous bases according to methods known per se. These salts can be obtained by the action of a metal base (alkali metal or alkaline earth metal base, for example), of ammonia, or an amine or of an amine salt on a compound of formula (I), in a solvent. The salt formed is separated by the usual methods.

These salts are also part of the invention.

When a product according to the invention exhibits at least one free basic function, pharmaceutically acceptable salts can be prepared by reaction between said product and an inorganic or organic acid. Pharmaceutically acceptable salts include chlorides, nitrates, sulfates, hydrogen sulfates, pyrosulfates, bisulfates, sulfites, bisulfites, phosphates, monohydrogenphosphates, dihydrogenphosphates, metaphosphates, pyrophosphates, acetates, propionates, acrylates, 4-hydroxybutyrates, caprylates, caproates, decanoates, oxalates, malonates, succinates, glutarates, adipates, pimelates, maleates, fumarates, citrates, tartrates, lactates, phenylacetates, mandelates, sebacates, suberates, benzoates, phthalates, methanesulfonates, propanesulfonates, xylenesulfonates, salicylates, cinnamates, glutamates, aspartates, glucuronates and galacturonates.

When a product according to the invention exhibits at least one free acidic function, pharmaceutically acceptable salts can be prepared by reaction between said product and an inorganic or organic base. Pharmaceutically acceptable bases include hydroxides of alkali metal or alkaline earth metal cations, such as Li, Na, K, Mg or Ca, and basic amine compounds, such as ammonia, arginine, histidine, piperidine, morpholine, piperazine or triethylamine.

The invention is also described by the following examples, given by way of illustration of the invention.

EXAMPLE 1

N-(3-Chloro-1H-indazol-5-yl)-2-methylsulfonylbenzenesulfonamide

N-(3-Chloro-1H-indazol-5-yl)-2-methylsulfonylbenzenesulfonamide can be obtained in the following way: a solution of 0.36 g of 2-methylsulfonylbenzenesulfonyl chloride and of 3.6 ml of tetrahydrofuran is added dropwise to a solution, cooled to 0° C., of 0.22 g of 5-amino-3-chloro-1H-indazole, of 15 ml of tetrahydrofuran and of 0.37 ml of triethylamine. After reacting for 30 minutes at a temperature in the region of 0° C. and 18 hours at a temperature in the region of 20° C., 30 ml of distilled water are added to the reaction medium. The medium is extracted with 30 ml and 15 ml of ethyl acetate. The organic phase is subsequently dried over magnesium sulfate, filtered and concentrated by evaporation under reduced pressure. The residue thus obtained is purified by chromatography on a silica column with a dichloromethane/methanol (99/1 by volume) mixture as eluent. The solid thus obtained is recrystallized from 45 ml of isopropanol. After drying under reduced pressure at 60° C., 0.05 g of N-(3-chloro-1H-indazol-5-yl)-2-methylsulfonylbenzenesulfonamide is thus obtained in the form of a white solid melting above 260° C. (analysis $C_{14}H_{12}ClN_3O_4S_2$ % calculated C, 43.58; H, 3.13; Cl, 9.19; N, 10.89; O, 16.59; S, 16.62; % found C, 43.72; H, 2.88, Cl, 7.94, N, 10.63; S, 16.80).

5-Amino-3-chloro-1H-indazole can be prepared as described by G. BOYER et al., in J. Chem. Res., Synop., (11), 350 (1990).

EXAMPLE 2

N-(3-Chloro-1H-indazol-5-yl)-3,4-dichlorobenzenesulfonamide

N-(3-Chloro-1H-indazol-5-yl)-3,4-dichlorobenzenesulfonamide can be obtained in the following way: a solution of 1.1 g of 3,4-dichlorobenzenesulfonyl chloride is added dropwise to a solution, cooled to 0° C. of 0.75 g of 5-amino-3-chloro-1H-indazole and of 14 ml of pyridine. After reacting for 10 minutes at a temperature in the region of 0° C. and 2 hours 30 minutes at a temperature in the region of 20° C., 50 ml of distilled water are added to the reaction medium. The medium is extracted with 50 ml and 25 ml of ethyl acetate. The organic phase is subsequently dried over magnesium sulfate, filtered and concentrated by evaporation under reduced pressure. The residue thus obtained is purified by chromatography on a silica column with a dichloromethane/methanol (99/1 by volume) mixture as eluent. The yellow oil thus obtained is again purified by chromatography on a silica column with dichloromethane as eluent. 0.08 g of N-(3-chloro-1H-indazol-5-yl)-3,4-dichlorobenzenesulfonamide is thus obtained in the form of a thick white oil (analysis $C_{13}H_8Cl_3N_3O_2S$ % calculated C, 41.46; H, 2.14; Cl, 28.24; N, 11.16; O, 8.50; S, 8.51% found C, 41.43; H, 2.58; N, 10.81; S, 7.84).

EXAMPLE 3

N-(3-Chloro-1H-indazol-5-yl)-3-fluorobenzenesulfonamide

N-(3-Chloro-1H-indazol-5-yl)-3-fluorobenzenesulfonamide can be obtained as described in Example 1 from 0.18 g of 5-amino-3-chloro-1H-indazole, 20 ml of tetrahydrofuran, 0.25 ml of triethylamine and 0.23 g of 3-fluorobenzenesulfonyl chloride. 0.13 g of N-(3-chloro-1H-indazol-5-yl)-3-fluorobenzenesulfonamide is thus obtained in the form of a yellow foam which decomposes at approximately 80° C. (analysis $C_{13}H_9ClFN_3O_2S$ % calculated: 47.93; H, 2.78; Cl, 10.88; F, 5.83; N, 12.90; O, 9.82; S, 9.84% found C, 48.11; H, 2.64; F, 5.14; N, 13.14; S, 8.22).

EXAMPLE 4

N-(3-Cyano-1H-indazol-5-yl)-3-fluorobenzenesulfonamide

N-(3-Cyano-1H-indazol-5-yl)-3-fluorobenzenesulfonamide can be obtained as described in Example 2 from 0.6 g of 5-amino-3-cyano-1H-indazole, 12 ml of pyridine and 0.73 g of 3-fluorobenzenesulfonyl chloride. 1 g of N-(3-cyano-1H-indazol-5-yl)-3-fluorobenzenesulfonamide is thus obtained in the form of a yellow solid melting at 227° C. (analysis $C_{14}H_9FN_4O_2S$ % calculated C, 53.16; H, 2.87; F, 6.01; N, 17.71; O, 10.12; S, 10.14% found C, 52.86; H, 2.63; F, 5.67; N, 16.04).

5-Amino-3-cyano-1H-indazole can be obtained in the following way: a suspension of 33 g of ferrous sulfate and 52 ml of distilled water is added portionwise to a suspension of 3.1 g of 3-cyano-5-nitro-1H-indazole and 145 ml of ethanol. The reaction medium is maintained with stirring at a temperature in the region of 20° C. for 30 minutes, and then 39 ml of 32% aqueous ammonia are added dropwise over 10 minutes. The black suspension thus obtained is brought to reflux for two hours, and is then brought back to a temperature in the region of 20° C. 300 ml of distilled water are added to the reaction medium, which is extracted with 300 ml and 150 ml of ethyl acetate. The organic phase is filtered through Clarcel, dried over magnesium sulfate and concentrated by evaporation under reduced pressure. The brown solid thus obtained is purified by chromatography on a silica column with a dichloromethane/methanol (99/1 by volume) mixture. After drying under reduced pressure, 1.1 g of 5-amino-3-cyano-1H-indazole are thus obtained in the form of a brown solid melting at 211° C.

3-Cyano-5-nitro-1H-indazole can be obtained as described by N. V. SAVITSKAYA et al. in J. Gen. Chem. USSR, (31), 3037 (1961).

EXAMPLE 5

N-(3-Cyano-1H-indazol-5-yl)-2-methylsulfonylbenzenesulfonamide

N-(3-Cyano-1H-indazol-5-yl)-2-methylsulfonylbenzenesulfonamide can be obtained as described in Example 2 from 0.55 g of 3-cyano-5-amino-1H-indazole, 10 ml of pyridine and 0.88 g of 2-methylsulfonylbenzenesulfonyl chloride. 0.15 g of N-(3-cyano-1H-indazol-5-yl)-2-methylsulfonylbenzenesulfonamide is thus obtained in the form of a yellow powder melting at 272° C. (analysis $C_{15}H_{12}N_4O_4S_2 \cdot 0.85H_2O$, % calculated C, 47.87; H, 3.21; N, 14.88; S, 17.04%, found C, 47.88; H, 3.01; N, 14.75; S, 17.45).

EXAMPLE 6

3-Fluoro-N-(3-phenyl-1H-indazol-5-yl)benzenesulfonamide

3-Fluoro-N-(3-phenyl-1H-indazol-5-yl)-benzenesulfonamide can be obtained in the following way: a solution of 0.4 g of N-(N-tert-butoxycarbonyl-3-phenyl-1H-indazol-5-yl)-3-fluorobenzenesulfonamide, of 3.5 ml of chloroform and of 0.127 ml of iodotrimethylsilane is maintained with stirring for 18 hours at a temperature in the region of 20° C. 10 ml of 5% aqueous ammonia are added to the reaction medium, which is extracted with 40 ml of dichloromethane.

The organic phase is dried over magnesium sulfate, filtered and concentrated by evaporation under reduced pressure. The residue thus obtained is purified by chromatography on a silica column with a dichloromethane/methanol (99/1 by volume) mixture. The gray solid thus obtained is recrystallized from 25 ml of dichloromethane in the presence of 3 S black. 0.1 g of 3-fluoro-N-(3-phenyl-1H-indazol-5-yl)benzenesulfonamide is thus obtained in the form of a white solid melting at 200° C. (analysis $C_{19}H_{14}FN_3O_2S$ % calculated C, 62.11; H, 3.84; F, 5.17; N, 11.44. % found C, 62.09; H, 3.69; F, 4.88; N, 11.44).

$^1$H N.M.R. (300 MHz, $(CD_3)_2SO$ d6, δ in ppm): 7.15 (dd, J=9 and 1.5 Hz: 1H); from 7.40 to 7.70 (mt: 8H); 7.61 (broad s: 1H); 7.78 (broad d, J=7.5 Hz: 2H); 10.21 (unresolved peak: 1H); 13.27 (broad s: 1H).

N-(N-tert-Butoxycarbonyl-3-phenyl-1H-indazol-5-yl)-3-fluorobenzenesulfonamide can be obtained as described in Example 1 from 0.4 g of 5-amino-N-tert-butoxycarbonyl-3-phenyl-1H-indazole, 15 ml of tetrahydrofuran, 0.36 ml of triethylamine and 0.27 g of 3-fluorobenzenesulfonyl chloride. 0.45 g of N-(N-tert-butoxycarbonyl-3-phenyl-1H-indazol-5-yl)-3-fluorobenzenesulfonamide is thus obtained in the form of an ochre solid melting at 100° C.

5-Amino-N-tert-butoxycarbonyl-3-phenyl-1H-indazole can be obtained in the following way: 0.12 g of 10% palladium-on-charcoal and 0.68 g of ammonium formate are added to a solution of 0.8 g of N-tert-butoxycarbonyl-5-nitro-3-phenyl-1H-indazole and of 14 ml of methanol. The suspension is maintained with stirring for 18 hours at a temperature in the region of 20° C. 50 ml of distilled water are added to the reaction medium which is extracted with 50 ml and 25 ml of ethyl acetate. The organic phases are pooled, dried over magnesium sulfate, filtered, and concentrated by evaporation under reduced pressure. The residue obtained is purified by chromatography on a silica column with dichloromethane as eluent. 0.6 g of 5-amino-N-tert-butoxycarbonyl-3-phenyl-1H-indazole is thus obtained in the form of an off-white solid melting at 191° C.

N-tert-Butoxycarbonyl-5-nitro-3-phenyl-1H-indazole can be obtained in the following way: 6.8 g of di-tert-butyl dicarbonate in solution in 70 ml of dichloromethane are added dropwise over 30 minutes to a solution, cooled to a temperature in the region of 0° C., of 5 g of 5-nitro-3-phenyl-1H-indazole, of 100 ml of dichloromethane, of 5.9 ml of triethylamine and of 0.6 g of 4-dimethylaminopyridine. Stirring is maintained for 18 hours at a temperature in the region of 20° C. 200 ml of distilled water are added to the reaction medium, which is extracted with 100 ml of dichloromethane. The organic phases are dried over magnesium sulfate, filtered and concentrated by evaporation under reduced pressure. The residue obtained is purified by chromatography on a silica column with dichloromethane as eluent. 6.9 g of N-tert-butoxycarbonyl-5-nitro-3-phenyl-1H-indazole are thus obtained in the form of a white solid melting at 110° C.

5-Nitro-3-phenyl-1H-indazole can be obtained as described in patent WO 0153268.

EXAMPLE 7

2-Methylsulfonyl-N-(3-phenyl-1H-indazol-5-yl)-benzenesulfonamide

2-Methylsulfonyl-N-(3-phenyl-1H-indazol-5-yl)benzenesulfonamide can be prepared as described in Example 1 from 0.5 g of 5-amino-3-phenyl-1H-indazole, 26 ml of tetrahydrofuran, 0.67 ml of triethylamine and 0.66 g of 2-methylsulfonylbenzenesulfonyl chloride. The residue obtained is purified by chromatography on a silica column with a dichloromethane/methanol (99/1 by volume) mixture as eluent. After recrystallization from 35 ml of isopropanol in the presence of 3 S black, 0.6 g of 2-methylsulfonyl-N-(3-phenyl-1H-indazol-5-yl)benzenesulfonamide is obtained in the form of a brown solid melting at 223° C. (analysis: $C_{20}H_{17}N_3O_4S_2$, % calculated C, 56.19; H, 4.01; N, 9.83; O, 14.97; S, 15.00% found C, 56.22; H, 4.08; N, 9.72; S, 14.48).

$^1$H N.M.R. (300 MHz, $(CD_3)_2SO$ d6, δ in ppm): 3.53 (s: 3H); 7.13 (dd, J=9 and 1.5 Hz: 1H); 7.43 (broad t, J=7.5 Hz: 1H); 7.50 (d, J=9 Hz: 1H); 7.53 (broad t, J=7.5 Hz: 2H); 7.67 (d, J=1.5 Hz: 1H); 7.77 (broad d, J=7.5 Hz: 2H); from 7.75 to 8.00 (mt: 3H); 8.26 (broad d, J=8 Hz: 1H); 9.36 (unresolved peak: 1H); 13.27 (broad s: 1H).

5-Amino-3-phenyl-1H-indazole can be obtained as described in Example 4 from 5 g of 5-nitro-3-phenyl-1H-indazole, 75 ml of ethanol, 77.5 g of ferrous sulfate, 65 ml of water and 50 ml of 32% aqueous ammonia. 2.1 g of 5-amino-3-phenyl-1H-indazole are thus obtained in the form of a white powder melting at 62° C.

EXAMPLE 8

3,4-Dichloro-N-(3-phenyl-1H-indazol-5-yl)benzenesulfonamide 3,4-Dichloro-N-(3-phenyl-1H-indazol-5-yl)benzenesulfonamide can be prepared as described in Example 1 from 1 g of 5-amino-3-phenyl-1H-indazole, 52 ml of tetrahydrofuran, 1.34 ml of triethylamine and 1.29 g of 3,4-dichlorobenzenesulfonyl chloride. The residue obtained is purified by chromatography on a silica column with a dichloromethane/methanol (99/1 by volume) mixture as eluent. After recrystallization from 35 ml of diisopropyl ether in the presence of 3 S black, 0.3 g of 3,4-dichloro-N-(3-phenyl-1H-indazol-5-yl)benzenesulfonamide is obtained in the form of a light gray solid melting at 216° C. (analysis: $C_{19}H_{13}Cl_2N_3O_2S$ % calculated C, 54.56; H, 3.13; Cl, 16.85; N, 10.05; O, 7.65; S, 7.67. % found C, 54.67; H, 2.90; Cl, 16.85; N, 10.08; S, 7.21).

EXAMPLE 9

3-Fluoro-N-(3-methyl-1H-indazol-5-yl)benzenesulfonamide

3-Fluoro-N-(3-methyl-1H-indazol-5-yl)benzenesulfonamide can be obtained as described in Example 6 from 1.35 g of N-(N-tert-butoxycarbonyl-3-methyl-1H-indazol-5-yl)-3-fluorobenzenesulfonamide, 13.5 ml of chloroform and 0.47 ml of iodotrimethylsilane. 0.6 g of 3-fluoro-N-(3-methyl-1H-indazol-5-yl)-benzenesulfonamide is thus obtained in the form of a white foam melting at 120° C. (analysis: $C_{14}H_{12}FN_3O_2S \cdot 0.39CH_2Cl_2$ % calculated, C, 55.07; H, 3.96; F, 6.22; N, 13.76; O, 10.48; S, 10.50. % found C, 54.99; H, 2.70; N, 13.81; S, 10.18).

N-(N-tert-Butoxycarbonyl-3-methyl-1H-indazol-5-yl)-3-fluorobenzenesulfonamide can be obtained as described in Example 1 from 0.9 g of 5-amino-N-tert-butoxycarbonyl-3-methyl-1H-indazole, 40 ml of tetrahydrofuran, 1 ml of triethylamine and 0.78 g of 3-fluorobenzenesulfonyl chloride. 0.1 g of N-(N-tert-butoxycarbonyl-3-methyl-1H-indazol-5-yl)-3-fluorobenzenesulfonamide is thus obtained in the form of a cream solid melting at 195° C.

5-Amino-N-tert-butoxycarbonyl-3-methyl-1H-indazole can be obtained as described in Example 6 from 3.4 g of N-tert-butoxycarbonyl-3-methyl-5-nitro-1H-indazole, 50 ml of methanol, 0.61 g of 10% palladium-on-charcoal and 3.53 g of ammonium formate. 2.7 g of 5-amino-N-tert-butoxycarbonyl-3-methyl-1H-indazole are thus obtained in the form of a cream solid melting at 185° C.

N-tert-Butoxycarbonyl-3-methyl-5-nitro-1H-indazole can be obtained as described in Example 6 from 1.9 g of 3-methyl-5-nitro-1H-indazole, 85 ml of dichloromethane, 3 ml of triethylamine, 0.31 g of 4-dimethylaminopyridine and 3.5 g of di-tert-butyl dicarbonate. 3.5 g of N-tert-butoxycarbonyl-3-methyl-5-nitro-1H-indazole are thus obtained in the form of a cream solid melting at 171° C.

3-Methyl-5-nitro-1H-indazole can be obtained in the following way: 13 ml of hydrazine hydrate are added to a solution of 16.3 g of 2-bromo-5-nitroacetophenone and of 400 ml of ethanol. The medium is maintained with stirring for 8 hours at reflux and is then brought back to a temperature in the region of 20° C. After having added 600 ml of distilled water, the aqueous phase is extracted with 600 ml and 300 ml of ethyl acetate. The organic phases are dried over magnesium sulfate, filtered and concentrated by evaporation under reduced pressure. The residue thus obtained is purified by chromatography on a silica column with dichloromethane/methanol (100/0 to 98/2 by volume) mixtures as eluent. 1.9 g of 3-methyl-5-nitro-1H-indazole are thus obtained in the form of an ochre solid melting at 220° C.

2-Bromo-5-nitroacetophenone can be obtained as described in patent WO 9322287.

EXAMPLE 10

2-Methylsulfonyl-N-(3-methyl-1H-indazol-5-yl)benzenesulfonamide

2-Methylsulfonyl-N-(3-methyl-1H-indazol-5-yl)benzenesulfonamide can be obtained as described in Example 6 from 1.45 g of N-(N-tert-butoxycarbonyl-3-methyl-1H-indazol-5-yl)-2-methylsulfonylbenzenesulfonamide, 12.6 ml of chloroform and 0.44 ml of iodotrimethylsilane. 0.35 g of 2-methylsulfonyl-N-(3-methyl-1H-indazol-5-yl)benzenesulfonamide is thus obtained in the form of a white solid melting above 260° C. (analysis: $C_{15}H_{15}N_3O_4S_2$ % calculated C, 49.30; H, 4.14; N, 11.50; O, 17.51; S, 17.55. % found C, 48.99; H, 4.45; N, 11.67; S, 17.23).

N-(N-tert-Butoxycarbonyl-3-methyl-1H-indazol-5-yl)-2-methylsulfonylbenzenesulfonamide can be obtained as described in Example 1 from 0.9 g of 5-amino-N-tert-butoxycarbonyl-3-methyl-1H-indazole, 55 ml of tetrahydrofuran, 1 ml of triethylamine and 1.02 g of 2-methylsulfonylbenzenesulfonyl chloride. 1.5 g of N-(N-tert-butoxycarbonyl-3-methyl-1H-indazol-5-yl)-2-methylsulfonylbenzenesulfonamide are thus obtained in the form of a pink solid melting at 228° C.

EXAMPLE 11

N-(3-Fluorophenyl)-(1H-indazol-5-yl)sulfonamide

N-(3-Fluorophenyl)-(1H-indazol-5-yl)sulfonamide can be obtained in the following way: 0.98 ml of 3-fluoroaniline is added dropwise to a solution, cooled to a temperature in the region of 0° C., of 2.57 g of (1H-indazol-5-yl)sulfonyl chloride in 40 ml of pyridine. Stirring is maintained for 2 hours at a temperature in the region of 0° C. and then for 18 hours at a temperature in the region of 20° C. The medium is concentrated by evaporation under reduced pressure, and the residue obtained is taken up with 50 ml of ethyl acetate and 40 ml of water. The organic phase is washed with 2 times 20 ml of water, dried over magnesium sulfate, filtered and concentrated by evaporation under reduced pressure. The residue obtained is purified by chromatography on a silica column with an ethyl acetate/cyclohexane (1/3 by volume) mixture as eluent. 8 mg of N-(3-fluorophenyl)-(1H-indazol-5-yl)sulfonamide are thus obtained in the form of an orange solid.

$^1$H N.M.R. (300 MHz, $(CD_3)_2SO$ d6 with addition of a few drops of $CD_3COOD$ d4, δ in ppm): 6.79 (ddd, J=9-8 and 2.5 Hz: 1H); from 6.90 to 7.00 (mt: 2H); 7.23 (td, J=8 and 7.5 Hz: 1H); 7.71 (mt: 2H); 8.27 (s: 1H); 8.34 (broad s: 1H).

(1H-Indazol-5-yl)sulfonyl chloride can be obtained in the following way: a solution of 762 mg of sodium nitrite in 1.2 ml of distilled water is added dropwise to a solution, cooled to approximately −5° C., of 1.37 g of 5-amino-1H-indazole in 7 ml of 100% acetic acid and 8 ml of hydrochloric acid (d=1.18), and stirring is maintained for 20 minutes at a temperature in the region of −10° C. The reaction medium is saturated with sulfur dioxide and, while continuing the introduction of sulfur dioxide, a solution of 1 g of copper (II) chloride in 1 ml of distilled water is added. The reaction medium is brought back to a temperature in the region of 20° C. and then warmed at a temperature in the region of 30° C. until sulfur dioxide is no longer being given off. The medium is concentrated by evaporation under reduced pressure. 2.57 g of a solid with a brick-red color are thus obtained, which solid is used at it is in the following step.

EXAMPLE 12

3-Fluoro-N-(3-iodo-1H-indazol-5-yl)benzenesulfonamide

3-Fluoro-N-(3-iodo-1H-indazol-5-yl)benzenesulfonamide can be obtained as described in Example 2 from 230 mg of 5-amino-3-iodo-1H-indazole, 5 ml of pyridine and 173 mg of 3-fluorobenzenesulfonyl chloride. 40 mg of 3-fluoro-N-(3-iodo-1H-indazol-5-yl)benzenesulfonamide are thus obtained in the form of a cream solid melting at 189° C.

$^1$H N.M.R. (300 MHz, $(CD_3)_2SO$ d6, δ in ppm): 7.05 (d, J=2 Hz: 1H); 7.17 (dd, J=9 and 2 Hz: 1H); from 7.40 to 7.70 (mt: 5H); 10.40 (broad unresolved peak: 1H); 13.50 (broad s: 1H).

5-Amino-3-iodo-1H-indazole can be obtained as described in Example 4 from 1 g of 3-iodo-5-nitro-1H-indazole, 20 ml of ethanol, 6.9 g of ferrous sulfate, 10.8 ml of distilled water and 8.2 ml of 32% aqueous ammonia. 230 mg of 5-amino-3-iodo-1H-indazole are thus obtained in the form of a yellow foam (Rf=0.12, silica gel thin layer chromatography, eluent: ethyl acetate/dichloromethane (2/8 by volume)).

3-Iodo-5-nitro-1H-indazole can be obtained as described by U. WRZECIONO et al. in Pharmazie, 34(1), 20 (1979).

EXAMPLE 13

2-Methylsulfonyl-N-(1H-indazol-5-yl)benzenesulfonamide

2-Methylsulfonyl-N-(1H-indazol-5-yl)benzenesulfonamide can be obtained as described in Example 2 from 1 g of 5-amino-1H-indazole, 20 ml of pyridine and 1.91 g of 2-methylsulfonylbenzenesulfonyl chloride. 0.64 g of 2-methylsulfonyl-N-(1H-indazol-5-yl)benzenesulfonamide is thus obtained in the form of a white solid melting at 245° C. (analysis $C_{14}H_{13}N_3O_4S_2$ % calculated C, 47.85; H, 3.73; N, 11.96; O, 18.21; S, 18.25. % found C, 47.42; H, 3.72; N, 11.64; S, 17.97).

EXAMPLE 14

3,4-Dichloro-N-(1H-indazol-5-yl)benzenesulfonamide 3,4-Dichloro-N-(1H-indazol-5-yl)benzenesulfonamide can be obtained as described in Example 2 from 1 g of 5-amino-1H-indazole, 20 ml of pyridine and 1.84 g of 3,4-dichlorobenzenesulfonyl chloride. 0.55 g of 3,4-dichloro-N-(1H-indazol-5-yl)benzenesulfonamide is thus obtained in the form of a green solid melting at 209° C. (analysis $C_{13}H_9Cl_2N_3O_2S$ % calculated C, 45.63; H, 2.65; Cl, 20.72; N, 12.28; O, 9.35; S, 9.37. % found C, 45.87; H, 2.72; Cl, 21.10; N, 12.27; S, 9.21).

EXAMPLE 15

3-Fluoro-N-(1H-indazol-5-yl)benzenesulfonamide

3-Fluoro-N-(1H-indazol-5-yl)benzenesulfonamide can be obtained as described in Example 1 from 0.4 g of 5-amino-1H-indazole, 20 ml of tetrahydrofuran, 0.83 ml of triethylamine and 0.88 g of 3-fluorobenzenesulfonyl chloride. 0.32 g of 3-fluoro-N-(1H-indazol-5-yl)-benzenesulfonamide is thus obtained in the form of a cream solid.

$^1$H N.M.R. (300 MHz, $(CD_3)_2SO$ d6, δ in ppm): 7.08 (dd, J=9 and 2 Hz: 1H); from 7.40 to 7.70 (mt: 6H); 8.02 (s: 1H); 10.20 (broad s: 1H); 13.06 (broad s: 1H).

EXAMPLE 16

3-Fluoro-N-(3-hydroxy-1H-indazol-5-yl)benzenesulfonamide

3-Fluoro-N-(3-hydroxy-1H-indazol-5-yl)benzenesulfonamide can be obtained as described in Example 2 from 51 mg of 5-amino-3-hydroxy-1H-indazole, 1.5 ml of pyridine and 69 mg of 3-fluorobenzenesulfonyl chloride. 6 mg of 3-fluoro-N-(3-hydroxy-1H-indazol-5-yl)benzenesulfonamide are thus obtained in the form of a white solid.

$^1$H N.M.R. (300 MHz, $(CD_3)_2SO$ d6, δ in ppm): 7.03 (dd, J=9 and 2 Hz: 1H); 7.19 (d, J=9 Hz: 1H); 7.30 (d, J=2 Hz: 1H); from 7.40 to 7.70 (mt: 4H); 10.07 (unresolved peak: 1H); 10.50 (very broad unresolved peak: 1H); 11.43 (very broad unresolved peak: 1H).

5-Amino-3-hydroxy-1H-indazole can be prepared as described in Example 4 from 360 mg of 3-hydroxy-5-nitro-1H-indazole, 20 ml of ethanol, 4.25 g of ferrous sulfate, 5 ml of 32% aqueous ammonia and 6.7 ml of distilled water. 40 mg of 5-amino-3-hydroxy-1H-indazole are thus obtained in the form of a greenish paste used as it is in the following step.

EXAMPLE 17

1H-Indazoly-5-yl 3-fluorobenzenesulfonate

1H-Indazol-5-yl 3-fluorobenzenesulfonate can be obtained in the following way: a suspension of 193 mg of 1-acetyl-1H-indazol-5yl 3-fluorobenzenesulfonate and of 0.19 ml of hydrochloric acid (d=1.18) in 1.65 ml of distilled water is brought to reflux for 16 hours. After returning to a temperature in the region of 20° C., the reaction medium is basified to a pH in the region of 8 with a saturated aqueous sodium hydrogencarbonate solution and extracted with two times 10 ml of dichloromethane. The pooled organic extracts are dried over calcium chloride, filtered and concentrated by evaporation under reduced pressure. The translucent oil obtained is taken up with 2 ml of diisopropyl ether and concentrated by trituration. The solid obtained is separated by filtration, washed with two times 1 ml of diisopropyl ether and dried under reduced pressure. 100 mg of 1H-indazol-5-yl 3-fluorobenzenesulfonate are thus obtained in the form of a whitish solid melting at 104° C. (analysis $C_{13}H_9FN_2O_3S$, % calculated C, 53.42; H, 3.10; F, 6.50; N, 9.58; O, 16.42; S, 10.97. % found C, 53.5; H, 2.9; F, 6.2; N, 9.6).

1-Acetyl-1H-indazol-5-yl 3-fluorobenzenesulfonate can be obtained in the following way: a solution de 0.15 g of 3-fluorobenzenesulfonyl chloride in 2 ml of tetrahydrofuran is run in dropwise into a solution, cooled to a temperature in the region of 0° C., of 132 mg of 1-acetyl-5-hydroxy-1H-indazole in 5 ml of anhydrous tetrahydrofuran and of 0.2 ml of triethylamine. The reaction medium is maintained with stirring for 3 hours at a temperature in the region of 0° C. and is then brought back to a temperature in the region of 20° C., hydrolyzed with 15 ml of distilled water and extracted with three times 15 ml of ethyl acetate. The pooled organic extracts are dried over magnesium sulfate, filtered and concentrated under reduced pressure. A white powder is thus obtained, which powder is resuspended in diisopropyl ether, separated by filtration, washed with diisopropyl ether and dried under reduced pressure. 193 mg of 1-acetyl-1H-indazol-5-yl 3-fluorobenzenesulfonate are thus obtained in the form of a white solid (Rf=0.50, silica gel thin layer chromatography, eluent: cyclohexane/dichloromethane (1/9 by volume)).

1-Acetyl-5-hydroxy-1H-indazole can be obtained in the following way: a suspension of 467 mg of 1-acetyl-5-benzyloxy-1H-indazole, 525 mg of ammonium formate, 1 g of 10% palladium-on-charcoal and 50 ml of acetone is brought to reflux for 3 hours. After returning to a temperature in the region of 20° C., the reaction medium is filtered through a bed of Celite 535. The filtrate is concentrated by evaporation under reduced pressure and the oil obtained is purified by chromatography on a silica column with a dichloromethane/methanol (98/2 by volume) mixture as eluent. 132 mg of 1-acetyl-5-hydroxy-1H-indazole are thus obtained in the form of a white solid (Rf=0.32, silica gel thin layer chromatography, eluent: methanol/dichloromethane (2/98 by volume)).

1-Acetyl-5-benzyloxy-1H-indazole can be obtained in the following way: 0.8 ml of acetic anhydride is run into a solution of 500 mg of 4-benzyloxy-2-methylaniline in 3 ml of toluene and the reaction medium is heated at a temperature in the region of 90° C. for 1 hour. 0.55 ml of tert-butyl nitrite is run in dropwise into this solution at approximately 90° C. Heating is continued for 1 hour 30 minutes and then the reaction medium is cooled to a temperature in the region of 20° C. and concentrated to dryness under reduced pressure. The solid residue is taken up with 5 ml of chloroform and the organic phase is washed with 4 ml of a 5% aqueous potassium carbonate solution, dried over magnesium sulfate, filtered and concentrated by evaporation under reduced pressure. The solid thus obtained is purified by chromatography on a silica column with a dichloromethane/cyclohexane (9/1 by volume) mixture as eluent. 467 mg of 1-acetyl-5-benzyloxy-1H-indazole are thus obtained in the form of a brown powder (Rf=0.54, silica gel thin layer chromatography, eluent: cyclohexane/dichloromethane (1/9 by volume)).

4-Benzyloxy-2-methylaniline can be prepared as described by T. GRAYBILL et al. in Bioorg. Med. Chem. Left., 5(4), 387 (1995).

EXAMPLE 18

N-Phenyl-5-(2-methylsulfonylbenzenesulfonylamino)-1H-indazole-3-carboxamide

N-Phenyl-5-(2-methylsulfonylbenzenesulfonylamino)-1H-indazole-3-carboxamide can be obtained as described in Example 2 from 40 mg of N-phenyl-5-amino-1H-indazole-3-carboxamide, 4 ml of pyridine and 40 mg of 2-methylsulfonylbenzenesulfonyl chloride. 50 mg of N-phenyl-5-(2-methylsulfonylbenzenesulfonylamino)-1H-indazole-3-carboxamide are thus obtained in the form of a pale yellow solid melting at 258° C. (analysis $C_{21}H_{18}N_4O_5S_2.0.48H_2O$, % calculated C, 53.61; H, 3.86; N, 11.91; O, 17.00; S, 13.63. % found C, 53.17; H, 3.48; N, 11.58; S, 14.08).

N-Phenyl-5-amino-1H-indazole-3-carboxamide can be prepared in the following way: 1.18 g of 0-(7-azabenzotriazol-1-yl)-N,N,N',N'-tetramethyluronium hexafluorophosphate, 1.1 ml of diisopropylethylamine and 0.28 ml of aniline are added to a solution of 0.5 g of 5-amino-1H-indazole-3-carboxylic acid in 24 ml of dimethylformamide. The medium is maintained with stirring at a temperature in the region of 20° C. for 18 hours. 100 ml of distilled water are added to the reaction medium, which is extracted with 100 ml and 50 ml of ethyl acetate. The pooled organic phases are dried over magnesium sulfate, filtered and concentrated by evaporation under reduced pressure. The residue thus obtained is purified by chromatography on a silica column with a dichloromethane/methanol (99/1 by volume) mixture as eluent. 40 mg of N-phenyl-5-amino-1H-indazole-3-carboxamide are thus obtained in the form of a green solid melting at 242° C.

5-Amino-1H-indazole-3-carboxylic acid can be prepared as described by G. BISTOCCHI et al. in Farmaco., 36(5), 315 (1981).

EXAMPLE 19

N-Methyl-5-(3-fluorobenzenesulfonylamino)-1H-indazole-3-carboxamide

N-Methyl-5-(3-fluorobenzenesulfonylamino)-1H-indazole-3-carboxamide can be obtained as described in Example 2 from 40 mg of N-methyl-5-amino-1H-indazole-3-carboxamide, 1.2 ml of pyridine and 40 mg of 3-fluorobenzenesulfonyl chloride. 20 mg of N-methyl-5-(3-fluorobenzenesulfonylamino)-1H-indazole-3-carboxamide are thus obtained in the form of an off-white solid melting above 260° C. (Analysis $C_{15}H_{13}N_4O_3S.0.74H_2O$ % calculated C, 51.72; H, 3.76; F, 5.45; N, 16.08; O, 13.78; S, 9.20. % found C, 51.74; H, 3.31; N, 15.71; S, 8.36).

N-Methyl-5-amino-1H-indazole-3-carboxamide can be prepared as in Example 18 from 0.5 g of 5-amino-1H-indazole-3-carboxylic acid, 24 ml of dimethylformamide, 1.18 g of 0-(7-azabenzotriazole-1-yl)-N,N,N',N'-tetramethyluronium hexafluorophosphate, 1.6 ml of diisopropylethylamine and 0.2 g of methylamine monohydrochloride. 60 mg of N-methyl-5-amino-1H-indazole-3-carboxamide are thus obtained in the form of a brown solid melting at 173° C.

EXAMPLE 20

5-(2-Methylsulfonylbenzenesulfonylamino)-1H-indazole-3-carboxamide and sodium 5-(2-methylsulfonylbenzenesulfonylamino)-1H-indazole-3-carboxylate 5-(2-Methylsulfonylbenzenesulfonylamino)-1H-indazole-3-carboxamide can be obtained in the following way: a solution of 6 ml of 10% sodium hydroxide and of 0.23 g of N-(3-cyano-1H-indazol-5-yl)-2-methylsulfonylbenzenesulfonamide is heated for 3 hours at a temperature in the region of 100° C. Ice is added to the reaction medium, which is acidified at approximately 5° C. with a 2N hydrochloric acid solution, to a pH of approximately 3, and is then extracted with 2 times 50 ml of ethyl acetate. The pooled organic phases are filtered, dried over magnesium sulfate, filtered again and concentrated by evaporation under reduced pressure. The residue thus obtained is purified by chromatography on a silica column with a dichloromethane/methanol (97.5/2.5 by volume) mixture as eluent. A first crop of 200 mg of yellow crystals is obtained, which crystals, taken up with 5 ml of diisopropyl ether, give, after filtration through a sintered glass funnel, washing with 2×2 ml of diisopropyl ether and drying at 50° C. under reduced pressure, 100 mg of 5-(2-methylsulfonylbenzenesulfonylamino)-1H-indazole-3-carboxamide in the form of a yellow solid melting above 260° C. (analysis $C_{15}H_{14}N_4O_5S_2.0.52H_2O$, % calculated C, 45.68; H, 3.58; N, 14.20; O, 20.28; S, 16.26. % found C, 45.67; H, 3.39; N, 13.79; S, 16.06).

On continuing the chromatography with a dichloromethane/methanol (9/1 by volume) mixture as eluent, a second crop of 100 mg of white crystals is obtained, which crystals, taken up in a mixture of methanol (5 ml) and dichloromethane (2.5 ml) at reflux, filtered through a sintered glass funnel, washed with 2×2.5 ml of methanol and dried at 50° C. under reduced pressure, result in 30 mg of sodium 5-(2-methylsulfonylbenzenesulfonylamino)-1H-indazole-3-carboxylate in the form of an off-white solid melting above 260° C. (analysis $C_{15}H_{12}N_3NaO_6S_2.0.36MeOH$, % calculated C, 43.16; H, 2.90; N, 10.07; Na, 5.51; O, 23.00; S, 15.36. % found C, 40.80; H, 2.30; N, 9.39; S, 15.41).

EXAMPLE 21

5-(3-Fluorobenzenesulfonylamino)-1H-indazole-3-carboxamide and 5-(3-fluorobenzenesulfonylamino)-1H-indazole-3-carboxylic acid 5-(3-Fluorobenzenesulfonylamino)-1H-indazole-3-carboxamide can be obtained as in Example 20 from 6 ml of 10% sodium hydroxide and 0.4 g of N-(3-cyano-1H-indazol-5-yl)-3-fluorobenzenesulfonamide. 0.2 g of 5-(3-fluorobenzenesulfonylamino)-1H-indazole-3-carboxamide is thus obtained in the form of a yellow solid melting at 272° C. (analysis $C_{14}H_{11}FN_4O_3S.0.23H_2O.0.48CH_3CO_2C_2H_5$ % calculated C, 50.29; H, 3.32; F, 5.68; N, 16.76; O, 14.36; S, 9.59. % found C, 50.42; H, 3.25; F, 5.57; N, 16.31; S, 9.14).

0.21 g of 5-(3-fluorobenzenesulfonylamino)-1H-indazole-3-carboxylic acid is also obtained in the form of a white solid melting above 260° C. (analysis C14H10FN3O4S, 0.71 CH2Cl2 % calculated C, 50.14; H, 3.01; F, 5.67; N, 12.53; O, 19.96; S, 9.56. % found C, 50.13; H, 2.66; F, 4.85; N, 12.96; S, 9.65).

EXAMPLE 22

N-Phenyl-5-(3-fluorobenzenesulfonylamino)-1H-indazole-3-carboxamide

N-Phenyl-5-(3-fluorobenzenesulfonylamino)-1H-indazole-3-carboxamide can be obtained as described in Example 18 from 0.45 g of 5-(3-fluorobenzenesulfonylamino)-1H-indazole-3-carboxylic acid, 11 ml of dimethylformamide, 0.56 g of 0-(7-azabenzotriazol-1-yl)-N,N,N',N'-tetramethyluronium hexafluorophosphate, 0.38 g of diisopropylethylamine and 0.14 g of aniline. 70 mg of N-phenyl-5-(3-fluorobenzenesulfonylamino)-1H-indazole-3-carboxamide are thus obtained in the form of a brown solid melting above 260° C. (Analysis: $C_{20}H_{15}FN_4O_3S.0.73H_2O$ % calculated C, 58.54; H, 3.68; F, 4.63; N, 13.65; O, 11.69; S, 7.81. % found C, 58.09; H, 3.18; N, 13.58; S, 7.43).

EXAMPLE 23

N-[5-(3-Fluorobenzenesulfonylamino)-1H-indazol-3-yl]-benzamide

N-[5-(3-Fluorobenzenesulfonylamino)-1H-indazol-3-yl] benzamide can be obtained as described in Example 2 from 0.45 g of N-(5-amino-1H-indazol-3-yl)benzamide, 10 ml of pyridine and 0.35 g of 3-fluorobenzenesulfonyl chloride. 0.6 g of N-[5-(3-fluorobenzenesulfonylamino)-1H-indazol-3-yl]-benzamide is thus obtained in the form of a white solid melting at 225° C. (analysis $C_{20}H_{15}FN_4O_3S$, % calculated C, 58.53; H, 3.68; F, 4.63; N, 13.65; O, 11.69; S, 7.81. % found C, 58.38; H, 3.42; N, 13.56; S, 7.44).

$^1$H N.M.R. (300 MHz, $(CD_3)_2SO$ d6, δ in ppm): 7.10 (dd, J=9 and 2 Hz: 1H); 7.39 (d, J=9 Hz: 1H); from 7.40 to 7.70 (mt: 7H); 7.42 (broad s: 1H); 8.07 (broad d, J=7.5 Hz: 2H); 10.20 (broad unresolved peak: 1H); 10.72 (broad s: 1H); 12.77 (broad s: 1H).

N-(5-Amino-1H-indazol-3-yl)benzamide can be obtained as described in Example 4 from 0.6 g of N-(5-nitro-1H-indazol-3-yl)benzamide, 21 ml of ethanol, 4.2 g of ferrous sulfate, 6.6 ml of water and 5.1 ml of 32% aqueous ammonia. 0.4 g of N-(5-amino-1H-indazol-3-yl)benzamide is thus obtained in the form of a yellow powder melting at 116° C.

N-(5-Nitro-1H-indazol-3-yl)benzamide can be obtained in the following way: 0.39 ml of benzoyl chloride is added dropwise to a solution, cooled to 0° C., of 0.6 g of 3-amino-5-nitro-1H-indazole and of 5 ml of pyridine. The medium is brought back to a temperature in the region of 20° C. and maintained with stirring for 18 hours. After addition of 20 ml of distilled water, the medium is extracted with 20 ml and 10 ml of ethyl acetate. The organic phases are pooled, dried over magnesium sulfate, filtered and concentrated by evaporation under reduced pressure. The residue thus obtained is purified by chromatography on a silica column with a dichloromethane/methanol (99/1 by volume) mixture as eluent. 0.9 g of N-(5-nitro-1H-indazol-3-yl)benzamide is thus obtained in the form of an orange solid melting at 231° C.

EXAMPLE 24

N-(1H-Indazol-5-yl)benzenesulfonamide

N-(1H-Indazol-5-yl)benzenesulfonamide can be obtained as described in Example 1 from 0.5 g of 5-amino-1H-indazole, 25 ml of tetrahydrofuran, 1.05 ml of triethylamine and 0.73 g of benzenesulfonyl chloride. 0.6 g of N-(1H-indazol-5-yl)benzenesulfonamide is thus obtained in the form of a cream solid melting at 179° C. (analysis $C_{13}H_{11}N_3O_2S$ % calculated C, 57.13; H, 4.06; N, 15.37; O, 11.71; S, 11.73. % found C, 56.90; H, 4.24; N, 14.21; S, 10.67).

EXAMPLE 25

3,4-Dichloro-N-(3-methyl-1H-indazol-5-yl)benzenesulfonamide 3,4-Dichloro-N-(3-methyl-1H-indazol-5-yl)benzenesulfonamide can be obtained as described in Example 6 from 0.8 g of N-(N-tert-butoxycarbonyl-3-methyl-1H-indazol-5-yl)-3,4-dichlorobenzenesulfonamide, 7.1 ml of chloroform and 0.25 ml of iodotrimethylsilane. 0.5 g of 3,4-dichloro-N-(3-methyl-1H-indazol-5-yl)benzenesulfonamide is thus obtained in the form of a white solid melting at 184° C. (analysis: $C_{14}H_{11}Cl_2N_3O_2S.0.04CH_2Cl_2$ % calculated, C, 47.21; H, 3.11; Cl, 19.90; N, 11.80; O, 8.98; S, 9.00. % found C, 47.65; H, 2.56; Cl, 19.97; N, 11.89; S, 8.92).

N-(N-tert-Butoxycarbonyl-3-methyl-1H-indazol-5-yl)-3,4-dichlorobenzenesulfonamide can be obtained as described in Example 1 from 1 g of 5-amino-N-tert-butoxycarbonyl-3-methyl-1H-indazole, 50 ml of tetrahydrofuran, 1.15 ml of triethylamine and 1.1 g of 3,4-dichlorobenzenesulfonyl chloride. 0.8 g of N-(N-tert-butoxycarbonyl-3-methyl-1H-indazol-5-yl)-3,4-dichlorobenzenesulfonamide is thus obtained in the form of a white solid melting at 171° C.

EXAMPLE 26

N-(3-Amino-1H-indazol-5-yl)-3-fluorobenzenesulfonamide

N-(3-Amino-1H-indazol-5-yl)-3-fluorobenzenesulfonamide can be obtained in the following way: a solution of 0.3 g of N-[5-(3-fluorobenzenesulfonylamino)-1H-indazol-3-yl] benzamide, of 24 ml of ethanol and of 1.08 ml of 37% hydrochloric acid is heated at a temperature in the region of 100° C. for 30 hours. The cooled reaction medium is concentrated under reduced pressure. 20 ml of water, and aqueous sodium hydroxide, to a pH in the region of 11, are added to the residue thus obtained, which is then extracted with three times 25 ml of ethyl acetate. The pooled organic phases are filtered, dried over magnesium sulfate, filtered again and concentrated by evaporation under reduced pressure. The residue thus obtained is purified by chromatography on a silica column with a dichloromethane/methanol (99/1 by volume) mixture as eluent. The solid thus obtained is recrystallized from 5 ml of isopropanol. 0.1 g of N-(3-amino-1H-indazol-5-yl)-3-fluorobenzenesulfonamide is thus obtained, after drying under reduced pressure at 60° C., in the form of a white solid melting at 216° C. (analysis $C_{13}H_{11}FN_4O_2S$ % calculated C, 50.97; H, 3.62; F, 6.20; N, 18.29; O, 10.45; S, 10.47. % found C, 50.80; H, 3.72; N, 18.14; S, 10.21).

EXAMPLE 27

3-Fluoro-N-(3-methylsulfonylamino-1H-indazol-5-yl)-benzenesulfonamide

3-Fluoro-N-(3-methylsulfonylamino-1H-indazol-5-yl) benzenesulfonamide can be obtained as described in Example 2 from 0.1 g of 5-amino-3-methylsulfonylamino-1H-indazole, 5 ml of pyridine and 83 mg of 3-fluorobenzenesulfonyl chloride. 30 mg of 3-fluoro-N-(3-methylsulfonylamino-1H-indazol-5-yl)benzenesulfonamide are thus obtained in the form of a beige solid melting at 230° C. (analysis $C_{14}H_{13}FN_4O_4S_2.0.57H_2O$ % calculated C, 43.75; H, 3.41; F, 4.94; N, 14.57; O, 16.65; S, 16.68. % found C, 43.75; H, 2.86; N, 14.77; S, 15.93).

5-Amino-3-methylsulfonylamino-1H-indazole can be obtained as described in Example 4 from 256 mg of 3-methylsulfonylamino-5-nitro-1H-indazole, 10 ml of ethanol, 2 g of ferrous sulfate, 3.2 ml of water and 2.4 ml of 32% aqueous ammonia. 0.1 g of 5-amino-3-methylsulfonylamino-1H-indazole is thus obtained in the form of an oil used as it is in the following step.

3-Methylsulfonylamino-5-nitro-1H-indazole can be obtained as described in Example 2 from 0.7 g of 3-amino- 5-nitro-1H-indazole, 23 ml of pyridine and 0.455 g of methylsulfonyl chloride. 0.85 g of 3-methylsulfonylamino-5-nitro-1H-indazole is thus obtained in the form of an orange powder used as it is in the following step.

3-Amino-5-nitro-1H-indazole can be prepared as described by E. PARNELL in Journal of Chemical Society, 2363 (1959).

EXAMPLE 28

N-[5-(3-Fluorobenzenesulfonylamino)-1H-indazol-3-yl)-acetamide

N-[5-(3-Fluorobenzenesulfonylamino)-1H-indazol-3-yl) acetamide can be obtained in the following way: 0.037 ml of acetyl chloride is added dropwise to a solution, cooled to 0° C., of 0.16 g of 3-fluoro-N-(3-amino-1H-indazol-5-yl)benzenesulfonamide and of 3.2 ml of pyridine. The reaction medium is then maintained with stirring at a temperature in the region of 25° C. overnight. After addition of 20 ml of water, the medium is extracted with three times 10 ml of ethyl acetate. The pooled organic phases are dried over magnesium sulfate, filtered and concentrated by evaporation under reduced pressure. The residue thus obtained is purified by chromatography on a silica column with a dichloromethane/methanol (97.5/2.5 by volume) mixture as eluent. The solid obtained is recrystallized from 6 ml of isopropanol. 0.1 g of N-[5-(3-fluorobenzenesulfonylamino)-1H-indazol-3-yl)acetamide is thus obtained, after drying under reduced pressure at 60° C., in the form of a white solid melting at 246° C. (analysis $C_{15}H_{13}FN_4O_3S.0.2H_2O$ % calculated C, 51.73; H, 3.76; F, 5.45; N, 16.08; O, 13.78; S, 9.20. % found C, 51.75; H, 2.82; F, 5.07; N, 16.04; S, 8.13).

EXAMPLE 29

N-Cyclohexyl-5-(2-methylsulfonylbenzenesulfonylamino)-1H-indazole-3-carboxamide

N-Cyclohexyl-5-(2-methylsulfonylbenzenesulfonylamino)-1H-indazole-3-carboxamide can be prepared as described in Example 2 from 0.25 g of 5-amino-N-cyclohexyl-1H-indazole-3-carboxamide, 5 ml of pyridine and 246 mg of 2-methylsulfonylbenzenesulfonyl chloride. 38 mg of N-cyclohexyl-5-(2-methylsulfonylbenzenesulfonylamino)-1H-indazole-3-carboxamide are thus obtained in the form of an off-white solid melting at a temperature above 260° C. (analysis $C_{21}H_{24}N_4O_5S_2$ % calculated C, 52.93; H, 5.08; N, 11.76; O, 16.79; S, 13.46. % found C, 52.62; H, 5.05; N, 11.19; S, 12.44).

5-Amino-N-cyclohexyl-1H-indazole-3-carboxamide can be obtained in the following way: a suspension of 1.57 g of N-cyclohexyl-5-nitro-1H-indazole-3-carboxamide, of 80 ml of methanol, of 1.37 g of ammonium formate and of 0.314 g of palladium hydroxide is brought to reflux for two hours. The reaction medium is then brought back to a temperature in the region of 25° C. and filtered through Celite® through a sintered glass funnel. The solid obtained is washed with methanol and the filtrate is concentrated by evaporation under reduced pressure. The oil thus obtained is taken up with 80 ml of dichloromethane and 80 ml of water. The organic phase is washed with two times 60 ml of distilled water and the aqueous phases thus obtained are extracted with 80 ml of dichloromethane. The pooled organic phases are dried over magnesium sulfate, filtered and concentrated by evaporation under reduced pressure. 1.17 g of 5-amino-N-cyclohexyl-1H-indazole-3-carboxamide are thus obtained in the form of a pale pink solid (Rf=0.40, silica gel thin layer chromatography, eluent: dichloromethane/methanol (9/1 by volume)).

N-Cyclohexyl-5-nitro-1H-indazole-3-carboxamide can be obtained in the following way: a solution of 2.5 g of 5-nitro-1H-indazole-3-carboxylic acid, of 150 ml of dichloromethane, of 75 ml of dimethylformamide, 0.16 g of 1-hydroxybenzotriazole and of 2.75 g 1-ethyl-3-[3-(dimethylamino)propyl]carbodiimide hydrochloride is stirred for 15 minutes at a temperature of 25° C. 1.7 ml of cyclohexylamine and 1.7 ml of triethylamine are then added. The reaction medium is maintained with stirring for 70 hours and concentrated by evaporation under reduced pressure. The residue thus obtained is taken up with 50 ml of dichloromethane and 50 ml of diisopropyl ethyl. After filtration, the paste obtained is taken up with 80 ml of distilled water and the solid form is filtered through a sintered glass funnel, washed with two times 50 ml of water and then dried under reduced pressure. The resulting solid is taken up with 50 ml of ethyl acetate, filtered through a sintered glass filter, washed with two times 25 ml of ethyl acetate and dried at 50° C. under reduced pressure. 1.57 g of N-cyclohexyl-5-nitro-1H-indazole-3-carboxamide are thus obtained in the form of a beige solid (Rf=0.90, silica gel thin layer chromatography, eluent: chloroform/methanol/20% aqueous ammonia (12/3/0.5 by volume)).

5-Nitro-1H-indazole-3-carboxylic acid can be prepared as described by G. BISTOCCHI and et. al., in Farmaco, 36(5), 315 (1981).

EXAMPLE 30

N-[3-(4-Chlorophenyl)-1H-indazol-5-yl]-2-methylsulfonylbenzenesulfonamide

N-[3-(4-Chlorophenyl)-1H-indazol-5-yl]-2-methylsulfonylbenzenesulfonamide can be obtained in the following way: a solution of 0.515 g 2-methylsulfonylbenzenesulfonyl chloride in 3 ml of tetrahydrofuran is added dropwise to a solution, cooled to 0° C., of 0.45 g of 5-amino-3-(4-chlorophenyl)-1H-indazole, of 15 ml of tetrahydrofuran and of 0.165 ml of pyridine. After reacting for 30 minutes at a temperature in the region of 0° C. and 2 hours at a temperature in the region of 20° C., 50 ml of distilled water are added to the reaction medium. The medium is extracted with 30 ml of ethyl acetate. The organic phase is then washed with 3 times 20 ml of distilled water and the aqueous phase is extracted again with 30 ml of ethyl acetate. The organic phases are pooled, dried over magnesium sulfate, filtered and concentrated to dryness by evaporation under reduced pressure. The residue thus obtained is purified by chromatography on a silica column with a dichloromethane/ethyl acetate (99/1 by volume) mixture as eluent. 0.79 g of N-[3-(4-chlorophenyl)-1H-indazol-5-yl]-2-methylsulfonylbenzenesulfonamide is thus obtained in the form of a white powder melting at 242° C. (analysis $C_{20}H_{16}ClN_3O_4S_2.0.65CH_3OH$ % calculated C, 52.01; H, 3.49; Cl, 7.67; N, 9.10; O, 13.85; S, 13.88. % found C, 52.02; H, 3.78; Cl, 7.91; N, 9.21; S, 13.45).

5-Amino-3-(4-chlorophenyl)-1H-indazole can be prepared as described in Example 4 from 1 g of 3-(4-chlorophenyl)-5-nitro-1H-indazole, 15 ml of ethanol, 13.5 g of ferrous sulfate, 13 ml of distilled water and 10 ml of 32% aqueous ammonia. 0.45 g of 5-amino-3-(4-chlorophenyl)-1H-indazole is thus obtained in the form of a salmon-pink powder melting at 163° C.

3-(4-Chlorophenyl)-5-nitro-1H-indazole can be prepared in the following way: a solution of 5.9 g of 2,4'-dichloro-5-nitrobenzophenone, of 4.8 ml of hydrazine hydrate and of 140 ml of ethanol is brought to reflux for 20 hours. The reaction medium is then brought back to a temperature in the region of 20° C. and the precipitate formed is filtered through a sintered glass funnel and washed with diisopropyl ether. The powder thus obtained is purified by chromatography on a silica column with dichloromethane as eluent. 3.5 g of 3-(4-chlorophenyl)-5-nitro-1H-indazole are thus obtained in the form of a yellow powder melting at 212° C.

2,4'-Dichloro-5-nitrobenzophenone can be obtained as described by F. D. BELLAMY et. al., in J. Med. Chem., 1991, 34(5), 1545.

EXAMPLE 31

N-[3-(4-Methoxyphenyl)-1H-indazol-5-yl]benzenesulfonamide

N-[3-(4-Methoxyphenyl)-1H-indazol-5-yl]benzenesulfonamide can be prepared as in Example 2 from 3.47 g of 5-amino-3-(4-methoxyphenyl)-1H-indazole, 1.29 ml of pyridine and 2.03 ml of benzenesulfonyl chloride. 1.7 g of N-[3-(4-methoxyphenyl)-1H-indazol-5-yl]benzenesulfonamide are thus obtained in the form of a white solid melting at 172° C. (analysis $C_{20}H_{17}N_3O_3S.0.2CH_2Cl_2$ % calculated C, 63.31; H, 4.52; N, 11.07; O, 12.65; S, 8.45. % found C, 62.90; H, 4.40; N, 11.00; S, 8.02).

5-Amino-3-(4-methoxyphenyl)-1H-indazole can be prepared as described in patent WO 0210137.

EXAMPLE 32

N-[3-(4-Methoxyphenyl)-1H-indazol-5-yl]-2-methylsulfonylbenzenesulfonamide

N-[3-(4-Methoxyphenyl)-1H-indazol-5-yl]-2-methylbenzenesulfonamide can be prepared as in Example 2 from 2.3 g of 5-amino-3-(4-methoxyphenyl)-1H-indazole, 0.94 ml of pyridine, 50 ml of tetrahydrofuran and 2.93 g of 2-methylsulfonylbenzenesulfonyl chloride. 1.62 g of N-[3-(4-methoxyphenyl)-1H-indazol-5-yl]-2-methylsulfonylbenzenesulfonamide are thus obtained in the form of a pale yellow solid melting at 244° C. (analysis $C_{21}H_{19}N_3O_5S_2$% calculated C, 55.13; H, 4.19; N, 9.18; O, 17.48; S, 14.02. % found C, 54.71; H, 4.19; N, 9.18; S, 13.87).

EXAMPLE 33

N-[3-(4-Fluorophenyl)-1H-indazol-5-yl]-2-methylsulfonylbenzenesulfonamide

N-[3-(4-Fluorophenyl)-1H-indazol-5-yl]-2-methylbenzenesulfonamide can be prepared as in Example 2 from 0.7 g of 5-amino-3-(4-fluorophenyl)-1H-indazole, 0.27 ml of pyridine, 18 ml of tetrahydrofuran and 866 mg of 2-methylsulfonylbenzenesulfonyl chloride. 0.54 g of N-[3-(4-fluorophenyl)-1H-indazol-5-yl]-2-methylsulfonylbenzenesulfonamide is thus obtained in the form of a pink solid melting at 209° C. (analysis $C_{20}H_{16}FN_3O_4S_2.0.62CH_2Cl_2$% calculated C, 53.93; H, 3.62; F, 4.26; N, 9.43; O, 14.37; S, 14.39. % found C, 53.93; H, 3.65; N, 9.44; S, 14.39).

5-Amino-3-(4-fluorophenyl)-1H-indazole can be prepared as described in patent WO 0210137.

EXAMPLE 34

N-[3-(4-Hydroxyphenyl)-1H-indazol-5-yl]benzenesulfonamide

N-[3-(4-Hydroxyphenyl)-1H-indazol-5-yl]benzenesulfonamide can be prepared in the following way: 6.56 ml of boron tribromide are added to a suspension, cooled to −60° C., of 0.8 g of N-[3-(4-methoxyphenyl)-1H-indazol-5-yl]benzenesulfonamide and of 150 ml of dichloromethane. The reaction mixture is then stirred at a temperature in the region of −60° C. for one hour, and then overnight at a temperature in the region of 25° C. The solution thus obtained is poured into 300 ml of an aqueous sodium hydrogencarbonate solution. The organic phase is washed with three times 200 ml of distilled water. The organic phases are pooled, dried over magnesium sulfate, filtered and concentrated to dryness by evaporation under reduced pressure. The residue thus obtained is purified by chromatography on a silica column with a dichloromethane/ethyl acetate (6/4 by volume) mixture as eluent. 20 mg of N-[3-(4-hydroxyphenyl)-1H-indazol-5-yl]benzenesulfonamide are thus obtained in the form of a white solid which decomposes at 190° C.

$^1$H N.M.R. (400 MHz, $(CD_3)_2SO$ d6, δ in ppm): 6.91 (d, J=8.5 Hz: 2H); 7.11 (dd, J=9 and 1.5 Hz: 1H); 7.43 (d, J=9 Hz: 1H); from 7.50 to 7.70 (mt: 6H); 7.72 (d, J=8.5 Hz: 2H); 9.64 (s: 1H); 10.05 (unresolved peak: 1H); 13.01 (broad s: 1H).

EXAMPLE 35

N-[3-(4-Hydroxyphenyl)-1H-indazol-5-yl]-2-methylsulfonylbenzenesulfonamide

N-[3-(4-Hydroxyphenyl)-1H-indazol-5-yl]-2-methylsulfonylbenzenesulfonamide can be prepared as described in Example 34 from 2 g of N-[3-(4-methoxyphenyl)-1H-indazol-5-yl]-2-methylsulfonylbenzenesulfonamide, 1 l of dichloromethane and 21 ml of boron tribromide. 395 mg of N-[3-(4-hydroxyphenyl)-1H-indazol-5-yl]-2-methylsulfonylbenzenesulfonamide are thus obtained in the form of a white solid which decomposes at 150° C. (analysis $C_{20}H_{17}N_3O_5S_2.0.26CH_2Cl_2$ % calculated C, 54.17H, 3.86; N, 9.47; O, 18.04; S, 14.46. % found C, 54.20; H, 3.76; N, 9.47; S, 14.26).

EXAMPLE 36

N-(3-Benzylamino-1H-indazol-5-yl)-2-methylsulfonylbenzenesulfonamide

N-(3-Benzylamino-1H-indazol-5-yl)-2-methylsulfonylbenzenesulfonamide can be prepared as in Example 2 from 0.12 g of 5-amino-3-benzylamino-1H-indazole, 10 ml of pyridine and 0.13 g of 2-methylsulfonylbenzenesulfonyl chloride. 0.1 g of N-(3-benzylamino-1H-indazol-5-yl)-2-methylsulfonylbenzenesulfonamide is thus obtained in the form of a yellow solid melting at 226° C. (analysis $C_{21}H_{20}N_4O_4S_2.0.62CH_2Cl_2$ % calculated C, 55.25; H, 4.42; N, 12.27; O, 14.02; S, 14.05. % found C, 55.35; H, 4.22; N, 12.12; S, 14.10).

5-Amino-3-benzylamino-1H-indazole can be obtained as described in Example 4 from 0.6 g of 3-benzylamino-5-nitro-1H-indazole, 22 ml of ethanol, 4.5 g of ferrous sulfate, 7 ml of water and 5.4 ml of 32% aqueous ammonia. 0.15 g of 5-amino-3-benzylamino-1H-indazole is thus obtained in the form of a brown powder melting at 196° C.

3-Benzylamino-5-nitro-1H-indazole can be prepared in the following way: a solution of 0.5 g of 3-amino-5-nitro-1H-indazole, of 10 ml of methanol, of 0.33 ml of benzaldehyde and of 0.24 g of sodium cyanoborohydride is brought to reflux for 4 hours. 30 ml of distilled water are added to the reaction medium cooled to a temperature in the region of 25° C., which is extracted with 3 times 15 ml of ethyl acetate. The organic phases are pooled, dried over magnesium sulfate, filtered and concentrated by evaporation under reduced pressure. The residue thus obtained is dissolved in 25 ml of methanol and 0.24 g of sodium cyanoborohydride are added. The pH of this solution is adjusted to approximately 2 by adding hydrochloric methanol, and stirred for 24 hours at a temperature in the region of 25° C. The suspension thus obtained is concentrated by evaporation under reduced pressure and 30 ml of water are added to the residue obtained. This aqueous phase is neutralized with 0.5 ml of aqueous ammonia, to pH 10, and extracted with 3 times 25 ml of ethyl acetate. The organic phases are pooled, dried over magnesium sulfate, filtered and concentrated by evaporation under reduced pressure. The residue thus obtained is purified by chromatography on a silica column with a dichloromethane/methanol (99/1 by volume) mixture as eluent. 250 mg of 3-benzylamino-5-nitro-1H-indazole are thus obtained in the form of an orange solid melting at 222° C.

EXAMPLE 37

N-(3-Methylamino-1H-indazol-5-yl)-2-methylsulfonylbenzenesulfonamide

N-(3-Methylamino-1H-indazol-5-yl)-2-methylsulfonylbenzenesulfonamide can be prepared as in Example 2 from 0.21 g of 5-amino-3-methylamino-1H-indazole, 25 ml of pyridine and 0.33 g of 2-methylsulfonylbenzenesulfonyl chloride. 0.3 g of N-(3-methylamino-1H-indazol-5-yl)-2-methylsulfonylbenzenesulfonamide is thus obtained in the form of a cream solid melting at 220° C. (analysis $C_{15}H_{16}N_4O_4S_2$ % calculated C, 47.36; H, 4.24; N, 14.73; O, 16.82; S, 16.86. % found C, 47.58; H, 4.35; N, 14.34; S, 16.52).

5-Amino-3-methylamino-1H-indazole can be obtained as described in Example 4 from 0.5 g of 3-methylamino-5-nitro-1H-indazole, 25 ml of ethanol, 5.2 g of ferrous sulfate, 8 ml of water and 6.2 ml of 32% aqueous ammonia. 0.1 g of 5-amino-3-methylamino-1H-indazole is thus obtained in the form of a cream powder melting at 215° C.

3-Methylamino-5-nitro-1H-indazole can be obtained in the following way: 2.4 ml of formic acid are added dropwise to a solution, cooled to 0° C., of 5 ml of acetic anhydride. The solution is then brought to 50° C. for one hour and then again cooled to −20° C. 3.5 g of 3-amino-5-nitro-1H-indazole in solution in 150 ml of tetrahydrofuran are then added and stirring is maintained at −20° C. for one hour. The reaction medium is concentrated by evaporation under reduced pressure and the residue thus obtained is dissolved in 50 ml of tetrahydrofuran. The solution thus obtained is cooled to 0° C. and 25 ml of borane-dimethyl sulfide complex (2M solution in tetrahydrofuran) are added dropwise. The reaction medium is brought slowly to a temperature in the region of 25° C. and then brought to reflux for 3 hours and again brought to a temperature in the region of 0° C. After addition of 100 ml of methanol, 50 ml of 3M hydrochloric methanol are added dropwise and the mixture is brought to reflux for one hour. The medium is brought to a temperature in the region of 25° C. and concentrated under reduced pressure by evaporation. The residue thus obtained is taken up with 100 ml of water and neutralized to pH 11 by addition of aqueous ammonia, and then extracted with 3 times 100 ml of ethyl acetate. The organic phases are pooled, dried over magnesium sulfate, filtered and concentrated by evaporation under reduced pressure. The residue thus obtained is purified by chromatography on a silica column with a dichloromethane/methanol (99/1 by volume) mixture as eluent. 1.1 g of 3-methylamino-5-nitro-1H-indazole are thus obtained in the form of an orange solid melting at 252° C.

EXAMPLE 38

N-(3-Bromo-1H-indazol-5-yl)-2-methylsulfonylbenzenesulfonamide

N-(3-Bromo-1H-indazol-5-yl)-2-methylsulfonylbenzenesulfonamide can be prepared as in Example 2 from 3.7 g of 5-amino-3-bromo-1H-indazole, 75 ml of pyridine and 4.54 g of 2-methylsulfonylbenzenesulfonyl chloride. 0.88 g of N-(3-bromo-1H-indazol-5-yl)-2-methylsulfonylbenzenesulfonamide is thus obtained in the form of a beige solid melting at a temperature above 260° C. (analysis $C_{14}H_{12}BrN_3O_4S_2$ % calculated C, 39.08; H, 2.81; Br, 18.57; N, 9.77; O, 14.87; S, 14.9. % found C, 39.58; H, 2.87; Br, 18.23; N, 9.38; S, 14.53.

5-Amino-3-bromo-1H-indazole can be prepared as described by M. BENCHIDMI et al., in Journal of Heterocyclic Chemistry, 16(8), 1599 (1979).

EXAMPLE 39

N-(3-Amino-1H-indazol-5-yl)-2-methylsulfonylbenzenesulfonamide

N-(3-Amino-1H-indazol-5-yl)-2-methylsulfonylbenzenesulfonamide can be obtained in the following way: 391 mg of 2-methylsulfonylbenzenesulfonyl chloride are added portionwise to a solution, cooled to −10° C., of 240 mg of 3,5-diamino-1H-indazole, of 2 ml of pyridine and of 3 ml of tetrahydrofuran. The medium is maintained with stirring for two hours at a temperature of −10° C. and then brought back to a temperature in the region of 25° C. After addition of 60 ml of water, aqueous ammonia (32%) and 30 ml of ethyl acetate, and settling out, the aqueous phase is extracted with 3 times 30 ml of ethyl acetate. The organic phases are pooled, dried over magnesium sulfate, filtered and concentrated by evaporation under reduced pressure. The residue thus obtained is purified by chromatography on a silica column with a chloroform/methanol/20% aqueous ammonia (12/3/0.5 by volume) mixture as eluent. 150 mg of a foam are thus obtained, which foam is taken up with 5 ml of ethyl acetate and filtered through a sintered glass funnel. 40 mg of N-(3-amino-1H-indazol-5-yl)-2-methylsulfonylbenzenesulfonamide are thus obtained in the form of a white solid melting at 246° C. (analysis $C_{14}H_{14}N_4O_4S_2.0.21AcOEt$ % calculated C, 45.89; H, 3.85; N, 15.29; O, 17.47; S, 17.50. % found C, 46.00; H, 3.79; N, 15.28; S, 17.68). 3,5-Diamino-1H-indazole can be obtained as described in patent DE1301319.

EXAMPLE 40

N-(3-Amino-1H-indazol-5-yl)-2,6-difluorobenzenesulfonamide

N-(3-Amino-1H-indazol-5-yl)-2,6-difluorobenzenesulfonamide can be obtained as described in Example 39 from 1 g of 3,5-diamino-1H-indazole, 10 ml of pyridine, 10 ml of tetrahydrofuran and 1.4 g of 2,6-difluorobenzenesulfonyl chloride. 179 mg of N-(3-amino-1H-indazol-5-yl)-2,6-difluorobenzenesulfonamide are thus obtained in the form of a gray solid melting at 241° C. (analysis $C_{13}H_{10}F_2N_4O_2S$ % calculated C, 48.15; H, 3.11; F, 11.72; N, 17.28; O, 9.87; S, 9.89. % found C, 47.81; H, 3.18; F, 11.64; N, 17.00; S, 9.67).

EXAMPLE 41

N-(3-Amino-1H-indazol-5-yl)-2,6-dichlorobenzenesulfonamide

N-(3-Amino-1H-indazol-5-yl)-2,6-dichlorobenzenesulfonamide can be obtained as described in Example 39 from 0.8 g of 3,5-diamino-1H-indazole, 8 ml of pyridine, 8 ml of tetrahydrofuran and 1.29 g of 2,6-dichlorobenzenesulfonyl chloride. 350 mg of N-(3-amino-1H-indazol-5-yl)-2,6-dichlorobenzenesulfonamide are thus obtained in the form of a pale yellow solid melting at 250° C. (analysis $C_{13}H_{10}Cl_2N_4O_2S$ % calculated C, 43.71; H, 2.82; Cl, 19.85; N, 15.68; O, 8.96; S, 8.98. % found C, 43.39; H, 2.92; Cl, 19.45; N, 15.31; S, 8.73).

EXAMPLE 42

N-(3-Amino-1H-indazol-5-yl)-3,5-difluorobenzenesulfonamide

N-(3-Amino-1H-indazol-5-yl)-3,5-difluorobenzenesulfonamide can be obtained as described in Example 39 from 2.1 g of 3,5-diamino-1H-indazole, 20 ml of pyridine, 20 ml of tetrahydrofuran and 1.47 g of 3,5-difluorobenzenesulfonyl chloride. 0.727 g of N-(3-amino-1H-indazol-5-yl)-3,5-difluorobenzenesulfonamide is thus obtained in the form of a white solid melting at 232° C. (analysis $C_{13}H_{10}F_2N_4O_2S$ % calculated C, 48.15; H, 3.11; F, 11.72; N, 17.28; O, 9.87; S, 9.89. % found C, 47.95; H, 3.14; F, 11.79; N, 17.06; S, 9.52).

EXAMPLE 43

N-[5-(2-Methylsulfonylbenzenesulfonylamino)-1H-indazol-3-yl)-acetamide

N-[5-(2-Methylsulfonylbenzenesulfonylamino)-1H-indazol-3-yl)-acetamide can be obtained as described in Example 28 from 0.5 g of N-(3-amino-1H-indazol-5-yl)-2-methylsulfonylbenzenesulfonamide, 3 ml of pyridine and 98 μl of acetyl chloride. 338 mg of N-[5-(2-methylsulfonylbenzenesulfonylamino)-1H-indazol-3-yl)-acetamide are thus obtained in the form of a white solid which decomposes at approximately 145° C. (analysis $C_{16}H_{16}N_4O_5S_2$ % calculated C, 47.05; H, 3.95; N, 13.72; O, 19.59; S, 15.7. % found C, 46.96; H, 4.27; N, 13.23; S, 14.91).

EXAMPLE 44

N-[5-(3,5-Difluorobenzenesulfonylamino)-1H-indazol-3-yl]acetamide

N-[5-(3,5-Difluorobenzenesulfonylamino)-1H-indazol-3-yl]acetamide can be obtained as described in Example 28 from 0.1 g of N-(3-amino-1H-indazol-5-yl)-3,5-difluorobenzenesulfonamide, 9 ml of pyridine and 0.024 ml of acetyl chloride. 338 mg of N-[5-(3,5-difluorobenzenesulfonylamino)-1H-indazol-3-yl)-acetamide are thus obtained in the form of a cream solid melting at 268° C.

$^1$H N.M.R. (300 MHz, $(CD_3)_2SO$ d6, δ in ppm): 2.10 (s: 3H); 7.05 (broad dd, J=9 and 2 Hz: 1H); from 7.25 to 7.45 (mt: 3H); 7.54 (broad s: 1H); 7.60 (tt, J=9 and 2.5 Hz: 1H); from 10.10 to 10.40 (broad unresolved peak: 1H); 10.36 (broad s: 1H); 12.67 (broad s: 1H).

EXAMPLE 45

N-[5-(2-Methylsulfonylbenzenesulfonylamino)-1H-indazol-3-yl]benzamide

N-[5-(2-Methylsulfonylbenzenesulfonylamino)-1H-indazol-3-yl]benzamide can be obtained as described in Example 28 from 0.5 g of N-(3-amino-1H-indazol-5-yl)-2-methylsulfonylbenzenesulfonamide, 3 ml of pyridine and 0.158 ml of benzoyl chloride. 435 mg of N-[5-(2-methylsulfonylbenzenesulfonylamino)-1H-indazol-3-yl)benzamide are thus obtained in the form of a pink solid which decomposes at approximately 200° C. (analysis $C_{21}H_{18}N_4O_5S_2.0.22CH_2Cl_2$ % calculated C, 53.60; H, 3.86; N, 11.91; O, 17.00; S, 13.63. % found C, 53.59; H, 3.89; N, 12.10; S, 13.53).

EXAMPLE 46

N-[5-(3,5-Difluorobenzenesulfonylamino)-1H-indazol-3-yl]benzamide

N-[5-(3,5-Difluorobenzenesulfonylamino)-1H-indazol-3-yl]benzamide can be obtained as described in Example 28 from 0.15 g of N-(3-amino-1H-indazol-5-yl)-3,5-difluorobenzenesulfonamide, 13.5 ml of pyridine and 0.06 ml of benzoyl chloride. 30 mg of N-[5-(3,5-difluorobenzenesulfonylamino)-1H-indazol-3-yl)benzamide are thus obtained in the form of a cream solid melting at 246° C. (analysis $C_{20}H_{14}F_2N_4O_3S.1.33H_2O$ % calculated C, 56.08; H, 3.29; F, 8.87; N, 13.08; O, 11.20; S, 7.48. % found C, 56.49; H, 3.38; N, 11.90; S, 6.95).

EXAMPLE 47

N-{2-[5-(3-Fluorobenzenesulfonylamino)-1H-indazol-3-yl]-phenyl}acetamide

N-{2-[5-(3-Fluorobenzenesulfonylamino)-1H-indazol-3-yl]phenyl}acetamide can be prepared in the following way: 1.86 ml of a saturated aqueous sodium hydrogencarbonate solution and 29.7 mg of tetrakis(triphenylphosphine)palladium[0] are successively added to a suspension, maintained under an argon atmosphere, of 528 mg of tert-butyl 3-iodo-5-(N-tert-butoxycarbonyl-3-fluorobenzenesulfonylamino) indazole-1-carboxylate and of 200 mg of 2-(acetylaminophenyl)boronic acid in 15 ml of dimethylformamide, and the mixture is maintained at reflux for 4 hours. After returning to a temperature in the region of 20° C., the reaction medium is concentrated under reduced pressure. The brown foam thus obtained is taken up with a mixture of dichloromethane and methanol and the remaining insoluble material is removed by filtration. The filtrate is concentrated to dryness by evaporation under reduced pressure and the residue thus isolated is purified by chromatography on a silica column with a dichloromethane/ethyl acetate (80/20 by volume) mixture as eluent. After trituration of the foam thus obtained with diisopropyl ether, filtration and drying, 83.4 mg of N-{2-[5-(3-fluorobenzenesulfonylamino)-1H-indazol-3-yl]-phenyl}acetamide hemihydrate are obtained in the form of a white solid melting at 135° C. (analysis $C_{21}H_{17}FN_4O_3S$ $0.5H_2O$ % calculated C, 58.18; H, 4.19; F, 4.38; N, 12.93; O, 12.92; S, 7.40. % found C, 58.26; H, 4.18; F, 4.60; N, 12.90; S, 7.25).

tert-Butyl 3-iodo-5-(N-tert-butoxycarbonyl-3-fluorobenzenesulfonylamino)-indazole-1-carboxylate can be obtained in the following way: 2.45 ml of triethylamine and then 269 mg of 4-(dimethylamino)-pyridine are added to a mixture, under argon, of 3.9 g of 3-fluoro-N-(3-iodo-1H-indazol-5-yl) benzenesulfonamide in 140 ml of dichloromethane. The mixture is cooled to a temperature in the region of 0° C., and then a solution of 4.55 g of di-tert-butyl dicarbonate in 20 ml of dichloromethane is added dropwise over 10 minutes. The reaction mixture is stirred at a temperature in the region of 0° C. for 0.5 hours and then at a temperature in the region of 20° C. for 5 hours. After addition of 40 ml of distilled water and settling out, the organic phase is washed with 2 times 20 ml of distilled water, dried over magnesium sulfate, decolorized with 3S black, filtered and then concentrated to dryness under reduced pressure (2 kPa) at a temperature in the region of 40° C. The evaporation residue is taken up in diisopropyl ether, triturated, filtered through a sintered glass funnel and then partially dried and dried under reduced pressure (3 kPa) at a temperature in the region of 40° C. 3.6 g of tert-butyl 3-iodo-5-(N-tert-butoxycarbonyl-3-fluorobenzenesulfonylamino)indazole-1-carboxylate are thus obtained in the form of a pale yellow solid.

$^1$H N.M.R. (300 MHz, $(CD_3)_2SO$ d6, δ in ppm): 1.29 (s: 9H); 1.69 (s: 9H); 7.61 (d, J=2 Hz: 1H); 7.70 (dd, J=9 and 2 Hz: 1H); from 7.70 to 7.95 (mt: 4H); 8.19 (d, J=9 Hz: 1H).

EXAMPLE 48

N-{2-[5-(2-Methylsulfonylbenzenesulfonylamino)-1H-indazol-3-yl]phenyl}acetamide

N-{2-[5-(2-Methylsulfonylbenzenesulfonylamino)-1H-indazol-3-yl]phenyl}acetamide can be obtained as described in Example 47 from 1.35 g of tert-butyl 3-iodo-5-(N-tert-butoxycarbonyl-2-methylsulfonylbenzenesulfonylamino)-indazole-1-carboxylate, 467 mg of 2-(acetylaminophenyl) boronic acid, 40 ml of dimethylformamide, 4.34 ml of a saturated aqueous sodium hydrogencarbonate solution and of 69 mg of tetrakis (triphenylphosphine)palladium[ ]. 360 mg of N-{2-[5-(2-methylsulfonylbenzenesulfonylamino)-1H-indazol-3-yl]phenyl}acetamide are thus obtained in the form of a white solid melting at 245° C. (analysis $C_{22}H_{20}N_4O_5S_2$ % calculated C, 54.53; H, 4.16; N, 11.56; O, 16.51; S, 13.24. % found C, 54.54; H, 4.15; N, 11.34; S, 13.14).

tert-Butyl 3-iodo-5-(N-tert-butoxycarbonyl-2-methylsulfonylbenzenesulfonylamino)indazole-1-carboxylate can be obtained in the following way: 37 ml of triethylamine and then 3.9 g of 4-(dimethylamino)pyridine are added to a mixture, under argon, of 63.6 g of N-(3-iodo-1H-indazol-5-yl)-2-methylsulfonylbenzenesulfonamide in 1.8 l of dichloromethane. The mixture is cooled to a temperature in the region of 0° C., and then a solution of 69.6 g of di-tert-butyl dicarbonate in 740 ml of dichloromethane is added dropwise over 1 hour. The reaction mixture is stirred at a temperature in the region of 0° C. for 0.5 hours and then at a temperature in the region of 20° C. for 18 hours. After addition of 1 l of water and settling out, the organic phase is washed with 3 times 700 ml of distilled water, dried over magnesium sulfate, filtered and then concentrated to dryness under reduced pressure (2 kPa) at a temperature in the region of 40° C. The residue thus obtained is purified by chromatography on a silica column (particle size 40-63 μm), eluting with a cyclohexane/ethyl acetate (70/30 by volume) mixture. The fractions containing the expected product are pooled and concentrated to dryness under reduced pressure (2 kPa) at a temperature in the region of 40° C. The residue is taken up in diisopropyl ether, triturated, filtered through a sintered glass funnel and then partially dried and dried under reduced pressure (3 kPa) at a temperature in the region of 40° C. 65 g of tert-butyl 3-iodo-5-(N-tert-butoxycarbonyl-2-methylsulfonylbenzenesulfonylamino)-indazole-1-carboxylate are thus obtained in the form of a pink powder (mass analysis: EI: m/z 677 (M$^+$·), m/z 477, m/z 303, m/z 258).

N-(3-Iodo-1H-indazol-5-yl)-2-methylsulfonylbenzenesulfonamide can be obtained as described in Example 2 from 25.7 g of 5-amino-3-iodo-1H-indazole, 440 ml of pyridine and 25.3 g of 2-(methylsulfonyl)benzenesulfonyl chloride. 39 g of N-(3-iodo-1H-indazol-5-yl)-2-methylsulfonylbenzenesulfonamide are thus obtained in the form of a brown solid (mass analysis: Cl: m/z 478 (M+H)$^+$, m/z 495 (M+NH$_4$)$^+$, m/z 260 (base peak)).

EXAMPLE 49

N-[3-(2-Aminophenyl)-1H-indazol-5-yl]-2-methyl-sulfonylbenzenesulfonamide

N-[3-(2-Aminophenyl)-1H-indazol-5-yl]-2-methylsulfonylbenzenesulfonamide can be obtained in the following way: 59 mg of powdered iron are added in small fractions to a solution, at reflux, of 280 mg of N-[3-(2-nitrophenyl)-1H-indazol-5-yl]-2-methylsulfonylbenzenesulfonamide, 10 ml of ethanol, 82 μl of distilled water and 51 μl of 12 N hydrochloric acid, and the reaction medium is then brought to reflux for 3 hours. After returning to a temperature in the region of 20° C., the suspension is filtered, and washed with ethanol. The filtrate is diluted with water and brought to a pH in the region of 10 with a 1 N sodium hydroxide solution. The filtrate is extracted with ethyl acetate and the remaining insoluble material is removed by filtration. The organic phase is washed with distilled water, dried with magnesium sulfate, treated with 3S black, filtered and concentrated to dryness under reduced pressure. The foam thus obtained is triturated with diisopropyl ether, filtered and dried. 40 mg of N-[3-(2-aminophenyl)-1H-indazol-5-yl]-2-methylsulfonylbenzenesulfonamide are thus obtained in the form of a white amorphous solid solvated with 1 mol of diisopropyl ether (analysis $C_{20}H_{18}N_4O_4S_2C_6H_{14}O$ % calculated C, 57.33; H, 5.92; N, 10.29; O, 14.69; S, 11.77. % found C, 57.41; H, 5.96; N, 10.01; S, 11.26).

N-[3-(2-Nitrophenyl)-1H-indazol-5-yl]-2-methylsulfonylbenzenesulfonamide can be obtained as described in Example 47 from 620 mg of tert-butyl 3-iodo-5-(N-tert-butoxycarbonyl-2-methylsulfonylbenzenesulfonylamino)indazole-1-carboxylate, 202 mg 2-nitrophenylboronic acid, 2 ml of a saturated aqueous sodium hydrogencarbonate solution, 31.7 mg of tetrakis(triphenylphosphine)palladium[0] and of 20 ml of dimethylformamide. 70 mg of N-[3-(2-nitrophenyl)-1H-indazol-5-yl]-2-methylsulfonylbenzenesulfonamide are thus obtained in the form of a yellow solid (Rf=0.53 silica gel thin layer chromatography, eluent: dichloromethane/ethyl acetate (80-20 by volume)).

$^1$H N.M.R. (300 MHz, $(CD_3)_2SO$ d6, δ in ppm): 3.54 (s: 3H); 7.15 (dd, J=9 and 2 Hz:1H); 7.35 (broad s: 1H); 7.51 (d, J=9 Hz: 1H); from 7.60 to 8.10 (mt: 7H); 8.25 (dd, J=7.5 and 1.5 Hz:1H); 9.45 (broad unresolved peak: 1H); 13.42 (unresolved peak: 1H).

EXAMPLE 50

2-Methylsulfonyl-N-(3-thiophen-2-yl-1H-indazol-5-yl)-benzenesulfonamide

2-Methylsulfonyl-N-(3-thiophen-2-yl-1H-indazol-5-yl)benzenesulfonamide can be obtained as described in Example 47 from 1.5 g of tert-butyl 3-iodo-5-(N-tert-butoxycarbonyl-2-methylsulfonylbenzenesulfonylamino)indazole-1-carboxylate, 339 mg of 2-thiopheneboronic acid, 50 ml of dimethylformamide, 4.8 ml of a saturated aqueous sodium hydrogencarbonate solution and 64 mg of tetrakis(triphenylphosphine)palladium[0]. 350 mg of 2-methylsulfonyl-N-(3-thiophen-2-yl-1H-indazol-5-yl)benzenesulfonamide are thus obtained in the form of an ochre solid melting at 246° C. (analysis $C_{18}H_{15}N_3O_4S_3$ % calculated C, 49.87; H, 3.49; N, 9.69; O, 14.76; S, 22.19. % found C, 49.82; H, 3.67; N, 9.08; S, 20.42).

EXAMPLE 51

2-Methylsulfonyl-N-(3-thiophen-3-yl-1H-indazol-5-yl)benzenesulfonamide

2-Methylsulfonyl-N-(3-thiophen-3-yl-1H-indazol-5-yl)benzenesulfonamide can be obtained as described in Example 47 from 1 g of tert-butyl 3-iodo-5-(N-tert-butoxycarbonyl-2-methylsulfonylbenzenesulfonylamino)indazole-1-carboxylate, 376 mg of 3-thiopheneboronic acid, 40 ml of dimethylformamide, 3.2 ml of a saturated aqueous sodium hydrogencarbonate solution and 42.7 mg of tetrakis(triphenylphosphine)palladium[0]. 108 mg of 2-methylsulfonyl-N-(3-thiophen-3-yl-1H-indazol-5-yl)benzenesulfonamide are thus obtained in the form of a white solid melting at 249° C. (analysis $C_{18}H_{15}N_3O_4S_3$ % calculated C, 49.87; H, 3.49; N, 9.69; O, 14.76; S, 22.19. % found C, 49.76; H, 3.53; N, 10.03; S, 21.78).

EXAMPLE 52

N-(3-Furan-3-yl-1H-indazol-5-yl)-2-methylsulfonyl-benzenesulfonamide

N-(3-Furan-3-yl-1H-indazol-5-yl)-2-methylsulfonylbenzenesulfonamide can be obtained as described in Example 47 from of 2 g of tert-butyl 3-iodo-5-(N-tert-butoxycarbonyl-2-methylsulfonylbenzenesulfonylamino)indazole-1-carboxylate, 660 mg of 3-furanboronic acid, 80 ml of dimethylformamide, 6.4 ml of a saturated aqueous sodium hydrogencarbonate solution and 85.4 mg of tetrakis(triphenylphosphine)palladium[0]. 440 mg of N-(3-furan-3-yl-1H-indazol-5-yl)-2-methylsulfonylbenzenesulfonamide are thus obtained in the form of a white solid melting at 249° C. (analysis —$C_{18}H_{15}N_3O_5S_2$ % calculated C, 51.79; H, 3.62; N, 10.07; O, 19.16; S, 15.36. % found C, 51.63; H, 3.55; N, 10.00; S, 15.13).

EXAMPLE 53

N-(3-Furan-2-yl-1H-indazol-5-yl)-2-methylsulfonyl-benzenesulfonamide

N-(3-Furan-2-yl-1H-indazol-5-yl)-2-methylsulfonylbenzenesulfonamide can be obtained as described in Example 47 from 1 g of tert-butyl 3-iodo-5-(N-tert-butoxycarbonyl-2-methylsulfonylbenzenesulfonylamino)indazole-1-carboxylate, 330 mg of 2-furanboronic acid, 40 ml of dimethylformamide, 3.2 ml of a saturated aqueous sodium hydrogencarbonate solution and 42.7 mg of tetrakis(triphenylphosphine)palladium[0]. 200 mg of N-(3-furan-2-yl-1H-indazol-5-yl)-2-methylsulfonylbenzenesulfonamide are thus obtained in the form of a white solid melting at 248° C. (analysis $C_{18}H_{15}N_3O_5S_2$ % calculated C, 51.79; H, 3.62; N, 10.07; O, 19.16; S, 15.36. % found C, 51.95; H, 3.75; N, 9.68; S, 14.75).

EXAMPLE 54

2-Methylsulfonyl-N-(3-pyridin-4-yl-1H-indazol-5-yl)benzenesulfonamide

2-Methylsulfonyl-N-(3-pyridin-4-yl-1H-indazol-5-yl)benzenesulfonamide can be obtained as described in Example 47 from 1 g of tert-butyl 3-iodo-5-(N-tert-butoxycarbonyl-2-methylsulfonylbenzenesulfonylamino)indazole-1-carboxylate, of 380 mg 4-pyridylboronic acid, 40 ml of dimethylformamide, 3.2 ml of a saturated aqueous sodium hydrogencarbonate solution and 42.7 mg of tetrakis(triphenylphosphine)palladium[0]. 100 mg of 2-methylsulfonyl-N-(3-pyridin-4-yl-1H-indazol-5-yl)benzenesulfonamide are thus obtained in the form of a white solid melting at 265° C. (analysis $C_{19}H_{16}N_4O_4S_2$ % calculated C, 53.26; H, 3.76; N, 13.08; O, 14.94; S, 14.97. % found C, 52.59; H, 3.30; N, 12.89; S, 15.14).

EXAMPLE 55

Methyl 3-[5-(2-methylsulfonylbenzenesulfonamino)-1H-indazol-3-yl]benzoate

Methyl 3-[5-(2-methylsulfonylbenzenesulfonamino)-1H-indazol-3-yl]benzoate can be obtained as described in Example 47 from 1 g of tert-butyl 3-iodo-5-(N-tert-butoxycarbonyl-2-methylsulfonylbenzenesulfonylamino)indazole-1-carboxylate, 530 mg of 3-methoxycarbonylphenylboronic acid, 30 ml of dimethylformamide, 3.2 ml of saturated aqueous sodium hydrogencarbonate solution and 42 mg of tetrakis(triphenylphosphine)palladium[0]. 239 mg of methyl 3-[5-(2-methylsulfonylbenzenesulfonamino)-1H-indazol-3-yl]benzoate are thus obtained in the form of an off-white solid melting at 202° C. (mass analysis: E1: m/z 485 ($M^+$), m/z 266 (base peak)).

EXAMPLE 56

3-[5-(2-Methylsulfonylbenzenesulfonamino)-1H-indazol-3-yl]benzoic acid

3-[5-(2-Methylsulfonylbenzenesulfonamino)-1H-indazol-3-yl]benzoic acid can be obtained in the following way: 64.7 mg of lithium hydroxide monohydrate and 2 ml of distilled water are added successively to a suspension of 220 mg of methyl 3-[5-(2-methylsulfonylbenzenesulfonamino)-1H-indazol-3-yl]benzoate, 2 ml of tetrahydrofuran and 2 ml of methanol, and the reaction medium is stirred for 16 hours at a temperature in the region of 20° C. The medium is then concentrated to dryness under reduced pressure and the evaporation residue is taken up with distilled water and the neutral materials are extracted with diethyl ether and then with ethyl acetate. The aqueous phase is acidified with 1N hydrochloric acid, to a pH in the region of 2. The precipitate formed is isolated by filtration, washed with distilled water then with diethyl ether, and dried under reduced pressure in an incubator at a temperature in the region of 50° C. for 2 hours. 153 mg of 3-[5-(2-methylsulfonylbenzenesulfonamino)-1H-indazol-3-yl]benzoic acid is thus obtained in the form of a whitish pink solid melting at a temperature above 260° C. (analysis $C_{21}H_{17}N_3O_6S_2$ % calculated C, 53.50; H, 3.63; N, 8.91; O, 20.36; S, 13.60. % found C, 52.59; H, 3.74; N, 8.68; O, 18.20; S, 13.02).

EXAMPLE 57

2-Methylsulfonyl-N-[3-(1H-pyrrolo[2,3-b]pyridin-2-yl)-1H-indazol-5-yl]benzenesulfonamide 2-Methylsulfonyl-N-[3-(1H-pyrrolo[2,3-b]pyridin-2-yl)-1H-indazol-5-yl]benzenesulfonamide can be obtained as described in Example 47 from 157.7 mg of tert-butyl 3-iodo-5-(N-tert-butoxycarbonyl-2-methylsulfonylbenzenesulfonylamino)indazole-1-carboxylate, 122 mg of 1-(tert-butoxycarbonyl)-7-azaindole-2-boronic acid, 7 ml of dimethylformamide, 500 µl of a saturated aqueous sodium hydrogencarbonate solution and 6.7 mg of tetrakis(triphenylphosphine)palladium[0]. 50 mg of 2-methylsulfonyl-N-[3-(1H-pyrrolo[2,3-b]pyridin-2-yl)-1H-indazol-5-yl]benzenesulfonamide are thus obtained in the form of a creamy yellow solid which decomposes at approximately 200° C. (LC/MS analysis: Tr 2.88 minutes MH$^+$=468).

1-(tert-Butoxycarbonyl)-7-azaindole-2-boronic acid can be prepared as described by E. Vasquez et al., in Journal of Organic Chemistry, 67, 7551-7552, (2002).

EXAMPLE 58

2-Methylsulfonyl-N-[3-(5-methoxy-1H-indol-2-yl)-1H-indazol-5-yl]benzenesulfonamide 2-Methylsulfonyl-N-[3-(5-methoxy-1H-indol-2-yl)-1H-indazol-5-yl]benzenesulfonamide can be obtained as described in Example 47 from 1.77 g of tert-butyl 3-iodo-5-(N-tert-butoxycarbonyl-2-methylsulfonylbenzenesulfonylamino)-indazole-1-carboxylate, 1.52 g 1-(tert-butoxycarbonyl)-5-methoxy-indole-2-boronic acid, 70 ml of dimethylformamide, 5.65 ml of a saturated aqueous sodium hydrogencarbonate solution and 151 mg of tetrakis(triphenylphosphine)palladium[0]. 250 mg of 2-methylsulfonyl-N-[3-(5-methoxy-1H-indol-2-yl)-1H-indazol-5-yl]benzenesulfonamide are thus obtained in the form of an amorphous cream solid (LC/MS analysis: Tr 3.52 minutes MH$^+$=497).

5-Methoxy-1-(tert-butoxycarbonyl)-7-azaindole-2-boronic acid can be obtained in the following way: 2.85 ml of 1.5 M solution of lithium diisopropylamide-tetrahydrofuran complex, in cyclohexane, is run, over 1 hour and maintaining the temperature at below 5° C., into a solution, maintained under an atmosphere of argon and cooled in an ice bath to between 0° C. and 5° C., of 2 g of 5-methoxy-1-tert-butoxy-7-azaindole in 10 ml of tetrahydrofuran and of 2.85 ml of triisopropyl borate. The temperature is maintained in the region of 0° C. for 30 minutes. The reaction mixture is then brought to a pH of between 2 and 3 by adding 1.5 ml of 2M hydrochloric acid. The reaction mixture is then settled out and the aqueous phase is extracted with 3 times 5 ml of ethyl acetate. The pooled organic extracts are dried over magnesium sulfate, filtered, and then concentrated to dryness under reduced pressure (2 kPa). 1.95 g of the dimer of 5-methoxy-1-(tert-butoxycarbonyl)-7-azaindole-2-boronic acid are obtained in the form of an amorphous cream solid (LC/MS analysis: Tr 3.29 minutes MH$^+$=435 UV %=95 (corresponding to the dimer of boronic acid)).

EXAMPLE 59

2-Methylsulfonyl-N-(3-pyridin-3-yl-1H-indazol-5-yl)benzenesulfonamide

2-Methylsulfonyl-N-(3-pyridin-3-yl-1H-indazol-5-yl)benzenesulfonamide can be prepared in the following way: 3.75 ml of saturated aqueous sodium hydrogencarbonate solution and 49 mg of tetrakis(triphenylphosphine)palladium [0] are added successively to a suspension, maintained under an atmosphere of argon, of 1 g of tert-butyl 3-iodo-5-(2-methylsulfonylbenzenesulfonylamino)indazole-1-carboxylate and of 200 mg of 3-pyridylboronic acid in 40 ml of dimethylformamide, and the mixture is maintained at reflux for 5 hours. After returning to a temperature in the region of 20° C., the reaction medium is poured onto 30 ml of distilled water and extracted with ethyl acetate. The pooled organic extracts are washed with distilled water, dried over magnesium sulfate, treated with 3S black, filtered and concentrated to dryness under reduced pressure. The brown oil obtained is purified by chromatography on a silica column with ethyl acetate as eluent. The foam thus obtained is recrystallized from 4 ml of acetonitrile at reflux. 120 mg of 2-methylsulfonyl-N-(3-pyridin-3-yl-1H-indazol-5-yl)benzenesulfonamide are thus obtained in the form of a beige solid melting above 260° C. (analysis $C_{19}H_{16}N_4O_4S_2$ % calculated C, 53.26; H, 3.76; N, 13.08; O, 14.94; S, 14.97. % found C, 52.31; H, 3.76; N, 12.94; S, 14.35).

tert-Butyl 3-iodo-5-(2-methylsulfonylbenzenesulfonylamino)indazole-1-carboxylate can be obtained in the following way: 22.6 ml of triethylamine and then 2.4 g of 4-(dimethylamino)pyridine are added to a suspension, under argon, of 38.8 g of N-(3-iodo-1H-indazol-5-yl)-2-methylsulfonylbenzenesulfonamide in 1.1 l of dichloromethane. The mixture is cooled to a temperature in the region of 0° C., and then a solution of 42.5 g of di-tert-butyl dicarbonate in 450 ml of dichloromethane is added dropwise over 45 minutes. The reaction mixture is stirred at a temperature in the region of 0° C. for 30 minutes and then at a temperature in the region of 20° C. for 16 hours. After the addition of 500 ml of distilled water and settling out, the organic phase is washed with 3 times 300 ml of distilled water, dried over magnesium sulfate, filtered, and then concentrated to dryness under reduced pressure (2 kPa) at a temperature in the region of 25° C. The residue thus obtained is triturated in diisopropyl ether and then filtered through a sintered glass funnel. The solid is partially dried, dried, and then purified by chromatography on a column of 1.2 kg of silica gel (particle size 40-63 µm), eluting successively with cyclohexane/ethyl acetate (80/20; 70/30; 50/50 by volume) mixtures and with pure ethyl acetate. The fractions containing the expected product are pooled and concentrated to dryness under reduced pressure (2 kPa) at a temperature in the region of 35° C. The residue is taken up and triturated in diisopropyl ether, filtered through a sintered glass funnel and then partially dried and dried. 31 g of tert-butyl 3-iodo-5-(2-methylsulfonylbenzenesulfonylamino)indazole-1-carboxylate are thus obtained in the form of an off-white solid (Rf=0.46, silica gel thin layer chromatography, eluent: cyclohexane/ethyl acetate (60-40 by volume)).

EXAMPLE 60

2-Methylsulfonyl-N-[3-(1H-pyrrol-2-yl)-1H-indazol-5-yl]benzenesulfonamide

2-Methylsulfonyl-N-[3-(1H-pyrrol-2-yl)-1H-indazol-5-yl]benzenesulfonamide can be obtained as described in Example 59 from 0.5 g of tert-butyl 3-iodo-5-(2-methylsulfonylbenzenesulfonylamino)indazole-1-carboxylate, 365 mg of 1-(tert-butyloxycarbonyl)pyrrole-2-boronic acid, 20 ml of dimethylformamide, 1.87 ml of saturated aqueous sodium hydrogencarbonate solution and 24.5 mg of tetrakis (triphenylphosphine)palladium[0]. 108 mg of 2-methylsulfonyl-N-[3-(1H-pyrrol-2-yl)-1H-indazol-5-yl]benzenesulfonamide are thus obtained in the form of a pale green solid melting at 255° C. (analysis $C_{18}H_{16}N_4O_4S_2$ % calculated: C, 51.91; H, 3.87; N, 13.45; O, 15.37; S, 15.40. % found C, 51.63; H, 3.87; N, 13.27; S, 15.21).

EXAMPLE 61

N-[3-(1H-Indol-2-yl)-1H-indazol-5-yl]-2-methylsulfonylbenzenesulfonamide

N-[3-(1H-Indol-2-yl)-1H-indazol-5-yl]-2-methylsulfonylbenzenesulfonamide can be obtained as described in Example 59 from 1 g of tert-butyl 3-iodo-5-(2-methylsulfonylbenzenesulfonylamino)indazole-1-carboxylate, 900 mg 1-(tert-butyloxycarbonyl)indole-2-boronic acid, 40 ml of dimethylformamide, 3.2 ml of saturated aqueous sodium hydrogencarbonate solution and 50 mg of tetrakis(triphenylphosphine)palladium[0]. 330 mg of N-[3-(1H-indol-2-yl)-1H-indazol-5-yl]-2-methylsulfonylbenzenesulfonamide are thus obtained in the form of a white solid melting above 260° C. (analysis $C_{22}H_{18}N_4O_4S_2$% calculated C, 56.63; H, 3.89; N, 12.01; O, 13.72; S, 13.75. % found C, 56.87H, 4.10: N, 13.81; S, 12.65).

EXAMPLE 62

N-[3-(3-Aminophenyl)-1H-indazol-5-yl]-2-methylsulfonylbenzenesulfonamide

N-[3-(3-Aminophenyl)-1H-indazol-5-yl]-2-methylsulfonylbenzenesulfonamide can be obtained as described in Example 59 from 0.5 g of tert-butyl 3-iodo-5-(2-methylsulfonylbenzenesulfonylamino)indazole-1-carboxylate, 276 mg of 3-aminophenylboronic acid, 20 ml of dimethylformamide, 1.6 ml of a saturated aqueous sodium hydrogencarbonate solution and 25 mg of tetrakis(triphenylphosphine)palladium[0]. 102 mg of N-[3-(3-aminophenyl)-1H-indazol-5-yl]-2-methylsulfonylbenzenesulfonamide are thus obtained in the form of a white solid melting at 220° C. (analysis $C_{20}H_{18}N_4O_4S_2$ % calculated C, 54.29; H, 4.10; N, 12.66; O, 14.46; S, 14.49. % found C, 53.48H, 4.11; N, 12.50; S, 13.95).

EXAMPLE 63

N-[3-(4-Dimethylaminophenyl)-1H-indazol-5-yl]-2-methylsulfonylbenzenesulfonamide N-[3-(4-Dimethylaminophenyl)-1H-indazol-5-yl]-2-methylsulfonylbenzenesulfonamide can be obtained as described in Example 59 from 1 g of tert-butyl 3-iodo-5-(2-methylsulfonylbenzenesulfonylamino)indazole-1-carboxylate, 570 mg of 4-dimethylaminophenylboronic acid, 40 ml of dimethylformamide, 3.2 ml of a saturated aqueous solution of sodium hydrogencarbonate and 50 mg of tetrakis(triphenylphosphine)palladium[0]. 200 mg of N-[3-(4-dimethylaminophenyl)-1H-indazol-5-yl]-2-methylsulfonylbenzenesulfonamide are thus obtained in the form of a yellow solid melting above 260° C. (analysis $C_{22}H_{22}N_4O_4S_2$ % calculated C, 56.15; H, 4.71; N, 11.91; O, 13.60; S, 13.63. % found C, 55.74; H, 4.81; N, 12.03; S, 13.34).

EXAMPLE 64

N-(3-Benzo[b]thiophen-3-yl-1H-indazol-5-yl)-2-methylsulfonylbenzenesulfonamide

N-(3-Benzo[b]thiophen-3-yl-1H-indazol-5-yl)-2-methylsulfonylbenzenesulfonamide can be obtained as described in Example 59 from 0.5 g of tert-butyl 3-iodo-5-(2-methylsulfonylbenzenesulfonylamino)indazole-1-carboxylate, 300 mg thianaphthene-3-boronic acid, 20 ml of dimethylformamide, 1.9 ml of saturated aqueous solution of sodium hydrogencarbonate and 25 mg of tetrakis(triphenylphosphine)palladium[0]. 150 mg of N-(3-benzo[b]thiophen-3-yl-1H-indazol-5-yl)-2-methylsulfonylbenzenesulfonamide are thus obtained in the form of a white solid melting at 235° C. (analysis $C_{22}H_{17}N_3O_4S_3$% calculated C, 54.64; H, 3.54; N, 8.69; O, 13.23; S, 19.89. % found C, 54.35; H, 3.68; N, 8.68; S, 20.12).

EXAMPLE 65

N-(3-Benzo[b]thiophen-2-yl-1H-indazol-5-yl)-2-methylsulfonylbenzenesulfonamide

N-(3-Benzo[b]thiophen-2-yl-1H-indazol-5-yl)-2-methylsulfonylbenzenesulfonamide can be obtained as described in Example 59 from 0.5 g of tert-butyl 3-iodo-5-(2-methylsulfonylbenzenesulfonylamino)indazole-1-carboxylate, 300 mg of thianaphthene-2-boronic acid, 20 ml of dimethylformamide, 1.9 ml of a saturated aqueous solution of sodium hydrogencarbonate and 25 mg of tetrakis(triphenylphosphine)palladium[0]. 150 mg of N-(3-benzo[b]thiophen-2-yl-1H-indazol-5-yl)-2-methylsulfonylbenzenesulfonamide are thus obtained in the form of a white solid melting at 270° C. (analysis $C_{22}H_{17}N_3O_4S_3$% calculated C, 54.64; H, 3.54; N, 8.69; O, 13.23; S, 19.89. % found C, 54.59H, 3.47; N, 8.79; S, 19.98).

EXAMPLE 66

N-[3-(4-Nitrophenyl)-1H-indazol-5-yl]-2-methylsulfonylbenzenesulfonamide

N-[3-(4-Nitrophenyl)-1H-indazol-5-yl]-2-methylsulfonylbenzenesulfonamide can be obtained as described in Example 59 from 5 g of tert-butyl 3-iodo-5-(2-methylsulfonylbenzenesulfonylamino)indazole-1-carboxylate, 2.9 g 4-nitrophenylboronic acid, 200 ml of dimethylformamide, 19 ml of a saturated aqueous solution of sodium hydrogencarbonate and 250 mg of tetrakis(triphenylphosphine)palladium [0]. 2.5 g of a yellow powder are thus obtained. 100 mg of this powder are recrystallized from 20 ml of acetonitrile. The resulting powder is washed with 2 times 1 ml of acetonitrile and 5 ml of diisopropyl ether. After drying at 50° C. under reduced pressure, 80 mg of N-[3-(4-nitrophenyl)-1H-indazol-5-yl]-2-methylsulfonylbenzenesulfonamide are obtained in the form of a pale yellow solid melting above 260° C. (analysis $C_{20}H_{16}N_4O_6S_2$ % calculated C, 50.84; H, 3.41; N, 11.86; O, 20.32; S, 13.57. % found C, 50.11; H, 3.35; N, 11.69; S, 13.14).

EXAMPLE 67

2-Methylsulfonyl-N-(3-quinolin-8-yl-1H-indazol-5-yl)benzenesulfonamide

2-Methylsulfonyl-N-(3-quinolin-8-yl-1H-indazol-5-yl) benzenesulfonamide can be obtained as described in Example 59 from 2 g of tert-butyl 3-iodo-5-(2-methylsulfonylbenzenesulfonylamino)indazole-1-carboxylate, 1.17 g of 8-quinolineboronic acid, 80 ml of dimethylformamide, 7.5 ml of a saturated aqueous sodium hydrogencarbonate solution and 98 mg of tetrakis(triphenylphosphine)palladium[0]. 30 mg of 2-methylsulfonyl-N-(3-quinolin-8-yl-1H-indazol-5-yl)benzenesulfonamide are thus obtained in the form of a pale yellow solid melting at 219° C. (analysis $C_{23}H_{18}N_4O_4S_2$% calculated C, 57.73; H, 3.79; N, 11.71; O, 13.37; S, 13.4. % found C, 57.10; H, 4.11; N, 11.19; S, 11.94).

EXAMPLE 68

Methyl 4-[5-(2-methylsulfonylbenzenesulfonamino)-1H-indazol-3-yl]benzoate

Methyl 4-[5-(2-methylsulfonylbenzenesulfonamino)-1H-indazol-3-yl]benzoate can be obtained as described in Example 59 from 1 g of tert-butyl 3-iodo-5-(2-methylsulfonylbenzenesulfonylamino)indazole-1-carboxylate, 631 mg of 4-methoxycarbonylphenylboronic acid, 40 ml of dimethylformamide, 3.75 ml of a saturated aqueous sodium hydrogencarbonate solution and of 49 mg of tetrakis(triphenylphosphine)palladium[0]. 190 mg of methyl 4-[5-(2-methylsulfonylbenzenesulfonamino)-1H-indazol-3-yl]benzoate are thus obtained in the form of a white solid melting at 244° C. (analysis $C_{22}H_{19}N_3O_6S_2$% calculated C, 54.42; H, 3.94; N, 8.65; O, 19.77; S, 13.21. % found C, 54.48; H, 3.63: N, 8.83; S, 13.17).

EXAMPLE 69

4-[5-(2-Methylsulfonylbenzenesulfonamino)-1H-indazol-3-yl]benzoic acid

4-[5-(2-methylsulfonylbenzenesulfonamino)-1H-indazol-3-yl]benzoic acid can be obtained as described in Example 56 from 166 mg of methyl 4-[5-(2-methylsulfonylbenzenesulfonamino)-1H-indazol-3-yl]benzoate, 2 ml of tetrahydrofuran, 2 ml of methanol, 48.7 mg of lithium hydroxide monohydrate and 2 ml of distilled water. 52.5 mg of 4-[5-(2-methylsulfonylbenzenesulfonamino)-1H-indazol-3-yl]benzoic acid hexahydrate are thus obtained in the form of a white solid melting at 199° C. (analysis $C_{21}H_{17}N_3O_6S_2.6H_2O$ % calculated C, 43.52; H, 5.04; N, 7.25; O, 33.12; S, 11.06. % found C, 42.86; H, 4.62; N, 7.04; S, 10.97).

EXAMPLE 70

N-[3-(4-Aminophenyl)-1H-indazol-5-yl]-2-methylsulfonylbenzenesulfonamide

N-[3-(3-Aminophenyl)-1H-indazol-5-yl]-2-methylsulfonylbenzenesulfonamide can be obtained as described in Example 49 from 200 mg of N-[3-(3-nitrophenyl)-1H-indazol-5-yl]-2-methylsulfonylbenzenesulfonamide, 6 ml of ethanol, 73 mg of powdered iron, 100 ml of distilled water and 40 μl of 12 N hydrochloric acid. 70 mg of N-[3-(3-aminophenyl)-1H-indazol-5-yl]-2-methylsulfonylbenzenesulfonamide are thus obtained in the form of light yellow crystals melting at 154° C. (analysis $C_{20}H_{18}N_4O_4S_2$ % calculated C, 54.29; H, 4.10; N, 12.66; O, 14.46; S, 14.49. % found C, 53.03; H, 4.26; N, 11.63; S, 13.22).

EXAMPLE 71

N-[3-(3-Cyanophenyl)-1H-indazol-5-yl]-2-methylsulfonylbenzenesulfonamide

N-[3-(3-Cyanophenyl)-1H-indazol-5-yl]-2-methylsulfonylbenzenesulfonamide can be obtained as described in Example 59 from 0.75 g of tert-butyl 3-iodo-5-(2-methylsulfonylbenzenesulfonylamino)indazole-1-carboxylate, 380 mg of 3-cyanophenylboronic acid, 30 ml of dimethylformamide, 2.85 ml of a saturated aqueous sodium hydrogencarbonate solution and 37 mg of tetrakis(triphenylphosphine)palladium[0]. 20 mg of N-[3-(3-cyanophenyl)-1H-indazol-5-yl]-2-methylsulfonylbenzenesulfonamide are thus obtained in the form of a white solid melting at 240° C. (analysis $C_{21}H_{16}N_4O_4S_2.H_2O$ % calculated C, 53.61; H, 3.86; N, 11.91; O, 17.00; S, 13.63. % found C, 53.95; H, 3.85: N, 11.68; S, 13.18).

EXAMPLE 72

2-Methylsulfonyl-N-(3-naphthalen-1-yl-1H-indazol-5-yl)-benzenesulfonamide

2-Methylsulfonyl-N-(3-naphthalen-1-yl-1H-indazol-5-yl)benzenesulfonamide can be obtained as described in Example 59 from 0.5 g of tert-butyl 3-iodo-5-(2-methylsulfonylbenzenesulfonylamino)indazole-1-carboxylate, 298 mg of 1-naphthaleneboronic acid, 20 ml of dimethylformamide, 1.9 ml of a saturated aqueous sodium hydrogencarbonate solution and 24.5 mg of tetrakis(triphenylphosphine)palladium[0]. 240 mg of 2-methylsulfonyl-N-(3-naphthalen-1-yl-1H-indazol-5-yl)benzenesulfonamide are thus obtained in the form of a white solid melting at 186° C. (analysis $C_{24}H_{19}N_3O_4S_2$ % calculated C, 60.36; H, 4.01; N, 8.80; O, 13.40; S, 13.43. % found C, 59.78; H, 4.05; N, 8.76; S, 13.34).

EXAMPLE 73

2-Methylsulfonyl-N-(3-naphthalen-2-yl-1H-indazol-5-yl)-benzenesulfonamide

2-Methylsulfonyl-N-(3-naphthalen-2-yl-1H-indazol-5-yl)benzenesulfonamide can be obtained as described in Example 59 from 0.5 g of tert-butyl 3-iodo-5-(2-methylsulfonylbenzenesulfonylamino)indazole-1-carboxylate, 298 mg of 2-naphthaleneboronic acid, 20 ml of dimethylformamide, 1.88 ml of a saturated aqueous sodium hydrogencarbonate solution and 24.5 mg of tetrakis(triphenylphosphine)palladium[0]. 120 mg of 2-methylsulfonyl-N-(3-naphthalen-2-yl-1H-indazol-5-yl)benzenesulfonamide are thus obtained in the form of a white solid melting at 221° C. (analysis $C_{24}H_{19}N_3O_4S_2$ % calculated C, 60.36; H, 4.01; N, 8.80; O, 13.40; S, 13.43. % found C, 60.09; H, 4.06; N, 8.55; S, 13.51).

EXAMPLE 74

N-{3-[(E)-2-(4-Fluorophenyl)vinyl]-1H-indazol-5-yl}-2-methylsulfonylbenzenesulfonamide N-{3-[(E)-2-(4-Fluorophenyl)vinyl]-1H-indazol-5-yl}-2-methylsulfonylbenzenesulfonamide can be obtained as described in Example 59 from 1 g of tert-butyl 3-iodo-5-(2-methylsulfonylbenzenesulfonylamino)-indazole-1-carboxylate, 575 mg trans-2-(4-fluorophenyl)vinylboronic acid, 28 ml of dimethylformamide, 3.25 ml of a saturated aqueous sodium hydrogencarbonate solution and 41 mg of tetrakis(triphenylphosphine)palladium[0]. 240 mg of N-{3-[(E)-2-(4-fluorophenyl)vinyl]-1H-indazol-5-yl}-2-methylsulfonylbenzenesulfonamide are thus obtained in the form of an off-white solid melting at 248° C. (analysis $C_{22}H_{18}FN_3O_4S_2$ % calculated C, 56.04; H, 3.85; F, 4.03; N, 8.91; O, 13.57; S, 13.60. % found C, 56.21; H, 4.09; F, 3.95; N, 8.64; S, 13.31).

EXAMPLE 75

N-{3-[2-(4-Fluorophenyl)ethyl]-1H-indazol-5-yl}-2-methylsulfonylbenzenesulfonamide N-{3-[2-(4-Fluorophenyl)ethyl]-1H-indazol-5-yl}-2-methylsulfonylbenzenesulfonamide can be obtained in the following way: a mixture of 300 mg of N-{3-[(E)-2-(4-fluorophenyl)vinyl]-1H-indazol-5-yl}-2-methylsulfonylbenzenesulfonamide, of 30 mg of 10% palladium-on-charcoal and of 8 ml of dimethylformamide is autoclaved under a pressure of 10 bar of hydrogen and the mixture is stirred at a temperature in the region of 20° C. for 1 hour until complete absorption of hydrogen. The medium is then filtered through a bed of Celite® 535, this is washed with dimethylformamide and the filtrate is concentrated to dryness under reduced pressure. The solid residue is taken up with dichloromethane and the insoluble material is isolated by filtration, washed with dichloromethane and then dried under reduced pressure. 220 mg of N-{3-[2-(4-fluorophenyl)ethyl]-1H-indazol-5-yl}-2-methylsulfonylbenzenesulfonamide is thus obtained in the form of an off-white solid melting at 234° C. (analysis $C_{22}H_{20}FN_3O_4S_2$ % calculated C, 55.81; H, 4.26; F, 4.01; N, 8.87; O, 13.51; S, 13.54. % found C, 55.80; H, 4.45; F, 3.85; N, 8.97; S, 12.80).

EXAMPLE 76

N-{3-[(E)-2-(4-Chlorophenyl)vinyl]-1H-indazol-5-yl}-2-methylsulfonylbenzenesulfonamide N-{3-[(E)-2-(4-Chlorophenyl)vinyl]-1H-indazol-5-yl}-2-methylsulfonylbenzenesulfonamide can be obtained as described in Example 59 from 1 g of tert-butyl 3-iodo-5-(2-methylsulfonylbenzenesulfonylamino)indazole-1-carboxylate, 631 mg of trans-2-(4-chlorophenyl)vinylboronic acid, 28 ml of dimethylformamide, 3.25 ml of a saturated aqueous sodium hydrogencarbonate solution and 48 mg of tetrakis(triphenylphosphine)-palladium[0]. 556 mg of N-{3-[(E)-2-(4-chlorophenyl)vinyl]-1H-indazol-5-yl}-2-methylsulfonylbenzenesulfonamide are thus obtained in the form of a pale yellow solid melting at 247° C. (analysis $C_{22}H_{18}ClN_3O_4S_2$ % calculated C, 54.15; H, 3.72; Cl, 7.27; N, 8.61; O, 13.11; S, 13.14. % found C, 54.32; H, 4.40; Cl, 5.65; N, 7.83; S, 11.93).

EXAMPLE 77

N-{3-[2-(4-Chlorophenyl)ethyl]-1H-indazol-5-yl}-2-methylsulfonylbenzenesulfonamide N-{3-[2-(4-Chlorophenyl)ethyl]-1H-indazol-5-yl}-2-methylsulfonylbenzenesulfonamide can be obtained as described in Example 75 from 465 mg of N-{3-[(E)-2-(4-chlorophenyl)vinyl]-1H-indazol-5-yl}-2-methylsulfonylbenzenesulfonamide, 47 mg of 10% palladium-on-charcoal and 8 ml of dimethylformamide. 145 mg of N-{3-[2-(4-chlorophenyl)-ethyl]-1H-indazol-5-yl}-2-methylsulfonylbenzenesulfonamide are thus obtained in the form of a white solid melting at 215° C. (analysis $C_{22}H_{20}ClN_3O_4S_2$ % calculated C, 53.92; H, 4.11; Cl, 7.24; N, 8.58; O, 13.06; S, 13.09. % found C, 52.86; H, 4.26; Cl, 7.72; N, 8.49; S, 12.52).

EXAMPLE 78

2-Methylsulfonyl-N-[3-((E)-styryl)-1H-indazol-5-yl]benzenesulfonamide

2-Methylsulfonyl-N-[3-((E)-styryl)-1H-indazol-5-yl]benzenesulfonamide can be prepared in the following way: 1.6 ml of a saturated aqueous sodium hydrogencarbonate solution and 21.35 mg of tetrakis(triphenylphosphine)palladium[0] are added successively to a suspension, maintained under an atmosphere of argon, of 500 mg of tert-butyl 3-iodo-5-(N-tert-butoxycarbonyl-2-methylsulfonylbenzenesulfonylamino)-indazole-1-carboxylate and of 220 mg of trans-2-phenylvinylboronic acid in 20 ml of dimethylformamide. The reaction medium is maintained at reflux for 5 hours. After returning to a temperature in the region of 20° C., the reaction medium is diluted with 20 ml of distilled water and extraction is carried out with ethyl acetate. The pooled organic extracts are washed with brine, dried over magnesium sulfate, filtered and concentrated under reduced pressure. The brown oil thus obtained is purified by chromatography on a silica cartridge (particle size 20-40 μm) with pure dichloromethane and then a dichloromethane/methanol (99/1 by volume) mixture as eluent. The yellow paste obtained is chromatographed for a second time on a silica cartridge (particle size 20-40 μm) with a cyclohexane/ethyl acetate (80/20 and then 70/30 by volume) mixture as eluent. 206 mg of 2-methylsulfonyl-N-[3-((E)-styryl)-1H-indazol-5-yl]benzenesulfonamide are thus obtained in the form of a white solid melting at 200° C.

$^1$H N.M.R. (300 MHz, $(CD_3)_2SO$ d6, δ in ppm), 3.56 (s, 3H); 7.09 (dd, J=8.5 and 1.5 Hz, 1H); 7.24 (d, J=16.5 Hz, 1H); 7.33 (broad t, J=7.5 Hz, 1H); from 7.40 to 7.50 (mt, 3H); 7.48 (d, J=16.5 Hz, 1H); 7.67 (d, J=7.5 Hz, 2H); from 7.75 to 7.85 (mt, 2H); 7.88 (split t, J=7.5 and 1.5 Hz, 1H); 7.96 (dd, J=7.5 and 1.5 Hz, 1H); 8.26 (dd, J=7.5 and 1.5 Hz, 1H); from 9.20 to 9.60 (broad unresolved peak: 1H); 13.18 (broad s, 1H).

EXAMPLE 79

Methyl(E)-3-[5(2-methylsulfonylbenzenesulfonylamino)-1H-indazol-3-yl]-acrylate

Methyl(E)-3-[5(2-methylsulfonylbenzenesulfonylamino)-1H-indazol-3-yl]-acrylate can be obtained in the following way: 40 μl of iodotrimethylsilane are added dropwise to a solution, maintained under an atmosphere of argon, of 150 mg of methyl(E)-3-[5(2-methylsulfonylbenzenesulfonylamino)-1-tert-butoxycarbonylindazol-3-yl]acrylate in 10 ml of chloroform, and the mixture is stirred at a temperature in the region of 20° C. for 16 hours. 5 ml of an aqueous solution containing 5% of aqueous ammonia are then added and the medium is extracted with dichloromethane. The pooled organic extracts are washed with distilled water, dried over magnesium sulfate, filtered and concentrated to dryness under reduced pressure. The white foam thus isolated is recrystallized from 8 ml of acetonitrile. 19 mg of methyl(E)-3-[5(2-methylsulfonylbenzenesulfonylamino)-1H-indazol-3-yl]-acrylate are thus obtained in the form of a white solid melting at 253° C. (analysis $C_{18}H_{17}N_3O_6S_2$ % calculated C, 49.65; H, 3.93; N, 9.65; O, 22.04; S, 14.73. % found C, 49.14; H, 3.92; N, 9.47; S, 14.23).

Methyl(E)-3-[5(2-methylsulfonylbenzenesulfonylamino)-1-tert-butoxycarbonylindazol-3-yl]acrylate can be obtained in the following way: 74 μL methyl acrylate are added dropwise to a solution, maintained under an atmosphere of argon and at a temperature in the region of 20° C., of 500 mg of tert-butyl 3-iodo-5-(2-methylsulfonylbenzenesulfonylamino)indazole-1-carboxylate, 1.2 ml of diisopropylethylamine, 121 mg of lithium chloride, 11.6 mg of palladium acetate in 15 ml of anhydrous dimethylformamide, and the reaction medium is then heated for 1 hour at 60° C. and then for 1 hour at 80° C. After returning to a temperature in the region of 20° C., 15 ml of distilled water are added and the reaction medium is extracted with ethyl acetate. The pooled organic extracts are washed with distilled water, dried over magnesium sulfate, filtered and concentrated to dryness under reduced pressure. The oil thus isolated is purified by chromatography on a column of silica gel with a cyclohexane/ethyl acetate (80/20 by volume) mixture as eluent. 90 mg of methyl(E)-3-[5(2-methylsulfonylbenzenesulfonylamino)-1- tert-butoxycarbonylindazol-3-yl]acrylate are thus obtained in the form of a white solid (Rf=0.90, silica gel thin layer chromatography, eluent: cyclohexane/ethyl acetate (50/50 by volume)).

$^1$H N.M.R. (300 MHz, $(CD_3)_2SO$ d6, δ in ppm), 1.64 (s, 9H); 3.55 (s, 3H); 3.82 (s, 3H); 6.73 (d, J=16.5 Hz, 1H); 7.42 (broad dd, J=9 and 2.5 Hz, 1H); 7.80 (d, J=16.5 Hz, 1H); from 7.80 to 7.95 (mt, 3H); 8.00 (d, J=9 Hz, 1H); 8.07 (dd, J=7.5 and 1.5 Hz, 1H); 8.25 (dd, J=7.5 and 1.5 Hz, 1H); from 9.80 to 10.10 (broad unresolved peak: 1H).

EXAMPLE 80

(E)-3-[5(2-Methylsulfonylbenzenesulfonylamino)-1H-indazol-3-yl]-acrylic acid (E)-3-[5(2-Methylsulfonylbenzenesulfonylamino)-1H-indazol-3-yl]acrylic acid can be obtained in the following way: 36 mg of lithium hydroxide monohydrate and 0.5 ml of distilled water are added successively to a suspension of 72 mg of methyl(E)-3-[5(2-methylsulfonylbenzenesulfonylamino)-1H-indazol-3-yl]acrylate, of 0.5 ml of tetrahydrofuran and of 0.5 ml of methanol, and the reaction mixture is stirred for 72 hours at a temperature in the region of 20° C. The medium is then diluted with 5 ml of distilled water, and acidified with 1N hydrochloric acid to a pH in the region of 2. The precipitate formed is isolated by filtration, washed with distilled water and then dried under a ventilated hood for 16 hours. 23 mg of (E)-3-[5(2-methylsulfonylbenzenesulfonylamino)-1H-indazol-3-yl]acrylic acid sesquihydrochloride are thus obtained in the form of a white solid melting at 170° C. (analysis $C_{17}H_{15}N_3O_6S_2$.1.5 HCl % calculated C, 42.88; H, 3.49; Cl, 11.17; N, 8.83; O, 20.16; S, 13.47. % found C, 42.41; H, 3.74; N, 8.56; S, 12.83).

EXAMPLE 81

N-[3-(1H-Benzimidazol-2-yl)-1H-indazol-5-yl]-2-methylsulfonylbenzenesulfonamide N-[3-(1H-benzimidazol-2-yl)-1H-indazol-5-yl]-2-methylsulfonylbenzenesulfonamide can be prepared in the following way: a solution of 175 mg of N-[3-(1H-benzimidazol-2-yl)-1-(2-trimethylsilanylethoxymethyl)-1H-indazol-5-yl]-2-methylsulfonylbenzenesulfonamide, of 7 ml of ethanol and of 42 ml of 2N hydrochloric acid is brought to 50° C. for 24 hours. After returning to a temperature in the region of 20° C., the reaction medium is brought to a pH in the region of 9 with a saturated aqueous sodium hydrogencarbonate solution, and extracted with ethyl acetate. The pooled organic extracts are washed with brine, dried over magnesium sulfate, filtered and concentrated to dryness under reduced pressure. The paste thus isolated is triturated in 5 ml of ethanol and the insoluble material is isolated by filtration, dried then triturated in 3 ml of acetonitrile, partially dried and dried. 49 mg of N-[3-(1H-benzimidazol-2-yl)-1H-indazol-5-yl]-2-methylsulfonylbenzenesulfonamide are thus obtained in the form of an ochre solid melting at a temperature above 260° C. (analysis $C_{21}H_{17}N_5O_4S_2$ % calculated C, 53.95; H, 3.66; N, 14.98; O, 13.69; S, 13.72. % found C, 52.45; H, 4.01; N, 14.65; S, 11.74).

N-[3-(1H-Benzimidazol-2-yl)-1-(2-trimethylsilanylethoxymethyl)-1H-indazol-5-yl]-2-methylsulfonylbenzenesulfonamide can be obtained as described in Example 2 from 130 mg of 3-(1H-benzimidazol-2-yl)-1-(2-trimethylsilanylethoxymethyl)-1H-indazol-5-ylamine, 5 ml of pyridine and 87 mg of 2-methylsulfonylbenzenesulfonyl chloride. 192 mg of N-[3-(1H-benzimidazol-2-yl)-1-(2-trimethylsilanylethoxymethyl)-1H-indazol-5-yl]-2-methylsulfonylbenzenesulfonamide are thus obtained in the form of an orange lac (Rf=0.53, silica gel thin layer chromatography, eluent: cyclohexane/ethyl acetate (50/50 by volume), mass analysis: Cl: m/z 598 (M+H)$^{+\cdot}$)

3-(1H-Benzimidazol-2-yl)-1-(2-trimethylsilanylethoxymethyl)-1H-indazol-5-ylamine can be obtained in the following way: 485 mg of powdered iron are added, in small fractions, to a solution, brought to reflux, of 350 mg of 3-(1H-benzimidazol-2-yl)-5-nitro-1-(2-trimethylsilanylethoxymethyl)-1H-indazole, of 15 ml of ethanol, of 200 μl of distilled water and of 320 μl 12N hydrochloric acid and the mixture is maintained at reflux for 16 hours. After returning to a temperature in the region of 20° C., the medium is diluted with 60 ml of ethanol, stirred, and then filtered through a bed of Celite® 535, which is then washed with ethanol. The filtrate is basified to a pH in the region of 9 with a saturated aqueous sodium hydrogencarbonate solution. The precipitate thus formed is removed by filtration, and washed with ethanol, and the filtrate is then concentrated to dryness under reduced pressure. The evaporation residue is dissolved in distilled water and extracted with ethyl acetate. The pooled organic extracts are dried over magnesium sulfate, filtered and concentrated to dryness under reduced pressure. 130 mg of 3-(1H-benzimidazol-2-yl)-1-(2-trimethylsilanylethoxymethyl)-1H-indazol-5-ylamine are thus obtained in the form of an orange lac (Rf=0.34, silica gel thin layer chromatography, eluent: cyclohexane/ethyl acetate (50/50 by volume); mass analysis: El: m/z 379 (M$^{+\cdot}$) (base peak), m/z 306).

3-(1H-Benzimidazol-2-yl)-5-nitro-1-(2-trimethylsilanylethoxymethyl)-1H-indazole can be obtained in the following way: a suspension of 720 mg of 5-nitro-1-(2-trimethylsilanylethoxymethyl)-1H-indazole-3-carboxaldehyde, of 216 mg of 1,2-phenylenediamine and of 77 mg of sulfur (0) in 70 ml of anhydrous dimethylformamide is heated at 95° C. for 16 hours. After returning to a temperature in the region of 20° C., the reaction medium is concentrated to dryness under reduced pressure and the evaporation residue is taken up with 20 ml of distilled water and 20 ml of ethyl acetate. The insoluble material floating at the surface is isolated by filtration, washed and dried and makes it possible to obtain a first crop of 160 mg of 3-(1H-benzimidazol-2-yl)-5-nitro-1-(2-trimethylsilanylethoxymethyl)-1H-indazole in the form of a yellow solid (Rf=0.22, silica gel thin layer chromatography, eluent: cyclohexane/ethyl acetate (75/25 by volume)). The filtrate is concentrated to dryness under reduced pressure and the solid residue is resuspended in a cyclohexane/ethyl acetate (80/20 by volume) mixture, isolated by filtration, washed and dried. A second crop of 200 mg of 3-(1H-benzimidazol-2-yl)-5-nitro-1-(2-trimethylsilanylethoxymethyl)-1H-indazole is thus obtained in the form of an orangey solid with the same Rf as the first crop (mass analysis: Cl: m/z 410 (M+H)$^{+})^+$ (base peak)).

5-Nitro-1-(2-trimethylsilanylethoxymethyl)-1H-indazole-3-carboxaldehyde can be obtained in the following way: 3.33 ml of a 20% by weight solution of diisobutylaluminum hydride in toluene are run into, over 15 minutes, a solution, maintained in the region of 0° C. and under an atmosphere of argon, of 760 mg of 3-(N-methoxy-N-methyl)-5-nitro-1-(2-trimethylsilanyl-ethoxymethyl)-1H-indazolecarboxamide in 25 ml of anhydrous tetrahydrofuran. The reaction medium is then stirred for 4 hours in the region of 0° C. At this temperature, a mixture of 2 ml of acetic acid in 16 ml of distilled water is then run in slowly. After stirring for 5 minutes, the insoluble material is removed by filtration through a bed of Celite®

535, which is washed with ethyl acetate. The filtrate is settled out and the aqueous phase is extracted with ethyl acetate. The pooled organic extracts are washed with distilled water and then a saturated aqueous sodium hydrogencarbonate solution, dried over magnesium sulfate, filtered and concentrated to dryness under reduced pressure. 725 mg of 5-nitro-1-(2-trimethylsilanylethoxymethyl)-1H-indazole-3-carboxaldehyde are thus obtained (Rf=0.41, silica gel thin layer chromatography, eluent: cyclohexane/ethyl acetate (75/25 by volume)), which is used extemporaneously in the following steps. $^1$H N.M.R. (300 MHz, $(CD_3)_2SO$ d6, δ in ppm), −0.08 (s, 9H); 0.86 (t, J=8 Hz, 2H); 3.63 (t, J=8 Hz, 2H); 6.03 (s, 2H); 8.19 (d, J=9 Hz, 1H); 8.46 (dd, J=9 and 3 Hz, 1H); 8.99 (d, J=3 Hz, 1H); 10.29 (s, 1H).

3-(N-Methoxy-N-methyl)-5-nitro-1-(2-trimethylsilanylethoxymethyl)-1H-indazolecarboxamide can be prepared in the following way: 390 mg of N-methoxymethylamine hydrochloride and then 0.56 ml of triethylamine are added successively to a solution of 674 mg of 5-nitro-1-(2-trimethylsilanylethoxymethyl)-1H-indazole-3-carboxylic acid, of 170 mg of 1-hydroxybenzotriazole monohydrate and of 240 mg of 1-ethyl-3-[3-(dimethylamino)propyl]-carbodiimide hydrochloride in 20 ml of dichloromethane. The reaction medium is stirred for 16 hours at a temperature in the region of 20° C., and then washed successively with a 5% aqueous sodium carbonate solution, twice with a total of 80 ml of 1N hydrochloric acid and twice with a total of 80 ml of distilled water. The organic phase is dried over calcium chloride, filtered and concentrated to dryness under reduced pressure. 280 mg of 3-(N-methoxy-N-methyl)-5-nitro-1-(2-trimethylsilanylethoxymethyl)-1H-indazolecarboxamide are thus obtained in the form of a yellow oil (Rf=0.76, silica gel thin layer chromatography, eluent: ethyl acetate/cyclohexane (60/40 by volume)).

5-Nitro-1-(2-trimethylsilanylethoxymethyl)-1H-indazole-3-carboxylic acid can be prepared in the following way: a solution of 2.07 g of 5-nitro-1H-indazole-3-carboxylic acid dissolved in 23 ml of anhydrous dimethylformamide is run into, over a period of 10 minutes, a suspension, maintained in the region of 0° C. and under an atmosphere of argon, of 690 mg of sodium hydride at 80% in dispersion in liquid petroleum jelly, and of 12 ml of anhydrous dimethylformamide. The temperature is then allowed to rise and stirring is carried out in the region of 20° C. over a total period of 2 hours. The medium is then cooled to a temperature in the region of −10° C. using a refrigerating mixture of ice and sodium chloride, and then 2.8 ml of 2-(trimethylsilyl)ethoxymethyl chloride are then run in over 10 minutes. The medium is then stirred for 48 hours at a temperature in the region of 20° C. before being concentrated to dryness under reduced pressure. The residue is taken up with distilled water and brought to a pH in the region of 2 with 1N hydrochloric acid, then extracted with ethyl acetate. The pooled organic extracts are washed with distilled water and then a saturated aqueous sodium hydrogencarbonate solution and a solution of brine, dried over magnesium sulfate, filtered and concentrated to dryness under reduced pressure. The oil thus isolated is purified by chromatography on silica gel with an ethyl acetate/methanol (95/5 by volume) mixture as eluent. 2.21 g of 5-nitro-1-(2-trimethylsilanylethoxymethyl)-1H-indazole-3-carboxylic acid are thus obtained in the form of yellow crystals (Rf=0.66, silica gel thin layer chromatography, eluent: ethyl acetate/methanol (90/10 by volume); mass analysis: IC: m/z 338 (M+H)$^+$, m/z 355 (M+NH$_4$)$^+$ (base peak)).

EXAMPLE 82

N-[3-(1H-Indol-2-yl)-1H-indazol-5-yl]benzenesulfonamide

N-[3-(1H-Indol-2-yl)-1H-indazol-5-yl]benzenesulfonamide can be obtained in the following way: 158.1 mg of N-tert-butoxycarbonylindole-2-boronic acid and 360 μl of a saturated sodium hydrogencarbonate solution and then 48.2 mg of tetrakis(triphenyl-phosphine)palladium[0] are added to a solution of 101.9 mg of tert-butyl 3-iodo-5-(N-tert-butoxycarbonylbenzenesulfonylamino)indazole-1-carboxylate in 4.5 ml of dimethylformamide. The suspension is heated in the region of 122° C. for 16 hours. After cooling to a temperature in the region of 20° C., the catalyst is filtered through a bed of Celite® 535, and the filtrate is concentrated to dryness under reduced pressure. The reaction crude is purified by preparative HPLS chromatography coupled to a mass detector (LC/MS, conditions A). The fractions containing the expected product are pooled and concentrated. 43.8 mg of N-[3-(1H-indol-2-yl)-1H-indazol-5-yl]benzenesulfonamide are obtained in the form of the trifluoroacetate salt (LC/MS analysis: Tr=3.49 minutes; [M+H]$^+$=389.13).

N-tert-Butoxycarbonylindole-2-boronic acid in dimer form can be prepared according to the procedure described by E. VASQUEZ et al., in Journal of Organic Chemistry, 67, 7551-52 (2002).

tert-Butyl 3-iodo-5-(N-tert-butoxycarbonylbenzenesulfonylamino)indazole-1-carboxylate can be prepared in the following way: 2 g of 5-amino-3-iodo-1H-indazole are dissolved in 40 ml of dichloromethane, 3.11 ml of pyridine are added, and then the temperature is reduced to 0° C. 1.08 ml of benzenesulfonyl chloride are then added dropwise. The medium is stirred for 30 minutes at 0° C. and then 16 hours at ambient temperature. The medium is treated with 40 ml of distilled water and then the insoluble material is filtered off and the aqueous phase is extracted with 50 ml of dichloromethane. The pooled organic phases are washed with a saturated sodium chloride solution and dried over magnesium sulfate. After evaporation of the solvent, the reaction crude is purified by flash chromatography (eluent: 98/2 dichloromethane/methanol; Rf=0.33). 2 g of a white solid are collected, which are dissolved in 50 ml of dichloromethane, and then 2.08 ml of triethylamine and 153 mg of 4-dimethylaminopyridine are added. The temperature of the medium is reduced to 0° C. A solution of 3.27 g of di-tert-butyl dicarbonate in 15 ml of dichloromethane is then added dropwise. The medium is stirred for 10 minutes at 0° C. and then for 5 hours at ambient temperature. The solvent is evaporated off and the crude is purified by flash chromatography (eluent=dichloromethane; Rf=0.26). 3 g of tert-butyl 3-iodo-5-(N-tert-butoxycarbonylbenzenesulfonylamino)indazole-1-carboxylate are collected in the form of a white solid melting at 166-168° C. (LC/MS analysis: Tr=4.39 minutes; [M+H]+=600.01; [M+H]+-tert-butyl=543.97).

EXAMPLE 83

2-Methylsulfonyl-N-(3-phenylamino-1H-indazol-5-yl)-benzenesulfonamide

2-Methylsulfonyl-N-(3-phenylamino-1H-indazol-5-yl)benzenesulfonamide can be obtained in the following way: the compound is prepared by reacting under microwave radiation on a Personal Chemistry Emrys Optimizer device. Four identical reactions are carried out. Each reaction is prepared as follows: 60 mg of tert-butyl 3-iodo-5-(N-tert-butoxycarbonyl-2-methylsulfonylbenzenesulfonylamino)-indazole-1-carboxylate are placed in a Personal Chemistry SmithProcessVial™ tube with a maximum volume of 5 ml. 404 mg of cesium carbonate, 35.9 mg of 2-dicyclohexylphosphino-2'-(N,N-dimethylamino)biphenyl, 12.1 mg of tris(dibenzylideneacetone)dipalladium[0] and 29 μl of aniline are then added. 4 ml of 1,2-dimethoxyethane are then added. The tube is sealed with the stopper provided for this purpose and the reaction is subjected to microwave radiation for 5 minutes at 120° C. The other parameters are those recommended by the constructor. The catalyst is filtered through Celite® 535 and the four reaction crudes are pooled, concentrated to dryness under reduced pressure in the rotary evaporator and purified by preparative LC/MS (conditions A). The fractions containing the protected intermediate compound are pooled and concentrated under reduced pressure. The yellow oil obtained is dissolved in 2 ml of dichloromethane and then 500 μl of trifluoroacetic acid are added. The solution is stirred for 2 hours at ambient temperature, until the starting product has disappeared. 10 ml of dichloromethane and 10 ml of a saturated sodium hydrogencarbonate solution are then added. When no more gas is being given off, the organic phase is dried over magnesium sulfate and the solvent is concentrated to dryness under reduced pressure and a rotary evaporator. 18.6 mg of 2-methylsulfonyl-N-(3-phenylamino-1H-indazol-5-yl)benzenesulfonamide are obtained in the form of a yellow oil (analytical LC/MS analysis: Tr=3.49 minutes; [M+H]+=443.09).

EXAMPLE 84

N-[3-(1H-Indol-2-yl)-1H-indazol-5-yl]-2-trifluoromethoxybenzenesulfonamide

N-[3-(1H-Indol-2-yl)-1H-indazol-5-yl]-2-trifluoromethoxybenzenesulfonamide can be obtained in the following way: 213.3 mg N-tert-butoxycarbonylindole-2-boronic acid in dimer form and 243 μl of a saturated sodium hydrogencarbonate solution and then 63.4 mg of tetrakis(triphenylphosphine)palladium[0] are added to a solution of 150 mg of tert-butyl 3-iodo-5-(N-tert-butoxycarbonyl-2-trifluoromethoxybenzenesulfonylamino)indazolecarboxylate in 4.5 ml of dimethylformamide. The suspension is heated in the region of 120° C. for 18 hours. After cooling to a temperature in the region of 20° C., the catalyst is filtered through sintered glass with Celite® 535, and the filtrate is concentrated to dryness under reduced pressure in a rotary evaporator. The reaction crude is purified by preparative HPLC chromatography coupled to a mass detector (LC/MS, conditions A). The fractions containing the expected product are pooled and concentrated, and then the base is released from the trifluoroacetate salt by being taken up in 10 ml of dichloromethane and washed with 10 ml of a saturated sodium hydrogencarbonate solution. The organic phase is dried over magnesium sulfate, filtered and concentrated to dryness under reduced pressure. 60.5 mg of N-[3-(1H-indol-2-yl)-1H-indazol-5-yl]-2-trifluoromethoxy-benzenesulfonamide are thus obtained in the form of a white solid melting at 172-174° C. (analytical LC/MS analysis: Tr=3.73 minutes; [M+H]+=473.07).

tert-Butyl 3-iodo-5-(N-tert-butoxycarbonyl-2-trifluoromethoxybenzenesulfonylamino)indazolecarboxylate can be prepared as described in Example 82 from 2 g of 5-amino-3-iodo-1H-indazole and 2.21 g of 3-trifluoromethoxybenzenesulfonyl chloride. The intermediate compound is purified by flash chromatography (eluent 99/1 dichloromethane/methanol; Rf=0.5). The pale yellow powder obtained (1.85 g) is then treated with 2.5 g of di-tert-butyl dicarbonate according to the procedure described. After purification by flash chromatography (eluent=dichloromethane; Rf=0.3), 2.31 g of tert-butyl 3-iodo-5-(N-tert-butoxycarbonyl-2-trifluoromethoxybenzenesulfonylamino)-indazolecarboxylate are collected in the form of a white solid melting at 110° C. (LC/MS analysis: Tr=4.52 minutes; [M+H]+=683.97; [M+H]+-tert-butyl=627.93).

EXAMPLE 85

3-Fluoro-N-[3-(1H-indol-2-yl)-1H-indazol-5-yl]benzenesulfonamide

3-Fluoro-N-[3-(1H-indol-2-yl)-1H-indazol-5-yl]benzenesulfonamide can be prepared in the following way: 236 mg of N-tert-butoxycarbonylindole-2-boronic acid in dimer form, 70.2 mg of tetrakis(triphenylphosphine)palladium[0] and 290 μl of a saturated sodium hydrogencarbonate solution are added to a solution of 150 mg of tert-butyl 3-iodo-5-(N-tert-butoxycarbonyl-3-fluorobenzenesulfonylamino)-1H-indazolecarboxylate in 5 ml of dimethylformamide. The medium is heated in the region of 120° C. for 15 hours. The catalyst is filtered through Celite® 535 and then, after evaporation of the solvent, the crude is purified by preparative LC/MS (conditions A). The fractions containing the expected product are concentrated and the product obtained is then dissolved in 3 ml of dichloromethane and then neutralized with 3 ml of a saturated sodium hydrogencarbonate solution. The organic phase is dried over magnesium sulfate, filtered and concentrated to dryness under reduced pressure. 45.9 mg of 3-fluoro-N-[3-(1H-indol-2-yl)-1H-indazol-5-yl]benzenesulfonamide are collected in the form of a black solid which decomposes at 134° C. (LC/MS analysis: Tr=3.56 minutes; [M+H]+=407.13).

EXAMPLE 86

4-Dimethylamino-2,3,5,6-tetrafluoro-N-[3-(1H-indol-2-yl)-1H-indazol-5-yl]benzenesulfonamide 4-Dimethylamino-2,3,5,6-tetrafluoro-N-[3-(1H-indol-2-yl)-1H-indazol-5-yl]-benzenesulfonamide can be prepared as follows: 211.5 mg of N-tert-butoxycarbonylindole-2-boronic acid in dimer form, 62.8 mg of tetrakis(triphenylphosphine)palladium[0] and 240 μl of a saturated sodium hydrogencarbonate solution are added to a solution of 150 mg of tert-butyl 3-iodo-5-(N-tert-butoxycarbonyl-2,3,4,5,6-pentafluorobenzenesulfonylamino)-indazolecarboxylate in 4.5 ml of dimethylformamide. The medium is heated in the region of 120° C. for 15 hours. The catalyst is filtered through Celite® 535 and then, after evaporation of the solvent, the crude is purified by preparative LC/MS (conditions A). The fractions containing the expected product are concentrated and the product obtained is then dissolved in 3 ml of dichloromethane then neutralized with 3 ml of a saturated hydrogencarbonate solution. The organic phase is dried over magnesium sulfate, filtered and concentrated to dryness under reduced pressure. 10.6 mg of 4-dimethylamino-2,3,5,6-tetrafluoro-N-[3-(1H-indol-2-yl)-1H-indazol-5-yl]benzenesulfonamide are collected in the form of a yellow oil (LC/MS analysis: Tr: 3.80 minutes; [M+H]+=504.09).

tert-Butyl 3-iodo-5-(N-tert-butoxycarbonyl-2,3,4,5,6-pentafluorobenzenesulfonylamino)indazolecarboxylate can be prepared as described in Example 85 using 2 g of 5-amino- 3-iodo-1H-indazole and 1.13 ml of pentafluorobenzenesulfonyl chloride. 1.77 g of an orangey solid, obtained by purification by flash chromatography (eluent 98/2 by volume dichloromethane/methanol), are obtained. This compound is then treated with 1.89 g of di-tert-butyl dicarbonate according to the procedure described in Example 82. The reaction crude is purified by flash chromatography (dichloromethane; Rf=0.63). 800 mg of tert-butyl 3-iodo-5-(N-tert-butoxycarbonyl-2,3,4,5,6-pentafluorobenzenesulfonylamino)indazolecarboxylate are collected in the form of a pinkish solid.

$^1$H N.M.R. (300 MHz, (CD$_3$)$_2$SO d6, δ in ppm), 1.36 (s, 9H); 1.69 (s, 9H); 7.61 (d, J=2 Hz, 1H); 7.70 (dd, J=9 and 2 Hz; 1H); 8.20 (d, J=9 Hz, 1H).

EXAMPLE 87

{N-[3-(1H-indol-2-yl)-1H-indazol-5-yl]}thiophene-2-sulfonamide

{N-[3-(1H-Indol-2-yl)-1H-indazol-5-yl]}thiophene-2-sulfonamide can be prepared in the following way: 250.3 mg of N-tert-butoxycarbonylindole-2-boronic acid in dimer form, 74.3 mg of tetrakis(triphenylphosphine)palladium[0] and 290 μl of a saturated sodium hydrogencarbonate solution are added to a solution of 155.8 mg of tert-butyl 3-iodo-5-(N-tert-butoxycarbonyl-2-thiophenesulfonylamino)indazolecarboxylate in 5 ml of dimethylformamide. The medium is heated in the region of 120° C. for 15 hours. The catalyst is filtered through Celite® 535 and then, after evaporation of the solvent, the crude is purified by preparative LC/MS (conditions A). The fractions containing the expected product are concentrated to dryness under reduced pressure and the product obtained is dissolved in 3 ml of dichloromethane then neutralized with 3 ml of a saturated sodium hydrogencarbonate solution. The organic phase is dried over magnesium sulfate and the solvent is evaporated off. 24.3 mg of {N-[3-(1H-indol-2-yl)-1H-indazol-5-yl]}thiophene-2-sulfonamide are collected in the form of a beige solid which decomposes at 130° C. (analysis: LC/MS Tr: 3.46 minutes; [M+H]$^+$=395.09).

tert-Butyl 3-iodo-5-(N-tert-butoxycarbonyl-2-thiophenesulfonylamino)-indazolecarboxylate can be prepared as described in Example 85 using 2 g of 5-amino-3-iodo-1H-indazole and 1.61 g of thiophene-2-sulfonyl chloride. The intermediate crude is purified by flash chromatography (98/2 by volume dichloromethane/methanol), resulting in 2.30 g of an orangey solid, which is then treated with 3.71 g of di-tert-butyl dicarbonate according to the procedure. After purification by flash chromatography (eluent: dichloromethane), 3.15 g of tert-butyl 3-iodo-5-(N-tert-butoxycarbonyl-2-thiophenesulfonylamino)indazolecarboxylate are obtained in the form of a white solid melting at 163° C. (LC/MS analysis: Tr=4.34 minutes; [M+H]$^+$=605.93; [M+H]$^+$-tert-butyl=549.90).

EXAMPLE 88

2-Methylsulfonyl-N-(3-phenylsulfanyl-1H-indazol-5-yl)-benzenesulfonamide

2-Methylsulfonyl-N-(3-phenylsulfanyl-1H-indazol-5-yl) benzenesulfonamide can be obtained in the following way: 3.8 ml of an aqueous 5N hydrochloric acid solution are added dropwise to a suspension of 0.38 g of 2-methylsulfonyl-N-[3-phenylsulfanyl-1-(2-trimethylsilanyl-ethoxymethyl)-1H-indazol-5-yl]benzenesulfonamide in 11.5 ml of absolute ethanol. The reaction mixture is then refluxed for 30 minutes and then cooled to a temperature in the region of 20° C. 4.6 ml of an aqueous 5N sodium hydroxide solution are then added and the mixture is stirred. The mixture is then concentrated to dryness under reduced pressure (2 kPa) at a temperature in the region of 40° C. and the residue is taken up in a mixture of 30 ml of ethyl acetate and 25 ml of water. After settling out, the aqueous phase is extracted with 2 times 30 ml of ethyl acetate. The organic extracts are pooled, dried over magnesium sulfate, filtered and then concentrated to dryness under reduced pressure (2 kPa) at a temperature in the region of 30° C. The residue thus obtained is purified by chromatography under argon pressure (50 kPa), on a cartridge of 25 g of silica (particle size 20-40 μm), eluting successively with pure dichloromethane then with a dichloromethane/methanol (99/1 by volume) mixture. The fractions containing the expected product are pooled and concentrated to dryness under reduced pressure (2 kPa) at a temperature in the region of 30° C. The solid thus obtained is taken up in 2 ml of isopropanol in the presence of 3S black and dissolved under hot conditions and the mixture is filtered through paper. After cooling to a temperature in the region of 20° C., the mixture is concentrated to dryness under reduced pressure (2 kPa) at a temperature in the region of 30° C. 98 mg of 2-methylsulfonyl-N-(3-phenylsulfanyl-1H-indazol-5-yl)benzenesulfonamide in the form of a white foam melting at 195° C. (analysis C$_{20}$H$_{17}$N$_3$O$_4$S$_3$ % calculated C, 52.27; H, 3.73; N, 9.14; O, 13.93; S, 20.93. % found C, 56.52; H, 5.54; N, 7.54; S, 16.89).

2-Methylsulfonyl-N-[3-phenylsulfanyl-1-(2-trimethylsilanylethoxymethyl)-1H-indazol-5-yl]benzenesulfonamide can be obtained in the following way: 0.44 g of 2-methylsulfonylbenzenesulfonyl chloride is added to a solution, at a temperature in the region of 0° C. and under argon, of 0.61 g of 5-amino-3-phenylsulfanyl-1-(2-trimethylsilanylethoxymethyl)-1H-indazole in 10 ml of pyridine. The reaction mixture is then stirred for 1 hour at a temperature in the region of 0° C. and then 2 hours at a temperature in the region of 20° C. After filtration through sintered glass, the filtrate is diluted with a mixture of 45 ml of ethyl acetate and 30 ml of water. After settling out, the organic phase is washed with 2 times 30 ml of water. The organic extracts are pooled, dried over magnesium sulfate, filtered and then concentrated to dryness under reduced pressure (2 kPa) at a temperature in the region of 25° C. The residue thus obtained is purified by chromatography under argon pressure (50 kPa), on a cartridge of 150 g of silica (particle size 20-40 μm), eluting successively with cyclohexane/ethyl acetate (90/10; 85/15; 70/30 by volume) mixtures. The fractions containing the expected product are pooled and concentrated to dryness under reduced pressure (2 kPa) at a temperature in the region of 20° C. 0.68 g of 2-methylsulfonyl-N-[3-phenylsulfanyl-1-(2-trimethylsilanylethoxymethyl)-1H-indazol-5-yl]benzenesulfonamide is thus obtained in the form of a burgundy-colored paste (Rf=0.35, silica gel thin layer chromatography, eluent: cyclohexane/ethyl acetate (70/30 by volume)).

5-Amino-3-phenylsulfanyl-1-(2-trimethylsilanylethoxymethyl)-1H-indazole can be obtained in the following way: a solution of 0.4 g of 5-nitro-3-phenylsulfanyl-1-(2-trimethylsilanylethoxymethyl)-1H-indazole in 16 ml of ethyl acetate containing 40 mg of 10% palladium-on-charcoal is hydrogenated under a pressure of 200 kPa at a temperature in the region of 25° C. for 18 hours. After filtration of the catalyst through Celite® under argon and washing with ethyl acetate, the filtrate is concentrated to dryness under reduced pressure (2 kPa) at a temperature in the region of 25° C. 0.33 g of crude 5-amino-3-phenylsulfanyl-1-(2-trimethylsilanylethoxymethyl)-1H-indazole is thus obtained in the form of a burgundy-colored oil. A second attempt using 1.1 g of 5-nitro-3-phenylsulfanyl-1-(2-trimethylsilanylethoxymethyl)-1H- indazole makes it possible to obtain, in the same way, 0.99 g of crude 5-amino-3-phenylsulfanyl-1-(2-trimethylsilanylethoxymethyl)-1H-indazole in the form of a burgundy-colored oil. The two crude products are pooled and purified by chromatography under argon pressure (50 kPa), on a column of 53 g of silica (particle size 40-63 µm), eluting successively with pure cyclohexane then with cyclohexane/ethyl acetate (97/3; 95/5; 90/10; 80/20 by volume) mixtures. The fractions containing the expected product are pooled and concentrated to dryness under reduced pressure (2 kPa) at a temperature in the region of 30° C. 0.78 g of 5-amino-3-phenylsulfanyl-1-(2-trimethylsilanylethoxymethyl)-1H-indazole is thus obtained in the form of a burgundy-colored oil (EI mass analysis: m/z 371 (M$^+$) (base peak)).

5-Nitro-3-phenylsulfanyl-1-(2-trimethylsilanylethoxymethyl)-1H-indazole can be obtained in the following way: 2 g of 3-iodo-5-nitro-1-(2-trimethylsilanylethoxymethyl)-1H-indazole and then 0.88 g of sodium thiophenate are added to a solution, under argon, of 0.11 g of palladium acetate, of 0.36 g of (R)-(+)-2,2'-bis(di-p-tolylphosphino)-1,1'-binaphthyl and of 0.64 g of sodium tert-butoxide in 40 ml of toluene. The reaction mixture is heated at a temperature in the region of 80° C. for 21 hours, and is then cooled to a temperature in the region of 20° C. After dilution with 100 ml of ethyl acetate and 80 ml of water and then settling out, the aqueous phase is extracted with 100 ml of ethyl acetate. The organic extracts are pooled, washed with 60 ml of a saturated aqueous sodium chloride solution, dried over magnesium sulfate, filtered and then concentrated to dryness under reduced pressure (2 kPa) at a temperature in the region of 25° C. The residue thus obtained is filtered through silica (particle size 15-35 µm), eluting with pure dichloromethane. The filtrate is concentrated to dryness under reduced pressure (2 kPa) at a temperature in the region of 20° C. The residue is purified by chromatography under argon pressure (50 kPa), on a column of 80 g of silica (particle size 40-63 µm), eluting successively with pure cyclohexane then with cyclohexane/ethyl acetate (95/5; 90/10 by volume) mixtures. The fractions containing the expected product are pooled and concentrated to dryness under reduced pressure (2 kPa) at a temperature in the region of 25° C. 1.08 g of 5-nitro-3-phenylsulfanyl-1-(2-trimethylsilanylethoxymethyl)-1H-indazole are thus obtained in the form of an orange oil (Rf=0.35, silica gel thin layer chromatography, eluent: cyclohexane/ethyl acetate (80/20 by volume)).

3-Iodo-5-nitro-1-(2-trimethylsilanylethoxymethyl)-1H-indazole can be obtained in the following way: 30 g of potassium hydroxide pellets are added to 30 ml of water at a temperature in the region of 0° C. After complete dissolution, 7 g of 3-iodo-5-nitro-1H-indazole, 50 ml of dichloromethane and then 82 mg of tetrabutylammonium bromide are added. The reaction mixture is stirred at a temperature in the region of 0° C. and 5 ml of 2-(trimethylsilyl)ethoxymethyl chloride are added over 15 minutes. The reaction mixture is stirred at a temperature in the region of 0° C. for 1.5 hours, and then 150 ml of water are added and the mixture is reheated to a temperature in the region of 20° C. After settling out, the aqueous phase is extracted with 2 times 70 ml of dichloromethane. The organic extracts are pooled, washed with 2 times 70 ml of water, dried over magnesium sulfate, filtered and then concentrated to dryness under reduced pressure (2 kPa) at a temperature in the region of 25° C. The residue thus obtained is dissolved in 40 ml of hot diisopropyl ether, filtered under hot conditions through paper and then recrystallized. The crystals are filtered through sintered glass, washed with 2 times 10 ml of diisopropyl ether and then dried under reduced pressure (2 kPa) at a temperature in the region of 20° C. 4.6 g of 3-iodo-5-nitro-1-(2-trimethylsilanylethoxymethyl)-1H-indazole are thus obtained in the form of a yellow solid (Rf=0.4, silica gel thin layer chromatography, eluent: cyclohexane/ethyl acetate (80/20 by volume)).

EXAMPLE 89

2-Methylsulfonyl-N-(3-phenylethynyl-1H-indazol-5-yl)-benzenesulfonamide

2-Methylsulfonyl-N-(3-phenylethynyl-1H-indazol-5-yl)benzenesulfonamide can be obtained in the following way: 0.23 g of 2-methylsulfonylbenzenesulfonyl chloride is added to a solution, at a temperature in the region of 0° C. and under argon, of 0.2 g of 5-amino-3-phenylethynyl-1H-indazole in 3.5 ml of pyridine. The reaction mixture is then stirred for 1.5 hours at 0° C. and then 2 hours at a temperature in the region of 20° C., and is then diluted with 10 ml of water. After settling out, the aqueous phase is washed with 3 times 15 ml of ethyl acetate. The organic extracts are pooled, washed with 3 times 5 ml of water, dried over magnesium sulfate, filtered and then concentrated to dryness under reduced pressure (2 kPa) at a temperature in the region of 20° C. The residue thus obtained is purified by chromatography under argon pressure (50 kPa), on a cartridge of 25 g of silica (particle size 20-40 µm), eluting with pure dichloromethane then successively with dichloromethane/methanol (99.5/0.5; 99/1 by volume) mixtures. The fractions containing the expected product are pooled and concentrated to dryness under reduced pressure (2 kPa) at a temperature in the region of 20° C. The residue is recrystallized from 5 ml of isopropanol in the presence of 3S black. The crystals are filtered through sintered glass, washed with diisopropyl ether, partially dried, and then dried under reduced pressure (3 kPa) at a temperature in the region of 50° C. for 2 hours. 66 mg of 2-methylsulfonyl-N-(3-phenylethynyl-1H-indazol-5-yl)benzenesulfonamide are obtained in the form of an off-white powder melting at 198° C. (analysis $C_{22}H_{17}N_3O_4S_2$ % calculated C, 58.52; H, 3.79; N, 9.31; O, 14.17; S, 14.20. % found C, 58.37; H, 3.88; N, 9.11; S, 13.73).

5-Amino-3-phenylethynyl-1-(2-trimethylsilanylethoxymethyl)-1H-indazole can be obtained in the following way: 18 ml of water, 0.2 ml of an aqueous 12N hydrochloric acid solution and 0.36 g of powdered iron are added to a solution of 0.84 g of 5-nitro-3-phenylethynyl-1-(2-trimethylsilanylethoxymethyl)-1H-indazole in 15 ml of absolute ethanol, at the reflux temperature of the solvent. The reaction mixture is then stirred at the reflux of the solvent for 4 hours, and is then cooled to a temperature in the region of 20° C. After filtration through Celite® and washing with absolute ethanol, the filtrate is concentrated to dryness under reduced pressure (2 kPa) at a temperature in the region of 35° C. The residue thus obtained is purified by chromatography under argon pressure (50 kPa), on a column of 60 g of silica (particle size 40-63 µm), eluting successively with cyclohexane/ethyl acetate (95/5; 90/10; 80/20; 70/30; 60/40; 50/50; 30/70 by volume) mixtures, and then with pure ethyl acetate and, finally, with pure ethanol. The fractions containing the expected product are pooled and concentrated to dryness under reduced pressure (2 kPa) at a temperature in the region of 35° C. 0.11 g of 5-amino-3-phenylethynyl-1-(2-trimethylsilanylethoxymethyl)-1H-indazole is thus obtained in the form of a brown oil (Rf=0.47, silica gel thin layer chromatography, eluent: cyclohexane/ethyl acetate (60/40 by volume)). 0.2 g of 5-amino-3-phenylethynyl-1H-indazole is also obtained in the form of a brown oil (Rf=0.17, silica gel thin layer chromatography, eluent: cyclohexane/ethyl acetate (60/40 by volume)).

5-Nitro-3-phenylethynyl-1-(2-trimethylsilanylethoxymethyl)-1H-indazole can be obtained in the following way: 0.16 g of triphenylphosphine, 0.54 g of tetrakis(triphenylphosphine)palladium(0) and 0.27 g of copper iodide are added to a solution, under argon, of 3 g of 3-iodo-5-nitro-1-(2-trimethylsilanylethoxymethyl)-1H-indazole in 200 ml of acetonitrile. After stirring for 10 minutes, 1.57 ml of phenylacetylene and 2 ml of triethylamine are added, and the reaction mixture is then refluxed for 16 hours. After cooling to a temperature in the region of 20° C., the reaction mixture is concentrated to dryness under reduced pressure (2 kPa) at a temperature in the region of 35° C. The residue is taken up in 150 ml of dichloromethane and then washed with 2 times 120 ml of water. The aqueous phases are pooled and extracted with 100 ml of dichloromethane. The organic extracts are pooled, dried over magnesium sulfate, filtered and then concentrated to dryness under reduced pressure (2 kPa) at a temperature in the region of 30° C. The residue is purified by chromatography under argon pressure (50 kPa), on a column of 200 g of silica (particle size 40-63 µm), eluting successively with pure cyclohexane then with cyclohexane/ethyl acetate (98/2; 97/3; 95/5; 90/10 by volume) mixtures. The fractions containing the expected product are pooled and concentrated to dryness under reduced pressure (2 kPa) at a temperature in the region of 35° C. 2.31 g of 5-nitro-3-phenylethynyl-1-(2-trimethylsilanylethoxymethyl)-1H-indazole are thus obtained in the form of a brown solid melting at 88° C.

EXAMPLE 90

2-Methylsulfonyl-N-(3-phenethyl-1H-indazol-5-yl)benzenesulfonamide

2-Methylsulfonyl-N-(3-phenethyl-1H-indazol-5-yl)benzenesulfonamide can be obtained in the following way: 5.6 ml of an aqueous 5N hydrochloric acid solution are added dropwise to a suspension of 0.56 g of 2-methylsulfonyl-N-[3-phenethyl-1-(2-trimethylsilanylethoxymethyl)-1H-indazol-5-yl]benzenesulfonamide in 17 ml of absolute ethanol. The reaction mixture is then refluxed for 30 minutes and then cooled to a temperature in the region of 20° C. 6.8 ml of an aqueous 5N sodium hydroxide solution are then added and the mixture is stirred. The mixture is then concentrated to dryness under reduced pressure (2 kPa) at a temperature in the region of 40° C. and the residue is taken up in a mixture of 35 ml of ethyl acetate and of 50 ml of water. After settling out, the aqueous phase is extracted with 2 times 30 ml of ethyl acetate. The organic extracts are pooled, washed with 2 times 20 ml of a saturated aqueous sodium chloride solution, dried over magnesium sulfate, filtered and then concentrated to dryness under reduced pressure (2 kPa) at a temperature in the region of 30° C. The residue thus obtained is purified by chromatography under argon pressure (50 kPa) on a column of 75 g of silica (particle size 40-63 µm), eluting with a dichloromethane/methanol (98/2 by volume) mixture. The fractions containing the expected product are pooled and concentrated to dryness under reduced pressure (2 kPa) at a temperature in the region of 30° C. The residue thus obtained is repurified by chromatography under argon pressure (50 kPa), on a column of silica (particle size 40-63 µm), eluting with a cyclohexane/ethyl acetate (70/30 by volume) mixture. The fractions containing the expected product are pooled and concentrated to dryness under reduced pressure (2 kPa) at a temperature in the region of 30° C. The residue thus obtained is taken up in 15 ml of diisopropyl ether, triturated, filtered and then dried. 130 mg of 2-methylsulfonyl-N-(3-phenethyl-1H-indazol-5-yl)benzenesulfonamide are thus obtained in the form of a white solid melting at 192° C. (CI mass analysis: m/z 456 (M+H)$^+$).

2-Methylsulfonyl-N-[3-phenethyl-1-(2-trimethylsilanylethoxymethyl)-1H-indazol-5-yl]benzenesulfonamide can be obtained in the following way: 0.6 g 2-methylsulfonylbenzenesulfonyl chloride is added portionwise to a solution, at a temperature in the region of 0° C. and under argon, of 0.83 g of 5-amino-3-phenethyl-1-(2-trimethylsilanyl-ethoxymethyl)-1H-indazole in 13 ml of pyridine. The reaction mixture is then stirred for 0.5 hours at a temperature in the region of 0° C. then 2 hours at a temperature in the region of 20° C., and is then diluted with 13 ml of water. After settling out, the aqueous phase is extracted with 3 times 30 ml of ethyl acetate. The organic extracts are pooled, washed with 2 times 15 ml of a saturated aqueous sodium chloride solution, dried over magnesium sulfate, filtered and then concentrated to dryness under reduced pressure (2 kPa) at a temperature in the region of 40° C. The residue thus obtained is purified by chromatography under argon pressure (50 kPa), on a cartridge of 70 g of silica (particle size 20-40 µm), eluting successively with pure cyclohexane then with a cyclohexane/ethyl acetate (80/20 by volume) mixture. The fractions containing the expected product are pooled and concentrated to dryness under reduced pressure (2 kPa) at a temperature in the region of 25° C. 0.56 g of 2-methylsulfonyl-N-[3-phenethyl-1-(2-trimethylsilanylethoxymethyl)-1H-indazol-5-yl]benzenesulfonamide are obtained in the form of a brown-colored paste (Rf=0.32, silica gel thin layer chromatography, eluent: cyclohexane/ethyl acetate (70/30 by volume)).

5-Amino-3-phenethyl-1-(2-trimethylsilanylethoxymethyl)-1H-indazole can be obtained in the following way: a solution of 0.9 g of 5-amino-3-phenylethynyl-1-(2-trimethylsilanylethoxymethyl)-1H-indazole in a mixture of 50 ml of absolute ethanol and of 2 ml of water containing 100 mg of 10% palladium-on-charcoal is hydrogenated under a pressure of 1000 kPa at a temperature in the region of 25° C. for 21.5 hours. After filtration of the catalyst through Celite® under argon and washing with ethanol, the filtrate is concentrated to dryness under reduced pressure (2 kPa) at a temperature in the region of 40° C. 0.83 g of crude 5-amino-3-phenethyl-1-(2-trimethylsilanylethoxymethyl)-1H-indazole is thus obtained in the form of a brown-colored oil (CI mass analysis: m/z 368 (M+H)$^+$).

EXAMPLE 91

2-Methylsulfonyl-N-[3-(3-trimethylsilanylethynylphenyl)-1H-indazol-5-yl]benzenesulfonamide 2-Methylsulfonyl-N-[3-(3-trimethylsilanylethynylphenyl)-1H-indazol-5-yl]benzenesulfonamide can be obtained in the following way: 0.28 g of trimethylsilylacetylene, 0.06 g of copper iodide, 0.03 g of triphenylphosphine, 0.11 g of tetrakis(triphenylphosphine)palladium(0) and 0.29 g of triethylamine are added successively to a solution, under argon, of 0.73 g of N-[3-(3-bromophenyl)-1H-indazol-5-yl]-2-methylsulfonylbenzenesulfonamide in 45 ml of acetonitrile. The reaction mixture is refluxed for 16 hours. After cooling to a temperature in the region of 20° C., 100 ml of water are added to the reaction mixture, which is allowed to settle out. The aqueous phase is extracted with 100 ml of ethyl acetate. The organic extracts are pooled, dried over magnesium sulfate, filtered and then concentrated to dryness under reduced pressure (2 kPa) at a temperature in the region of 40° C. The residue is purified by chromatography on a silica column (particle size 40-63 µm), eluting with pure dichloromethane. The fractions containing the expected product are pooled and concentrated to dryness under reduced pressure (2 kPa) at a temperature in the region of 40° C. The residue is repurified by HPLC chromatography/MS, on a C18 grafted silica column of the X Terra™ type (particle size 5 µm; length×diameter=100×30 mm), eluting with an acetonitrile/water (65/35 by volume) mixture at a flow rate of 20 ml/min. The fractions containing the expected product are pooled and concentrated to dryness under reduced pressure (2 kPa) at a temperature in the region of 40° C. The residue is taken up in 20 ml of ethyl acetate and recrystallized in the presence of 3S black and magnesium sulfate. The crystals are filtered off through sintered glass, washed, partially dried and then dried. 0.05 g of 2-methylsulfonyl-N-[3-(3-trimethylsilanylethynylphenyl)-1H-indazol-5-yl]-benzenesulfonamide is thus obtained in the form of a white crystalline solid melting at 110° C. (analysis LC/MS Tr: 4.25 minutes; [M+.]=523).

N-[3-(3-Bromophenyl)-1H-indazol-5-yl]-2-methylsulfonylbenzenesulfonamide can be obtained in the follow way: 1.6 g of (3-bromophenyl)boronic acid, 8.7 ml of a saturated aqueous sodium hydrogencarbonate solution and 0.11 g of tetrakis(triphenylphosphine)palladium[0] are added successively to a suspension, maintained under an atmosphere of argon, of 2.3 g of tert-butyl 3-iodo-5-(2-methylsulfonylbenzenesulfonylamino)indazole-1-carboxylate in 90 ml of dimethylformamide. The reaction mixture is refluxed for 5 hours. After cooling to a temperature in the region of 20° C., the reaction mixture is hydrolyzed with 200 ml of water and extracted with 200 ml and then 100 ml of ethyl acetate. The pooled organic extracts are dried over magnesium sulfate, filtered and then concentrated to dryness under reduced pressure (2 kPa) at a temperature in the region of 40° C. The brown oil thus obtained is purified by chromatography on a silica column (particle size 63-200 µm), eluting with a dichloromethane/methanol (99/1 by volume) mixture. The fractions containing the expected product are pooled and concentrated to dryness under reduced pressure (2 kPa) at a temperature in the region of 40° C. 1.4 g of N-[3-(3-bromophenyl)-1H-indazol-5-yl]-2-methylsulfonylbenzenesulfonamide are obtained in the form of a yellow lac. This product is repurified by chromatography on a silica column (particle size 63-200 µm), with pure dichloromethane as eluent. The fractions containing the expected product are pooled and concentrated to dryness under reduced pressure (2 kPa) at a temperature in the region of 40° C. 0.73 g of N-[3-(3-bromophenyl)-1H-indazol-5-yl]-2-methylsulfonylbenzenesulfonamide are obtained in the form of a white foam melting at 104° C.

EXAMPLE 92

2-Methylsulfonyl-N-(6-methyl-3-phenyl-1H-indazol-5-yl)-benzenesulfonamide

2-Methylsulfonyl-N-(6-methyl-3-phenyl-1H-indazol-5-yl)benzenesulfonamide can be obtained in the following way: 0.45 g of 2-methylsulfonylbenzenesulfonyl chloride is added to a solution, at a temperature in the region of 0° C. and under argon, of 0.4 g of 5-amino-6-methyl-3-phenyl-1H-indazole in 35 ml of pyridine. The reaction mixture is then stirred for 10 minutes at a temperature in the region of 0° C. then 16 hours at a temperature in the region of 20° C., and is then diluted with 50 ml of water. After settling out, the aqueous phase is extracted with 50 ml and then 25 ml of ethyl acetate. The organic extracts are pooled, dried over magnesium sulfate, filtered and then concentrated to dryness under reduced pressure (2 kPa) at a temperature in the region of 40° C. The residue thus obtained is purified by chromatography on a silica column (particle size 63-200 µm), eluting with a dichloromethane/methanol (99/1 by volume) mixture. The fractions containing the expected product are pooled and concentrated to dryness under reduced pressure (2 kPa) at a temperature in the region of 40° C. The residue is taken up and recrystallized from 20 ml of diethyl ether. The crystals are filtered off through sintered glass, washed with 2 times 10 ml of diisopropyl ether, partially dried and then dried under reduced pressure (3 kPa) at a temperature in the region of 50° C. 0.27 g of 2-methylsulfonyl-N-(6-methyl-3-phenyl-1H-indazol-5-yl)benzenesulfonamide are obtained in the form of a beige powder melting at 239° C. (analysis $C_{21}H_{19}N_3O_4S_2$ % calculated C, 57.13; H, 4.34; N, 9.52; O, 14.49; S, 14.52. % found C, 56.66; H, 4.52; N, 9.41; S, 14.15).

5-Amino-6-methyl-3-phenyl-1H-indazole can be obtained in the following way: 0.5 ml of water and 0.18 ml of an aqueous 12N hydrochloric acid solution are added to a solution of 0.53 g of 6-methyl-5-nitro-3-phenyl-1H-indazole in 30 ml of ethanol. The reaction mixture is then heated at the reflux of the solvent and 0.36 g of powdered iron are added in 2 steps. The reaction mixture is then stirred at the reflux of the solvent for 4.5 hours and is then cooled to a temperature in the region of 20° C. and treated with 50 ml of ice-cold water. The mixture is then basified with an aqueous 32% ammonium hydroxide solution, to a pH in the region of 11. After settling out, the aqueous phase is extracted with one times 50 ml then 2 times 25 ml of ethyl acetate. The organic extracts are pooled, dried over magnesium sulfate, filtered and then concentrated to dryness under reduced pressure (2 kPa) at a temperature in the region of 40° C. The residue thus obtained is purified by chromatography on a silica column (particle size 63-200 µm), eluting with a cyclohexane/ethyl acetate (75/25 by volume) mixture. The fractions containing the expected product are pooled and concentrated to dryness under reduced pressure (2 kPa) at a temperature in the region of 40° C. 0.4 g of 5-amino-6-methyl-3-phenyl-1H-indazole is thus obtained in the form of a beige crystalline solid melting at 133° C.

6-Methyl-5-nitro-3-phenyl-1H-indazole can be obtained in the following way: 0.43 g of potassium nitrate is added over 5 minutes to a solution, cooled to a temperature in the region of 0° C., of 0.8 g of 6-methyl-3-phenyl-1H-indazole in 8 ml of an aqueous 98% sulfuric acid solution. The reaction mixture is stirred at a temperature in the region of 0° C. for 5 minutes and is then heated at a temperature in the region of 35-40° C. for 10 minutes and again cooled to a temperature in the region of 0° C. and stirred for 1 hour. The mixture is then poured into 50 g of ice, stirred at a temperature in the region of 0° C. for 1 hour, then filtered through sintered glass. The solid obtained is washed with 3 times 30 ml of water and partially dried and is then redissolved in 100 ml of ethyl acetate and the mixture is dried over magnesium sulfate, filtered and then concentrated to dryness under reduced pressure (2 kPa) at a temperature in the region of 40° C. The residue thus obtained is purified by chromatography on a silica column (particle size 40-63 µm), eluting successively with cyclohexane/ethyl acetate (90/10; 80/20 by volume) mixtures. The fractions containing the expected product are pooled and concentrated to dryness under reduced pressure (2 kPa) at a temperature in the region of 40° C. 0.46 g of 6-methyl-5-nitro-3-phenyl-1H-indazole is thus obtained in the form of a yellow crystalline solid melting at 164° C.

6-Methyl-3-phenyl-1H-indazole can be obtained as described in Example 1, by iodination of 6-methyl-1H-indazole followed by a reaction of the Suzuki type as described in Example 4. 6-Methyl-1H-indazole can be prepared according to J. Heterocycl. Chem. 1984, 21(4), 1063.

EXAMPLE 93

5-Fluoro-2-methylsulfonyl-N-(3-phenyl-1H-indazol-5-yl)-benzenesulfonamide

5-Fluoro-2-methylsulfonyl-N-(3-phenyl-1H-indazol-5-yl)benzenesulfonamide can be prepared as described in Example 2 from 0.52 g of 5-amino-3-phenyl-1H-indazole, 5 ml of pyridine and 0.68 g of 5-fluoro-2-methylsulfonylbenzenesulfonyl chloride. The residue obtained is purified by chromatography on a column of 50 g of silica (particle size 40-63 μm), eluting with pure dichloromethane. After recrystallization from 5 ml of acetonitrile and washing with acetonitrile and then with diisopropyl ether, 0.07 g of 5-fluoro-2-methylsulfonyl-N-(3-phenyl-1H-indazol-5-yl)benzenesulfonamide is obtained in the form of a white solid melting at 224° C. (analysis: $C_{20}H_{16}FN_3O_4S_2$, % calculated C, 53.92; H, 3.62; F, 4.26; N, 9.43; O, 14.37; S, 14.40. % found C, 53.74; H, 3.31; N, 9.35; S, 14.10).

5-Fluoro-2-methylsulfonylbenzenesulfonyl chloride can be obtained in the following way: 4.2 ml of an aqueous concentrated hydrochloric acid solution are added to a solution of 1 g of 5-fluoro-2-methylsulfonylphenylamine in 3.7 ml of 100% acetic acid. The reaction mixture is cooled to a temperature in the region of −5° C., and then a solution of 0.4 g of sodium nitrate in 0.63 ml of water is added dropwise. The reaction mixture is stirred at a temperature in the region of −10° C. for 20 minutes, and is then sparged with sulfur dioxide for one hour. A solution of 0.53 g of copper(II) chloride in 0.6 ml of water is then added at a temperature in the region of −5° C., followed, 2 minutes later, by 6.9 ml of 100% acetic acid, and the sparging with sulfur dioxide is then recommenced. After 40 minutes, the sparging is stopped and the mixture is left to reheat to a temperature in the region of 20° C. and then stirred for 1.5 hours. The reaction mixture is then warmed in a water bath in order to remove the excess sulfur dioxide, and it is then concentrated to dryness under reduced pressure (2 kPa) at a temperature in the region of 40° C. 2 g of crude. 5-fluoro-2-methylsulfonylbenzenesulfonyl chloride are thus obtained in the form of an ochre solid which is used directly in the following step (Rf=0.5, silica gel thin layer chromatography, eluent: dichloromethane)).

5-Fluoro-2-methylsulfonylphenylamine can be obtained in the following way: 1.25 ml of water and 0.47 ml of an aqueous 12N hydrochloric acid solution are added to a solution of 1.2 g of 4-fluoro-1-methylsulfonyl-2-nitrobenzene in 80 ml of ethanol. The reaction mixture is then heated at the reflux of the solvent and 0.92 g of powdered iron are added portionwise. The reaction mixture is then stirred at the reflux of the solvent for 2 hours, then at a temperature in the region of 20° C. for 16 hours. It is then filtered through sintered glass and the solid is washed with ethanol. The filtrate is concentrated to dryness under reduced pressure (2 kPa) at a temperature in the region of 40° C. The residue is taken up in a mixture of water and ethyl acetate and then basified with an aqueous sodium hydrogencarbonate solution, to a pH in the region of 10, and allowed to settle out. The aqueous phase is extracted with 4 times 50 ml of ethyl acetate. The organic extracts are pooled, washed with water, dried over magnesium sulfate, treated with 3S black, filtered and then concentrated to dryness under reduced pressure (2 kPa) at a temperature in the region of 40° C. 1 g of 5-fluoro-2-methylsulfonylphenylamine is thus obtained in the form of a beige oil which crystallizes (Rf=0.33, silica gel thin layer chromatography, eluent: dichloromethane).

4-Fluoro-1-methylsulfonyl-2-nitrobenzene can be obtained in the following way: 1.3 g of 4-fluoro-1-methylsulfinyl-2-nitrobenzene in 15 ml of dichloromethane are added dropwise to a suspension, stirred at a temperature in the region of −5° C. under argon, of 1.5 g of 3-chloroperoxybenzoic acid in 15 ml of dichloromethane. The reaction mixture is then stirred at a temperature in the region of 0° C. for 30 minutes and is then left to reheat to a temperature in the region of 20° C. It is then filtered through sintered glass and the solid is washed with dichloromethane. The filtrate is washed with an aqueous sodium hydrogencarbonate solution then with water, dried over magnesium sulfate, treated with 3S black, filtered and then concentrated to dryness under reduced pressure (2 kPa) at a temperature in the region of 40° C. The residue thus obtained is purified by chromatography on a column of 125 g of silica (particle size 40-63 μm), eluting with pure dichloromethane. The fractions containing the expected product are pooled and concentrated to dryness under reduced pressure (2 kPa) at a temperature in the region of 40° C. 1.2 g of 4-fluoro-1-methylsulfonyl-2-nitrobenzene are thus obtained in the form of a yellow foam (Rf=0.43, silica gel thin layer chromatography, eluent: dichloromethane)).

4-Fluoro-1-methylsulfinyl-2-nitrobenzene can be obtained in the following way: 4.7 g of magnesium monoperoxyphthalate are added portionwise to a solution, under argon, of 1.9 g of 4-fluoro-1-methylsulfanyl-2-nitrobenzene in 6 ml of methanol and 30 ml of dichloromethane. The reaction mixture is then stirred at a temperature in the region of 20° C. for 3 hours, and is then filtered through sintered glass and the solid is washed with dichloromethane. The filtrate is washed with an aqueous sodium hydrogencarbonate solution then with water, dried over magnesium sulfate, treated with 3S black, filtered and then concentrated to dryness under reduced pressure (2 kPa) at a temperature in the region of 40° C. The residue thus obtained is purified by chromatography on a column of 125 g of silica (particle size 40-63 μm), eluting with pure dichloromethane. The fractions containing the expected product are pooled and concentrated to dryness under reduced pressure (2 kPa) at a temperature in the region of 40° C. 1.3 g of 4-fluoro-1-methylsulfinyl-2-nitrobenzene are thus obtained in the form of a yellow foam (Rf=0.23, silica gel thin layer chromatography, eluent: dichloromethane/ethyl acetate 90/10)).

4-Fluoro-1-methylsulfanyl-2-nitrobenzene can be prepared according to *J. Fluorine Chem.* 1981, 17, 233.

EXAMPLE 94

4-Amino-N-(3-phenyl-1H-indazol-5-yl)benzene-sulfonamide

4-Amino-N-(3-phenyl-1H-indazol-5-yl)benzenesulfonamide can be obtained in the following way: 1.5 ml of an aqueous 5N hydrochloric acid solution are added to a suspension of 0.3 g of N-[4-(3-phenyl-1H-indazol-5-ylsulfamoyl)-phenyl]acetamide in 6 ml of 95% ethanol. The reaction mixture is then refluxed for 30 minutes then cooled to a temperature in the region of 20° C. 20 ml of water and 1 ml of an aqueous 32% ammonium hydroxide solution are then added to the reaction mixture, which is then extracted successively with 30 ml and 15 ml of ethyl acetate. The organic extracts are pooled, dried over magnesium sulfate, filtered and then concentrated to dryness under reduced pressure (2 kPa) at a temperature in the region of 40° C. The residue thus obtained is purified by chromatography on a silica column (particle size 40-63 μm), eluting with a dichloromethane/methanol (95/5 by volume) mixture. The fractions containing the expected product are pooled and concentrated to dryness under reduced pressure (2 kPa) at a temperature in the region of 40° C. The solid thus obtained is taken up in 9 ml of ethanol in the presence of 3S black and dissolved under hot conditions, and the mixture is filtered under hot conditions through sintered glass and then recrystallized. The crystals are filtered off through sintered glass, washed with 0.5 ml of 95% ethanol then with 2 times 2 ml of diisopropyl ether, partially dried and then dried under reduced pressure (3 kPa) at a temperature in the region of 50° C. 70 mg of 4-amino-N-(3-phenyl-1H-indazol-5-yl)benzenesulfonamide are thus obtained in the form of a light beige powder melting at 249° C. (Cl mass analysis: m/z 365 (M+H)$^+$).

EXAMPLE 95

N-[4-(3-Phenyl-1H-indazol-5-ylsulfamoyl)phenyl]acetamide

N-[4-(3-Phenyl-1H-indazol-5-ylsulfamoyl)phenyl]acetamide can be prepared as described in Example 2 from 0.45 g of 5-amino-3-phenyl-1H-indazole, 42 ml of pyridine and 0.5 g of 4-acetylaminobenzenesulfonyl chloride. The residue obtained is purified by chromatography on a silica column (particle size 63-200 μm), eluting successively with dichloromethane/methanol (98.5/1.5; 95/5 by volume) mixtures. 0.45 g of N-[4-(3-phenyl-1H-indazol-5-ylsulfamoyl)phenyl]acetamide is thus obtained in the form of a purple crystalline solid melting at 167° C. (El mass analysis: m/z 406 (M$^+$), m/z 208 (base peak)).

EXAMPLE 96

N-(3-Phenyl-1H-indazol-5-yl)pyridine-3-sulfonamide

N-(3-Phenyl-1H-indazol-5-yl)-pyridine-3-sulfonamide can be prepared as described in Example 2 from 0.5 g of 5-amino-3-phenyl-1H-indazole, 45 ml of pyridine and 0.46 g of pyridine-3-sulfonyl chloride. The residue obtained is purified by chromatography on a silica column (particle size 40-63 μm), eluting with a dichloromethane/methanol (97.5/2.5 by volume) mixture. The solid thus obtained is taken up in 20 ml of acetonitrile in the presence of 3S black and dissolved under hot conditions, and the mixture is filtered under hot conditions through sintered glass and then recrystallized. The crystals are filtered off through sintered glass, washed with 2 times 2.5 ml of acetonitrile then 5 ml of diisopropyl ether, partially dried and then dried under reduced pressure (3 kPa) at a temperature in the region of 50° C. 0.35 g of N-(3-phenyl-1H-indazol-5-yl)pyridine-3-sulfonamide is thus obtained in the form of a white crystalline solid melting at 225° C. (analysis: $C_{18}H_{14}N_4O_2S$, % calculated C, 61.7; H, 4.03; N, 15.99; O, 9.13; S, 9.15. % found C, 61.58; H, 4.01; N, 16.16; S, 9.18).

EXAMPLE 97

3-Nitro-N-(3-phenyl-1H-indazol-5-yl)benzenesulfonamide

3-Nitro-N-(3-phenyl-1H-indazol-5-yl)benzenesulfonamide can be obtained in the following way: 0.89 g of 3-nitrobenzenesulfonyl chloride is added to a solution, at a temperature in the region of 0° C. and under argon, of 0.7 g of 5-amino-3-phenyl-1H-indazole in 15 ml of THF. The reaction mixture is cooled to a temperature in the region of 0° C., and then a solution of 0.33 ml of pyridine in 4 ml of THF is added over 10 minutes. The reaction mixture is stirred at a temperature in the region of 0° C. for 0.5 hours then at a temperature in the region of 20° C. for 3 hours. It is then diluted with 70 ml of water and 30 ml of ethyl acetate. After settling out, the organic phase is washed with 3 times 50 ml of water, dried over magnesium sulfate, filtered and then concentrated to dryness under reduced pressure (2 kPa) at a temperature in the region of 40° C. The residue thus obtained is purified by chromatography on a silica column (particle size 63-200 μm), eluting with pure dichloromethane then with a dichloromethane/methanol (98/2 by volume) mixture. The fractions containing the expected product are pooled and concentrated to dryness under reduced pressure (2 kPa) at a temperature in the region of 40° C. The residue is taken up in 20 ml isopropanol and filtered through sintered glass. The solid is washed with 10 ml of diisopropyl ether, partially dried and then dried. 0.41 g of 3-nitro-N-(3-phenyl-1H-indazol-5-yl)benzenesulfonamide is thus obtained in the form of a white powder melting at 228° C. (analysis: $C_{19}H_{14}N_4O_4S$ (0.44 $CH_2Cl_2$), % calculated C, 57.85; H, 3.58; N, 14.21; O, 16.23; S, 8.13. % found C, 57.84; H, 3.19; N, 14.22; S, 7.81).

EXAMPLE 98

3-Amino-N-(3-phenyl-1H-indazol-5-yl)benzenesulfonamide

3-Amino-N-(3-phenyl-1H-indazol-5-yl)benzenesulfonamide can be obtained in the following way: 0.06 ml of an aqueous hydrochloric acid solution is added to a solution of 0.28 g of 3-nitro-N-(3-phenyl-1H-indazol-5-yl)benzenesulfonamide in 15 ml of absolute ethanol and 0.3 ml of water. The reaction mixture is refluxed, then 0.12 g of powdered iron is added in small portions. The reaction mixture is refluxed for 2 hours and is then cooled to a temperature in the region of 20° C. 30 ml of water are added to the mixture, which is filtered through Celite®, and the solid is washed with water then ethyl acetate. The filtrate is basified with an aqueous 32% ammonium hydroxide solution to a pH in the region of 12, and is then extracted with 3 times 20 ml of ethyl acetate. The organic extracts are pooled, washed with 3 times 10 ml of water, dried over magnesium sulfate, filtered and then concentrated to dryness under reduced pressure (2 kPa) at a temperature in the region of 40° C. The solid residue is washed successively with diisopropyl ether then dichloromethane, partially dried and dried. 0.12 g of 3-amino-N-(3-phenyl-1H-indazol-5-yl)benzenesulfonamide is thus obtained in the form of an off-white powder melting at 205° C.

$^1$H N.M.R. (300 MHz, $(CD_3)_2SO$ d6, δ in ppm): 5.57 (broad s, 2H); 6.72 (broad dd, J=8.5 and 2 Hz, 1H); 6.85 (broad d, J=8.5 Hz, 1H); 6.95 (mt, 1H); 7.15 (mt, 2H); 7.43 (broad t, J=7.5 Hz, 1H); 7.49 (d, J=8.5 Hz, 1H); 7.55 (t, J=7.5 Hz, 2H); 7.61 (broad d, J=2 Hz, 1H); 7.78 (d, J=7.5 Hz, 2H); 9.95 (unresolved peak: 1H).

EXAMPLE 99

N-(3-Phenyl-1H-indazol-5-yl)cyclohexanesulfonamide

N-(3-Phenyl-1H-indazol-5-yl)cyclohexanesulfonamide can be prepared as described in Example 2 from 0.5 g of 5-amino-3-phenyl-1H-indazole, 45 ml of pyridine and 0.43 g of cyclohexylsulfonyl chloride. The residue obtained is purified by chromatography on a silica column (particle size 40-63 µm), eluting with a dichloromethane/methanol (97.5/2.5 by volume) mixture. The solid thus obtained is taken up in 40 ml of dichloromethane in the presence of 3S black and dissolved under hot conditions, and the mixture is filtered under hot conditions through sintered glass and then recrystallized. The crystals are filtered off through sintered glass, washed with 2 times 5 ml of dichloromethane then 10 ml of diisopropyl ether, partially dried and then dried under reduced pressure (3 kPa) at a temperature in the region of 50° C. 0.2 g of N-(3-phenyl-1H-indazol-5-yl)cyclohexanesulfonamide is thus obtained in the form of a white crystalline solid melting at 160° C. (EI mass analysis: m/z 355 (M+), m/z 208 (base peak)).

Cyclohexylsulfonyl chloride can be prepared according to EP 0 788 796 A1.

EXAMPLE 100

N-(3-Phenyl-1H-indazol-5-yl)-piperidine-4-sulfonamide

N-(3-Phenyl-1H-indazol-5-yl)piperidine-4-sulfonamide can be obtained in the following way: 1.89 g of ethanethiol, then 1.45 g of boron trifluoride etherate, are added dropwise to a solution, under argon, of 0.5 g of benzyl 4-(3-phenyl-1H-indazol-5-ylsulfamoyl)piperidine-1-carboxylate in 5 ml of dichloromethane. The reaction mixture is stirred at a temperature in the region of 20° C. for 16 hours and is then concentrated to dryness under reduced pressure (2 kPa) at a temperature in the region of 40° C. The residue is taken up in 10 ml of water, basified with 5 ml of an aqueous 32% ammonium hydroxide solution, and then extracted successively with 30 ml and 15 ml of ethyl acetate. The organic extracts are pooled, dried over magnesium sulfate, filtered and then concentrated to dryness under reduced pressure (2 kPa) at a temperature in the region of 40° C. The residue thus obtained is purified by chromatography on a silica column (particle size 40-63 µm), eluting successively with dichloromethane/methanol (99/1; 95/5 by volume) mixtures. The fractions containing the expected product are pooled and concentrated to dryness under reduced pressure (2 kPa) at a temperature in the region of 40° C. The residue taken up in 6 ml of acetonitrile in the presence of 3S black, and dissolved under hot conditions, and the mixture is filtered under hot conditions through sintered glass and then recrystallized. The crystals are filtered off through sintered glass, washed with 2 times 0.5 ml then 1 ml of acetonitrile, partially dried and then dried under reduced pressure (3 kPa) at a temperature in the region of 50° C. 0.04 g of N-(3-phenyl-1H-indazol-5-yl)piperidine-4-sulfonamide is thus obtained in the form of a white crystalline solid melting at 230° C. (analysis: $C_{18}H_{20}N_4O_2S$, % calculated C, 60.65; H, 5.66; N, 15.72; O, 8.98; S, 9. % found C, 60.62; H, 5.85; N, 15.39; S, 8.72).

Benzyl 4-(3-phenyl-1H-indazol-5-ylsulfamoyl)piperidine-1-carboxylate can be prepared as described in Example 2 from 0.7 g of 5-amino-3-phenyl-1H-indazole, 63 ml of pyridine and 1.2 g of benzyl 4-chlorosulfonyl-piperidine-1-carboxylate. The residue obtained is purified by chromatography on a silica column (particle size 40-63 µm), eluting with a dichloromethane/methanol (98.5/1.5 by volume) mixture. 0.5 g of benzyl 4-(3-phenyl-1H-indazol-5-ylsulfamoyl)piperidine-1-carboxylate is thus obtained in the form of an ochre crystalline solid which is used directly in the following step.

Benzyl 4-chlorosulfonyl-piperidine-1-carboxylate can be prepared according to WO 00/46221.

EXAMPLES 101-104

Preparation of a Library of

4 N-(3-aryl-1H-indazol-5-yl)-2-methylsulfonylbenzenesulfonamides;
N-[3-(3,5-bistrifluoromethylphenyl)-1H-indazol-5-yl]-2-methylsulfonylbenzenesulfonamide;
N-[3-(3,5-difluorophenyl)-1H-indazol-5-yl]-2-methylsulfonylbenzenesulfonamide;
2-methylsulfonyl-N-[3-(2-methylsulfanylphenyl)-1H-indazol-5-yl]benzenesulfonamide;
N-[3-(1H-indol-5-yl)-1H-indazol-5-yl]-2-methylsulfonylbenzenesulfonamide.

TABLE 1

Reagents used

| MDLNUMBER | Name | Empirical formula | Molecular weight |
|---|---|---|---|
| MFCD00051850 | 3,5-bis(trifluoromethyl)benzeneboronic acid | $C_8H_5BF_6O_2$ | 257.93 |
| MFCD01318138 | 3,5-difluorophenylboronic acid | $C_6H_5BF_2O_2$ | 157.91 |
| MFCD01318165 | (2-methylthio)phenylboronic acid | $C_7H_9BO_2S$ | 168.02 |
| MFCD01319013 | 5-indolylboronic acid | $C_8H_8BNO_2$ | 160.97 |

The boronic acids described above (295 µmol) are distributed in 4 filtering reactors of a Bohdan 48-well miniblock, and then a solution of 0.1 g of tert-butyl 3-iodo-5-(N-tert-butoxycarbonyl-2-methylsulfonylbenzenesulfonylamino)-indazole-1-carboxylate in 2 ml of dimethylformamide, 0.32 ml of a saturated aqueous sodium hydrogencarbonate solution and 4.3 mg of tetrakis(triphenylphosphine)palladium(0) are successively added. After closing of the reactors, the reaction mixtures thus obtained are stirred at a temperature in the region of 105° C. for 20 hours. After cooling to a temperature in the region of 20° C., the reaction mixtures are filtered and then diluted with 2 ml of ethyl acetate and 2 ml of water each, stirred and allowed to settle out. The organic phases are separated (Myriad Allex automated device) and, for each sample thus obtained, a 15 µl sample is analyzed by LC/MS, then they are concentrated to dryness under reduced pressure (Genevac HT8 centrifugal evaporator) at a temperature in the region of 40° C. The residues are dissolved in dimethyl sulfoxide so as to have concentrations of 0.1 mg/µl and the corresponding solutions are purified by LCMS (conditions B). After purification by LC/MS, the fractions containing the expected products are concentrated to dryness under reduced pressure (Genevac HT8 centrifugal evaporator) at a temperature in the region of 40° C., and the residues are weighed (Mettler Toledo Automated Workstation LA200), dissolved at a concentration of 10 mM in dimethyl sulfoxide (Zinsser) and then analyzed by LC/MS. The fractions containing the expected products having satisfactory purity are pooled and a 10 µl sample diluted in 10 µl of dimethyl sulfoxide is analyzed by LC/MS. The following compounds were isolated and characterized by their retention time (Tr) and molecular peak by mass spectrometry.

| Example | Name | PM | Formula | UV purity | Tr (min.) | Molecular ion detected |
|---|---|---|---|---|---|---|
| 101 | N-[3-(3,5-bistrifluoromethylphenyl)-1H-indazol-5-yl]-2-methylsulfonylbenzenesulfonamide | 563 | $C_{22}H_{15}F_6N_3O_4S_2$ | 96 | 4.53 | 564 |
| 102 | N-[3-(3,5-difluorophenyl)-1H-indazol-5-yl]-2-methylsulfonylbenzenesulfonamide | 463 | $C_{20}H_{15}F_2N_3O_4S_2$ | 90 | 4.08 | 464 |
| 103 | 2-methylsulfonyl-N-[3-(2-methylsulfanylphenyl)-1H-indazol-5-yl]benzenesulfonamide | 473 | $C_{21}H_{19}N_3O_4S_3$ | 91 | 3.87 | 474 |
| 104 | N-[3-(1H-indol-5-yl)-1H-indazol-5-yl]-2-methylsulfonylbenzenesulfonamide | 466 | $C_{22}H_{18}N_4O_4S_2$ | 93 | 3.66 | 467 |

EXAMPLE 105

2-Methylsulfonyl-N-(3-o-tolyl-1H-indazol-5-yl)benzenesulfonamide

2-Methylsulfonyl-N-(3-o-tolyl-1H-indazol-5-yl)benzenesulfonamide can be prepared as described in Examples 101-104 from 40.1 mg of α-tolylboronic acid (heating for 4 hours). 9.3 mg of 2-methylsulfonyl-N-(3-o-tolyl-1H-indazol-5-yl)benzenesulfonamide in solution in dimethyl sulfoxide at 10 mM are thus obtained ($C_{21}H_{19}N_3O_4S_2$; molecular weight 441.53; LC/MS analysis: UV purity: 93%; analytical Tr: 3.93 min; theoretical m/z: 441; molecular ion detected: 442).

EXAMPLES 106-159

Preparation of a Library of 54 N-(3-phenyl-1H-indazol-5-yl)sulfonamides

Preparation of 54 solutions of various sulfonyl chlorides RSO2Cl:

The 54 reagents (lines of 1 to 54 of Table 2) are weighed and then diluted in tetrahydrofuran (THF) or N-methylpyrrolidone (NMP) so as to obtain ready-to-use solutions with a titer of 0.166 mol/liter.

TABLE 2 reagents used

| | NAME | Formula | Molecular weight | Solvent |
|---|---|---|---|---|
| 1 | Naphthalene-1-sulfonyl chloride | $C_{10}H_7ClO_2S$ | 226.00 | THF |
| 2 | Dansyl chloride | $C_{12}H_{12}ClNO_2S$ | 269.75 | NMP |
| 3 | Naphthalene-2-sulfonyl chloride | $C_{10}H_7ClO_2S$ | 226.68 | THF |
| 4 | 2-Trifluoromethylbenzenesulfonyl chloride | $C_7H_4ClF_3O_2S$ | 244.62 | THF |
| 5 | Thiophene-2-sulfonyl chloride | $C_4H_3ClO_2S_2$ | 182.65 | THF |
| 6 | Quinoline-8-sulfonyl chloride | $C_9H_6ClNO_2S$ | 227.67 | NMP |
| 7 | Benzenesulfonyl chloride | $C_6H_5ClO_2S$ | 176.62 | THF |
| 8 | 2-Nitrobenzenesulfonyl chloride | $C_6H_4ClNO_4S$ | 221.62 | THF |
| 9 | 2,4,6-Triisopropylbenzenesulfonyl chloride | $C_{15}H_{23}ClO_2S$ | 302.86 | THF |
| 10 | 2-Mesitylenesulfonyl chloride | $C_9H_{11}ClO_2S$ | 218.70 | THF |
| 11 | 4-Bromobenzenesulfonyl chloride | $C_6H_4BrClO_2S$ | 255.52 | THF |
| 12 | 4-Fluorobenzenesulfonyl chloride | $C_6H_4ClFO_2S$ | 194.61 | THF |
| 13 | N-Acetylsulfanilyl chloride | $C_8H_8ClNO_3S$ | 233.67 | NMP |
| 14 | 4-Nitrobenzenesulfonyl chloride | $C_6H_4ClNO_4S$ | 221.62 | THF |
| 15 | 4-Methoxybenzenesulfonyl chloride | $C_7H_7ClO_3S$ | 206.65 | THF |
| 16 | 4-tert-Butylbenzenesulfonyl chloride | $C_{10}H_{13}ClO_2S$ | 232.73 | THF |
| 17 | 4-Methylbenzenesulfonyl chloride | $C_7H_7ClO_2S$ | 190.65 | THF |
| 18 | Isopropanesulfonyl chloride | $C_3H_7ClO_2S$ | 142.60 | THF |
| 19 | Methanesulfonyl chloride | $CH_3ClO_2S$ | 114.55 | THF |
| 20 | Phenylmethanesulfonyl chloride | $C_7H_7ClO_2S$ | 190.65 | THF |
| 21 | 2-Vinylbenzenesulfonyl chloride | $C_8H_7ClO_2S$ | 202.66 | THF |
| 22 | Ethanesulfonyl chloride | $C_2H_5ClO_2S$ | 128.58 | THF |
| 23 | 1-Propanesulfonyl chloride | $C_3H_7ClO_2S$ | 142.60 | THF |
| 24 | 1-Butanesulfonyl chloride | $C_4H_9ClO_2S$ | 156.63 | THF |
| 25 | 3-Trifluoromethylbenzenesulfonyl chloride | $C_7H_4ClF_3O_2S$ | 244.62 | THF |
| 26 | 2,5-Dimethoxybenzenesulfonyl chloride | $C_8H_9ClO_4S$ | 236.67 | THF |
| 27 | 2-Methylbenzenesulfonyl chloride | $C_7H_7ClO_2S$ | 190.65 | THF |
| 28 | 3-(Chlorosulfonyl)benzoic acid | $C_7H_5ClO_4S$ | 220.63 | THF |
| 29 | 2-Fluorobenzenesulfonyl chloride | $C_6H_4ClFO_2S$ | 194.61 | THF |
| 30 | 5-Chlorothiophene-2-sulfonyl chloride | $C_4H_2Cl_2O_2S_2$ | 217.09 | THF |
| 31 | 3-CHLOROBENZENESULFONYL CHLORIDE | $C_6H_4Cl_2O_2S$ | 211.07 | THF |
| 32 | 3,5-DICHLOROBENZENESULFONYL CHLORIDE | $C_6H_3Cl_3O_2S$ | 245.51 | THF |
| 33 | M-TOLUENESULFONYL CHLORIDE | $C_7H_7ClO_2S$ | 190.65 | THF |
| 34 | 2-BROMOBENZENESULFONYL CHLORIDE | $C_6H_4BrClO_2S$ | 255.52 | THF |

TABLE 2-continued reagents used

| | NAME | Formula | Molecular weight | Solvent |
|---|---|---|---|---|
| 35 | 2-(BENZOYLAMINOMETHYL)THIOPHENE-5-SULFONYL CHLORIDE | $C_{12}H_{10}ClNO_3S_2$ | 315.80 | THF |
| 36 | 3-BROMOBENZENESULFONYL CHLORIDE | $C_6H_4BrClO_2S$ | 255.52 | THF |
| 37 | 2-(TRIFLUOROMETHOXY)BENZENESULFONYL CHLORIDE | $C_7H_4ClF_3O_3S$ | 260.62 | THF |
| 38 | 4-CYANOBENZENESULFONYL CHLORIDE | $C_7H_4ClNO_2S$ | 201.63 | THF |
| 39 | 2-CYANOBENZENESULFONYL CHLORIDE | $C_7H_4ClNO_2S$ | 201.63 | THF |
| 40 | 4-(N-BUTOXY)BENZENESULPHONYL CHLORIDE | $C_{10}H_{13}ClO_3S$ | 248.73 | THF |
| 41 | 4-ACETAMIDO-3-CHLOROBENZENESULFONYL CHLORIDE | $C_8H_7Cl_2NO_3S$ | 268.12 | NMP |
| 42 | BANSYL CHLORIDE | $C_{18}H_{24}ClNO_2S$ | 353.91 | THF |
| 43 | (−)-CAMPHOR-10-SULFONYL CHLORIDE | $C_{10}H_{15}ClO_3S$ | 250.74 | THF |
| 44 | BENZOFURAZAN-4-SULPHONYL CHLORIDE | $C_6H_3ClN_2O_3S$ | 218.62 | THF |
| 45 | 5-(ISOXAZOL-3YL)THIOPHENE-2-SULFONYL CHLORIDE | $C_7H_4ClNO_3S_2$ | 249.69 | THF |
| 46 | 2-NITRO-ALPHA-TOLUENESULFONYL CHLORIDE | $C_7H_6ClNO_4S$ | 235.64 | THF |
| 47 | 3,4-DIFLUOROBENZENESULPHONYL CHLORIDE | $C_6H_3ClF_2O_2S$ | 212.60 | THF |
| 48 | 5-CHLORO-3-METHYLBENZO[B]THIOPHENE-2-SULFONYL CHLORIDE | $C_9H_6Cl_2O_2S_2$ | 281.18 | THF |
| 49 | 3-CYANOBENZENESULFONYL CHLORIDE | $C_7H_4ClNO_2S$ | 201.63 | THF |
| 50 | 4-METHYLSULFONYLBENZENESULFONYL CHLORIDE | $C_7H_7ClO_4S_2$ | 254.71 | THF |
| 51 | 3-METHOXYBENZENESULPHONYL CHLORIDE | $C_7H_7ClO_3S$ | 206.65 | THF |
| 52 | 3-PHENYLBENZENESULFONYLCHLORIDE | $C_{12}H_9ClO_2S$ | 252.72 | THF |
| 53 | 3,5-DIFLUOROBENZENESULFONYL CHLORIDE | $C_6H_3ClF_2O_2S$ | 212.60 | THF |
| 54 | 2-AMINO-3,5-DICHLOROPHENYLSULFONYL CHLORIDE | $C_6H_4Cl_3NO_2S$ | 260.53 | NMP |

Setting Up of the Reactions:

Using an automated laboratory device, 336 μL of pyridine are distributed in 71 filtering reactors (ACT496, Advanced Chem Tech) each containing 50 μmol of 5-amino-3-phenyl-1H-indazole in THF (1.5 ml). The reaction mixtures thus obtained are stirred and cooled to 0° C. and then 301 μL of each of the solutions of sulfonyl derivatives described above are added thereto.

While maintaining the stirring for 16 hours, the temperature is allowed to come back up to 20° C., and then the reaction media are filtered. The filtrates are evaporated to dryness, and then the evaporation residues are each taken up with 500 μl of DMSO then stirred for 1 hour. For each sample in solution in DMSO thus obtained, a 15 μL sample is analyzed by LC/MS and then the residual solutions are purified by LCMS (conditions A). After purification by LC/MS, the fractions containing the desired compounds are (optionally pooled) evaporated to dryness (Savant AES 2000 or Genevac HT8 centrifugal evaporator), weighed (Mettler Toledo Automated Workstation LA200), and diluted to 10 mM in DMSO (Zinsser Winlissy, Zinsser Analytical). Each solution obtained is analyzed by LC/MS.

The following compounds were isolated and characterized by their retention time and molecular peak in mass spectrometry.

| Example | NAME | PM | Formula | UV purity | Tr (min) | Molecular ion detected |
|---|---|---|---|---|---|---|
| 106 | N-(3-Phenyl-1H-indazol-5-yl)-naphthalene-1-sulfonamide | 399.47 | $C_{23}H_{17}N_3O_2S$ | 100 | 3.95 | 400.24 |
| 107 | 5-Dimethylamino-N-(3-phenyl-1H-indazol-5-yl)naphthalene-1-sulfonamide | 442.54 | $C_{25}H_{22}N_4O_2S$ | 92.35 | 3.75 | 443.29 |
| 108 | N-(3-Phenyl-1H-indazol-5-yl)-naphthalene-2-sulfonamide | 399.47 | $C_{23}H_{17}N_3O_2S$ | 96.48 | 3.99 | 400.25 |
| 109 | N-(3-Phenyl-1H-indazol-5-yl)-2-trifluoromethylbenzenesulfonamide | 417.41 | $C_{20}H_{14}F_3N_3O_2S$ | 100 | 3.94 | 418.22 |
| 110 | N-(3-Phenyl-1H-indazol-5-yl)-thiophene-2-sulfonamide | 355.44 | $C_{17}H_{13}N_3O_2S_2$ | 92.63 | 3.68 | 356.19 |
| 111 | N-(3-Phenyl-1H-indazol-5-yl)quinoline-8-sulfonamide | 400.46 | $C_{22}H_{16}N_4O_2S$ | 90.41 | 3.75 | 401.24 |
| 112 | N-(3-Phenyl-1H-indazol-5-yl)benzenesulfonamide | 349.41 | $C_{19}H_{15}N_3O_2S$ | 92.84 | 3.72 | 350.25 |

-continued

| Example | NAME | PM | Formula | UV purity | Tr (min) | Molecular ion detected |
|---|---|---|---|---|---|---|
| 113 | 2-Nitro-N-(3-phenyl-1H-indazol-5-yl)benzenesulfonamide | 394.41 | $C_{19}H_{14}N_4O_4S$ | 92.19 | 3.81 | 395.22 |
| 114 | 2,4,6-Triisopropyl-N-(3-phenyl-1H-indazol-5-yl)-benzenesulfonamide | 475.65 | $C_{28}H_{33}N_3O_2S$ | 73.77 | 4.8 | 476.35 |
| 115 | 2,4,6-Trimethyl-N-(3-phenyl-1H-indazol-5-yl)-benzenesulfonamide | 391.49 | $C_{22}H_{21}N_3O_2S$ | 100 | 4.11 | 392.26 |
| 116 | 4-Bromo-N-(3-phenyl-1H-indazol-5-yl)-benzenesulfonamide | 428.31 | $C_{19}H_{14}BrN_3O_2S$ | 100 | 4.01 | 428.11 |
| 117 | 4-Fluoro-N-(3-phenyl-1H-indazol-5-yl)-benzenesulfonamide | 367.40 | $C_{19}H_{14}FN_3O_2S$ | 100 | 3.8 | 368.23 |
| 118 | N-[4-(3-Phenyl-1H-indazol-5-ylsulfamoyl)phenyl]acetamide | 406.46 | $C_{21}H_{18}N_4O_3S$ | 96.71 | 3.36 | 407.23 |
| 119 | 4-Nitro-N-(3-phenyl-1H-indazol-5-yl)benzenesulfonamide | 394.41 | $C_{19}H_{14}N_4O_4S$ | 96.64 | 3.85 | 395.21 |
| 120 | 4-Methoxy-N-(3-phenyl-1H-indazol-5-yl)-benzenesulfonamide | 379.44 | $C_{20}H_{17}N_3O_3S$ | 100 | 3.72 | 380.23 |
| 121 | 4-tert-Butyl-N-(3-phenyl-1H-indazol-5-yl)-benzenesulfonamide | 405.52 | $C_{23}H_{23}N_3O_2S$ | 94.05 | 4.22 | 406.28 |
| 122 | 4-Methyl-N-(3-phenyl-1H-indazol-5-yl)-benzenesulfonamide | 363.44 | $C_{20}H_{17}N_3O_2S$ | 100 | 3.84 | 364.25 |
| 123 | 1-Methyl-N-(3-phenyl-1H-indazol-5-yl)ethanesulfonamide | 315.39 | $C_{16}H_{17}N_3O_2S$ | 100 | 3.54 | 316.24 |
| 124 | N-(3-Phenyl-1H-indazol-5-yl)-methanesulfonamide | 287.34 | $C_{14}H_{13}N_3O_2S$ | 100 | 3.29 | 288.20 |
| 125 | 1-Phenyl-N-(3-phenyl-1H-indazol-5-yl)-methanesulfonamide | 363.44 | $C_{20}H_{17}N_3O_2S$ | 95.77 | 3.81 | 364.25 |
| 126 | (E)-2-Phenyl-N-(3-phenyl-1H-indazol-5-yl)-ethylenesulfonamide | 375.45 | $C_{21}H_{17}N_3O_2S$ | 96.89 | 3.88 | 376.23 |
| 127 | N-(3-Phenyl-1H-indazol-5-yl)-ethanesulfonamide | 301.37 | $C_{15}H_{15}N_3O_2S$ | 100 | 3.4 | 302.21 |
| 128 | N-(3-Phenyl-1H-indazol-5-yl)propanesulfonamide | 315.39 | $C_{16}H_{17}N_3O_2S$ | 100 | 3.58 | 316.25 |
| 129 | N-(3-Phenyl-1H-indazol-5-yl)-butanesulfonamide | 329.42 | $C_{17}H_{19}N_3O_2S$ | 100 | 3.74 | 330.26 |
| 130 | 3-Trifluoromethyl-N-(3-phenyl-1H-indazol-5-yl)-benzenesulfonamide | 417.41 | $C_{20}H_{14}F_3N_3O_2S$ | 100 | 4.02 | 418.20 |
| 131 | 2,5-Dimethoxy-N-(3-phenyl-1H-indazol-5-yl)-benzenesulfonamide | 409.46 | $C_{21}H_{19}N_3O_4S$ | 100 | 3.73 | 410.24 |
| 132 | 2-Methyl-N-(3-phenyl-1H-indazol-5-yl)-benzenesulfonamide | 363.44 | $C_{20}H_{17}N_3O_2S$ | 100 | 3.83 | 364.25 |
| 133 | 3-(3-Phenyl-1H-indazol-5-ylsulfamoyl)benzoic acid | 393.42 | $C_{20}H_{15}N_3O_4S$ | 93.37 | 3.42 | 394.21 |
| 134 | 2-Fluoro-N-(3-phenyl-1H-indazol-5-yl)-benzenesulfonamide | 367.40 | $C_{19}H_{14}FN_3O_2S$ | 100 | 3.75 | 368.23 |
| 135 | 5-Chloro-N-(3-phenyl-1H-indazol-5-yl)thiophene-2-sulfonamide | 389.88 | $C_{17}H_{12}ClN_3O_2S_2$ | 100 | 3.98 | 390.15 |
| 136 | 3-Chloro-N-(3-phenyl-1H-indazol-5-yl)-benzenesulfonamide | 383.86 | $C_{19}H_{14}ClN_3O_2S$ | 100 | 3.94 | 384.18 |
| 137 | 3,5-Dichloro-N-(3-phenyl-1H-indazol-5-yl)-benzenesulfonamide | 418.30 | $C_{19}H_{13}Cl_2N_3O_2S$ | 100 | 4.21 | 418.13 |
| 138 | 3-Methyl-N-(3-phenyl-1H-indazol-5-yl)-benzenesulfonamide | 363.44 | $C_{20}H_{17}N_3O_2S$ | 100 | 3.84 | 364.25 |
| 139 | 2-Bromo-N-(3-phenyl-1H-indazol-5-yl)-benzenesulfonamide | 428.31 | $C_{19}H_{14}BrN_3O_2S$ | 100 | 3.87 | 428.11 |

-continued

| Example | NAME | PM | Formula | UV purity | Tr (min) | Molecular ion detected |
|---|---|---|---|---|---|---|
| 140 | N-[5-(3-Phenyl-1H-indazol-5-ylsulfamoyl)thiophen-2-ylmethyl]benzamide | 488.59 | $C_{25}H_{20}N_4O_3S_2$ | 100 | 3.72 | 489.20 |
| 141 | 3-Bromo-N-(3-phenyl-1H-indazol-5-yl)-benzenesulfonamide | 428.31 | $C_{19}H_{14}BrN_3O_2S$ | 96.49 | 3.97 | 428.12 |
| 142 | N-(3-Phenyl-1H-indazol-5-yl)-2-trifluoromethoxybenzenesulfonamide | 433.41 | $C_{20}H_{14}F_3N_3O_3S$ | 96.55 | 3.99 | 434.20 |
| 143 | 4-Cyano-N-(3-phenyl-1H-indazol-5-yl)-benzenesulfonamide | 374.42 | $C_{20}H_{14}N_4O_2S$ | 100 | 3.74 | 375.22 |
| 144 | 2-Cyano-N-(3-phenyl-1H-indazol-5-yl)-benzenesulfonamide | 374.42 | $C_{20}H_{14}N_4O_2S$ | 69.03 | 3.67 | 375.23 |
| 145 | 4-Butoxy-N-(3-phenyl-1H-indazol-5-yl)-benzenesulfonamide | 421.52 | $C_{23}H_{23}N_3O_3S$ | 95.16 | 4.27 | 422.27 |
| 146 | N-[2-Chloro-4-(3-phenyl-1H-indazol-5-ylsulfamoyl)phenyl]-acetamide | 440.91 | $C_{21}H_{17}ClN_4O_3S$ | 100 | 3.57 | 441.21 |
| 147 | 5-Dibutylamino-N-(3-phenyl-1H-indazol-5-yl)naphthalene-1-sulfonamide | 526.70 | $C_{31}H_{34}N_4O_2S$ | 97 | 4.56 | 527.32 |
| 148 | C-(7,7-Dimethyl-2-oxo-bicyclo[2.2.1]hept-1-yl)-N-(3-phenyl-1H-indazol-5-yl)-methanesulfonamide | 423.53 | $C_{23}H_{25}N_3O_3S$ | 94.77 | 3.95 | 424.29 |
| 149 | N-(3-Phenyl-1H-indazol-5-yl)-benzo[1,2,5]oxadiazole-4-sulfonamide | 391.41 | $C_{19}H_{13}N_5O_3S$ | 96.86 | 3.77 | 392.20 |
| 150 | N-(3-Phenyl-1H-indazol-5-yl)-(5-isoxazol-3-ylthiophene)-2-sulfonamide | 422.48 | $C_{20}H_{14}N_4O_3S_2$ | 93.42 | 3.78 | 423.16 |
| 151 | C-(2-Nitrophenyl)-N-(3-phenyl-1H-indazol-5-yl)-methanesulfonamide | 408.44 | $C_{20}H_{16}N_4O_4S$ | 96.32 | 3.77 | 409.23 |
| 152 | 3,4-Difluoro-N-(3-phenyl-1H-indazol-5-yl)-benzenesulfonamide | 385.39 | $C_{19}H_{13}F_2N_3O_2S$ | 96.53 | 3.9 | 386.19 |
| 153 | N-(3-Phenyl-1H-indazol-5-yl)-(5-chloro-3-methylbenzo[b]thiophene)-2-sulfonamide | 453.97 | $C_{22}H_{16}ClN_3O_2S_2$ | 96.36 | 4.33 | 454.15 |
| 154 | 3-Cyano-N-(3-phenyl-1H-indazol-5-yl)-benzenesulfonamide | 374.42 | $C_{20}H_{14}N_4O_2S$ | 96.71 | 3.71 | 375.22 |
| 155 | 4-Methanesulfonyl-N-(3-phenyl-1H-indazol-5-yl)-benzenesulfonamide | 427.50 | $C_{20}H_{17}N_3O_4S_2$ | 100 | 3.55 | 428.18 |
| 156 | 3-Methoxy-N-(3-phenyl-1H-indazol-5-yl)-benzenesulfonamide | 379.44 | $C_{20}H_{17}N_3O_3S$ | 100 | 3.78 | 380.23 |
| 157 | N-(3-Phenyl-1H-indazol-5-yl)-biphenyl-3-sulfonamide | 425.51 | $C_{25}H_{19}N_3O_2S$ | 94.46 | 4.16 | 426.23 |
| 158 | 3,5-Difluoro-N-(3-phenyl-1H-indazol-5-yl)-benzenesulfonamide | 385.39 | $C_{19}H_{13}F_2N_3O_2S$ | 100 | 3.93 | 386.20 |
| 159 | 2-Amino-4,6-dichloro-N-(3-phenyl-1H-indazol-5-yl)-benzenesulfonamide | 433.32 | $C_{19}H_{14}Cl_2N_4O_2S$ | 100 | 4.02 | 433.15 |

EXAMPLE 160

4-Trifluoromethoxy-N-(3-phenyl-1H-indazol-5-yl) benzenesulfonamide

4-Trifluoromethoxy-N-(3-phenyl-1H-indazol-5-yl)benzenesulfonamide can be prepared as described in the library of Examples 106-159 starting with 4-trifluoromethoxyphenylsulfonate chloride and of 5-amino-2-phenyl-1H-indazole.

EXAMPLES 161-225

Preparation of a Library of 65 N-(3-aryl-1H-indazol-5-yl)-2-methylsulfonylbenzenesulfonamides Preparation of the Reagents:

A solution of tert-butyl 3-iodo-5-(N-tert-butoxycarbonyl-2-methylsulfonylbenzenesulfonylamino)indazole-1-carboxylate in dimethylformamide is prepared so as to obtain a concentration of 99 mM.

The following 65 boronic acids (Table 3) are weighed and diluted in dimethylformamide so as to obtain a solution with a concentration of 1.47 mM.

TABLE 3

| | Identifier | Name | Formula | Molecular weight |
|---|---|---|---|---|
| 1 | MFCD00002104 | 4-bromophenylboronic acid | $C_6H_6BbrO_2$ | 200.83 |
| 2 | MFCD00007193 | 3-nitrophenylboronic acid | $C_6H_6BNO_4$ | 166.93 |
| 3 | MFCD00013930 | 2,4-dichlorophenylboronic acid | $C_6H_5BCl_2O_2$ | 190.82 |
| 4 | MFCD00039138 | 4-tolylboronic acid | $C_7H_9BO_2$ | 135.96 |
| 5 | MFCD00040198 | 3-methylphenylboronic acid | $C_7H_9BO_2$ | 135.96 |
| 6 | MFCD00042703 | n-(5-dimethylamino-1-naphthalenesulfonyl)-3-aminobenzeneboronic acid | $C_{18}H_{19}BN_2O_4S$ | 370.24 |
| 7 | MFCD00051800 | 3-chloro-4-fluorobenzeneboronic acid | $C_6H_5BclFO_2$ | 174.37 |
| 8 | MFCD00051935 | 3,5-dichlorophenylboronic acid | $C_6H_5BCl_2O_2$ | 190.82 |
| 9 | MFCD00092336 | 4-dibenzofuranboronic acid | $C_{12}H_9BO_3$ | 212.01 |
| 10 | MFCD00093311 | 4-biphenylboronic acid | $C_{12}H_{11}BO_2$ | 198.03 |
| 11 | MFCD00093312 | 4-phenoxyphenylboronic acid | $C_{12}H_{11}BO_3$ | 214.03 |
| 12 | MFCD00093410 | 4-(methylthio)phenylboronic acid | $C_7H_9BO_2S$ | 168.02 |
| 13 | MFCD00136929 | 2-biphenylboronic acid | $C_{12}H_{11}BO_2$ | 198.03 |
| 14 | MFCD00151850 | 2-thiopheneboronic acid | $C_4H_5BO_2S$ | 127.96 |
| 15 | MFCD00151854 | 3-(trifluoromethyl)phenylboronic acid | $C_7H_6BF_3O_2$ | 189.93 |
| 16 | MFCD00151855 | 4-(trifluoromethyl)benzeneboronic acid | $C_7H_6BF_3O_2$ | 189.93 |
| 17 | MFCD00161354 | 3-chlorophenylboronic acid | $C_6H_6BClO_2$ | 156.38 |
| 18 | MFCD00161359 | 3-methoxyphenylboronic acid | $C_7H_9BO_3$ | 151.96 |
| 19 | MFCD00185689 | 3,5-dimethylphenylboronic acid | $C_8H_{11}BO_2$ | 149.98 |
| 20 | MFCD00236019 | benzo[b]furane-2-boronic acid | $C_8H_7BO_3$ | 161.95 |
| 21 | MFCD00236030 | 5-chlorothiophene-2-boronic acid | $C_4H_4BClO_2S$ | 162.4 |
| 22 | MFCD00236042 | 3-fluorophenylboronic acid | $C_6H_6BFO_2$ | 139.92 |
| 23 | MFCD00236047 | 2-methoxyphenylboronic acid | $C_7H_9BO_3$ | 151.96 |
| 24 | MFCD00239386 | 3-bromophenylboronic acid | $C_6H_6BBrO_2$ | 200.83 |
| 25 | MFCD00239441 | 4-vinylphenylboronic acid | $C_8H_9BO_2$ | 147.97 |
| 26 | MFCD00274219 | 3-ethoxyphenylboronic acid | $C_8H_{11}BO_3$ | 165.98 |
| 27 | MFCD00674012 | 2-chlorophenylboronic acid | $C_6H_6BClO_2$ | 156.38 |
| 28 | MFCD00674013 | 2-fluorophenylboronic acid | $C_6H_6BFO_2$ | 139.92 |
| 29 | MFCD00674027 | 2-ethoxyphenylboronic acid | $C_8H_{11}BO_3$ | 165.98 |
| 30 | MFCD00674028 | 4-ethoxyphenylboronic acid | $C_8H_{11}BO_3$ | 165.98 |
| 31 | MFCD00792672 | 4-(hydroxymethyl)phenylboronic acid | $C_7H_9BO_3$ | 151.96 |
| 32 | MFCD00807405 | 3,4-difluorobenzene-boronic acid | $C_6H_5BF_2O_2$ | 157.91 |
| 33 | MFCD00859377 | 4-ethylphenylboronic acid | $C_8H_{11}BO_2$ | 149.98 |
| 34 | MFCD00994627 | (3-fluoro-4-benzyloxyphenyl)boronic acid | $C_{13}H_{12}BFO_3$ | 246.04 |
| 35 | MFCD01009694 | (3,4-dimethylphenyl)boronic acid | $C_8H_{11}BO_2$ | 149.98 |
| 36 | MFCD01009695 | 3,4-methylenedioxyphenylboronic acid | $C_7H_7BO_4$ | 165.94 |
| 37 | MFCD01009697 | 4-tert-butylbenzeneboronic acid | $C_{10}H_{15}BO_2$ | 178.04 |
| 38 | MFCD01074574 | 3,4-dimethoxyphenylboronic acid | $C_8H_{11}BO_4$ | 181.98 |
| 39 | MFCD01074590 | 2,4-dimethoxyphenylboronic acid | $C_8H_{11}BO_4$ | 181.98 |
| 40 | MFCD01074603 | (3-hydroxyphenyl)boronic acid | $C_6H_7BO_3$ | 137.93 |
| 41 | MFCD01074614 | (4-isopropylphenyl)boronic acid | $C_9H_{13}BO_2$ | 164.01 |
| 42 | MFCD01074628 | 4-hydroxybenzeneboronic acid | $C_6H_7BO_3$ | 137.93 |
| 43 | MFCD01074634 | (3-isopropylphenyl)boronic acid | $C_9H_{13}BO_2$ | 164.01 |
| 44 | MFCD01074640 | 3-amino-4-methylbenzeneboronic acid | $C_7H_{10}BNO_2$ | 150.97 |
| 45 | MFCD01074646 | 3,4-dichlorophenylboronic acid | $C_6H_5BCl_2O_2$ | 190.82 |
| 46 | MFCD01074648 | 4-(trifluoromethoxy)benzeneboronic acid | $C_7H_6BF_3O_3$ | 205.93 |
| 47 | MFCD01074667 | 4-acetylphenylboronic acid | $C_8H_9BO_3$ | 163.97 |
| 48 | MFCD01075703 | 2,3-dichlorophenylboronic acid | $C_6H_5BCl_2O_2$ | 190.82 |
| 49 | MFCD01075705 | (4-benzyloxyphenyl)boronic acid | $C_{13}H_{13}BO_3$ | 228.05 |
| 50 | MFCD01075707 | 2-fluorobiphenyl-4-boronic acid | $C_{12}H_{10}BFO_2$ | 216.02 |
| 51 | MFCD01075725 | 3,5-dibromophenylboronic acid | $C_6H_5BBr_2O_2$ | 279.72 |
| 52 | MFCD01318110 | 4-bromo-2-fluorobenzeneboronic acid | $C_6H_5BBrFO_2$ | 218.82 |
| 53 | MFCD01318146 | 4-(ethylthiophenyl)boronic acid | $C_8H_{11}BO_2S$ | 182.05 |
| 54 | MFCD01318183 | 2,3,4-trimethoxyphenylboronic acid | $C_9H_{13}BO_5$ | 212.01 |
| 55 | MFCD01318966 | 5-chloro-2-methoxyphenylboronic acid | $C_7H_8BClO_3$ | 186.4 |
| 56 | MFCD01318968 | 4-cyanophenylboronic acid | $C_7H_6BNO_2$ | 146.94 |
| 57 | MFCD01318998 | 2,4-difluorophenylboronic acid | $C_6H_5BF_2O_2$ | 157.91 |
| 58 | MFCD01319014 | 4-iodophenylboronic acid | $C_6H_6BIO_2$ | 247.82 |
| 59 | MFCD01320697 | 3-(trifluoromethoxy)benzeneboronic acid | $C_7H_6BF_3O_3$ | 205.93 |

TABLE 3-continued

| Identifier | Name | Formula | Molecular weight |
|---|---|---|---|
| 60 MFCD01630820 | [(4-methylsulfonyl)phenyl]boronic acid | $C_7H_9BO_4S$ | 200.02 |
| 61 MFCD01863170 | 2,3-difluorophenylboronic acid | $C_6H_5BF_2O_2$ | 157.91 |
| 62 MFCD01863524 | 2,3-dimethylbenzeneboronic acid | $C_8H_{11}BO_2$ | 149.98 |
| 63 MFCD01863527 | (4-fluoro-3-methylphenyl)boronic acid | $C_7H_8BFO_2$ | 153.95 |
| 64 MFCD02683107 | 4-chloro-o-tolueneboronic acid | $C_7H_8BClO_2$ | 170.4 |
| 65 MFCD02683115 | 3-fluoro-4-methylbenzeneboronic acid | $C_7H_8BFO_2$ | 153.95 |

Setting Up of the Reactions:

65 sintered glass reactors are arranged on two Miniblock reaction blocks (Mettler-Toledo, Viroflay, France), and 1.75 ml of the solution of tert-butyl 3-iodo-5-(N-tert-butoxycarbonyl-2-methylsulfonylbenzenesulfonylamino)-indazole-1-carboxylate prepared above are distributed into each one of the reactors using a Zinsser automated diluting device (Zinsser Analytical, Frankfurt, Germany). 200 µl of each solution of boronic acid described above (Table 3) are then added, followed by 320 µl of a saturated sodium hydrogencarbonate solution. A suspension of tetrakis(triphenylphosphine)-palladium(0) in dimethylformamide is then distributed (50 µl per well), and the reactors are then closed and heated to a temperature in the region of 105° C. using a suitable heating jacket (Mettler-Toledo, Viroflay, France). After one night at this temperature, the reaction mixtures are filtered, under hot conditions, in suitable collecting racks (Mettler-Toledo, Viroflay, France) equipped with 75×100 mm hemolysis tubes, and then, after returning to ambient temperature, each reaction medium is diluted with 2 ml of ethyl acetate and transferred into a 13×100 mm tube for liquid-liquid extraction (Zinsser Winlissy, Zinsser Analytical, Frankfurt, Germany). The following extraction sequence is applied twice to each reaction medium: addition of 2 ml of distilled water, mixing, settling out, removal of the aqueous phase, which is returned to its tube of origin. At the end of these operations, the organic extracts are transferred (Zinsser Winlissy, Zinsser Analytical, Frankfurt, Germany) into pre-tared tubes (AWS LA200, Mettler-Toledo, Viroflay, France); before evaporation, 10 µl of each organic extract are transferred (Zinsser Winlissy, Zinsser Analytical, Frankfurt, Germany) into a microtitration plate and diluted with 40 µl of dimethyl sulfoxide, thus constituting 65 crude samples used for the LC/MS analysis. The tared tubes containing the organic extracts are finally evaporated to dryness (Genevac HT8 or Savant centrifugal evaporator), thus providing the crude samples. Before purification, the samples are prepared in the following way: each sample is solubilized in 1 ml of dimethyl sulfoxide, and filtered in a filtering plate. The filtrates are then distributed in two wells each of 500 µl and subjected to purification by LC/MS (conditions B).

After purification by LC/MS, the fractions containing the desired compounds are (optionally pooled) evaporated to dryness (Savant AES 2000 or Genevac HT8 centrifugal evaporator), weighed (Mettler Toledo Automated Workstation LA200), and diluted to 10 mM in dimethyl sulfoxide (Zinsser Winlissy, Zinsser Analytical). Each solution obtained is analyzed by LC/MS. The following compounds were isolated and characterized by their retention time and molecular peak in mass spectrometry.

| Example | NAME | MW | Formula | UV purity | Tr (min) | Molecular ion detected |
|---|---|---|---|---|---|---|
| 161 | N-[3-(4-Bromophenyl)-1H-indazol-5-yl]-2-methanesulfonylbenzenesulfonamide | 506.40 | $C_{20}H_{16}BrN_3O_4S_2$ | 100 | 4.14 | 506.12 |
| 162 | 2-Methanesulfonyl-N-[3-(3-nitrophenyl)-1H-indazol-5-yl]-benzenesulfonamide | 472.50 | $C_{20}H_{16}N_4O_6S_2$ | 100 | 3.90 | 473.21 |
| 163 | N-[3-(2,4-Dichlorophenyl)-1H-indazol-5-yl]-2-methanesulfonylbenzenesulfonamide | 496.40 | $C_{20}H_{15}Cl_2N_3O_4S_2$ | 87 | 4.11 | 496.14 |
| 164 | 2-Methanesulfonyl-N-(3-p-tolyl-1H-indazol-5-yl)-benzenesulfonamide | 441.53 | $C_{21}H_{19}N_3O_4S_2$ | 94.02 | 3.96 | 442.25 |
| 165 | 2-Methanesulfonyl-N-(3-m-tolyl-1H-indazol-5-yl)-benzenesulfonamide | 441.53 | $C_{21}H_{19}N_3O_4S_2$ | 100 | 3.96 | 442.24 |
| 166 | N-{3-[5-(2-Methanesulfonylbenzenesulfonylamino)-1H-indazol-3-yl]phenyl}-5-dimethylaminonaphthalene-1-sulfonamide | 675.80 | $C_{32}H_{29}N_5O_6S_3$ | 93.74 | 3.80 | 676.2 |
| 167 | N-[3-(3-Chloro-4-fluorophenyl)-1H-indazol-5-yl]-2-methanesulfonylbenzenesulfonamide | 479.93 | $C_{20}H_{15}ClFN_3O_4S_2$ | 82.48 | 4.12 | 480.17 |
| 168 | N-[3-(3,5-Dichlorophenyl)-1H-indazol-5-yl]-2-methanesulfonylbenzenesulfonamide | 496.39 | $C_{20}H_{15}Cl_2N_3O_4S_2$ | 100 | 4.43 | 496.14 |

-continued

| Example | NAME | MW | Formula | UV purity | Tr (min) | Molecular ion detected |
|---|---|---|---|---|---|---|
| 169 | N-(3-(Dibenzofuran-4-yl)-1H-indazol-5-yl)-2-methanesulfonylbenzenesulfonamide | 517.58 | $C_{26}H_{19}N_3O_5S_2$ | 51.3 | 4.23 | 518.21 |
| 170 | N-(3-Biphenyl-4-yl-1H-indazol-5-yl)-2-methanesulfonylbenzenesulfonamide | 503.60 | $C_{26}H_{21}N_3O_4S_2$ | 100 | 4.32 | 504.25 |
| 171 | 2-Methanesulfonyl-N-[3-(4-phenoxyphenyl)-1H-indazol-5-yl]benzenesulfonamide | 519.60 | $C_{26}H_{21}N_3O_5S_2$ | 100 | 4.29 | 520.23 |
| 172 | 2-Methanesulfonyl-N-[3-(4-methylsulfanylphenyl)-1H-indazol-5-yl]-benzenesulfonamide | 473.60 | $C_{21}H_{19}N_3O_4S_3$ | 100 | 3.99 | 474.22 |
| 173 | N-(3-Biphenyl-2-yl-1H-indazol-5-yl)-2-methanesulfonylbenzenesulfonamide | 503.60 | $C_{26}H_{21}N_3O_4S_2$ | 100 | 4.07 | 504.25 |
| 174 | 2-Methanesulfonyl-N-(3-thiophen-2-yl-1H-indazol-5-yl)-benzenesulfonamide | 433.53 | $C_{18}H_{15}N_3O_4S_3$ | 100 | 3.79 | 434.19 |
| 175 | N-[3-(3-Trifluoromethylphenyl)-1H-indazol-5-yl]-2-methanesulfonylbenzenesulfonamide | 495.50 | $C_{21}H_{16}F_3N_3O_4S_2$ | 96.66 | 4.16 | 496.21 |
| 176 | N-[3-(4-Trifluoromethylphenyl)-1H-indazol-5-yl]-2-methanesulfonylbenzenesulfonamide | 495.50 | $C_{21}H_{16}F_3N_3O_4S_2$ | 100 | 4.17 | 496.21 |
| 177 | N-[3-(3-Chlorophenyl)-1H-indazol-5-yl]-2-methanesulfonylbenzenesulfonamide | 461.95 | $C_{20}H_{16}ClN_3O_4S_2$ | 100 | 4.06 | 462.19 |
| 178 | 2-Methanesulfonyl-N-[3-(3-methoxyphenyl)-1H-indazol-5-yl]benzenesulfonamide | 457.53 | $C_{21}H_{19}N_3O_5S_2$ | 96.37 | 3.84 | 458.24 |
| 179 | 2-Methanesulfonyl-N-[3-(3,5-dimethylphenyl)-1H-indazol-5-yl]benzenesulfonamide | 455.55 | $C_{22}H_{21}N_3O_4S_2$ | 100 | 4.11 | 456.27 |
| 180 | N-(3-Benzofuran-2-yl-1H-indazol-5-yl)-2-methanesulfonylbenzenesulfonamide | 467.52 | $C_{22}H_{17}N_3O_5S_2$ | 100 | 4.05 | 468.22 |
| 181 | N-[3-(5-Chlorothiophen-2-yl)-1H-indazol-5-yl]-2-methanesulfonylbenzenesulfonamide | 467.97 | $C_{18}H_{14}ClN_3O_4S_3$ | 96.06 | 4.16 | 468.15 |
| 182 | N-[3-(3-Fluorophenyl)-1H-indazol-5-yl]-2-methanesulfonylbenzenesulfonamide | 445.49 | $C_{20}H_{16}FN_3O_4S_2$ | 100 | 3.90 | 446.22 |
| 183 | 2-Methanesulfonyl-N-[3-(2-methoxyphenyl)-1H-indazol-5-yl]benzenesulfonamide | 457.53 | $C_{21}H_{19}N_3O_5S_2$ | 88.85 | 3.75 | 458.24 |
| 184 | N-[3-(3-Bromophenyl)-1H-indazol-5-yl]-2-methanesulfonylbenzenesulfonamide | 506.40 | $C_{20}H_{16}BrN_3O_4S_2$ | 100 | 4.12 | 506.13 |
| 185 | 2-Methanesulfonyl-N-[3-(4-vinylphenyl)-1H-indazol-5-yl]-benzenesulfonamide | 453.54 | $C_{22}H_{19}N_3O_4S_2$ | 100 | 4.05 | 454.25 |
| 186 | N-[3-(3-Ethoxyphenyl)-1H-indazol-5-yl]-2-methanesulfonylbenzenesulfonamide | 471.55 | $C_{22}H_{21}N_3O_5S_2$ | 100 | 3.97 | 472.25 |
| 187 | N-[3-(2-Chlorophenyl)-1H-indazol-5-yl]-2-methanesulfonylbenzenesulfonamide | 461.95 | $C_{20}H_{16}ClN_3O_4S_2$ | 100 | 3.84 | 462.19 |
| 188 | N-[3-(2-Fluorophenyl)-1H-indazol-5-yl]-2-methanesulfonylbenzenesulfonamide | 445.49 | $C_{20}H_{16}FN_3O_4S_2$ | 100 | 3.78 | 446.23 |
| 189 | N-[3-(2-Ethoxyphenyl)-1H-indazol-5-yl]-2-methanesulfonylbenzenesulfonamide | 471.55 | $C_{22}H_{21}N_3O_5S_2$ | 100 | 3.86 | 472.25 |
| 190 | N-[3-(4-Ethoxyphenyl)-1H-indazol-5-yl]-2-methanesulfonylbenzenesulfonamide | 471.55 | $C_{22}H_{21}N_3O_5S_2$ | 100 | 3.95 | 472.26 |
| 191 | N-[3-(4-Hydroxymethylphenyl)-1H-indazol-5-yl]-2-methanesulfonylbenzenesulfonamide | 457.53 | $C_{21}H_{19}N_3O_5S_2$ | 84.92 | 3.30 | 458.23 |
| 192 | N-[3-(3,4-Difluorophenyl)-1H-indazol-5-yl]-2-methanesulfonylbenzenesulfonamide | 463.48 | $C_{20}H_{15}F_2N_3O_4S_2$ | 100 | 4.00 | 464.22 |
| 193 | N-[3-(4-Ethylphenyl)-1H-indazol-5-yl]-2-methanesulfonylbenzenesulfonamide | 455.55 | $C_{22}H_{21}N_3O_4S_2$ | 95.74 | 4.12 | 456.27 |

-continued

| Example | NAME | MW | Formula | UV purity | Tr (min) | Molecular ion detected |
|---|---|---|---|---|---|---|
| 194 | N-[3-(4-Benzyloxy-3-fluorophenyl)-1H-indazol-5-yl]-2-methanesulfonylbenzenesulfonamide | 551.61 | $C_{27}H_{22}FN_3O_5S_2$ | 100 | 4.29 | 552.22 |
| 195 | 2-Methanesulfonyl-N-[3-(3,4-dimethylphenyl)-1H-indazol-5-yl]benzenesulfonamide | 455.55 | $C_{22}H_{21}N_3O_4S_2$ | 94.09 | 4.08 | 456.27 |
| 196 | N-[3-(Benzo[1,3]dioxol-5-yl)-1H-indazol-5-yl]-2-methanesulfonylbenzenesulfonamide- | 471.51 | $C_{21}H_{17}N_3O_6S_2$ | 100 | 3.75 | 472.21 |
| 197 | N-[3-(4-tert-Butylphenyl)-1H-indazol-5-yl]-2-methanesulfonylbenzenesulfonamide | 483.61 | $C_{24}H_{25}N_3O_4S_2$ | 100 | 4.38 | 484.29 |
| 198 | 2-Methanesulfonyl-N-[3-(3,4-dimethoxyphenyl)-1H-indazol-5-yl]benzenesulfonamide | 487.55 | $C_{22}H_{21}N_3O_6S_2$ | 100 | 3.62 | 488.25 |
| 199 | 2-Methanesulfonyl-N-[3-(2,4-dimethoxyphenyl)-1H-indazol-5-yl]benzenesulfonamide | 487.55 | $C_{22}H_{21}N_3O_6S_2$ | 96.96 | 3.74 | 488.25 |
| 200 | N-[3-(3-Hydroxyphenyl)-1H-indazol-5-yl]-2-methanesulfonylbenzenesulfonamide | 443.50 | $C_{20}H_{17}N_3O_5S_2$ | 96.2 | 3.48 | 444.22 |
| 201 | N-[3-(4-Isopropylphenyl)-1H-indazol-5-yl]-2-methanesulfonylbenzenesulfonamide | 469.58 | $C_{23}H_{23}N_3O_4S_2$ | 100 | 4.26 | 470.28 |
| 202 | N-[3-(4-Hydroxyphenyl)-1H-indazol-5-yl]-2-methanesulfonylbenzenesulfonamide | 443.50 | $C_{20}H_{17}N_3O_5S_2$ | 92.7 | 3.39 | 444.22 |
| 203 | N-[3-(3-Isopropylphenyl)-1H-indazol-5-yl]-2-methanesulfonylbenzenesulfonamide | 469.58 | $C_{23}H_{23}N_3O_4S_2$ | 100 | 4.24 | 470.28 |
| 204 | N-[3-(3-Amino-4-methylphenyl)-1H-indazol-5-yl]-2-methanesulfonylbenzenesulfonamide | 456.54 | $C_{21}H_{20}N_4O_4S_2$ | 95.71 | 3.07 | 457.25 |
| 205 | N-[3-(3,4-Dichlorophenyl)-1H-indazol-5-yl]-2-methanesulfonylbenzenesulfonamide | 496.39 | $C_{20}H_{15}Cl_2N_3O_4S_2$ | 100 | 4.33 | 496.15 |
| 206 | N-[3-(4-Trifluoromethoxyphenyl)-1H-indazol-5-yl]-2-methanesulfonylbenzenesulfonamide | 511.50 | $C_{21}H_{16}F_3N_3O_5S_2$ | 96.28 | 4.25 | 512.2 |
| 207 | N-[3-(4-Acetylphenyl)-1H-indazol-5-yl]-2-methanesulfonylbenzenesulfonamide | 469.54 | $C_{22}H_{19}N_3O_5S_2$ | 67.65 | 3.68 | 470.23 |
| 208 | N-[3-(2,3-Dichlorophenyl)-1H-indazol-5-yl]-2-methanesulfonylbenzenesulfonamide | 496.39 | $C_{20}H_{15}Cl_2N_3O_4S_2$ | 100 | 4.01 | 496.14 |
| 209 | N-[3-(4-Benzyloxyphenyl)-1H-indazol-5-yl]-2-methanesulfonylbenzenesulfonamide | 533.62 | $C_{27}H_{23}N_3O_5S_2$ | 69.31 | 4.24 | 534.24 |
| 210 | N-[3-(2-Fluorobiphenyl-4-yl)-1H-indazol-5-yl]-2-methanesulfonylbenzenesulfonamide | 521.59 | $C_{26}H_{20}FN_3O_4S_2$ | 100 | 4.38 | 522.23 |
| 211 | N-[3-(3,5-Dibromophenyl)-1H-indazol-5-yl]-2-methanesulfonylbenzenesulfonamide | 585.30 | $C_{20}H_{15}Br_2N_3O_4S_2$ | 96.31 | 4.53 | 584 |
| 212 | N-[3-(4-Bromo-2-fluorophenyl)-1H-indazol-5-yl]-2-methanesulfonylbenzenesulfonamide | 524.39 | $C_{20}H_{15}BrFN_3O_4S_2$ | 95.83 | 4.10 | 524.11 |
| 213 | N-[3-(4-Ethylsulfanylphenyl)-1H-indazol-5-yl]-2-methanesulfonylbenzenesulfonamide | 487.62 | $C_{22}H_{21}N_3O_4S_3$ | 100 | 4.15 | 488.23 |
| 214 | 2-Methanesulfonyl-N-[3-(2,3,4-trimethoxyphenyl)-1H-indazol-5-yl]-benzenesulfonamide | 517.58 | $C_{23}H_{23}N_3O_7S_2$ | 96.8 | 3.69 | 518.24 |
| 215 | N-[3-(5-Chloro-2-methoxyphenyl)-1H-indazol-5-yl]-2-methanesulfonylbenzenesulfonamide | 491.97 | $C_{21}H_{18}ClN_3O_5S_2$ | 96.88 | 4.01 | 492.18 |
| 216 | N-[3-(4-Cyanophenyl)-1H-indazol-5-yl]-2-methanesulfonylbenzenesulfonamide | 452.51 | $C_{21}H_{16}N_4O_4S_2$ | 91.57 | 3.78 | 453.23 |
| 217 | N-[3-(2,4-Difluorophenyl)-1H-indazol-5-yl]-2-methanesulfonylbenzenesulfonamide | 463.48 | $C_{20}H_{15}F_2N_3O_4S_2$ | 100 | 3.87 | 464.21 |
| 218 | N-[3-(4-Iodophenyl)-1H-indazol-5-yl]-2-methanesulfonylbenzenesulfonamide | 553.40 | $C_{20}H_{16}IN_3O_4S_2$ | 64.54 | 4.24 | 554.08 |

-continued

| Example | NAME | MW | Formula | UV purity | Tr (min) | Molecular ion detected |
|---------|------|-----|---------|-----------|----------|------------------------|
| 219 | N-[3-(3-Trifluoromethoxyphenyl)-1H-indazol-5-yl]-2-methanesulfonylbenzenesulfonamide | 511.50 | $C_{21}H_{16}F_3N_3O_5S_2$ | 84.36 | 4.20 | 512.19 |
| 220 | 2-Methanesulfonyl-N-[3-(4-methanesulfonylphenyl)-1H-indazol-5-yl]-benzenesulfonamide | 505.59 | $C_{21}H_{19}N_3O_6S_3$ | 100 | 3.51 | 506.19 |
| 221 | N-[3-(2,3-Difluorophenyl)-1H-indazol-5-yl]-2-methanesulfonylbenzenesulfonamide | 463.48 | $C_{20}H_{15}F_2N_3O_4S_2$ | 100 | 3.85 | 464.21 |
| 222 | N-[3-(4-Fluoro-3-methylphenyl)-1H-indazol-5-yl]-2-methanesulfonylbenzenesulfonamide | 459.52 | $C_{21}H_{18}FN_3O_4S_2$ | 90.18 | 4.03 | 460.23 |
| 223 | N-[3-(3-Benzyloxyphenyl)-1H-indazol-5-yl]-2-methanesulfonylbenzenesulfonamide | 533.62 | $C_{27}H_{23}N_3O_5S_2$ | 100 | 4.29 | 534.24 |
| 224 | N-[3-(3-Fluoro-4-methylphenyl)-1H-indazol-5-yl]-2-methanesulfonylbenzenesulfonamide | 459.52 | $C_{21}H_{18}FN_3O_4S_2$ | 100 | 4.07 | 460.23 |
| 225 | N-[3-(2,5-Dichlorophenyl)-1H-indazol-5-yl]-2-methanesulfonylbenzenesulfonamide | 496.39 | $C_{20}H_{15}Cl_2N_3O_4S_2$ | 89.45 | 4.07 | 496.14 |

Analysis by LC/MS:

The LC/MS analyses were carried out on a Micromass device model LCT connected to an HP 1100 device. The abundance of the products was measured using an HP G1315A diode array detector over a wave range of 200-600 nm and a Sedex 65 light scattering detector. The acquisition of the mass spectra was carried out over a range of 180 to 800. The data were analyzed using the Micromass MassLynx software. The separation was carried out on a Hypersil BDS C18, 3 μm (50×4.6 mm), column, eluting with a linear gradient of 5 to 90% of acetonitrile containing 0.05% (v/v) of trifluoroacetic acid (TFA) in water containing 0.05% (v/v) TFA over 3.5 min at a flow rate of 1 mL/mn. The total time of analysis, including the column reequilibration period, is 7 min.

Purification by LC/MS; Conditions A:

The products were purified by LC/MS using a Waters FractionsLynx system composed of a Waters gradient pump model 600, a Waters regeneration pump model 515, a Waters Reagent Manager dilution pump, a Waters autoinjecter model 2700, two Rheodyne valves model LabPro, a Waters diode array detector model 996, a Waters mass spectrometer model ZMD and a Gilson fraction collector model 204. The system was controlled by Waters FractionLynx software. The separation was carried out alternately on two Waters Symmetry columns ($C_{18}$, 5 μM, 19×50 mm, catalogue reference 186000210), one column undergoing regeneration with a 95/5 (v/v) water/acetonitrile mixture containing 0.07% (v/v) of trifluoroacetic acid, while the other column was in the process of separation. The columns were eluted using a linear gradient of 5 to 95% of acetonitrile containing 0.07% (v/v) of trifluoroacetic acid in water containing 0.07% (v/v) of trifluoroacetic acid, at a flow rate of 10 mL/mn. On leaving the separating column, one thousandth of the effluent is separated with LC Packing Accurate, diluted with methyl alcohol at a flow rate of 0.5 mL/mn and sent to the detectors, in a proportion of 75% to the diode array detector and the remaining 25% to the mass spectrometer. The remainder of the effluent (999/1000) is sent to the fraction collector, where the flow is eliminated as long as the mass of the expected product is not detected by the FractionLynx software. The FractionLynx software is provided with the molecular formulae of the expected products, and triggers collection of the product when the mass signal detected corresponds to the ion $[M+H]^+$ and/or to $[M+Na]^+$. In certain cases, depending on the results of analytical LC/MS, when an intense ion corresponding to $[M+2H]^{++}$ has been detected, the FractionLynx software is also provided with the value corresponding to half the calculated molecular mass (MW/2). Under these conditions, collection is also triggered when the mass signal for the ion $[M+2H]^{++}$ and/or $[M+Na^+ H]^{++}$ is detected. The products were collected in tared glass tubes. After collection, the solvents were evaporated off, in a Savant AES 2000 or Genevac HT8 centrifugal evaporator, and the product masses were determined by weighing the tubes after evaporation of the solvents.

Purification by LC/MS; Conditions B:

The products were purified by preparative chromatography coupled to detection by mass spectrometry on the Waters system controlled by the Mass Lynx software for the detection (positive electrospray mode), along with Fraction Lynx for the collection. The purification was carried out on an X Terra® column ($C_{18}$ grafted phase, 5 μm) 100 mm in length and 30 mm in diameter. The flow rate of the eluent was fixed at 20 ml/min. Either a water/acetonitrile/trifluoroacetic acid at 0.05% (v/v) gradient is used, the composition of which varies in a linear fashion over time in the following way:

| 0 min | water: 50% (v/v) | acetonitrile: 50% (v/v) |
| 6 min | water: 50% (v/v) | acetonitrile: 50% (v/v) |
| 12 min | water: 5% (v/v) | acetonitrile: 95% (v/v) |
| 15 min | water: 5% (v/v) | acetonitrile: 95% (v/v) | or an isocratic system is used, composed of: 60% (v/v) water/acetonitrile: 40% (v/v)/trifluoroacetic acid at 0.05% (v/v).

After collection, the solvents were evaporated off in a Genevac HT8 centrifugal evaporator and the product masses were determined by weighing the tubes after evaporation of the solvents.

EXAMPLE 226

3-(1H-Benzimidazol-2-yl)-1 indazol-5-yl-2-methanesulfonylbenzenesulfonate 200 mg of 5-benzyloxy-1H-indazole-3-carboxylic acid are dissolved in 2.5 ml of DMF and 140 μl of N,N'-diisopropylcarbodiimide are then added. The suspension is stirred for one hour at ambient temperature. The acid thus activated is added dropwise to a solution of 80.4 mg of 1,2-phenylenediamine in 0.5 ml of DMF. The suspension is stirred at ambient temperature for 20 hours. The suspension is filtered and the DMF is evaporated off in a rotary evaporator. The reaction crude is purified by flash chromatography (eluent cyclohexane/ethyl acetate, 60:40). 434.7 mg of a yellow solid are collected, which solid is suspended in 5 ml of ethanol. 1 ml of 37% HCl is then added. The medium is heated at 80° C. for 18 hours. The solvent is evaporated off, and the crude is taken up with 20 ml of ethyl acetate and 10 ml of a saturated sodium bicarbonate solution. After stirring for 10 minutes, the organic phase is dried over magnesium sulfate and the solvent is evaporated off. The reaction crude is purified by flash chromatography (eluent: 1/1 ethyl acetate/cyclohexane; Rf of expected product=0.29). 101 mg of a pale yellow solid are collected.

Analyses:
LC/MS: Tr=3.28 min; [M+H]+=341.26

82.5 mg of 3-(1H-benzimidazol-2-yl)-5-benzyloxy-1H-indazole previously prepared are suspended in 4 ml of methanol, and 1 ml of cyclohexene and 82.5 mg of 10% palladium-on-charcoal are then added. The suspension is brought to reflux for 8 hours. The catalyst is filtered through sintered glass filled with celite and the solvent is then evaporated off. 59.5 mg of 3-(1H-benzimidazol-2-yl)-1H-indazol-5-ol are collected in the form of a yellow oil.

Analyses:
LC/MS: Tr=2.26 min; [M+H]+=251.19

59.5 mg of 3-(1H-benzimidazol-2-yl)-1H-indazol-5-ol are dissolved in 3 ml of dichloromethane, then 35.1 mg of 2-methylsulfonylbenzenesulfonyl chloride and 99 μl of triethylamine are added. The solution is stirred for 24 hours at ambient temperature. After evaporation of the solvent, the reaction crude is purified by flash chromatography (eluent: 60/40 ethyl acetate/cyclohexane). 69.2 mg of 3-(1H-benzimidazol-2-yl)-1H-indazol-5-yl 2-methanesulfonylbenzenesulfonate are collected in the form of a white solid.

Analyses:
LC/MS: Tr=2.82 min; [M+H]+=469.07

EXAMPLES 227 TO 232

Compounds of the following general formula (IL)

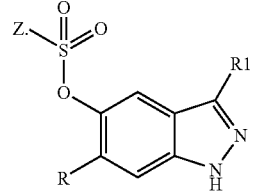

(IL)

for which Z and R1 have the same meaning as in the formula (I), can be prepared by protection of position 1 of the indazole (IIG) (step b), coupling between the iodinated derivative (IIH) and a boronic acid RI—B(OH)$_2$, (in Examples 227-232: indol-2-boronic acid), then debenzylation of the coupling product (IIK), condensation thereof on a sulfonyl chloride Z-SO$_2$Cl and deprotection of the NH at position 1 on the indazole so as to produce the expected product (IL):

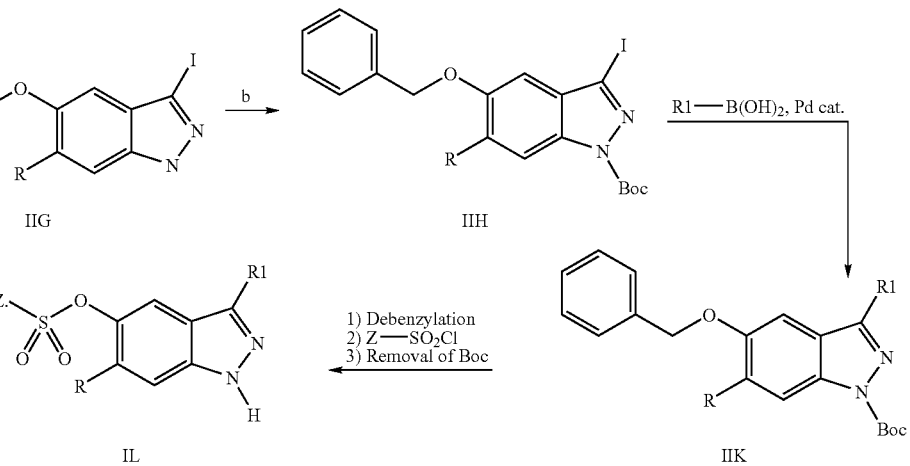

[1) debenzylation 3) Boc removal]

| Example | Z | R1 | Molar mass (g/mol) |
|---|---|---|---|
| 227 | 2-sulfonylmethylphenyl | indol-2-yl | 467.52 |
| 228 | phenyl | indol-2-yl | 389.43 |
| 229 | 2,6-dichlorophenyl | indol-2-yl | 458.32 |
| 230 | 2-trifluoromethoxyphenyl | indol-2-yl | 473.43 |
| 231 | 3-fluorophenyl | indol-2-yl | 407.42 |
| 232 | 2-thienyl | indol-2-yl | 395.46 |

Determination of the Activity of the Compounds—Experimental Protocols

1. FAK

The inhibitory activity of the compounds on FAK is determined by measuring the inhibition of the autophosphorylation of the enzyme using a time resolved fluorescence (HTRF) assay.

The complete cDNA of human FAK, the N-terminal end of which was labeled with histidine, was cloned into a baculovirus expression vector pFastBac HTc. The protein was expressed and purified to approximately 70% homogeneity.

The kinase activity is determined by incubating the enzyme (6.6 µg/ml) with various concentrations of test compound in a 50 mM Hepes buffer, pH=7.2, containing 10 mM $MgCl_2$, 100 µM $Na_3VO_4$ and 15 µM d'ATP for 1 hour at 37° C. The enzyme reaction is stopped by adding Hepes buffer, pH=7.0, containing 0.4 mM KF, 133 mM EDTA and 0.1% BSA, and the labeling is carried out, over 1 to 2 hours at ambient temperature, by adding to this buffer an anti-Histidine antibody labeled with XL665 and a monoclonal antibody phosphospecific for tyrosine, conjugated to europium cryptate (Eu—K). The characteristics of the two fluorophores are available in G. Mathis et al., Anticancer Research, 1997, 17, pages 3011-3014. The transfer of energy from the excited europium cryptate to the XL665 acceptor is proportional to the degree of autophosphorylation of FAK. The long-lived signal specific for XL-665 is measured in a Packard Discovery plate counter. All the assays are carried out in duplicate and the mean of the two assays is calculated. The inhibition of the FAK autophosphorylation activity with compounds of the invention is expressed as percentage inhibition compared to a control whose activity is measured in the absence of test compound. The [signal at 665 nm/signal at 620 nm] ratio is used for the calculation of the % inhibition.

2. KDR

The inhibitory effect of the compounds is determined in an assay of substrate phosphorylation by the KDR enzyme in vitro using a scintillation technique (96-well plate, NEN).

The cytoplasmic domain of the human KDR enzyme was cloned in the form of a GST fusion into the baculovirus expression vector pFastBac. The protein was expressed in SF21 cells and purified to approximately 60% homogeneity.

The KDR kinase activity is measured in 20 mM MOPS, 10 mM $MgCl_2$, 10 mM $MnCl_2$, 1 mM DTT, 2.5 mM EGTA, 10 mM β-glycerophosphate, pH=7.2, in the presence of 10 mM $MgCl_2$, 100 µM $Na_3VO_4$, 1 mM NaF. 10 µl of the compound are added to 70 µl of kinase buffer containing 100 ng of KDR enzyme at 4° C. The reaction is triggered by adding 20 µl of solution containing 2 µg of substrate (SH2-SH3 fragment of PLCγ expressed in the form of a GST fusion protein), 2 µCi γ$^{33}$P[ATP] and 2 µM cold ATP. After incubation for 1 hour at 37° C., the reaction is stopped by adding 1 volume (100 µl) of 200 mM EDTA. The incubation buffer is removed and the wells are washed three times with 300 µl of PBS. The radioactivity is measured in each well using Top Count NXT radioactivity counter (Packard).

The background noise is determined by measuring the radioactivity in four different wells containing the radioactive ATP and the substrate alone.

A control for total activity is measured in four different wells containing all the reagents (γ$^{33}$P-[ATP], KDR and PLCγ substrate) but in the absence of compound.

The inhibition of the KDR activity with the compound of the invention is expressed as percentage inhibition of the control activity determined in the absence of compound.

The compound SU5614 (Calbiochem) (1 µM) is included in each plate as an inhibition control.

3. Aurora2

The inhibitory effect of compounds with respect to the Aurora2 kinase is determined with a radioactivity scintillation assay using nickel chelate.

A complete recombinant Aurora2 enzyme, the N-terminal end of which was labeled with histidine, was expressed in E. coli and purified to a quality close to homogeneity.

The C-terminal fragment (Q1687-H2101) of a NuMA (Nuclear protein that associates with the Mitotic Apparatus) expressed in E. coli, and the N-terminal end of which was labeled with histidine, was purified by nickel chelate chromatography and used as substrate in the Aurora2 kinase assay.

In order to determine the kinase activity, the NuMA substrate is equilibrated by chromatography on a Pharmacia PD10 column, in a buffer (50 mM Tris-HCl, pH7.5, 50 mM NaCl, 10 mM $MgCl_2$) to which 10% (v/v) of glycerol and 0.05% (w/v) of NP40 have been added.

The kinase activity of Aurora2 is measured by scintillation with nickel chelate (New England Nuclear, model SMP107). Each well contains 100 µl of the following solution: 0.02 µM of Aurora2; 0.5 µM of NuMA substrate; 1 µM of ATP to which 0.5 µCi of ATP-[$^{33}$P] has been added. The solutions are incubated for 30 minutes at 37° C. The assay buffer is then removed and the wells are rinsed twice with 300 µl of kinase buffer. The radioactivity is measured in each well using a Packard Model Top Count NXT device.

The background noise is deduced from the measurement of radioactivity by measuring, in duplicate, in wells containing the radioactive ATP alone containing buffered kinase treated in the same way as the other samples.

The activity of the control is determined by measuring, in duplicate, the radioactivity in the complete assay mixture (ATP, Aurora2 and the NuMA substrate) in the absence of test compound.

The inhibition of the Aurora2 with a compound of the invention is expressed as percentage inhibition of the control activity in the absence of test compound. Staurosporine is added to each plate as an inhibition control.

4. Src

The inhibition of the Src kinase is evaluated by measuring the phosphorylation of the biotinylated cdc2 substrate (Pierce) detected by fluorescence (DELFIA) using an antiphosphotyrosine antibody labeled with Europium, in 96-well Wallac plates. The c-Src protein used is a recombinant human protein produced in Baculovirus, comprising the SH3 and SH2 and the catalytic domains. The enzyme, the substrate and the various concentrations of test compounds are placed in the well in a 50 mM Tris buffer containing 10 mM $MgCl_2$. The reaction is initiated by adding 10 µM of ATP. After incubation for 60 minutes at 30° C., the reaction is stopped by adding 75 mM EDTA. 50 µl are taken from each well and transferred into a plate coated with streptavidin. After incubation for 30 minutes at 25° C., the wells are washed with a washing buffer (Wallac) and then the antiphosphotyrosine antibody (PY20-Europium [Perkin Elmer]) is added in a volume of 75 µl. The plate is incubated for 30 minutes at 25° C. and then an "Enhancer" solution (Wallac) is added before reading the fluorescence using a fluorimeter (Perkin Elmer). The background noise is evaluated in triplicate in wells containing the substrate and the antibody in the absence of enzyme. The activity of the enzyme is measured (in triplicate) in the wells containing all the reagents in the absence of compound. The inhibition of the Src activity is expressed as percentage inhibition of the activity of the control determined in the absence of compound. The compound PP2 (Calbiochem) is included at various concentrations in each experiment as an inhibition control.

5. Tie2

The coding sequence of human Tie2 corresponding to the amino acids of the intracellular domain 776-1124 was generated by PCR using the cDNA isolated from human placenta as model. This sequence was introduced into a baculovirus expression vector pFastBacGT in the form of a GST fusion protein.

The inhibitory effect of the molecules is determined in an assay of phosphorylation of PLC by Tie2 in the presence of GST-Tie2 purified to approximately 80% homogeneity. The substrate is composed of the SH2-SH3 fragments of PLC expressed in the form of a GST fusion protein.

The kinase activity of Tie2 is measured in a 20 mM MOPS buffer, pH 7.2, containing 10 mM $MgCl_2$, 10 mM $MnCl_2$, 1 mM DTT and 10 mM of glycerophosphate. A reaction mixture composed of 70 µl of kinase buffer containing 100 ng of GST-Tie2 enzyme per well is placed in a FlashPlate 96-well plate kept on ice. 10 µl of the test molecule diluted in DMSO at a maximum concentration of 10% are then added. For a given concentration, each measurement is carried out in quadruplicate. The reaction is initiated by adding 20 µl of solution containing 2 µg of GST-PLC, 2 µM of cold ATP and 1 µCi of $^{33}$P[ATP]. After incubation for 1 hour at 37° C., the reaction is stopped by adding 1 volume (100 µl) of 200 mM EDTA. After removing the incubation buffer, the wells are washed three times with 300 µl of PBS. The radioactivity is measured on a Wallac MicroBeta1450.

The inhibition of the Tie2 activity is calculated and expressed as percentage inhibition compared to the control activity determined in the absence of compound.

6. IGF1R

The inhibitory activity of the compounds on IGF1R is determined by measuring the inhibition of the autophosphorylation of the enzyme using a time resolved fluorescence (HTRF) assay.

The human IGF1R cytoplasmic domain was cloned, as a fusion with glutathione S-transferase (GST), into the baculovirus expression vector pFastBac-GST. The protein was expressed in SF21 cells and purified to approximately 80% homogeneity.

The kinase activity was determined by incubating the enzyme with various concentrations of test compound in a 50 mM Hepes buffer, pH 7.5, containing mM $MnCl_2$, 50 mM NaCl, 3% glycerol, 0.025% Tween 20 and 120 mM of ATP. The enzyme reaction is stopped by adding 100 mM Hepes buffer, pH 7.0, containing 0.4 M KF, 133 mM EDTA and 0.1% BSA containing an anti-GST antibody labeled with XL665 and an antiphosphotyrosine antibody conjugated to europium cryptate (Eu—K). The characteristics of the two fluorophores, XL-665 and Eu—K, are available in G. Mathis et al., Anticancer Research, 1997, 17, pages 3011-3014. The transfer of energy from the excited europium cryptate to the acceptor XL665 is proportional to the degree of autophosphorylation of IGF1R. The long-lived signal specific for XL-665 is measured in a Victor analyzer plate counter (Perkin-Elmer). The inhibition of the IGF1R autophosphorylation activity with compounds of the invention is expressed as percentage inhibition compared to a control whose activity is measured in the absence of test compound.

7. CDK2

The inhibition of the CDK2/cyclinE kinase is evaluated by measuring the phosphorylation of the peptide substrate Rb-biotinylated, detected by fluorescence, in 96-well scintillation plates (Flashplates) coated with streptavidin.

Each point is assayed in duplicate.

Sequence of the Rb-biotinylated peptide: Biotin-SAC-PLNLPLQNNHTMDMYLSPVRSPKKKGSTTR-OH Kinase Buffer:

| HEPES, pH 8.0 | 50 mM |
|---|---|
| $MgCl_2$ $6H_2O$ | 10 mM |
| DTT | 1 mM |

Protocol:
1. Preparation of the substrate: fresh solution at 1 mg/ml in PBS.
2. Introduce 4 µg per well into the scintillation plate.
3. Incubate for 2 hours at ambient temperature.
4. Prepare series of dilutions at 1 mM, 300 µM, 100 µM, 30 µM and 10 µM in DMSO from a stock solution of inhibitor at 10 mM in DMSO.
5. Wash the scintillation plate with 3 times 300 µl of PBS to remove the unbound peptide substrate.
6. Add the CDK2/cyclinE kinase: 200 ng per well, in 90 µl of kinase buffer (with the exception of the "without enzyme" control wells).
7. Add the test inhibitor to each of the wells, at a final concentration for 100 µl of 10 µM, 3 µM, 1 µM, 0.3 µM and 0.1 µM.
8. Agitate the scintillation plate gently for 1 minute.
9. Incubate for 30 minutes on ice.
10. Initiate the reaction with 10 µl of kinase buffer having a final concentration per well of 1 µM of cold ATP and of 1 µCi of ATP-$^{33}$P.
11. Agitate the scintillation plate gently for 1 minute.
12. Incubate for 45 minutes at ambient temperature (without agitation).
13. Wash the scintillation plate 3 times with 300 µl of PBS.
14. Indirect measurement of the radioactivity corresponding to the incorporation of ATP-$^{33}$P, originating from the kinase, into the phosphorylation site of Rb.

8. CDK4

The inhibition of the CDK4/cyclinD1 kinase is evaluated by measuring the phosphorylation of the peptide substrate Rb-biotinylated, detected by fluorescence, in 96-well scintillation plates (Flashplates) coated with streptavidin.

Each point is assayed in duplicate.

Sequence of the Rb-biotinylated peptide: biotin-RPPTL-SPIPHIPRSPYKFPSSPLR

Kinase Buffer:

| HEPES, pH 8.0 | 50 mM |
|---|---|
| $MgCl_2$ $6H_2O$•pH 7.0 | 10 mM |
| DTT | 1 mM |

Protocol:
1. Preparation of the substrate: fresh solution at 1 mg/ml in PBS.
2. Introduce 100 µg per well into the scintillation plate.
3. Incubate for 2 hours at ambient temperature.
4. Prepare series of dilutions at 1 mM, 300 µM, 100 µM, 30 µM and 10 µM in DMSO from a stock solution of inhibitor at 10 mM in DMSO.

5. Wash the scintillation plate with 3 times 300 μl of PBS to remove the unbound peptide substrate.
6. Add the CDK4/cyclinD1 kinase: 70 ng per well, in 90 μl of kinase buffer (with the exception of the "without enzyme" control wells).
7. Add 1 μl of test inhibitor to each of the wells, at a final concentration for 100 μl of 10 μM, 3 μM, 1 μM, 0.3 μM and 0.1 μM.
8. Agitate the scintillation plate gently for 1 minute.
9. Incubate for 30 minutes on ice.
10. Initiate the reaction with 10 μl of kinase buffer having a final concentration per well of 1 μM of cold ATP and of 1 μCi of ATP-$^{33}$P.
11. Agitate the scintillation plate gently for 1 minute.
12. Incubate for 45 minutes at ambient temperature (without agitation).
13. Wash the scintillation plate 3 times with 300 μl of PBS.
14. Indirect measurement of the radioactivity corresponding to the incorporation of ATP-$^{33}$P, originating from the kinase, into the phosphorylation site of Rb.

TABLE 1

| Structure | Example | % inhib at 10 or 30* μM | KDR | Aurora2 | SRC | TIE2 | IGF1R | CDK2 | CDK4 |
|---|---|---|---|---|---|---|---|---|---|
| 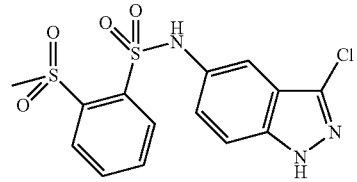 | 1 | 70* | 7 | 86 | | 18 | | | |
| 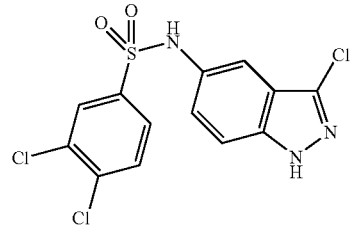 | 2 | 75* | 43 | | | | | | |
| 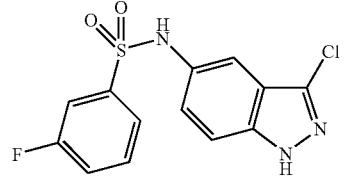 | 3 | 71* | 22 | 46 | | 15 | | | |
| 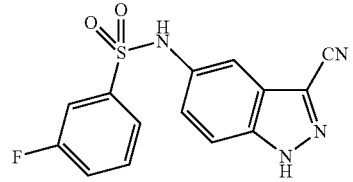 | 4 | 85* | 24 | | | | | | |
| 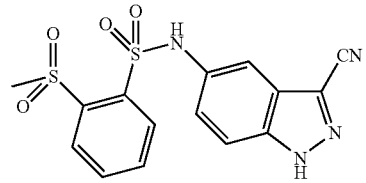 | 5 | 80* | 26 | | | | | | |

TABLE 1-continued
| Structure | Example | % inhib at 10 or 30* μM | % inhib at 10 μM | | | | | | |
| --- | --- | --- | --- | --- | --- | --- | --- | --- | --- |
| | | | KDR | Auro ra2 | SRC | TIE 2 | IGF1 R | CDK 2 | CDK 4 |
| 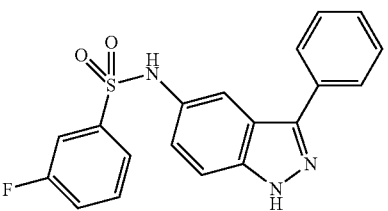 | 6 | 82 | 85 | 95 | 55 | 74 | | | |
| 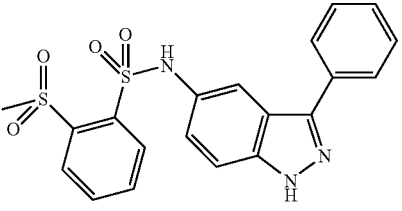 | 7 | 89 | 70 | 97 | 89 | 86 | | | |
| 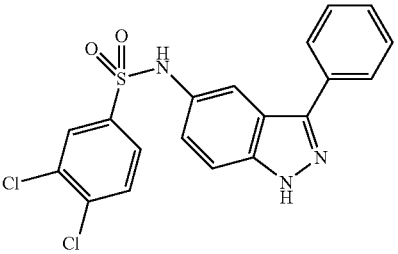 | 8 | 76* | 81 | 59 | | 56 | | | |
| 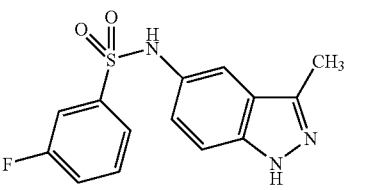 | 9 | 68* | 18 | 61 | | 29 | | | |
| 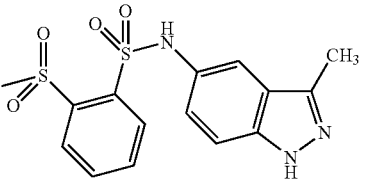 | 10 | 66* | 20 | 90 | | 33 | | | |
| 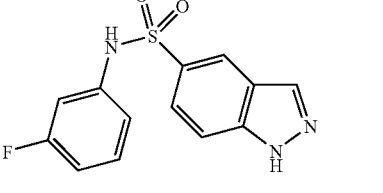 | 11 | 59 | 7 | | | | | | |

TABLE 1-continued

| Structure | Example | % inhib at 10 or 30* µM | % inhib at 10 µM |||||||
|---|---|---|---|---|---|---|---|---|---|
| | | | KDR | Aurora2 | SRC | TIE 2 | IGF1 R | CDK 2 | CDK 4 |
| (structure) | 12 | 92* | 39 | | | | | | |
| (structure) | 13 | 83* | 0 | 76 | | 22 | | | |
| (structure) | 14 | 42 | | | | | | | |
| (structure) | 15 | 67* | 13 | | | | | | |
| (structure) | 16 | 58 | 8 | | | | | | |
| (structure) | 17 | 59 | 46 | | | | | | |
| (structure) | 18 | 89 | 18 | 97 | | | | | |

TABLE 1-continued
| Structure | Example | % inhib at 10 or 30* µM | % inhib at 10 µM | | | | | | |
|---|---|---|---|---|---|---|---|---|---|
| | | | KDR | Aurora2 | SRC | TIE2 | IGF1R | CDK2 | CDK4 |
| 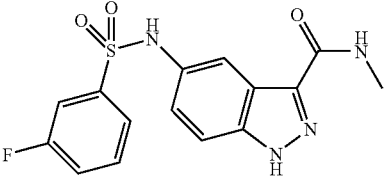 | 19 | 85 | 73 | | | | | | |
| 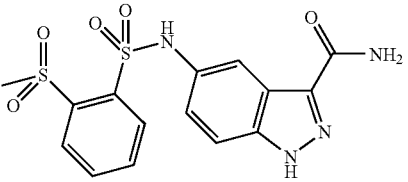 | 20 | 76 | 28 | | | | | | |
| 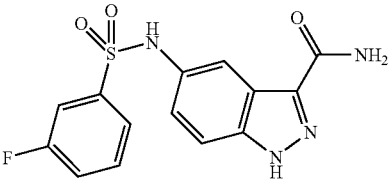 | 21 | 76* | 80 | | | | | | |
| 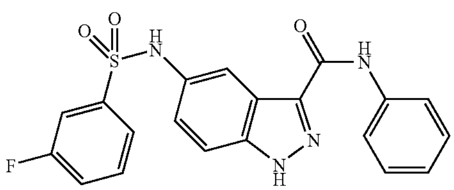 | 22 | 89 | 18 | 84 | | | | | |
| 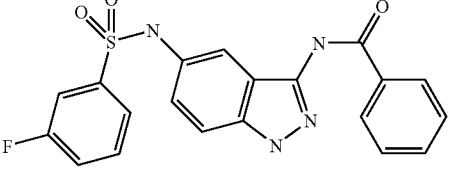 | 23 | 93 | | 99 | | | | | |
| 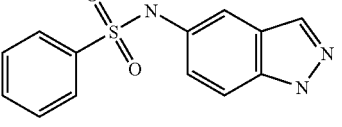 | 24 | 76 | 10 | 60 | | | | | |
| 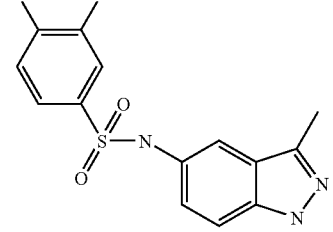 | 25 | 38* | 11 | 50 | | | | | |

TABLE 1-continued

| Structure | Example | % inhib at 10 or 30* µM | % inhib at 10 µM | | | | | |
|---|---|---|---|---|---|---|---|---|
| | | | KDR | Aurora2 | SRC | TIE 2 | IGF1R | CDK 2 | CDK 4 |
| [3-fluorophenyl-SO2-NH-indazole] | 26 | 96 | 24 | 95 | | | 34 | 39 | |
| [3-fluorophenyl-SO2-NH-indazole-N(SO2Me)] | 27 | 6 | 13 | 76 | | | | | |
| [3-fluorophenyl-SO2-NH-indazole-NHAc] | 28 | 84 | 24 | 92 | | | | | |
| [2-(methylsulfonyl)phenyl-SO2-NH-indazole-C(O)NH-cyclohexyl] | 29 | 0 | 8 | 80 | | | 96 | | |
| [2-(methylsulfonyl)phenyl-SO2-NH-indazole-3-(4-chlorophenyl)] | 30 | 88 | 85 | 100 | 72 | | 96 | 73 | |

TABLE 1-continued
| Structure | Example | % inhib at 10 or 30* μM | % inhib at 10 μM | | | | | |
|---|---|---|---|---|---|---|---|---|
| | | | KDR | Aurora2 | SRC | TIE 2 | IGF1R | CDK 2 | CDK 4 |
| 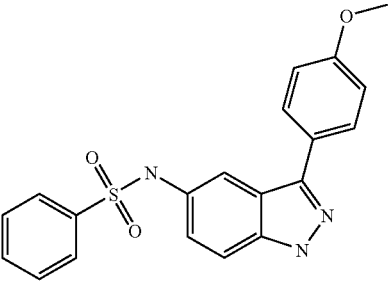 | 31 | 75 | 98 | 90 | | | | | |
| 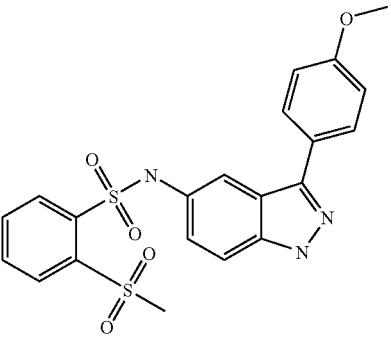 | 32 | 97 | 87 | 92 | | | | 93 | |
| 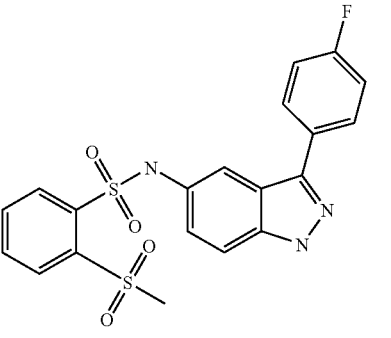 | 33 | 94 | 68 | 89 | | | | 94 | |
| 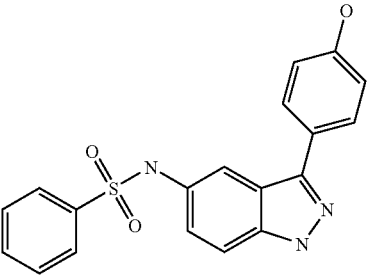 | 34 | 87 | 96 | 100 | | | | 89 | |

TABLE 1-continued

Results

| Structure | Example | % inhib at 10 or 30* μM | % inhib at 10 μM ||||||
|---|---|---|---|---|---|---|---|---|
| | | | KDR | Aurora2 | SRC | TIE 2 | IGF1R | CDK 2 | CDK 4 |
| (structure) | 35 | 97 | 80 | 94 | | | | 94 | |
| (structure) | 36 | 92 | 23 | 80 | | | | 92 | |
| (structure) | 37 | 67 | 8 | 36 | | | | 51 | |
| (structure) | 38 | 69 | 3 | 86 | 56 | | | | |
| (structure) | 39 | 96 | 20 | 81 | | | | 72 | |
| (structure) | 40 | 55 | 22 | 70 | | | | 12 | |

TABLE 1-continued
| Structure | Example | % inhib at 10 or 30* μM | % inhib at 10 μM | | | | | |
|---|---|---|---|---|---|---|---|---|
| | | | KDR | Aurora2 | SRC | TIE2 | IGF1R | CDK2 | CDK4 |
| 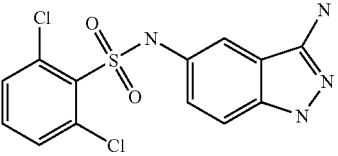 | 41 | 71 | 36 | 90 | | | | 18 | |
| 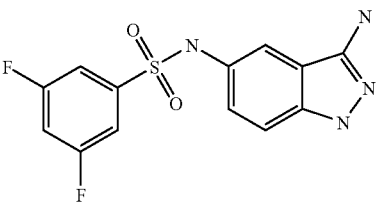 | 42 | 100 | 25 | 50 | | | | 0 | |
| 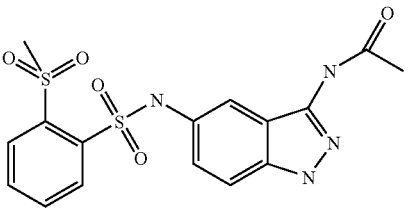 | 43 | 83 | 25 | 85 | | | | 96 | |
| 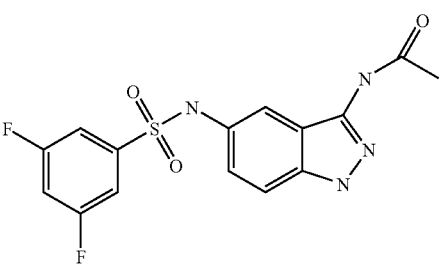 | 44 | 95 | 37 | | | | | 82 | |
| 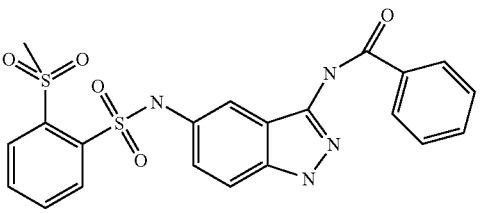 | 45 | 100 | 55 | 95 | | | | 95 | |
| 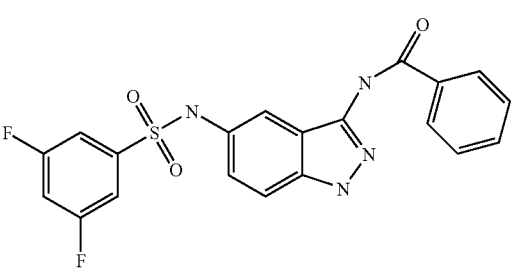 | 46 | 90 | 82 | 95 | | | | 82 | |

TABLE 1-continued
| Structure | Example | % inhib at 10 or 30* μM | % inhib at 10 μM | | | | | |
|---|---|---|---|---|---|---|---|---|
| | | | KDR | Aurora2 | SRC | TIE 2 | IGF1R | CDK 2 | CDK 4 |
| 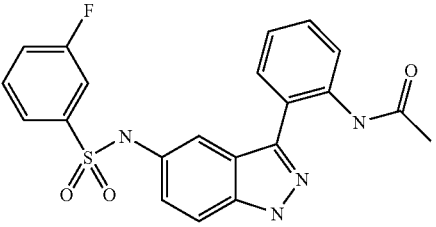 | 47 | 32 | 25 | 65 | | | | | |
| 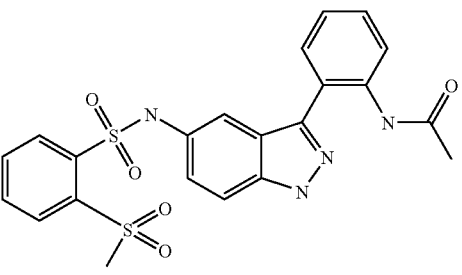 | 48 | 5 | 9 | 42 | | | | | |
| 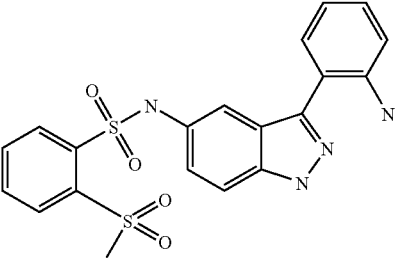 | 49 | 40 | 18 | 17 | | | | 50 | |
| 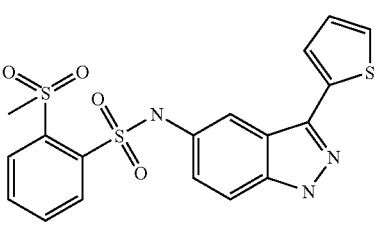 | 50 | 99 | 80 | 91 | | | | 63 | |
| 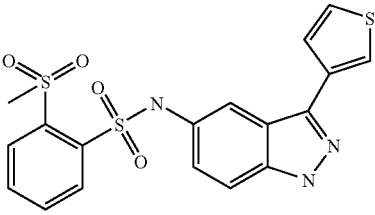 | 51 | 90 | 55 | 88 | | | | | |
| 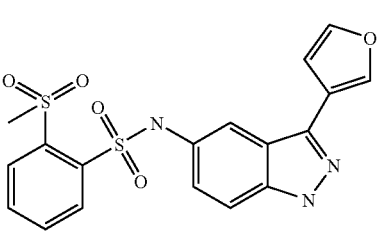 | 52 | 93 | 49 | 84 | | | | 80 | |

TABLE 1-continued
| Structure | Example | % inhib at 10 or 30* µM | KDR | Auro ra2 | SRC | TIE 2 | IGF1 R | CDK 2 | CDK 4 |
|---|---|---|---|---|---|---|---|---|---|
| 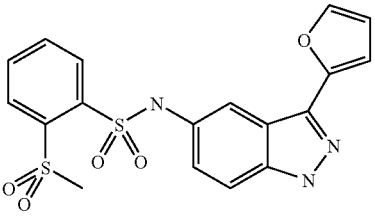 | 53 | 96 | 42 | 91 | | | | 76 | |
| 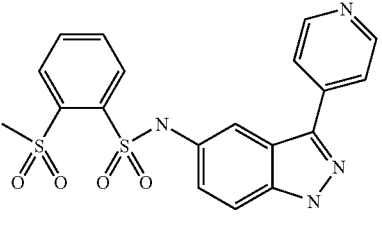 | 54 | 96 | 76 | 100 | | | | 87 | |
| 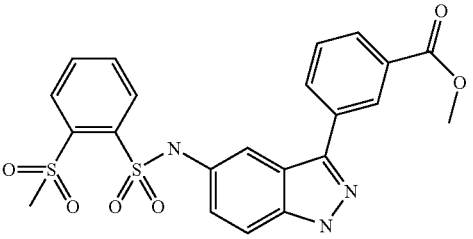 | 55 | 98 | 51 | 94 | | | | 64 | |
| 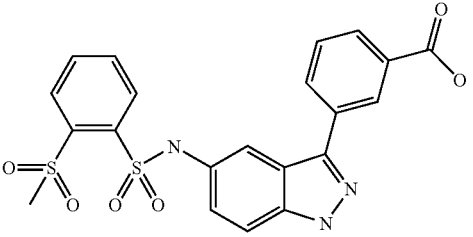 | 56 | 81 | 82 | 87 | | | | | |
| 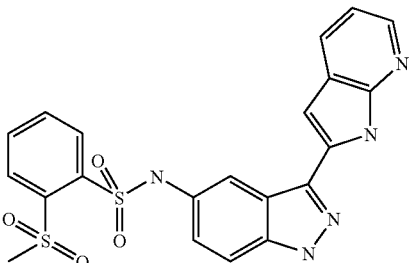 | 57 | 48 | 22 | 53 | | | | 0 | |

TABLE 1-continued
| Structure | Example | % inhib at 10 or 30* μM | % inhib at 10 μM ||||||
|---|---|---|---|---|---|---|---|---|
| | | | KDR | Aurora2 | SRC | TIE2 | IGF1R | CDK2 | CDK4 |
| 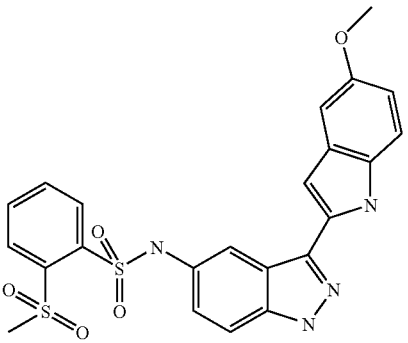 | 58 | 97 | 97 | 100 | | | | 100 | |
| 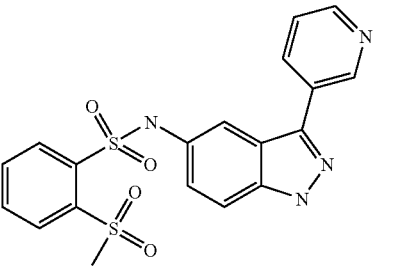 | 59 | 95 | 40 | 100 | | | | 88 | |
| 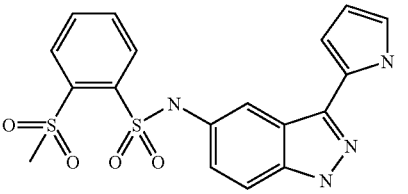 | 60 | 99 | 64 | 100 | 98 | | | 99 | |
| 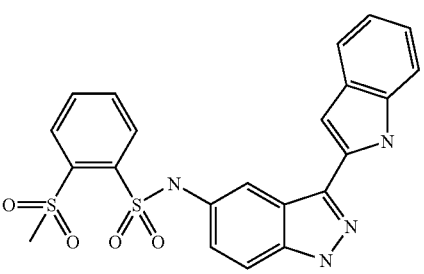 | 61 | 99 | 98 | 100 | 99 | | | 99 | |
| 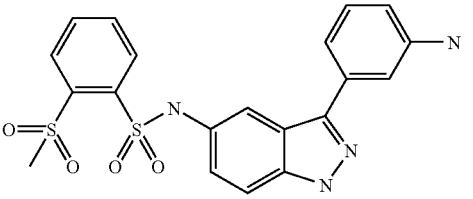 | 62 | 99 | 74 | 100 | 95 | | | 88 | |

TABLE 1-continued

| Structure | Example | % inhib at 10 or 30* μM | % inhib at 10 μM ||||||
|---|---|---|---|---|---|---|---|---|
| | | | KDR | Aurora2 | SRC | TIE2 | IGF1R | CDK2 | CDK4 |
| | 63 | 94 | 0 | 100 | 46 | | | 81 | |
| | 64 | 30 | 41 | 72 | 86 | | | | |
| | 65 | 86 | 73 | 100 | 96 | | | 63 | |
| | 66 | 75 | 20 | 100 | 90 | | | | |
| | 67 | 79 | 28 | 90 | | | | | |

TABLE 1-continued
| Structure | Example | % inhib at 10 or 30* μM | % inhib at 10 μM | | | | | | |
| --- | --- | --- | --- | --- | --- | --- | --- | --- | --- |
| | | | KDR | Aurora2 | SRC | TIE 2 | IGF1 R | CDK 2 | CDK 4 |
| 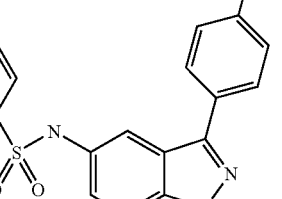 | 68 | 91 | 85 | 95 | | | | | |
| 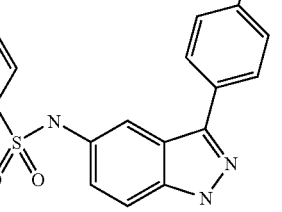 | 69 | 98 | 73 | 99 | | | | 61 | |
| 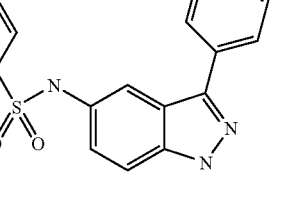 | 70 | 99 | 71 | 98 | | | | 85 | |
| 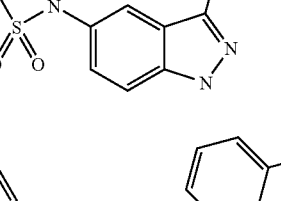 | 71 | 97 | 83 | 93 | | | | 90 | |
| 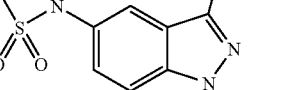 | 72 | 21 | 41 | 78 | 77 | | | | |

TABLE 1-continued
| Structure | Example | % inhib at 10 or 30* μM | KDR | Aurora2 | SRC | TIE2 | IGF1R | CDK2 | CDK4 |
|---|---|---|---|---|---|---|---|---|---|
| 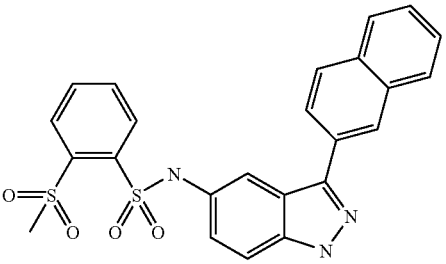 | 73 | 87 | 38 | 100 | 40 | | | | |
| 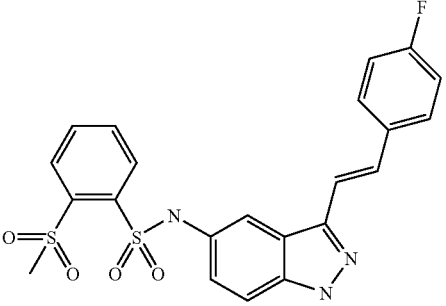 | 74 | 99 | 95 | 99 | | | 95 | | |
| 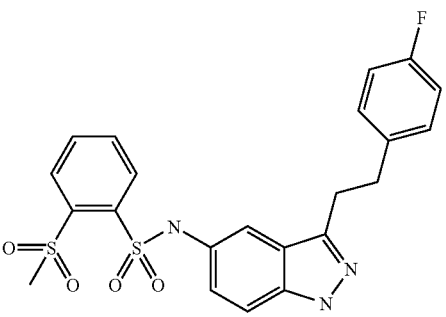 | 75 | 82 | 35 | 87 | | | | | |
| 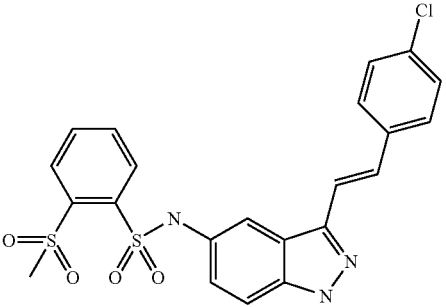 | 76 | 96 | 92 | 99 | | | 96 | | |

TABLE 1-continued

| Structure | Example | % inhib at 10 or 30* μM | % inhib at 10 μM | | | | | |
|---|---|---|---|---|---|---|---|---|
| | | | KDR | Aurora2 | SRC | TIE 2 | IGF1R | CDK 2 | CDK 4 |
| (structure) | 77 | 73 | 36 | 93 | | | | | |
| (structure) | 78 | 94 | 97 | 100 | | | | 96 | |
| (structure) | 79 | 98 | 50 | 95 | | | | 37 | |
| (structure) | 80 | 66 | 32 | 89 | | | | | |
| (structure) | 81 | 98 | 93 | 100 | 100 | | | 99 | |

TABLE 1-continued

| Structure | Example | % inhib at 10 or 30* μM | KDR | Aurora2 | SRC | TIE2 | IGF1R | CDK2 | CDK4 |
|---|---|---|---|---|---|---|---|---|---|
| 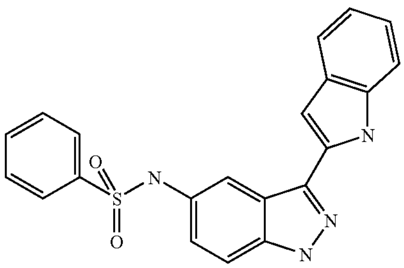 | 82 | 93 | 100 | 100 | | | | 100 | |
| 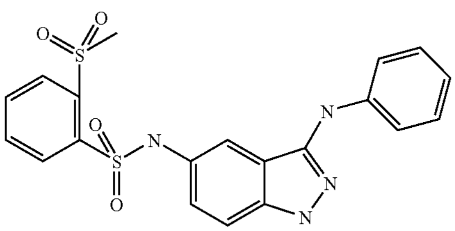 | 83 | 92 | 60 | 93 | | | | 100 | |
| 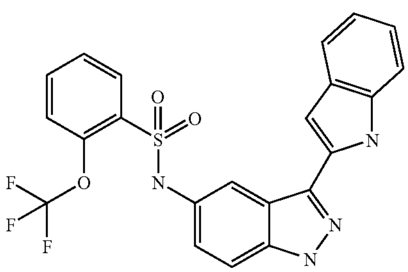 | 84 | 90 | 98 | 100 | | | | 94 | |
| 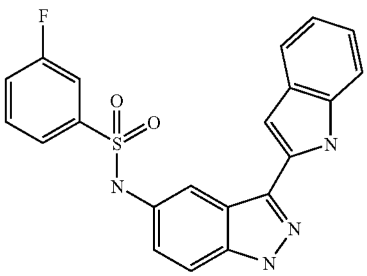 | 85 | 95 | 99 | 100 | | | | 99 | |
| 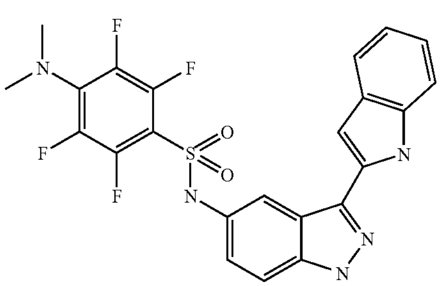 | 86 | 40 | 85 | 86 | | | | 53 | |

TABLE 1-continued
| Structure | Example | % inhib at 10 or 30* μM | % inhib at 10 μM | | | | | |
|---|---|---|---|---|---|---|---|---|
| | | | KDR | Aurora2 | SRC | TIE2 | IGF1R | CDK2 | CDK4 |
| 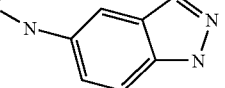 | 87 | 91 | 100 | 100 | | | | | |
| 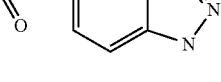 | 88 | 21 | 25 | 55 | | | 82 | | |
| 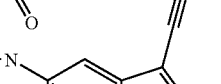 | 89 | 92 | 85 | 92 | | | 90 | | |
|  | 90 | 89 | 45 | 100 | | | | | |
| 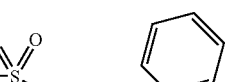 | 91 | 95 | 35 | 11 | | | 7 | | |

TABLE 1-continued

| Structure | Example | % inhib at 10 or 30* μM | % inhib at 10 μM | | | | | |
|---|---|---|---|---|---|---|---|---|
| | | | KDR | Aurora2 | SRC | TIE2 | IGF1R | CDK2 | CDK4 |
| | 92 | 27 | 66 | 70 | | | | 62 | |
| | 93 | 94 | 83 | 89 | | | | 87 | |
| | 94 | 36 | 88 | 65 | | | | 70 | |
| | 95 | 0 | 34 | 30 | | | | 73 | |
| | 96 | 67 | 91 | 100 | 83 | | | | |

TABLE 1-continued

| Structure | Example | % inhib at 10 or 30* μM | % inhib at 10 μM ||||||
|---|---|---|---|---|---|---|---|---|
| | | | KDR | Aurora2 | SRC | TIE 2 | IGF1R | CDK 2 | CDK 4 |
| | 97 | 50 | 96 | 93 | 76 | | | | |
| | 98 | 53 | 91 | 94 | 78 | | | | |
| | 99 | 44 | 46 | 79 | | | | | |
| | 100 | 94 | 74 | 44 | | | | 13 | |
| | 101 | 84 | 39 | 30 | | | | 28 | |

TABLE 1-continued

| Structure | Example | % inhib at 10 or 30* μM | % inhib at 10 μM ||||||
|---|---|---|---|---|---|---|---|---|
| | | | KDR | Aurora2 | SRC | TIE2 | IGF1R | CDK2 | CDK4 |
| | 102 | 90 | 77 | 96 | | | | 74 | |
| | 103 | 61 | 25 | 40 | | | | 19 | |
| | 104 | 85 | 75 | 97 | | | | 73 | |
| | 105 | 71 | 28 | 49 | | | | 25 | |

TABLE 1-continued
| Structure | Example | % inhib at 10 or 30* μM | % inhib at 10 μM | | | | | | |
|---|---|---|---|---|---|---|---|---|---|
| | | | KDR | Aurora2 | SRC | TIE 2 | IGF1R | CDK 2 | CDK 4 |
| 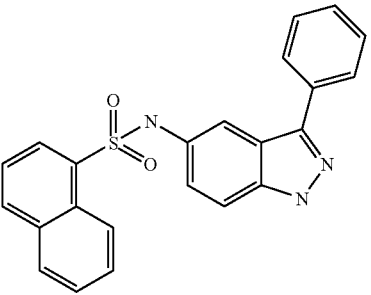 | 106 | 43 | 79 | 92 | | | | 90 | |
| 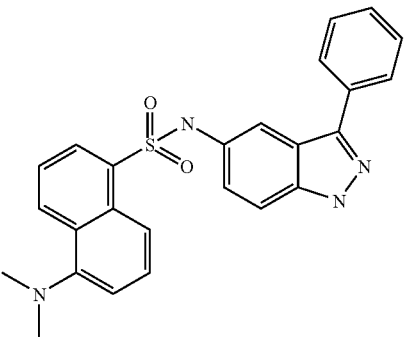 | 107 | 10 | 51 | 43 | | | | 84 | |
| 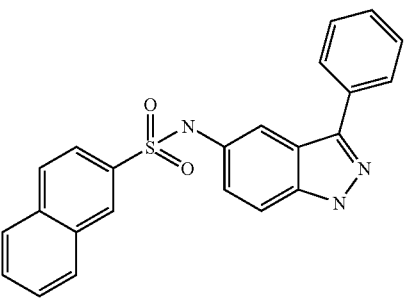 | 108 | 8 | 72 | 44 | | | | 78 | |
| 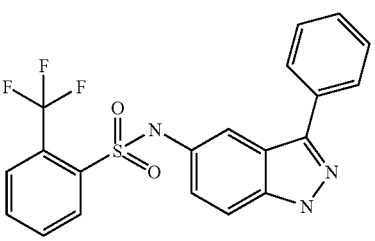 | 109 | 61 | 91 | 100 | 42 | | | 81 | |
| 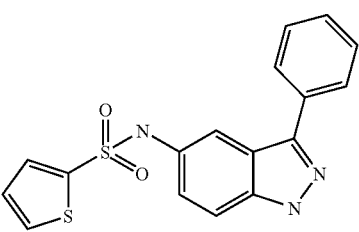 | 110 | 66 | 91 | 100 | 45 | | | 80 | |

TABLE 1-continued

| Structure | Example | % inhib at 10 or 30* μM | % inhib at 10 μM ||||||
|---|---|---|---|---|---|---|---|---|
| | | | KDR | Aurora2 | SRC | TIE2 | IGF1R | CDK2 | CDK4 |
| (quinoline-8-sulfonamide linked to 3-phenyl-1H-indazol-5-yl) | 111 | 66 | 83 | 100 | | | | 99 |
| (benzenesulfonamide linked to 3-phenyl-1H-indazol-5-yl) | 112 | 75 | 93 | 100 | 47 | | | 84 |
| (2-nitrobenzenesulfonamide linked to 3-phenyl-1H-indazol-5-yl) | 113 | 73 | 88 | 100 | 23 | | | 81 |
| (2,4,6-triisopropylbenzenesulfonamide linked to 3-phenyl-1H-indazol-5-yl) | 114 | 48 | 90 | 98 | | | | 50 |
| (2,4,6-trimethylbenzenesulfonamide linked to 3-phenyl-1H-indazol-5-yl) | 115 | 31 | 78 | 70 | | | | 79 |

TABLE 1-continued
| Structure | Example | % inhib at 10 or 30* μM | % inhib at 10 μM | | | | | |
|---|---|---|---|---|---|---|---|---|
| | | | KDR | Aurora2 | SRC | TIE2 | IGF1R | CDK2 | CDK4 |
| 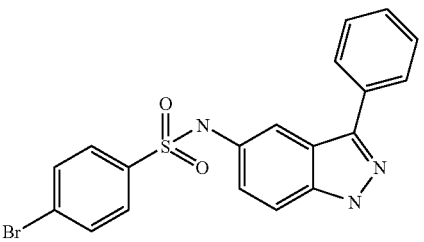 | 116 | 20 | 81 | 69 | | | | | |
| 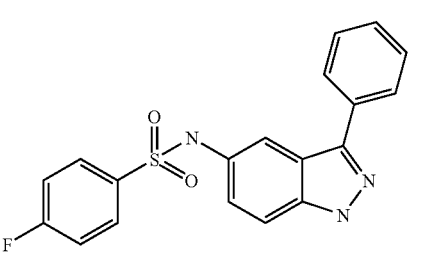 | 117 | 53 | 93 | 100 | 39 | | | 56 | |
| 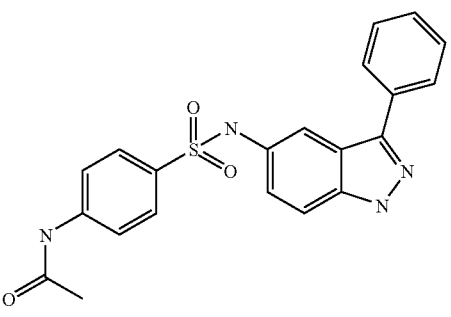 | 118 | 8 | 53 | 52 | | | | | |
| 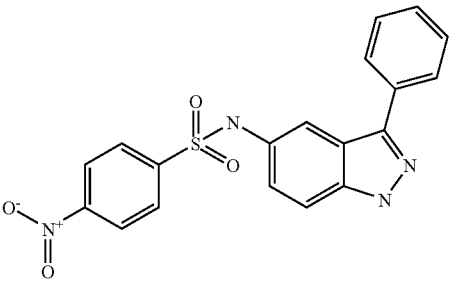 | 119 | 25 | 78 | 50 | | | | 50 | |
| 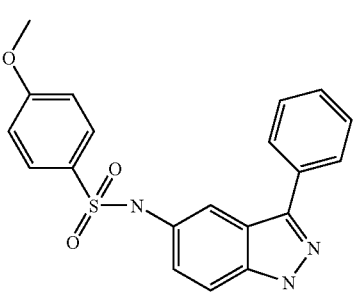 | 120 | 36 | 69 | 52 | | | | | |

TABLE 1-continued
| Structure | Example | % inhib at 10 or 30* μM | KDR | Aurora2 | SRC | TIE 2 | IGF1R | CDK 2 | CDK 4 |
|---|---|---|---|---|---|---|---|---|---|
| 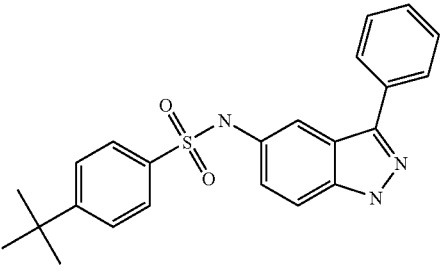 | 121 | 5 | 39 | 27 | | | | | |
| 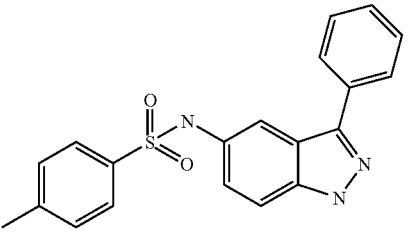 | 122 | 23 | 72 | 65 | | | | | |
| 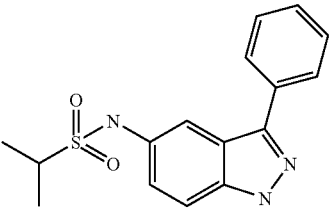 | 123 | 30 | 62 | 82 | | | | | |
| 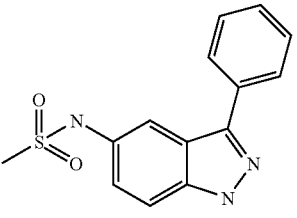 | 124 | 16 | 55 | 60 | | | | | |
| 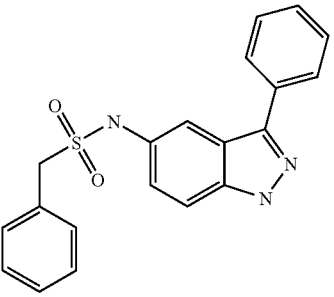 | 125 | 17 | 56 | 65 | | | | | |

TABLE 1-continued
| Structure | Example | % inhib at 10 or 30* μM | % inhib at 10 μM | | | | | |
|---|---|---|---|---|---|---|---|---|
| | | | KDR | Aurora2 | SRC | TIE 2 | IGF1 R | CDK 2 | CDK 4 |
| 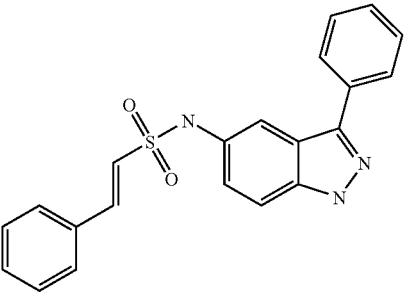 | 126 | 7 | 58 | 50 | | | | | |
| 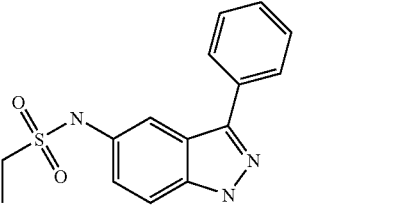 | 127 | 32 | 63 | 78 | | | | | |
| 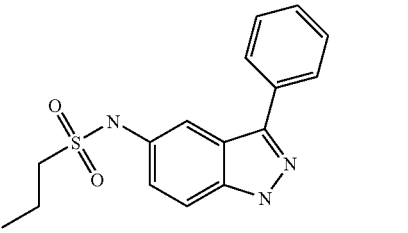 | 128 | 55 | 49 | 87 | | | | | |
| 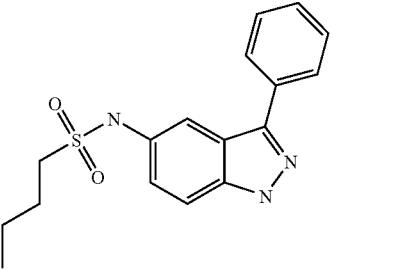 | 129 | 46 | 58 | 64 | | | | 30 | |
| 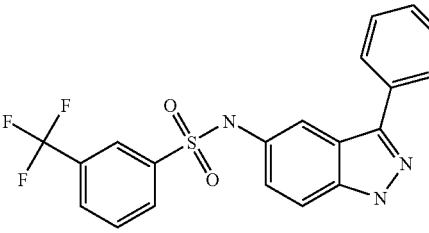 | 130 | 26 | 94 | 69 | 18 | | | | |

TABLE 1-continued

| Structure | Example | % inhib at 10 or 30* μM | % inhib at 10 μM | | | | | |
|---|---|---|---|---|---|---|---|---|
| | | | KDR | Aurora2 | SRC | TIE 2 | IGF1R | CDK 2 | CDK 4 |
| | 131 | 64 | 95 | 97 | 36 | | | 51 | |
| | 132 | 51 | 96 | 100 | 18 | | | 77 | |
| | 133 | 12 | 96 | 67 | 24 | | | 40 | |
| | 134 | 67 | 90 | 100 | 44 | | | 81 | |
| | 135 | 50 | 91 | 100 | 54 | | | 65 | |

TABLE 1-continued
Results
| Structure | Example | % inhib at 10 or 30* μM | % inhib at 10 μM ||||||
|---|---|---|---|---|---|---|---|---|
| | | | KDR | Aurora2 | SRC | TIE2 | IGF1R | CDK2 | CDK4 |
| 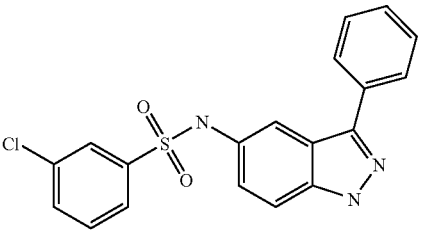 | 136 | 59 | 98 | 85 | 62 | | | | |
| 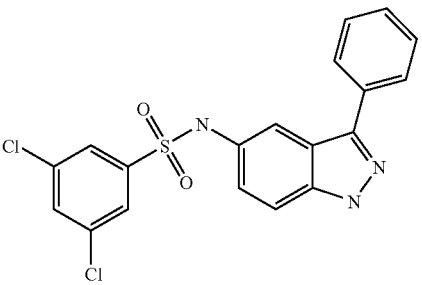 | 137 | 53 | 96 | 80 | 59 | | | | |
| 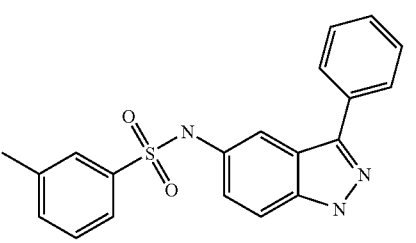 | 138 | 47 | 92 | 99 | 39 | | | 72 | |
| 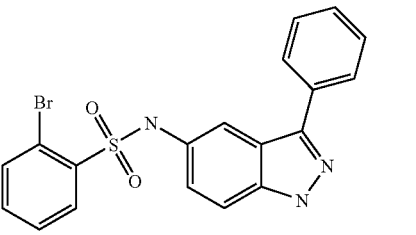 | 139 | 53 | 96 | 96 | 51 | | | | |
| 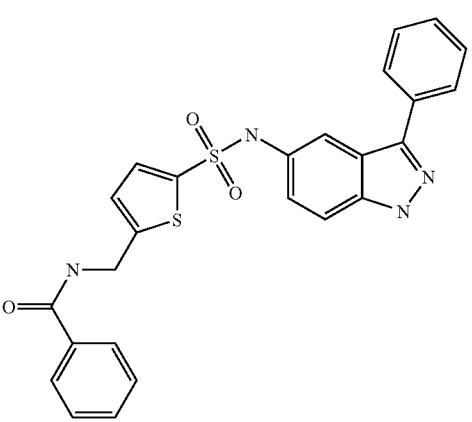 | 140 | 6 | 70 | 71 | | | | 40 | |

TABLE 1-continued
| Structure | Example | % inhib at 10 or 30* µM | KDR | Aurora2 | SRC | TIE 2 | IGF1R | CDK 2 | CDK 4 |
|---|---|---|---|---|---|---|---|---|---|
| 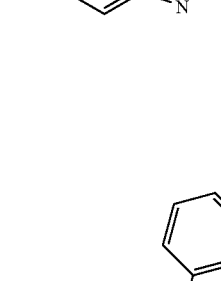 | 141 | 38 | 97 | 80 | 43 | | | | |
| 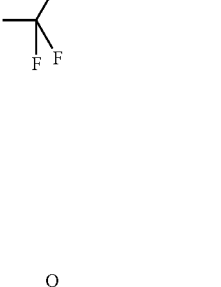 | 142 | 40 | 85 | 100 | | | | 74 | |
| 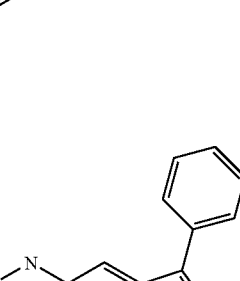 | 143 | 23 | 87 | 64 | | | | | |
| 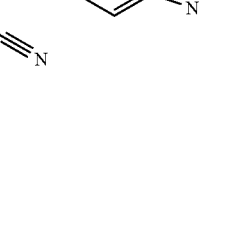 | 144 | 70 | 72 | 100 | | | | 69 | |

TABLE 1-continued

| Structure | Example | % inhib at 10 or 30* μM | % inhib at 10 μM | | | | | |
|---|---|---|---|---|---|---|---|---|
| | | | KDR | Aurora2 | SRC | TIE2 | IGF1R | CDK2 | CDK4 |
| [structure] | 145 | 0 | 14 | 26 | | | | | |
| [structure] | 146 | 14 | 47 | 57 | | | | | |
| [structure] | 147 | 0 | 96 | 86 | 88 | | | | |
| [structure] Chiral | 148 | 36 | 61 | 77 | | | | 30 | |

TABLE 1-continued
| | | | | % inhib at 10 µM | | | | | |
|---|---|---|---|---|---|---|---|---|---|
| Structure | Example | % inhib at 10 or 30* µM | KDR | Aurora2 | SRC | TIE 2 | IGF1 R | CDK 2 | CDK 4 |
| 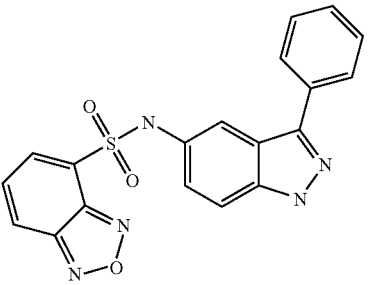 | 149 | 78 | 57 | 100 | | | | 67 | |
| 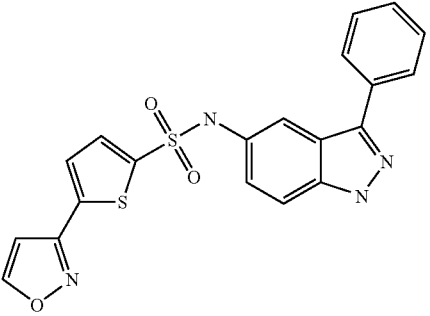 | 150 | 3 | 75 | 82 | | | | | |
| 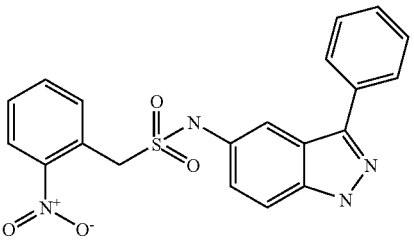 | 151 | 33 | 63 | 84 | | | | | |
| 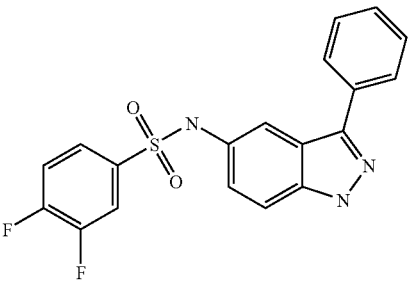 | 152 | 71 | 93 | 92 | 43 | | | 67 | |
| 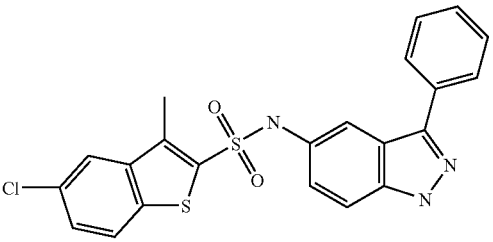 | 153 | 0 | 24 | 25 | | | | | |

TABLE 1-continued
| Structure | Example | % inhib at 10 or 30* μM | % inhib at 10 μM |||||||
| | | | KDR | Aurora2 | SRC | TIE2 | IGF1R | CDK2 | CDK4 |
|---|---|---|---|---|---|---|---|---|---|
| 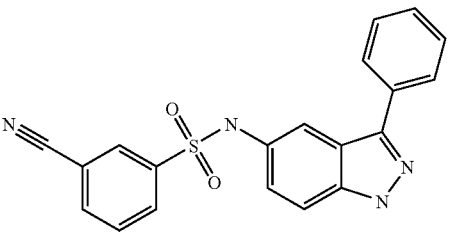 | 154 | 54 | 96 | 95 | 44 | | | 75 | |
| 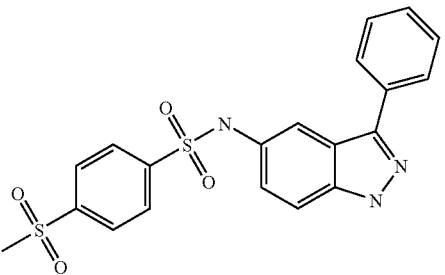 | 155 | 5 | 61 | 61 | | | | 50 | |
| 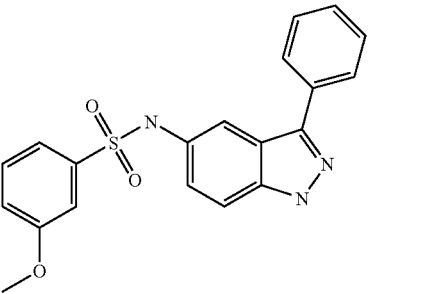 | 156 | 56 | 94 | 99 | 57 | | | 68 | |
| 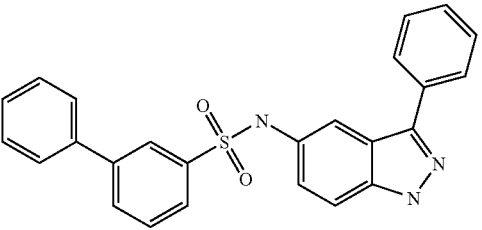 | 157 | 0 | 63 | 38 | | | | | |
| 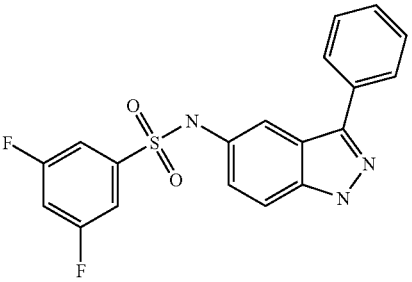 | 158 | 95 | 96 | 100 | 75 | | | 68 | |

TABLE 1-continued

| | | | Results | | | | | |
| | | | | % inhib at 10 µM | | | | |
| Structure | Example | % inhib at 10 or 30* µM | KDR | Aurora2 | SRC | TIE 2 | IGF1 R | CDK 2 | CDK 4 |
| --- | --- | --- | --- | --- | --- | --- | --- | --- | --- |
| 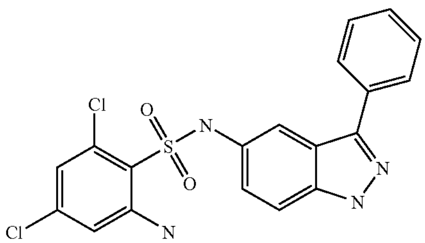 | 159 | 53 | 86 | 77 | | | | 58 | |
| 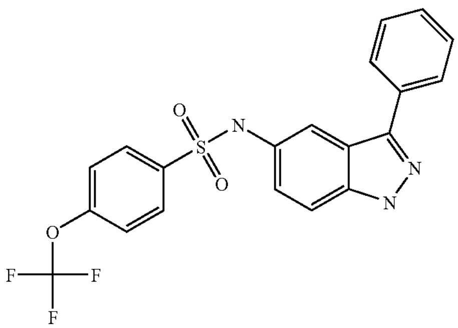 | 160 | 3 | 51 | 26 | | | | | |
| 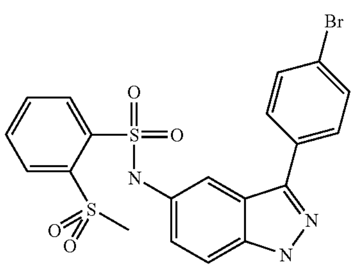 | 161 | 61 | 65 | 89 | | | | 75 | |
| 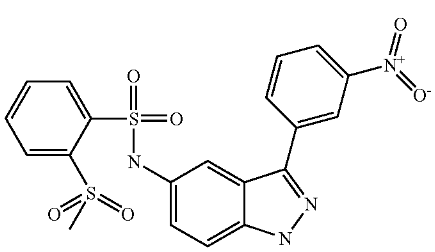 | 162 | 97 | 57 | 91 | | | | 82 | |
| 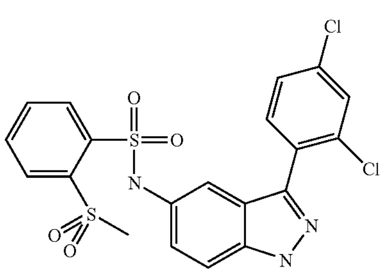 | 163 | 61 | 61 | 64 | | | | 23 | |

TABLE 1-continued

Results

| Structure | Example | % inhib at 10 or 30* μM | % inhib at 10 μM | | | | | | |
|---|---|---|---|---|---|---|---|---|---|
| | | | KDR | Aurora2 | SRC | TIE 2 | IGF1 R | CDK 2 | CDK 4 |
| (structure 164) | 164 | 90 | 71 | 91 | | | | 66 | |
| (structure 165) | 165 | 96 | 58 | 92 | | | | 71 | |
| (structure 166) | 166 | 53 | 33 | 61 | | | | 20 | |
| (structure 167) | 167 | 91 | 44 | 90 | | | | 77 | |
| (structure 168) | 168 | 95 | 49 | 87 | | | | 50 | |
| (structure 169) | 169 | 22 | 66 | 52 | | | | 13 | |

TABLE 1-continued

| Structure | Example | % inhib at 10 or 30* μM | KDR | Aurora2 | SRC | TIE 2 | IGF1R | CDK 2 | CDK 4 |
|---|---|---|---|---|---|---|---|---|---|
| | 170 | 62 | 60 | 69 | | | | 41 | |
| | 171 | 25 | 40 | 59 | | | | 20 | |
| | 172 | 92 | 71 | 94 | | | | 84 | |
| | 173 | 62 | 32 | 77 | | | | 27 | |
| | 174 | 100 | 53 | 93 | | | | 65 | |

TABLE 1-continued

| Structure | Example | % inhib at 10 or 30* µM | KDR | Aurora2 | SRC | TIE2 | IGF1R | CDK2 | CDK4 |
|---|---|---|---|---|---|---|---|---|---|
| 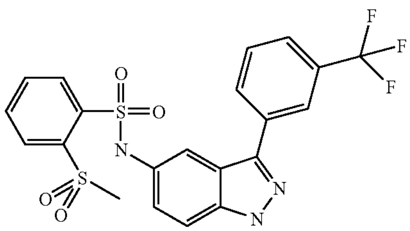 | 175 | 90 | 68 | 88 | | | | 81 | |
| 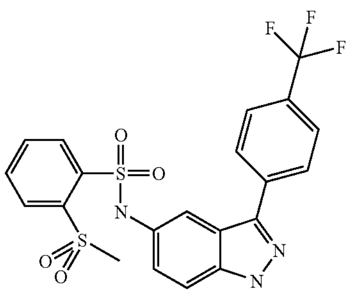 | 176 | 66 | 70 | 88 | | | | 83 | |
| 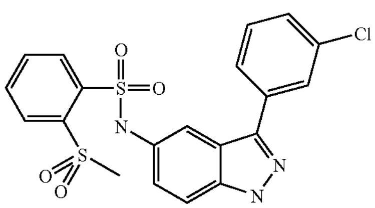 | 177 | 97 | 71 | 95 | | | | 80 | |
| 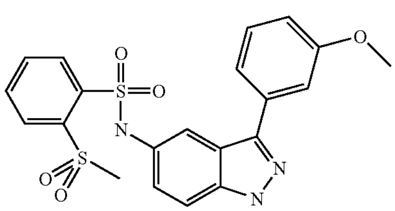 | 178 | 95 | 44 | 90 | | | | 67 | |
| 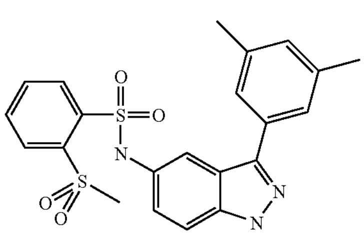 | 179 | 96 | 49 | 93 | | | | 72 | |
| 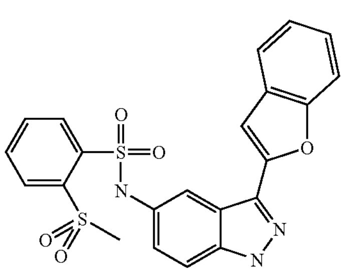 | 180 | 95 | 29 | 99 | | | | 93 | |

TABLE 1-continued

| Structure | Example | % inhib at 10 or 30* μM | % inhib at 10 μM | | | | | | |
|---|---|---|---|---|---|---|---|---|---|
| | | | KDR | Aurora2 | SRC | TIE2 | IGF1R | CDK2 | CDK4 |
| 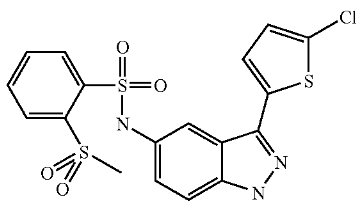 | 181 | 83 | 49 | 94 | | | | 55 | |
| 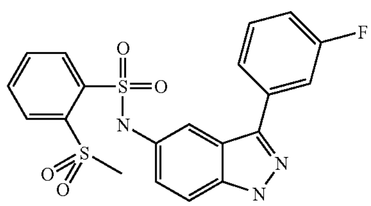 | 182 | 96 | 68 | 94 | | | | 69 | |
| 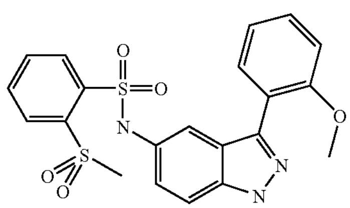 | 183 | 82 | 37 | 90 | | | | 50 | |
| 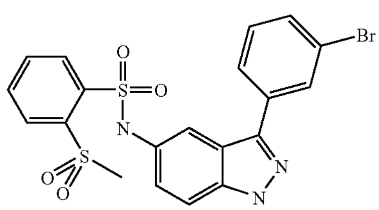 | 184 | 96 | 61 | 93 | | | | 73 | |
| 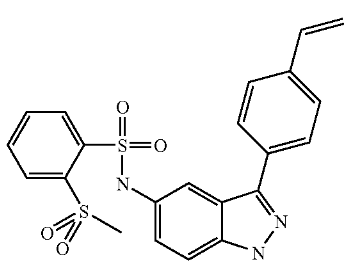 | 185 | 92 | 58 | 94 | | | | 77 | |
| 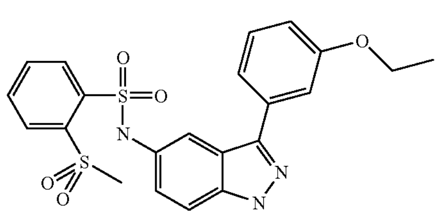 | 186 | 94 | 35 | 90 | | | | 60 | |

TABLE 1-continued

Results

| Structure | Example | % inhib at 10 or 30* μM | % inhib at 10 μM ||||||
|---|---|---|---|---|---|---|---|---|---|
| | | | KDR | Aurora2 | SRC | TIE 2 | IGF1R | CDK 2 | CDK 4 |
| (structure) | 187 | 46 | 49 | 67 | | | | 52 | |
| (structure) | 188 | 91 | 64 | 74 | | | | 61 | |
| (structure) | 189 | 70 | 20 | 62 | | | | 31 | |
| (structure) | 190 | 96 | 50 | 95 | | | | 74 | |
| (structure) | 191 | 96 | 45 | 88 | | | | 73 | |
| (structure) | 192 | 90 | 47 | 89 | | | | 72 | |

TABLE 1-continued
Results
| Structure | Example | % inhib at 10 or 30* µM | % inhib at 10 µM | | | | | |
|---|---|---|---|---|---|---|---|---|
| | | | KDR | Aurora2 | SRC | TIE 2 | IGF1 R | CDK 2 | CDK 4 |
| 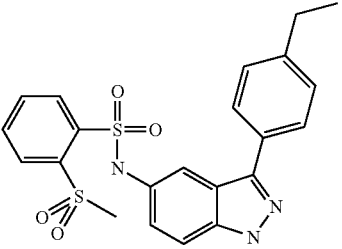 | 193 | 76 | 56 | 88 | | | | 65 | |
| 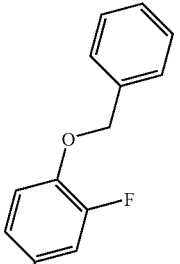 | 194 | 44 | 39 | 58 | | | | 41 | |
| 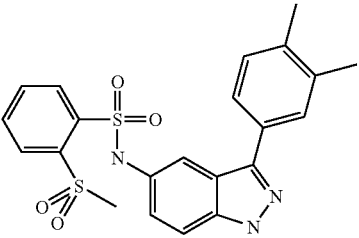 | 195 | 91 | 47 | 91 | | | | 75 | |
| 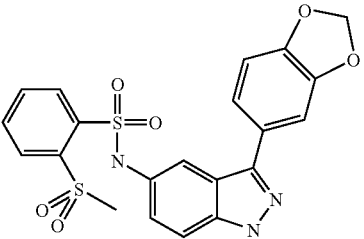 | 196 | 94 | 73 | 94 | | | | 76 | |
| 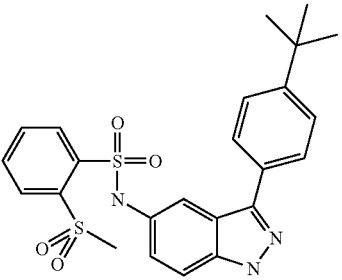 | 197 | 43 | 41 | 73 | | | | 0 | |

TABLE 1-continued

| Structure | Example | % inhib at 10 or 30* μM | KDR | Aurora2 | SRC | TIE 2 | IGF1R | CDK 2 | CDK 4 |
|---|---|---|---|---|---|---|---|---|---|
| 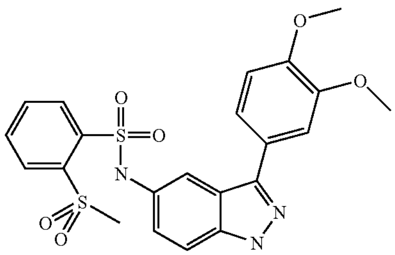 | 198 | 98 | 66 | 98 | | | | 76 | |
| 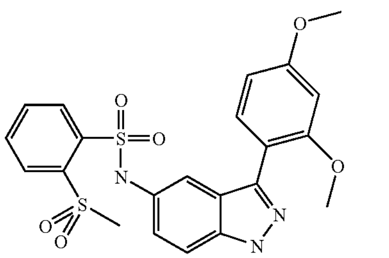 | 199 | 87 | 45 | 87 | | | | 27 | |
| 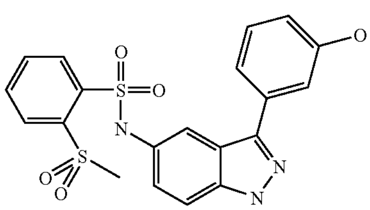 | 200 | 93 | 64 | 94 | | | | 73 | |
| 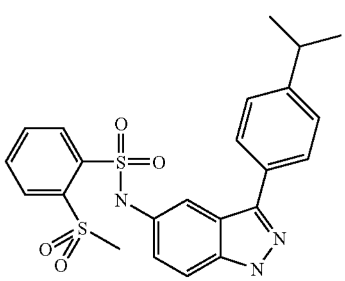 | 201 | 55 | 50 | 82 | | | | 24 | |
| 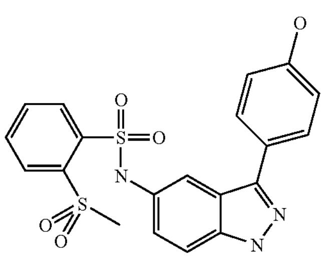 | 202 | 97 | 79 | 96 | | | | 83 | |

TABLE 1-continued

| Structure | Example | % inhib at 10 or 30* μM | % inhib at 10 μM | | | | | |
|---|---|---|---|---|---|---|---|---|
| | | | KDR | Aurora2 | SRC | TIE 2 | IGF1R | CDK 2 | CDK 4 |
| (structure) | 203 | 86 | 39 | 84 | | | | 59 | |
| (structure) | 204 | 97 | 67 | 95 | | | | 78 | |
| (structure) | 205 | 90 | 42 | 86 | | | | 66 | |
| (structure) | 206 | 58 | 48 | 85 | | | | 61 | |
| (structure) | 207 | 91 | 45 | 94 | | | | 56 | |

TABLE 1-continued
| Structure | Example | % inhib at 10 or 30* μM | % inhib at 10 μM |||||||
|---|---|---|---|---|---|---|---|---|---|
| | | | KDR | Aurora2 | SRC | TIE 2 | IGF1R | CDK 2 | CDK 4 |
| 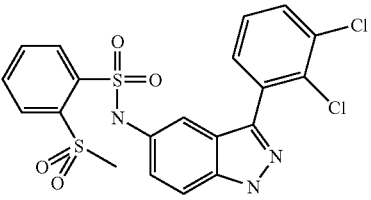 | 208 | −1 | 25 | 56 | | | | 0 | |
| 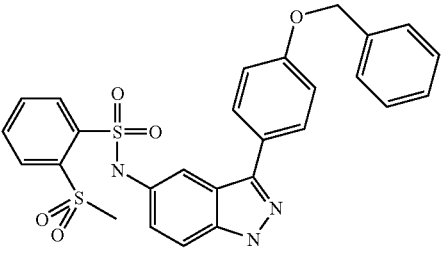 | 209 | 55 | 34 | 67 | | | | 16 | |
| 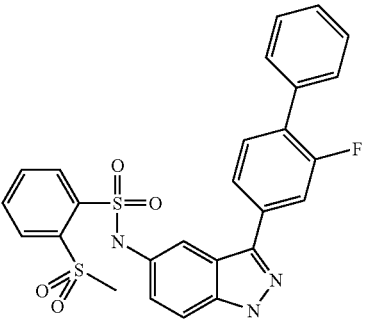 | 210 | 70 | 50 | 65 | | | | 0 | |
| 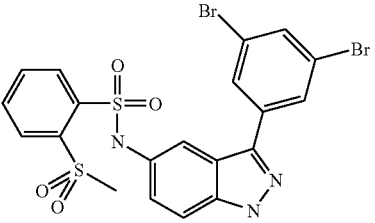 | 211 | 95 | 21 | 79 | | | | 45 | |
| 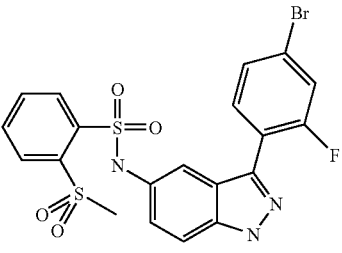 | 212 | 72 | 47 | 86 | | | | 65 | |

TABLE 1-continued

| Structure | Example | % inhib at 10 or 30* µM | % inhib at 10 µM ||||||
|---|---|---|---|---|---|---|---|---|
| | | | KDR | Aurora2 | SRC | TIE 2 | IGF1R | CDK 2 | CDK 4 |
| | 213 | 80 | 68 | 89 | | | | 77 | |
| | 214 | 60 | 56 | 67 | | | | 21 | |
| | 215 | 97 | 39 | 86 | | | | | |
| | 216 | 96 | 32 | 91 | | | | 86 | |
| | 217 | 95 | 70 | 92 | | | | 83 | |

TABLE 1-continued

Results

| Structure | Example | % inhib at 10 or 30* μM | % inhib at 10 μM ||||||
|---|---|---|---|---|---|---|---|---|
| | | | KDR | Aurora2 | SRC | TIE2 | IGF1R | CDK2 | CDK4 |
| | 218 | 15 | 37 | 68 | | | | 20 | |
| | 219 | 87 | 31 | 86 | | | | 60 | |
| | 220 | 96 | 88 | 95 | | | | 75 | |
| | 221 | 94 | 60 | 84 | | | | 50 | |
| | 222 | 94 | 49 | 92 | | | | 66 | |
| | 223 | 70 | 23 | 31 | | | | 0 | |

TABLE 1-continued

Results

| Structure | Example | % inhib at 10 or 30* μM | % inhib at 10 μM | | | | | | |
|---|---|---|---|---|---|---|---|---|---|
| | | | KDR | Aurora2 | SRC | TIE2 | IGF1R | CDK2 | CDK4 |
| 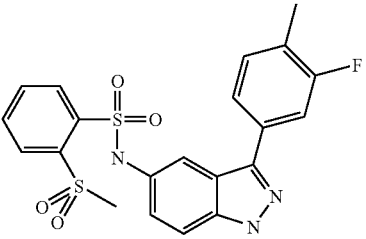 | 224 | 91 | 71 | 92 | | | | 70 | |
| 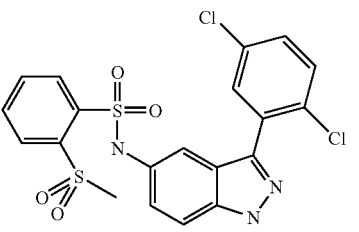 | 225 | 51 | 12 | 49 | | | | 27 | |
| 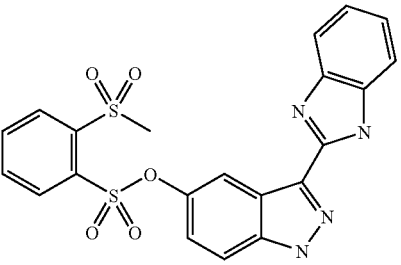 | 226 | | | 100 | | | | | |
| 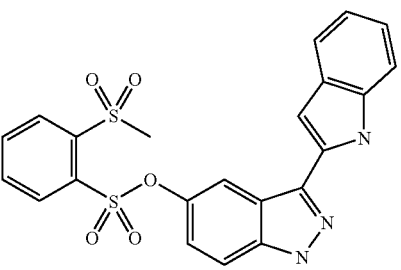 | 227 | | | 100 | | | | | |

What is claimed is:

1. A compound of the formula (IA):

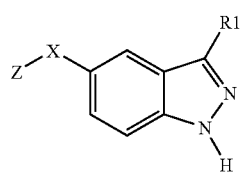

Formula (IA)

wherein:

R1 is substituted or unsubstituted heteroaryl selected from the group consisting of thiophenyl, benzo[b]thiophenyl, indolyl, pyrrol[2,3-b]pyridinyl, furanyl, dibenzofuranyl, benzofuranyl, pyridinyl, pyrrol-1-yl, pyrrol-2-yl, pyrrol-3-yl, benzimidazolyl and quinolinyl; and Z is selected from the group consisting of alkyl, alkenyl, aryl, cycloalkyl, substituted alkyl, substituted alkenyl, substituted aryl, and substituted cycloalkyl;

R is chosen from hydrogen or C1-C3 alkyl;

X is selected from the group consisting of $S(O_2)$—NH; $S(O_2)$—O; NH—$S(O_2)$; and O—$S(O_2)$; or an enantiomer, stereoisomer, rotamer or a tautomer thereof, or a pharmaceutically acceptable salt or solvate thereof;

with the proviso that the compound of formula (IA) is not one of the following compounds:

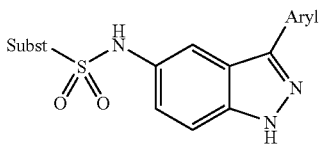

wherein
  (i) Aryl is chosen from 6-(2-dimethylaminomethyl-5-methylmorpholin-4-yl)-1H-benzimidazol-2-yl, 6-(4-methylpiperazin-1-yl)-1H-benzimidazol-2-yl, 6-(1,4'-bipiperidin-1'-yl)-1H-benzimidazol-2-yl and 6-(N,N-dialkylamino)-1H-benzimidazol-2-yl, and Subst is independently chosen from methyl, ethyl, trifluoromethyl, phenyl, or 4-methoxyphenyl,
  (ii) Aryl is thien-2-yl and Subst is 3,5-bis(trifluoromethyl)phenyl.

2. The compound as set forth in claim 1, wherein X is S(O$_2$)—NH or S(O$_2$)—O.

3. The compound as set forth in claim 1, wherein Z is substituted aryl.

4. The compound as set forth in claim 3, wherein Z is phenyl substituted with one to three substituents.

5. The compound as set forth in claim 4, wherein Z is phenyl substituted with one or more substituents selected independently from the group consisting of: fluorine, chlorine, trifluoromethoxy, dimethylamino, and methylsulfonyl.

6. The compound as set forth in claim 1, wherein X is SO$_2$—NH.

7. The compound as set forth in claim 1, wherein R is hydrogen.

8. The compound as set forth in claim 1, wherein R1 is selected from the group consisting of thiophen-2-yl, 5-methoxy-1H-indol-2-yl, benzofuran-2-yl, 1H-indol-2-yl, pyrrol-2-yl, 1H-benzimidazol-2-yl, pyrid-4-yl and pyrid-3-yl.

9. The compound as set forth in claim 8, wherein Z is chosen from 2-methylsulfonylphenyl, 3-fluorophenyl, 2-trifluoromethoxyphenyl, and phenyl.

10. The compound as set forth in claim 1, wherein R1 is selected from the group consisting of 5-methoxy-1H-indol-2-yl, 1H-indol-2-yl, 1H-benzimidazol-2-yl, pyrid-4-yl, pyrid-3-yl, and benzothiophen-2-yl.

11. The compound as set forth in claim 1, which is chosen from the group consisting of:
  2-methylsulfonyl-N-(3-thiophen-2-yl-1H-indazol-5-yl)benzenesulfonamide;
  2-methylsulfonyl-N-(3-thiophen-3-yl-1H-indazol-5-yl)benzenesulfonamide;
  N-(3-furan-3-yl-1H-indazol-5-yl)-2-methylsulfonylbenzenesulfonamide;
  N-(3-furan-2-yl-1H-indazol-5-yl)-2-methylsulfonylbenzenesulfonamide;
  2-methylsulfonyl-N-(3-pyridin-4-yl-1H-indazol-5-yl)benzenesulfonamide;
  2-methylsulfonyl-N-[3-(1H-pyrrolo[2,3-b]pyridin-2-yl)-1H-indazol-5-yl]benzenesulfonamide;
  2-methylsulfonyl-N-[3-(5-methoxy-1H-indol-2-yl)-1H-indazol-5-yl]benzenesulfonamide;
  2-methylsulfonyl-N-(3-pyridin-3-yl-1H-indazol-5-yl)benzenesulfonamide;
  2-methylsulfonyl-N-[3-(1H-pyrrol-2-yl)-1H-indazol-5-yl]benzenesulfonamide;
  N-[3-(1H-indol-2-yl)-1H-indazol-5-yl]-2-methylsulfonylbenzenesulfonamide;
  N-(3-benzo[b]thiophen-3-yl-1H-indazol-5-yl)-2-methylsulfonylbenzenesulfonamide;
  N-(3-benzo[b]thiophen-2-yl-1H-indazol-5-yl)-2-methylsulfonylbenzenesulfonamide;
  2-methylsulfonyl-N-(3-quinolin-8-yl-1H-indazol-5-yl)benzenesulfonamide;
  N-[3-(1H-benzimidazol-2-yl)-1H-indazol-5-yl]-2-methylsulfonylbenzenesulfonamide;
  N-[3-(1H-indol-2-yl)-1H-indazol-5-yl]benzenesulfonamide;
  N-[3-(1H-indol-2-yl)-1H-indazol-5-yl]-2-trifluoromethoxybenzenesulfonamide;
  3-fluoro-N-[3-(1H-indol-2-yl)-1H-indazol-5-yl]benzenesulfonamide;
  4-dimethylamino-2,3,5,6-tetrafluoro-N-[3-(1H-indol-2-yl)-1H-indazol-5-yl]benzenesulfonamide;
  N-[3-(1H-indol-5-yl)-1H-indazol-5-yl]-2-methylsulfonylbenzenesulfonamide;
  N-(3-(dibenzofuran-4-yl)-1H-indazol-5-yl)-2-methanesulfonyl-benzenesulfonamide;
  2-methanesulfonyl-N-(3-thiophen-2-yl-1H-indazol-5-yl)benzenesulfonamide;
  N-(3-benzofuran-2-yl-1H-indazol-5-yl)-2-methanesulfonyl-benzenesulfonamide;
  N-[3-(5-chlorothiophen-2-yl)-1H-indazol-5-yl]-2-methanesulfonyl-benzenesulfonamide;
  3-(1H-benzimidazol-2-yl)-1H-indazol-5-yl-2-methanesulfonylbenzenesulfonate;
  3-(1H-indol-2-yl)-1H-indazol-5-yl-2-methanesulfonyl-benzenesulfonate;
  3-(1H-indol-2-yl)-1H-indazol-5-yl-benzenesulfonate;
  3-(1H-indol-2-yl)-1H-indazol-5-yl-2,6-dichlorobenzenesulfonate;
  3-(1H-indol-2-yl)-1H-indazol-5-yl-2-trifluoromethoxy-benzenesulfonate; and
  3-(1H-indol-2-yl)-1H-indazol-5-yl-3-fluorobenzenesulfonate.

12. A pharmaceutical composition comprising one or more compounds as set forth in claim 1, in combination with a pharmaceutically acceptable excipient.

13. A compound of the formula (I):

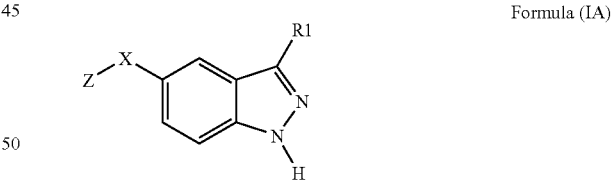

Formula (IA)

wherein:
  R1 is substituted or unsubstituted heteroaryl selected from the group consisting of thiophenyl, benzo[b]thiophenyl, indolyl, pyrrol[2,3-b]pyridinyl, furanyl, dibenzofuranyl, benzofuranyl, pyridinyl, pyrrol-1-yl, pyrrol-2-yl, pyrrol-3-yl, benzimidazolyl and quinolinyl;
  X is selected from the group consisting of S(O$_2$)—NH; S(O$_2$)—O; NH—S(O$_2$); and O—S(O$_2$);
  Z is selected from the group consisting of alkyl, aryl, cycloalkyl, substituted alkyl, substituted aryl, and substituted cycloalkyl; or
  an enantiomer, stereoisomer, rotamer or a tautomer thereof, or a pharmaceutically acceptable salt or solvate thereof;

with the proviso that the compound of formula (IA) is not one of the following compounds:

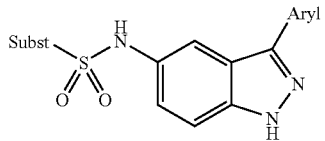

wherein
(i) Aryl is chosen from 6-(2-dimethylaminomethyl-5-methylmorpholin-4-yl)-1H-benzimidazol-2-yl, 6-(4-methylpiperazin-1-yl)-1H-benzimidazol-2-yl, 6-(1,4'-bipiperidin-1'-yl)-1H-benzimidazol-2-yl and 6-(N,N-dialkylamino)-1H-benzimidazol-2-yl, and Subst is independently chosen from methyl, ethyl, trifluoromethyl, phenyl, or 4-methoxyphenyl, or (ii) Aryl is thien-2-yl and Subst is 3,5-bis(trifluoromethyl)phenyl.

14. A pharmaceutical composition comprising one or more compounds as set forth in claim 13, in combination with a pharmaceutically acceptable excipient.

* * * * *